US007910105B2

(12) United States Patent
Young et al.

(10) Patent No.: US 7,910,105 B2
(45) Date of Patent: Mar. 22, 2011

(54) METHODS FOR TREATING AND PREVENTING FIBROSIS

(75) Inventors: Deborah A. Young, Melrose, MA (US); Thomas A. Wynn, Silver Spring, MD (US); Mary Collins, Natick, MA (US); Michael J. Grusby, Newton, MA (US)

(73) Assignees: Wyeth LLC, Madison, NJ (US); The United States of America as represented by the Department of Health and Human Services, Washington, DC (US); President and Fellows of Harvard College, Cambridge, MA (US)

( * ) Notice: Subject to any disclaimer, the term of this patent is extended or adjusted under 35 U.S.C. 154(b) by 336 days.

(21) Appl. No.: 11/402,885

(22) Filed: Apr. 13, 2006

(65) Prior Publication Data

US 2006/0257403 A1 Nov. 16, 2006

Related U.S. Application Data

(60) Provisional application No. 60/671,374, filed on Apr. 14, 2005.

(51) Int. Cl.
*A61K 39/395* (2006.01)
*A61K 38/20* (2006.01)

(52) U.S. Cl. ....................................... 424/145.1; 514/12

(58) Field of Classification Search ........................ None
See application file for complete search history.

(56) References Cited

U.S. PATENT DOCUMENTS

| | | | | |
|---|---|---|---|---|
| 5,624,821 | A | 4/1997 | Winter et al. | 435/69.6 |
| 5,648,260 | A | 7/1997 | Winter et al. | 435/252.3 |
| 5,665,772 | A | 9/1997 | Cottens et al. | 514/514 |
| 5,693,761 | A | 12/1997 | Queen et al. | 536/23.53 |
| 5,693,762 | A | 12/1997 | Queen et al. | 530/387.3 |
| 5,714,147 | A | 2/1998 | Capon et al. | 424/178.1 |
| 6,057,128 | A | 5/2000 | Donaldson et al. | 435/69.1 |
| 6,136,310 | A | 10/2000 | Hanna et al. | 424/154.1 |
| 6,258,562 | B1 | 7/2001 | Salfeld et al. | 435/69.6 |
| 6,307,024 | B1 | 10/2001 | Novak et al. | 530/351 |
| 6,350,892 | B1 | 2/2002 | Banville et al. | 556/436 |
| 6,576,744 | B1 | 6/2003 | Presnell et al. | 530/351 |
| 6,777,539 | B2 | 8/2004 | Sprecher et al. | 530/350 |
| 6,929,932 | B2 | 8/2005 | Presnell et al. | 435/69.52 |
| 7,189,400 | B2 | 3/2007 | Carter et al. | 424/185.1 |
| 7,198,789 | B2 * | 4/2007 | Carter et al. | 424/130.1 |
| 7,276,478 | B2 | 10/2007 | Sivakumar et al. | 424/85.2 |
| 7,314,623 | B2 | 1/2008 | Grusby et al. | 424/185.1 |
| 7,495,085 | B2 | 2/2009 | Valge-Archer et al. | 530/387.9 |
| 2003/0118592 | A1 | 6/2003 | Ledbetter et al. | 424/178.1 |
| 2003/0133939 | A1 | 7/2003 | Ledbetter et al. | 424/178.1 |
| 2004/0009150 | A1 | 1/2004 | Nelson et al. | 424/85.2 |
| 2004/0016010 | A1 | 1/2004 | Kasaian et al. | 800/18 |
| 2004/0058445 | A1 | 3/2004 | Ledbetter et al. | 435/372 |
| 2005/0136049 | A1 | 6/2005 | Ledbetter et al. | 424/132.1 |
| 2005/0175614 | A1 | 8/2005 | Ledbetter et al. | 424/145.1 |
| 2005/0180970 | A1 | 8/2005 | Ledbetter et al. | 424/143.1 |
| 2005/0186216 | A1 | 8/2005 | Ledbetter et al. | 424/155.1 |
| 2005/0202012 | A1 | 9/2005 | Ledbetter et al. | 424/144.1 |
| 2005/0202023 | A1 | 9/2005 | Ledbetter et al. | 424/155.1 |
| 2005/0202028 | A1 | 9/2005 | Ledbetter et al. | 424/178.1 |
| 2005/0202534 | A1 | 9/2005 | Ledbetter et al. | 435/69.1 |
| 2005/0238646 | A1 | 10/2005 | Ledbetter et al. | 424/144.1 |
| 2006/0024268 | A1 | 2/2006 | Kasaian et al. | 424/85.2 |
| 2006/0039902 | A1 | 2/2006 | Young et al. | 424/133.1 |
| 2006/0159655 | A1 | 7/2006 | Collins et al. | 424/85.2 |
| 2008/0167241 | A1 | 7/2008 | Donaldson et al. | 514/12 |
| 2008/0241098 | A1 | 10/2008 | Young et al. | 424/85.2 |
| 2009/0197803 | A1 | 8/2009 | Grusby et al. | 514/12 |

FOREIGN PATENT DOCUMENTS

| | | | |
|---|---|---|---|
| WO | WO 99/47675 | | 9/1999 |
| WO | WO 00/53761 | | 9/2000 |
| WO | WO 00/56772 | | 9/2000 |
| WO | WO 01/55112 | | 8/2001 |
| WO | WO 01/85792 | | 11/2001 |
| WO | WO 03/028630 | | 4/2003 |
| WO | WO 03/087320 | | 10/2003 |
| WO | WO 2004/007682 | | 1/2004 |
| WO | WO 2004/083249 | | 9/2004 |
| WO | WO2004083249 | * | 9/2004 |

(Continued)

OTHER PUBLICATIONS

Elliot Marshall, Science, Mar. 2006, vol. 311, pp. 1688-1689.*

Alfarano et al. (2005) "The Biomolecular Interaction Network Database and related tools 2005 update" *Nuc. Acids Res. Database Issue* 33:D418-24.

Bonecchi et al. (1998) "Divergent Effects of Interleukin-4 and Interferon-γ on Macrophage-Derived Chemokine Production: An Amplification Circuit of Polarized T Helper 2 Responses" *Blood* 92:2668-71.

Chiaramonte et al. (1999) "An IL-13 inhibitor blocks the development of hepatic fibrosis during a T-helper type 2—dominated inflammatory response" *J. Clin. Invest.* 104:777-85.

(Continued)

*Primary Examiner* — Bridget E Bunner
*Assistant Examiner* — Fozia M Hamud
(74) *Attorney, Agent, or Firm* — Fitzpatrick, Cella, Harper & Scinto

(57) ABSTRACT

The present invention provides methods of screening for compositions useful for treating, ameliorating, or preventing fibrosis and/or fibrosis-associated conditions by measuring changes in the level(s) of IL-21 and/or IL-21 receptor (IL-21R) (e.g., the level of expression of IL-21 and/or IL-21R protein and/or mRNA, the level of activity of IL-21 and/or IL-21R, the level of interaction of IL-21 with IL-21R). The invention further provides antagonists of IL-21 or IL-21R for the treatment of fibrosis and/or fibrosis-associated conditions. Further provided herein are methods of diagnosing, prognosing, and monitoring the progress (e.g., the course of treatment) of fibrosis and/or fibrosis-associated conditions by measuring the level of IL-21 and/or IL-21R (i.e., the level of activity of IL-21 and/or IL-21R, the level of expression of IL-21 and/or IL-21R (e.g., the level of IL-21 and/or IL-21R gene products), and/or the level of interaction of IL-21 with IL-21R).

8 Claims, 46 Drawing Sheets

FOREIGN PATENT DOCUMENTS

| | | |
|---|---|---|
| WO | WO 2004/084835 | 10/2004 |
| WO | WO 2005/030196 A2 | 4/2005 |
| WO | WO 2005/112983 | 12/2005 |
| WO | WO 2006/135385 | 12/2006 |
| WO | WO 2009/100035 | 8/2009 |

OTHER PUBLICATIONS

Chiaramonte et al. (2003) "Regulation and Function of the Interleukin 13 Receptor α 2 During a T Helper Cell Type 2—dominant Immune Response" *J. Exp. Med.* 197:687-701.

Collins et al. (2003) "IL-21 and IL-21 receptor: a new cytokine pathway modulates innate and adaptive immunity" *Immunol. Res.* 28:131-40.

Distler et al. (2005) "Expression of Interleukin-21 Receptor in Epidermis from Patients with Systemic Sclerosis" Arthirtis Rheum. 52:856-64.

Davis et al. (2005) "Crystal structure of prostate-specific membrane antigen, a tumor marker and peptidase" *Proc. Natl. Acad. Sci. USA* 102:5981-86.

Di Carlo et al. (2004) "IL-21 Induces Tumor Rejection by Specific CTL and IFN-γ-Dependent CXC Chemokines in Syngeneic Mice" *J. lmmunol.* 172:1540-47.

Elit (2002) "CCI-779 Wyeth" *Curr. Opin. Investig. Drugs* 3(8):1249-53.

Fallon et al. (2000) "Schistosome Infection of Transgenic Mice Defines Distinct and Contrasting Pathogenic Roles for IL-4 and IL-13: IL-13 Is a Profibrotic Agent" *J. Immunol.* 164:2585-91.

Fichtner-Feigl et al. (2006) "IL-13 signaling through the IL-13α2 receptor is involved in induction of TGF-beta1 production and fibrosis" *Nat. Med.* 12:99-106.

Gordon (2003) "Alternative activation of macrophages" *Nat. Rev. Immunol.* 3:23-35.

Guo et al. (2000) "Biochemical Characterization of Endogenously Formed Eosinophilic Crystals in the Lungs of Mice" *J. Biol. Chem.* 275:8032-37.

Habib et al. (2003) "IL-21: a novel IL-2-family lymphokine that modulates B, T, and natural killer cell responses" *J. Allergy Clin. Immunol.* 112:1033-45.

Halpin and Harbury (2004) "DNA Display II. Genetic Manipulation of Combinatorial Chemistry Libraries for Small-Molecule Evolution" *PLoS Biology* 2:1022-30.

Herbert et al. (2004) "Alternative macrophage activation is essential for survival during schistosomiasis and downmodulates T helper 1 responses and immunopathology" *Immunity* 20:623-35.

Hesse et al. (2000) "NOS-2 Mediates the Protective Anti-Inflammatory and Antifibrotic Effects of the Th1-Inducing Adjuvant, IL-12, in a Th2 Model of Granulomatous Disease" *Am. J. Pathol.* 157:945-55.

Hesse et al. (2001) "Differential Regulation of Nitric Oxide Synthase-2 and Arginase-1 by Type 1/Type 2 Cytokines In Vivo: Granulomatous Pathology Is Shaped by the Pattern of L-Arginine Metabolism" *J. Immunol.* 167:6533-44.

Hoffmann et al. (1999) "Studies with Double Cytokine-Deficient Mice Reveal That Highly Polarized Th1- and Th2-Type Cytokine and Antibody Responses Contribute Equally to Vaccine-Induced Immunity to *Schistosoma mansoni*" *J. lmmunol.* 163:927-938.

Hoffmann et al. (2000) "IL-10 and the Dangers of Immune Polarization: Excessive Type 1 and Type 2 Cytokine Responses Induce Distinct Forms of Lethal Immunopathology in Murine Schistosomiasis" *J. Immunol.* 164:6406-16.

Huang and Houghton (2002) "Inhibitors of mammalian target of rapamycin as novel antitumor agents: From bench to clinic" *Curr. Opin. Investig. Drugs* 3:295-304.

Jakubzick et al. (2003) "Impact of Interleukin-13 Responsiveness on the Synthetic and Proliferative Properties of Th1- and Th2-Type Pulmonary Granuloma Fibroblasts" *Am. J. Pathol.* 162:1475-86.

Jankovic et al. (1999) "Schistosome-Infected IL-4 Receptor Knockout (KO) Mice, in Contrast to IL-4 KO Mice, Fail to Develop Granulomatous Pathology While Maintaining the Same Lymphokine Expression Profile" *J. Immunol.* 163:337-42.

Jin et al. (2004) "Distinct Activation Signals Determine Whether IL-21 Induces B Cell Costimulation, Growth Arrest, or Bim-Dependent Apoptosis" *J. Immunol.* 173:657-65.

Kaplan et al. (1998) "Th2 Cells Are Required for the *Schistosoma mansoni* Egg-Induced Granulomatous Response" *J. Immunol.* 160:1850-56.

Karp (2000) "An ontology for biological function based on molecular interactions" *Bioinformatics Ontology* 16:269-85.

Kasaian et al. (2002) "IL-21 limits NK cell responses and promotes antigen-specific T cell activation: a mediator of the transition from innate to adaptive immunity" *Immunity* 16:559-69.

Kaviratne et al. (2004) "IL-13 Activates a Mechanism of Tissue Fibrosis That Is Completely TGF-β Independent" *J. Immunol.* 173:4020-29.

Kishida et al. (2003) "Interleukin (IL)-21 and IL-15 genetic transfer synergistically augments therapeutic antitumor immunity and promotes regression of metastatic lymphoma" *Mol. Ther.* 8:552-58.

Kraan et al. (2004) "Differential effects of leflunomide and methotrexate on cytokine production in rheumatoid arthritis" *Ann. Rheum. Dis.* 63:1056-61.

Krstenansky and Mao (1987) "Antithrombin properties of C-terminus of hirudin using synthetic unsulfated $N^{\alpha}$-acetyl-hirudin$_{45-65}$" FEBS Letters 211:10-16.

Lee et al. (2001) "Interleukin-13 Induces Tissue Fibrosis by Selectively Stimulating and Activating Transforming Growth Factor β1" *J. Exp. Med.* 194:809-21.

Liu et al. (2004) "Regulation of Found in Inflammatory Zone 1 Expression in Bleomycin-Induced Lung Fibrosis: Role of IL-4/IL-13 and Mediation via STAT-6" *J. Immunol.* 173:3425-31.

Ma et al. (2003) "IL-21 Activates Both Innate and Adaptive Immunity to Generate Potent Antitumor Responses that Require Perforin but Are Independent of IFN-γ" *J. Immunol.* 171:608-15.

Mallat et al. (2001) "Interleukin-18/Interleukin-18 Binding Protein Signaling Modulates Atherosclerotic Lesion Development and Stability" *Circ. Res.* 89:e41-45.

Mantovani et al. (2005) "Macrophage Polarization Comes of Age" *Immunity* 23:344-46.

Mehta et al. (2003) "IL-21 Induces the Apoptosis of Resting and Activated Primary B Cells" *J. Immunol.* 170:4111-18.

Mehta et al. (2004) "Biology of IL-21 and the IL-21 receptor" *Immunol. Rev.* 202:84-95.

Mehta et al. (2005) "NFATc2 and T-bet contribute to T-helper-cell-subset-specific regulation of IL-21 expression" *Proc. Natl. Acad. Sci.* U.S.A. 102:2016-21.

Mentink-Kane et al. (2004) "IL-13 receptor α 2 down-modulates granulomatous inflammation and prolongs host survival in schistosomiasis" *Proc. Natl. Acad. Sci.* U.S.A. 101:586-90.

Morimoto et al. (2006) "Functional Importance of Regional Differences in Localized Gene Expression of Receptors for IL-13 in Murine Gut" *J. Immunol.* 176:491-95.

Munder et al. (1998) "Alternative Metabolic States in Murine Macrophages Reflected by the Nitric Oxide Synthase/Arginase Balance: Competitive Regulation by CD4+ T Cells Correlates with Th1/Th2 Phenotype" *J. Immunol.* 160:5347-54.

Wynn (2004) "Fibrotic disease and the T(H)1/T(H)2 paradigm" *Nat. Rev. Immunol.* 4:583-594.

Wynn et al. (2004) "Immunopathogenesis of schistosomiasis" *Immunol. Rev.* 201:156-67.

Yusuf-Makagiansar et al. (2002) "Inhibition of LFA-1/ICAM-1 and VLA-4/VCAM-1 as a therapeutic approach to inflammation and autoimmune diseases" *Med. Res. Rev.* 22:146-67.

Zeng et al. (2005) "Synergy of IL-21 and IL-15 in regulating CD8+ T cell expansion and function" *J. Exp. Med.* 201:139-48.

Zheng et al. (2003) "Cytokine regulation of IL-13Rα2 and IL-13Rα1 in vivo and in vitro" *J. Allergy Clin. Immunol.* 111:720-28.

Zhu et al. (2004) "Acidic mammalian chitinase in asthmatic Th2 inflammation and IL-13 pathway activation" *Science* 304:1678-82.

International Search Report and Written Opinion for PCT/US2006/013829, mailed Aug. 21, 2006.

Urban, et al., "IFN Inhibits Inflammatory Responses and Protective Immunity in Mice Infected with the Nematode Parasite, *Nippostrongylus brasiliensis*," J. Immunol. 151:7086-94 (1993).

Nair et al. (2005) "Chitinase and Fizz Family Members Are a Generalized Feature of Nematode Infection with Selective Upregulation of Ym1 and Fizz1 by Antigen-Presenting Cells" *Infect. Immun.* 73:385-94.

Ozaki et al. (2000) "Cloning of a type I cytokine receptor most related to the IL-2 receptor β chain" *Proc. Natl. Acad. Sci.* U.S.A. 97:11439-44.

Ozaki et al. (2002) "A critical role for IL-21 in regulating immunoglobulin production" *Science* 298:1630-34.

Parrish-Novak et al. (2000) "Interleukin 21 and its receptor are involved in NK cell expansion and regulation of lymphocyte function" *Nature* 408:57-63.

Pearce and MacDonald (2002) "The immunobiology of schistosomiasis" *Nat. Rev. Immunol.* 2:499-511.

Pene et al. (2004) "Cutting Edge: IL-21 Is a Switch Factor for the Production of IgG1 and IgG3 by Human B Cells" *J. Immunol.* 172:5154-57.

Pesce et al. (2006) "The IL-21 Receptor Augments Th2 Effector Function and Alternative Macrophage Activation" J. Clin. Invest. 116:2044-55.

Remington: The Science and Practice of Pharmacy, $21^{st}$ Ed. (Ed. A.R. Gennaro), pp. 692-1017, Lippincott, Williams & Wilkins, Baltimore, M.D., 2005.

Sandler et al. (2003) "Global Gene Expression Profiles During Acute Pathogen-Induced Pulmonary Inflammation Reveal Divergent Roles for Th1 and Th2 Responses in Tissue Repair" *J. Immunol.* 171:3655-67.

Sivakumar et al. (2004) "Interleukin-21 is a T-helper cytokine that regulates humoral immunity and cell-mediated anti-tumour responses" *Immunology* 112:177-82.

Suto et al. (2002) "Interleukin 21 prevents antigen-induced IgE production by inhibiting germ line Cϵ transcription of IL-4-stimulated B cells" *Blood* 100:4565-73.

van der Poll et al. (1997) "Effect of a Recombinant Dimeric Tumor Necrosis Factor Receptor on Inflammatory Responses to Intravenous Endotoxin in Normal Humans" *Blood* 89:3727-34.

Verkman (2004) "Drug discovery in academia" *Am. J. Physiol. Cell Physiol.* 286:465-74.

Vosshenrich and Di Santo (2001) "Cytokines: IL-21 joins the γc-dependent network?" *Curr. Biol.* 11:R175-77.

Wood et al. (2003) "Enhanced Interleukin (IL)-13 Responses in Mice Lacking IL-13 Receptor α 2" *J. Exp. Med.* 197:703-09.

Wurster et al. (2002) "Interleukin 21 Is a T Helper (Th) Cell 2 Cytokine that Specifically Inhibits the Differentiation of Naive Th Cells into Interferon γ-producing Th1 Cells" *J. Exp. Med.* 196:969-77.

Wynn (2003) "IL-13 effector functions" *Annu. Rev. Immunol.* 21:425-56.

Parrish-Novak et al., "Interleukin-21 and the IL-21 receptor: novel effectors of NK and T cell responses" J. Leukoc. Biol. 72:856-63 (2002).

Clinical Rheumatology (Mason and Currey's), $4^{th}$ edn., H.L.F. Currey (ed.), Edinburgh: Churchill Livingstone (1986); ISBN 0-443-0364-1; Barnes, C.G., Rheumatoid Arthritis (Chapter 4), pp. 53-58 (English translation).

* cited by examiner

```
1       GTCGACGCGG CGGTACCAGC TGTCTGCCCA CTTCTCCTGT GGTGTGCCTC
51      ACGGTCACTT GCTTGTCTGA CCGCAAGTCT GCCCATCCCT GGGGCAGCCA
101     ACTGGCCTCA GCCCGTGCCC CAGGCGTGCC CTGTCTCTGT CTGGCTGCCC
151     CAGCCCTACT GTCTTCCTCT GTGTAGGCTC TGCCCAGATG CCCGGCTGGT
201     CCTCAGCCTC AGGACTATCT CAGCAGTGAC TCCCCTGATT CTGGACTTGC
251     ACCTGACTGA ACTCCTGCCC ACCTCAAACC TTCACCTCCC ACCACCACCA
301     CTCCGAGTCC CGCTGTGACT CCCACGCCCA GGAGACCACC CAAGTGCCCC
351     AGCCTAAAGA ATGGCTTTCT GAGAAAGACC CTGAAGGAGT AGGTCTGGGA
401     CACAGCATGC CCCGGGGCCC AGTGGCTGCC TTACTCCTGC TGATTCTCCA
451     TGGAGCTTGG AGCTGCCTGG ACCTCACTTG CTACACTGAC TACCTCTGGA
501     CCATCACCTG TGTCCTGGAG ACACGGAGCC CCAACCCCAG CATACTCAGT
551     CTCACCTGGC AAGATGAATA TGAGGAACTT CAGGACCAAG AGACCTTCTG
601     CAGCCTACAC AGGTCTGGCC ACAACACCAC ACATATATGG TACACGTGCC
651     ATATGCGCTT GTCTCAATTC CTGTCCGATG AAGTTTTCAT TGTCAATGTG
701     ACGGACCAGT CTGGCAACAA CTCCCAAGAG TGTGGCAGCT TTGTCCTGGC
751     TGAGAGCATC AAACCAGCTC CCCCCTTGAA CGTGACTGTG GCCTTCTCAG
801     GACGCTATGA TATCTCCTGG GACTCAGCTT ATGACGAACC CTCCAACTAC
851     GTGCTGAGGG GCAAGCTACA ATATGAGCTG CAGTATCGGA ACCTCAGAGA
901     CCCCTATGCT GTGAGGCCGG TGACCAAGCT GATCTCAGTG GACTCAAGAA
951     ACGTCTCTCT TCTCCCTGAA GAGTTCCACA AAGATTCTAG CTACCAGCTG
1001    CAGGTGCGGG CAGCGCCTCA GCCAGGCACT TCATTCAGGG GGACCTGGAG
1051    TGAGTGGAGT GACCCCGTCA TCTTTCAGAC CCAGGCTGGG GAGCCCGAGG
1101    CAGGCTGGGA CCCTCACATG CTGCTGCTCC TGGCTGTCTT GATCATTGTC
1151    CTGGTTTTCA TGGGTCTGAA GATCCACCTG CCTTGGAGGC TATGGAAAAA
1201    GATATGGGCA CCAGTGCCCA CCCCTGAGAG TTTCTTCCAG CCCCTGTACA
1251    GGGAGCACAG CGGGAACTTC AAGAAATGGG TTAATACCCC TTTCACGGCC
1301    TCCAGCATAG AGTTGGTGCC ACAGAGTTCC ACAACAACAT CAGCCTTACA
1351    TCTGTCATTG TATCCAGCCA AGGAGAAGAA GTTCCCGGGG CTGCCGGGTC
1401    TGGAAGAGCA ACTGGAGTGT GATGGAATGT CTGAGCCTGG TCACTGGTGC
```

Figure 1A

```
1451  ATAATCCCCT TGGCAGCTGG CCAAGCGGTC TCAGCCTACA GTGAGGAGAG
1501  AGACCGGCCA TATGGTCTGG TGTCCATTGA CACAGTGACT GTGGGAGATG
1551  CAGAGGGCCT GTGTGTCTGG CCCTGTAGCT GTGAGGATGA TGGCTATCCA
1601  GCCATGAACC TGGATGCTGG CCGAGAGTCT GGCCCTAATT CAGAGGATCT
1651  GCTCTTGGTC ACAGACCCTG CTTTTCTGTC TTGCGGCTGT GTCTCAGGTA
1701  GTGGTCTCAG GCTTGGAGGC TCCCCAGGCA GCCTACTGGA CAGGTTGAGG
1751  CTGTCATTTG CAAAGGAAGG GGACTGGACA GCAGACCCAA CCTGGAGAAC
1801  TGGGTCCCCA GGAGGGGGCT CTGAGAGTGA AGCAGGTTCC CCCCCTGGTC
1851  TGGACATGGA CACATTTGAC AGTGGCTTTG CAGGTTCAGA CTGTGGCAGC
1901  CCCGTGGAGA CTGATGAAGG ACCCCCTCGA AGCTATCTCC GCCAGTGGGT
1951  GGTCAGGACC CCTCCACCTG TGGACAGTGG AGCCCAGAGC AGCTAGCATA
2001  TAATAACCAG CTATAGTGAG AAGAGGCCTC TGAGCCTGGC ATTTACAGTG
2051  TGAACATGTA GGGGTGTGTG TGTGTGTGTG TGTGTGTGTG TGTGTGTGTG
2101  TGTGTGTGTG TGTGTGTGTG TGTCTTGGGT TGTGTGTTAG CACATCCATG
2151  TTGGGATTTG GTCTGTTGCT ATGTATTGTA ATGCTAAATT CTCTACCCAA
2201  AGTTCTAGGC CTACGAGTGA ATTCTCATGT TTACAAACTT GCTGTGTAAA
2251  CCTTGTTCCT TAATTTAATA CCATTGGTTA AATAAAATTG GCTGCAACCA
2301  ATTACTGGAG GGATTAGAGG TAGGGGGCTT TTGAGTTACC TGTTTGGAGA
2351  TGGAGAAGGA GAGAGGAGAG ACCAAGAGGA GAAGGAGGAA GGAGAGGAGA
2401  GGAGAGGAGA GGAGAGGAGA GGAGAGGAGA GGAGAGGAGA GGAGAGGAGA
2451  GGCTGCCGTG AGGGGAGAGG GACCATGAGC CTGTGGCCAG GAGAAACAGC
2501  AAGTATCTGG GGTACACTGG TGAGGAGGTG GCCAGGCCAG CAGTTAGAAG
2551  AGTAGATTAG GGGTGACCTC CAGTATTTGT CAAAGCCAAT TAAAATAACA
2601  AAAAAAAAAA AAAAGCGGCC GCTCTAGA
```

1 MPRGPVAALL LLILHGAWSC LDLTCYTDYL WTITCVLETR SPNPSILSLT

51 WQDEYEELQD QETFCSLHRS GHNTTHIWYT CHMRLSQFLS DEVFIVNVTD

101 QSGNNSQECG SFVLAESIKP APPLNVTVAF SGRYDISWDS AYDEPSNYVL

151 RGKLQYELQY RNLRDPYAVR PVTKLISVDS RNVSLLPEEF HKDSSYQLQV

201 RAAPQPGTSF RGTWSEWSDP VIFQTQAGEP EAGWDPHMLL LLAVLIIVLV

251 FMGLKIHLPW RLWKKIWAPV PTPESFFQPL YREHSGNFKK WVNTPFTASS

301 IELVPQSSTT TSALHLSLYP AKEKKFPGLP GLEEQLECDG MSEPGHWCII

351 PLAAGQAVSA YSEERDRPYG LVSIDTVTVG DAEGLCVWPC SCEDDGYPAM

401 NLDAGRESGP NSEDLLLVTD PAFLSCGCVS GSGLRLGGSP GSLLDRLRLS

451 FAKEGDWTAD PTWRTGSPGG GSESEAGSPP GLDMDTFDSG FAGSDCGSPV

501 ETDEGPPRSY LRQWVVRTPP PVDSGAQSS

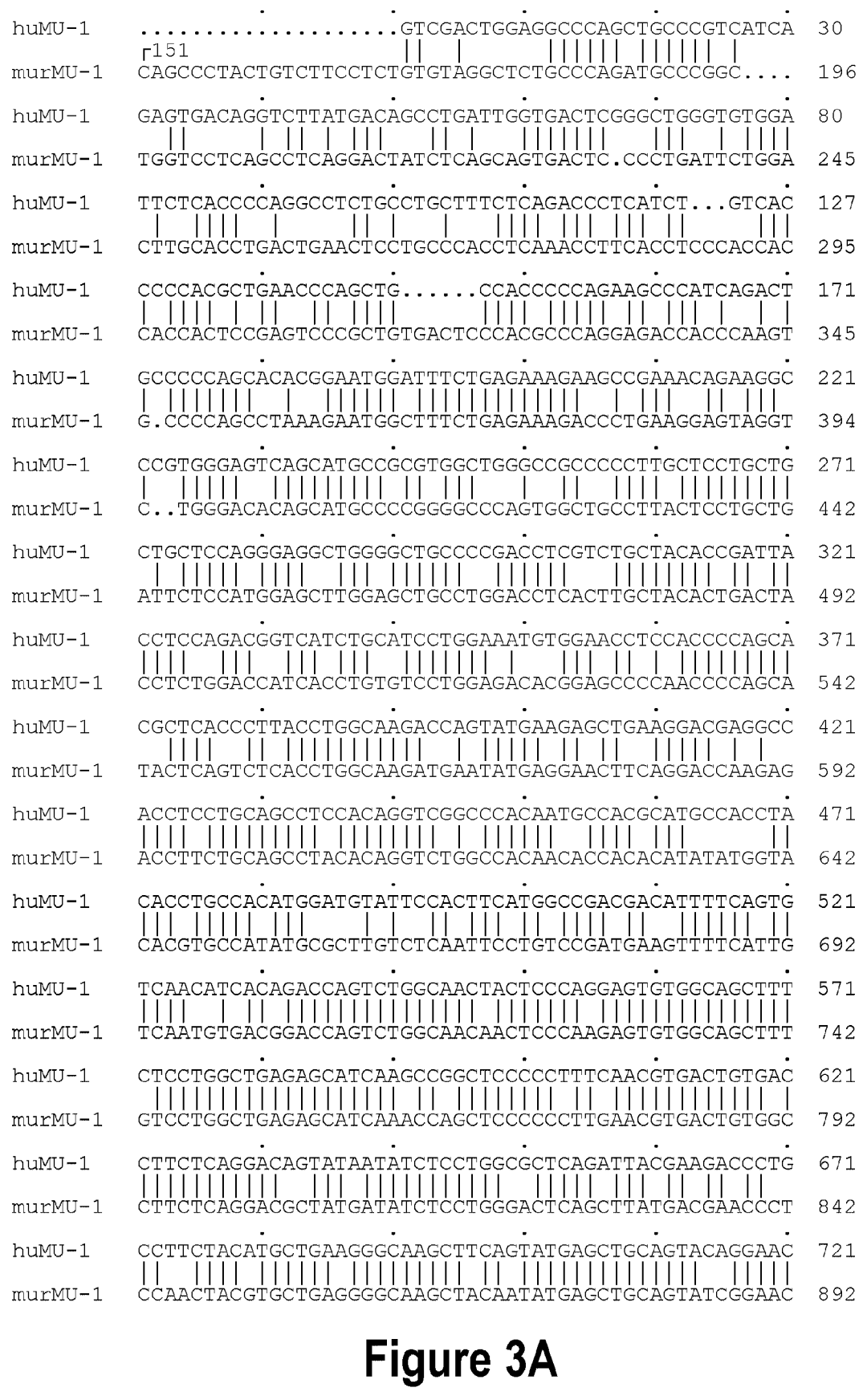

```
huMU-1    ....................GTCGACTGGAGGCCCAGCTGCCCGTCATCA  30
          ┌151
murMU-1   CAGCCCTACTGTCTTCCTCTGTGTAGGCTCTGCCCAGATGCCCGGC....  196

huMU-1    GAGTGACAGGTCTTATGACAGCCTGATTGGTGACTCGGGCTGGGTGTGGA  80
murMU-1   TGGTCCTCAGCCTCAGGACTATCTCAGCAGTGACTC.CCCTGATTCTGGA  245

huMU-1    TTCTCACCCCAGGCCTCTGCCTGCTTTCTCAGACCCTCATCT...GTCAC  127
murMU-1   CTTGCACCTGACTGAACTCCTGCCCACCTCAAACCTTCACCTCCCACCAC  295

huMU-1    CCCCACGCTGAACCCAGCTG......CCACCCCCAGAAGCCCATCAGACT  171
murMU-1   CACCACTCCGAGTCCCGCTGTGACTCCCACGCCCAGGAGACCACCCAAGT  345

huMU-1    GCCCCCAGCACACGGAATGGATTTCTGAGAAAGAAGCCGAAACAGAAGGC  221
murMU-1   G.CCCCAGCCTAAAGAATGGCTTTCTGAGAAAGACCCTGAAGGAGTAGGT  394

huMU-1    CCGTGGGAGTCAGCATGCCGCGTGGCTGGGCCGCCCCCTTGCTCCTGCTG  271
murMU-1   C..TGGGACACAGCATGCCCCGGGGCCCAGTGGCTGCCTTACTCCTGCTG  442

huMU-1    CTGCTCCAGGGAGGCTGGGGCTGCCCCGACCTCGTCTGCTACACCGATTA  321
murMU-1   ATTCTCCATGGAGCTTGGAGCTGCCTGGACCTCACTTGCTACACTGACTA  492

huMU-1    CCTCCAGACGGTCATCTGCATCCTGGAAATGTGGAACCTCCACCCCAGCA  371
murMU-1   CCTCTGGACCATCACCTGTGTCCTGGAGACACGGAGCCCCAACCCCAGCA  542

huMU-1    CGCTCACCCTTACCTGGCAAGACCAGTATGAAGAGCTGAAGGACGAGGCC  421
murMU-1   TACTCAGTCTCACCTGGCAAGATGAATATGAGGAACTTCAGGACCAAGAG  592

huMU-1    ACCTCCTGCAGCCTCCACAGGTCGGCCCACAATGCCACGCATGCCACCTA  471
murMU-1   ACCTTCTGCAGCCTACACAGGTCTGGCCACAACACCACACATATATGGTA  642

huMU-1    CACCTGCCACATGGATGTATTCCACTTCATGGCCGACGACATTTTCAGTG  521
murMU-1   CACGTGCCATATGCGCTTGTCTCAATTCCTGTCCGATGAAGTTTTCATTG  692

huMU-1    TCAACATCACAGACCAGTCTGGCAACTACTCCCAGGAGTGTGGCAGCTTT  571
murMU-1   TCAATGTGACGGACCAGTCTGGCAACAACTCCCAAGAGTGTGGCAGCTTT  742

huMU-1    CTCCTGGCTGAGAGCATCAAGCCGGCTCCCCCTTTCAACGTGACTGTGAC  621
murMU-1   GTCCTGGCTGAGAGCATCAAACCAGCTCCCCCCTTGAACGTGACTGTGGC  792

huMU-1    CTTCTCAGGACAGTATAATATCTCCTGGCGCTCAGATTACGAAGACCCTG  671
murMU-1   CTTCTCAGGACGCTATGATATCTCCTGGGACTCAGCTTATGACGAACCCT  842

huMU-1    CCTTCTACATGCTGAAGGGCAAGCTTCAGTATGAGCTGCAGTACAGGAAC  721
murMU-1   CCAACTACGTGCTGAGGGGCAAGCTACAATATGAGCTGCAGTATCGGAAC  892
```

Figure 3A

```
huMU-1   CGGGGAGACCCCTGGGCTGTGAGTCCGAGGAGAAAGCTGATCTCAGTGGA  771
murMU-1  CTCAGAGACCCCTATGCTGTGAGGCCGGTGACCAAGCTGATCTCAGTGGA  942

huMU-1   CTCAAGAAGTGTCTCCCTCCTCCCCCTGGAGTTCCGCAAAGACTCGAGCT  821
murMU-1  CTCAAGAAACGTCTCTCTTCTCCCTGAAGAGTTCCACAAAGATTCTAGCT  992

huMU-1   ATGAGCTGCAGGTGCGGGCAGGGCCCATGCCTGGCTCCTCCTACCAGGGG  871
murMU-1  ACCAGCTGCAGGTGCGGGCAGCGCCTCAGCCAGGCACTTCATTCAGGGGG  1042

huMU-1   ACCTGGAGTGAATGGAGTGACCCGGTCATCTTTCAGACCCAGTCAGAGGA  921
murMU-1  ACCTGGAGTGAGTGGAGTGACCCCGTCATCTTTCAGACCCAGGCTGGGGA  1092

huMU-1   GTTAAAGGAAGGCTGGAACCCTCACCTGCTGCTTCTCCTCCTGCTTGTCA  971
murMU-1  GCCCGAGGCAGGCTGGGACCCTCACATGCTG...CTGCTCCTGGCTGTCT  1139

huMU-1   TAGTCTTCATTCCTGCCTTCTGGAGCCTGAAGACCCATCCATTGTGGAGG  1021
murMU-1  TGATCATTGTCCTGGTTTTCATGGGTCTGAAGATCCACCTGCCTTGGAGG  1189

huMU-1   CTATGGAAGAAGATATGGG...CCGTCCCCAGCCCTGAGCGGTTCTTCAT  1068
murMU-1  CTATGGAAAAAGATATGGGCACCAGTGCCCACCCCTGAGAGTTTCTTCCA  1239

huMU-1   GCCCCTGTACAAGGGCTGCAGCGGAGACTTCAAGAAATGGGTGGGTGCAC  1118
murMU-1  GCCCCTGTACAGGGAGCACAGCGGGAACTTCAAGAAATGGGTTAATACCC  1289

huMU-1   CCTTCACTGGCTCCAGCCTGGAGCTGGGACCCTGGAGCCCAGAGGTGCCC  1168
murMU-1  CTTTCACGGCCTCCAGCATAGAGTTGGTGCCACAGAGTTCCACAACAACA  1339

huMU-1   TCCACCCTGGAGGTGTACAGCTGCCACCCACCACGGAGCCCGGCCAAGAG  1218
murMU-1  TCAGCCTTACATCTGT...............CATTGTATCCAGCCAAGGA  1374

huMU-1   GCTGCAGCTCACGGAGCTACAAGAACCAGCAGAGCTGGTGGAGTCTGACG  1268
murMU-1  GAAGAAGTTCCCGGGGCTGCCGGGTCTGGAAGAGCAACTGGAGTGTGATG  1424

huMU-1   GTGTGCCCAAGCCCAGCTTCTGG.........CCGACAGCCCAGAACTCG  1309
murMU-1  GAATGTCTGAGCCTGGTCACTGGTGCATAATCCCCTTGGCAGCTGGCCAA  1474

huMU-1   GGGGGCTCAGCTTACAGTGAGGAGAGGGATCGGCCATACGGCCTGGTGTC  1359
murMU-1  GCGGTCTCAGCCTACAGTGAGGAGAGAGACCGGCCATATGGTCTGGTGTC  1524

huMU-1   CATTGACACAGTGACTGTGCTAGATGCAGAGGGGCCATGCACCTGGCCCT  1409
murMU-1  CATTGACACAGTGACTGTGGGAGATGCAGAGGGCCTGTGTGTCTGGCCCT  1574

huMU-1   GCAGCTGTGAGGATGACGGCTACCCAGCCCTGGACCTGGATGCTGGCCTG  1459
murMU-1  GTAGCTGTGAGGATGATGGCTATCCAGCCATGAACCTGGATGCTGGCCGA  1624

huMU-1   GAGCCCAGCCCAGGCCTAGAGGACCCACTCTTGGATGCAGGGACCACAGT  1509
murMU-1  GAGTCTGGCCCTAATTCAGAGGATCTGCTCTTGGTCACAGACCCTGCTTT  1674
```

Figure 3B

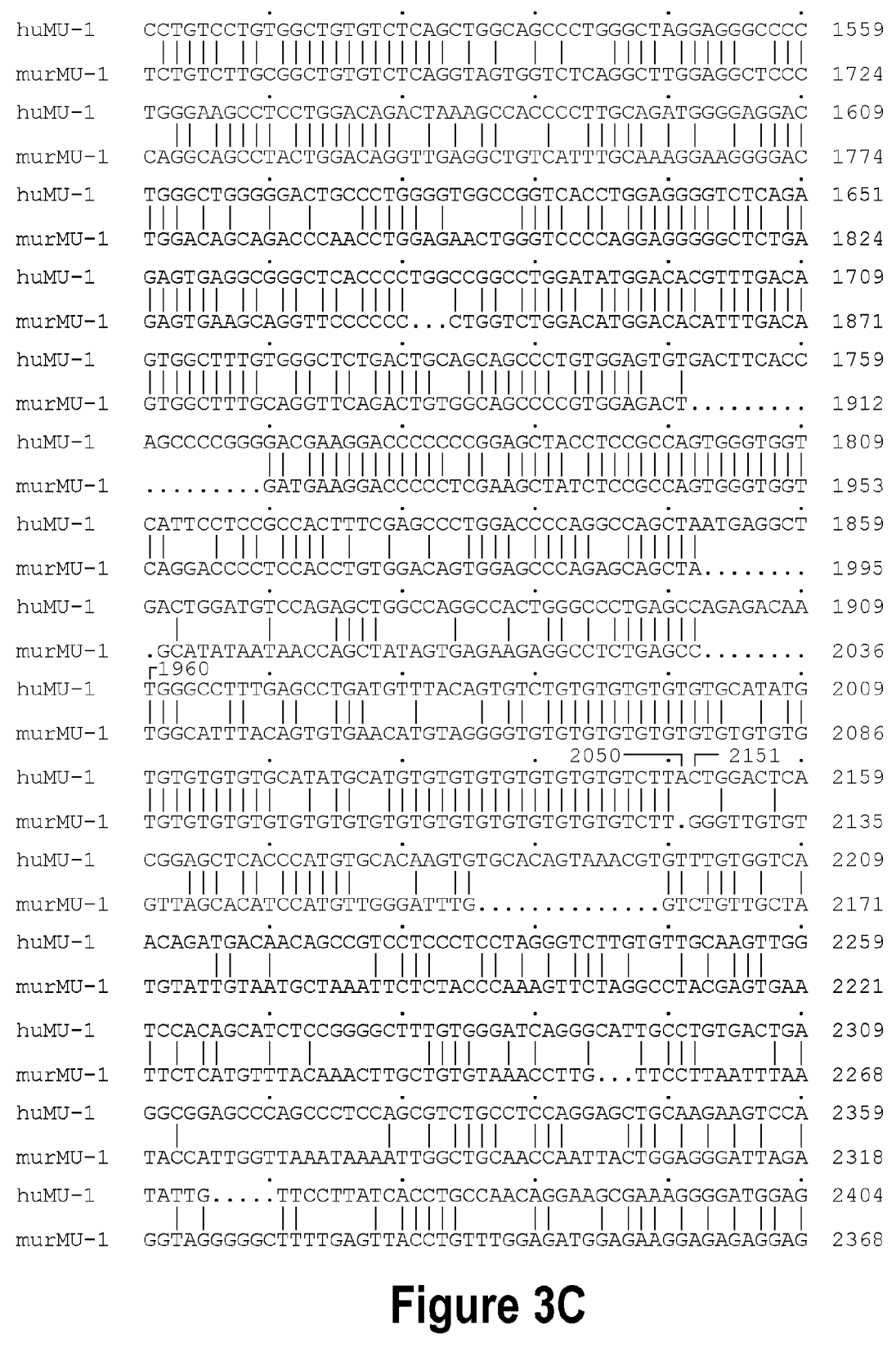

```
huMU-1    CCTGTCCTGTGGCTGTGTCTCAGCTGGCAGCCCTGGGCTAGGAGGGCCCC  1559
murMU-1   TCTGTCTTGCGGCTGTGTCTCAGGTAGTGGTCTCAGGCTTGGAGGCTCCC  1724

huMU-1    TGGGAAGCCTCCTGGACAGACTAAAGCCACCCCTTGCAGATGGGGAGGAC  1609
murMU-1   CAGGCAGCCTACTGGACAGGTTGAGGCTGTCATTTGCAAAGGAAGGGGAC  1774

huMU-1    TGGGCTGGGGGACTGCCCTGGGGTGGCCGGTCACCTGGAGGGGTCTCAGA  1651
murMU-1   TGGACAGCAGACCCAACCTGGAGAACTGGGTCCCCAGGAGGGGGCTCTGA  1824

huMU-1    GAGTGAGGCGGGCTCACCCCTGGCCGGCCTGGATATGGACACGTTTGACA  1709
murMU-1   GAGTGAAGCAGGTTCCCCCC...CTGGTCTGGACATGGACACATTTGACA  1871

huMU-1    GTGGCTTTGTGGGCTCTGACTGCAGCAGCCCTGTGGAGTGTGACTTCACC  1759
murMU-1   GTGGCTTTGCAGGTTCAGACTGTGGCAGCCCCGTGGAGACT.........  1912

huMU-1    AGCCCCGGGGACGAAGGACCCCCCGGAGCTACCTCCGCCAGTGGGTGGT  1809
murMU-1   .........GATGAAGGACCCCCTCGAAGCTATCTCCGCCAGTGGGTGGT  1953

huMU-1    CATTCCTCCGCCACTTTCGAGCCCTGGACCCCAGGCCAGCTAATGAGGCT  1859
murMU-1   CAGGACCCCTCCACCTGTGGACAGTGGAGCCCAGAGCAGCTA........  1995

huMU-1    GACTGGATGTCCAGAGCTGGCCAGGCCACTGGGCCCTGAGCCAGAGACAA  1909
murMU-1   .GCATATAATAACCAGCTATAGTGAGAAGAGGCCTCTGAGCC........  2036
          ┌1960
huMU-1    TGGGCCTTTGAGCCTGATGTTTACAGTGTCTGTGTGTGTGTGTGCATATG  2009
murMU-1   TGGCATTTACAGTGTGAACATGTAGGGGTGTGTGTGTGTGTGTGTGTGTG  2086
                                               2050──┐ ┌─ 2151
huMU-1    TGTGTGTGTGCATATGCATGTGTGTGTGTGTGTGTGTGTCTTACTGGACTCA  2159
murMU-1   TGTGTGTGTGTGTGTGTGTGTGTGTGTGTGTGTGTGTCTT.GGGTTGTGT  2135

huMU-1    CGGAGCTCACCCATGTGCACAAGTGTGCACAGTAAACGTGTTTGTGGTCA  2209
murMU-1   GTTAGCACATCCATGTTGGGATTTG..............GTCTGTTGCTA  2171

huMU-1    ACAGATGACAACAGCCGTCCTCCCTCCTAGGGTCTTGTGTTGCAAGTTGG  2259
murMU-1   TGTATTGTAATGCTAAATTCTCTACCCAAAGTTCTAGGCCTACGAGTGAA  2221

huMU-1    TCCACAGCATCTCCGGGGCTTTGTGGGATCAGGGCATTGCCTGTGACTGA  2309
murMU-1   TTCTCATGTTTACAAACTTGCTGTGTAAACCTTG...TTCCTTAATTTAA  2268

huMU-1    GGCGGAGCCCAGCCCTCCAGCGTCTGCCTCCAGGAGCTGCAAGAAGTCCA  2359
murMU-1   TACCATTGGTTAAATAAAATTGGCTGCAACCAATTACTGGAGGGATTAGA  2318

huMU-1    TATTG.....TTCCTTATCACCTGCCAACAGGAAGCGAAAGGGGATGGAG  2404
murMU-1   GGTAGGGGGCTTTTGAGTTACCTGTTTGGAGATGGAGAAGGAGAGAGGAG  2368
```

Figure 3C

```
huMU-1    TGAGCCCATGGTGACCTCGGGAATGGCAATTTTTTGGGCGGCCCCTGGAC    2454
          || |     || ||     || |  |       ||| |  |     |
murMU-1   AGACCAAGAGGAGAAGGAGGAAGGAGAGGAGAGGAGAGGAGAGGAGAGGA    2418

huMU-1    GAAGGTCTGAATCCCGACTCTGATACCTTCTGGCTGTGCTACCTGAGCCA    2504
          || |    ||    ||    ||    |    |   |||      || |
murMU-1   GAGGAGAGGAGAGGAGA.GGAGAGGAGAGGAGAGGCTGCCGTGAGGGGAG    2467

huMU-1    AGTCGCCTCCCCTCTCTGGGCTAGAGTTTCCTTATCCAGACAGTGGGGAA    2554
          ||  ||        |||| |  |||  |      |    |    |  ||
murMU-1   AGGGACCATGAGCCTGTGGCCAGGAGAAACAGCA............AGTA    2505

huMU-1    GGCATGACACACCTGGGGGAAATTGGCGATGTCACCCGTGTACGGTACGC    2604
          |  ||||  | |  |  ||||   |  ||  |   || ||  |     |
murMU-1   TCTGGGGTACACTGGTGAGGAGGTGGCCAGGCCAGC..AGTTAGAAGAGT    2553

huMU-1    AGCCCAGAGCAGACCCTCAATAAACGTCAGCTTCCTTCAAAAAAAAAAAA    2654
          ||  ||| |    ||||  ||  ||  |||| |  |   |||| || ||||
murMU-1   AGATTAGGGGTGACCTCCAGTATTTGTCAAAGCCAATTAAAATAACAAAA    2603

huMU-1    AAAAATCTAGA...............    2665
          ||||| | |
murMU-1   AAAAAAAAAAAGCGGCCGCTCTAGA      2628
```

Fig. 4

```
Human MU-1    MPRGWAAPLLLLLLQGGWGCPDLVCYTDYLQTVICILEMWNLHPSTLTLT  50
              ||||  | ||||:| | |  | || |||||| |: |:||  .|| |·||
MurineMU-1    MPRGPVAALLLLILHGAWSCLDLTCYTDYLWTITCVLETRSPNPSILSLT  50

Human MU-1    WQDQYEELKDEATSCSLHRSAHNATHATYTCHMDVFHFMADDIFSVNITD  100
              |||:||||·|: | |||||| || ||  |||||  · |:·|::| ||:||
MurineMU-1    WQDEYEELQDQETFCSLHRSGHNTTHIWYTCHMRLSQFLSDEVFIVNVTD  100

Human MU-1    QSGNYSQECGSFLLAESIKPAPPFNVTVTFSGQYNISWRSDYEDPAFYML  150
              |||| ||||||||·||||||||||| |||| |||·|·||| | |::|·  ·|·|
MurineMU-1    QSGNNSQECGSFVLAESIKPAPPLNVTVAFSGRYDISWDSAYDEPSNYVL  150

Human MU-1    KGKLQYELQYRNRGDPWAVSPRRKLISVDSRSVSLLPLEFRKDSSYELQV  200
              :|||||||||||  ||:|| |  |||||||||·|||||  ||  |||||:|||
MurineMU-1    RGKLQYELQYRNLRDPYAVRPVTKLISVDSRNVSLLPEEFHKDSSYQLQV  200

Human MU-1    RAGPMPGSSYQGTWSEWSDPVIFQTQSEELKEGWNPHLLLLLLVIVFIP  250
              || | ||·|:·||||||||||||||||·  | · ||·||:||||  ·|: :
MurineMU-1    RAAPQPGTSFRGTWSEWSDPVIFQTQAGEPEAGWDPHMLLLLAVLIIVL.  249

Human MU-1    AFWSLKTHPLWRLWKKIWA.VPSPERFFMPLYKGCSGDFKKWVGAPFTGS  299
                 | ||  |  |||||||||| ||·|| ||  |||:   ||·||||||  ||| |
MurineMU-1    VFMGLKIHLPWRLWKKIWAPVPTPESFFQPLYREHSGNFKKWVNTPFTAS  299

Human MU-1    SLELGPWSPEVPSTLEVYSCHPPRSPAKRLQLTELQEPAELVESDGVPKP  349
              |:|| | |  | |   |   |   |||  ·  |   |  ·| ||· ·|
MurineMU-1    SIELVPQSSTTTSAL.....HLSLYPAKEKKFPGLPGLEEQLECDGMSEP  344

Human MU-1    SFW...PTAQNSGGSAYSEERDRPYGLVSIDTVTVLDAEGPCTWPCSCED  396
              |   | |  ||||||||||||||||||||||| |||| | ||||||||
MurineMU-1    GHWCIIPLAAGQAVSAYSEERDRPYGLVSIDTVTVGDAEGLCVWPCSCED  394

Human MU-1    DGYPALDLDAGLEPSPGLEDPLLDAGTTVLSCGCVSAGSPGLGGPLGSLL  446
              |||||:·||||  |  |  || ||   |||||||  |  |||  |||   ||||
MurineMU-1    DGYPAMNLDAGRESGPNSEDLLLVTDPAFLSCGCVSGSGLRLGGSPGSLL  444

Human MU-1    DRLKPPLADGEDWAGGLPWGGRSPGGVSESEAGSPLAGLDMDTFDSGFVG  496
              |||:  |   ||   |   |||| ||||||||   |||||||||||| |
MurineMU-1    DRLRLSFAKEGDWTADPWRTGSPGGGSESEAGSP.PGLDMDTFDSGFAG  493

Human MU-1    SDCSSPVECDFTSPGDEGPPRSYLRQWVV.IPPPLSSPGPQAS*  539
              |||  ||||     ||||||||||||||||  |||· | | |·|
MurineMU-1    SDCGSPVET......DEGPPRSYLRQWVVRTPPPVDS.GAQSS.  529
```

```
             1                                                     50
     humu    ~~~MPRGWAA PLLLLL..LQ GGWG...... CPDLVCYTDY LQTVICILEM
  mousemu    ~~~MPRGPVA ALLLLI..LH GAWS...... CLDLTCYTDY LWTITCVLET
humil2rbc    MAAPALSWRL PLLILLLPLA TSWASAAVNG TSQFTCFYNS RANISCVWSQ
             51                                                   100
     humu    WN..LHPSTL TLTWQDQYEE LKDEATSCSL HRSAHNATHA TYTCHM....
  mousemu    RS..PNPSIL SLTWQDEYEE LQDQETFCSL HRSGHNTTHI WYTCHM....
humil2rbc    DGALQDTSCQ VHAWPDR... .RRWNQTCEL ....LPVSQA SWACNLILGA
             101                                                  150
     humu    .DVFHFMADD IFSVNITDQS GN..YSQECG SFLLAESIKP APPFNVTVTF
   mousem    .RLSQFLSDE VFIVNVTDQS GN..NSQECG SFVLAESIKP APPLNVTVAF
humil2rbc    PDSQKLTTVD IVTLRVLCRE GVRWRVMAIQ DFKPFENLRL MAPISLQVVH
             151                                                  200
     humu    ..SGQYNISW RSDYEDPAFY MLKGKLQYEL QYRNRGDPWA VSPRRKLISV
  mousemu    ..SGRYDISW DSAYDEPSNY VLRGKLQYEL QYRNLRDPYA VRPVTKLISV
humil2rbc    VETHRCNISW E..ISQASHY FER.HLEFEA RTLSPGHTWE EAP...LLTL
             201                                                  250
     humu    DSRSVSLLPL EFRKDSSYEL QVRAGPMPGS SYQGTWSEWS DPVIFQTQS.
  mousemu    DSRNVSLLPE EFHKDSSYQL QVRAAPQPGT SFRGTWSEWS DPVIFQTQA.
humil2rbc    KQKQEWICLE TLTPDTQYEF QVRVKPLQGE F..TTWSPWS QPLAFRTKPA
             251                                                  300
     humu    ..EELKEGWN PHLLLLL... LLVIVFIPAF WSLKTHPLWR LWKKIWA.VP
  mousemu    ..GEPEAGWD PHMLLLL... AVLIIVL.VF MGLKIHLPWR LWKKIWAPVP
humil2rbc    ALGKDTIPWL GHLLVGLSGA FGFIILVYLL INCRNTGPW. LKKVLKCNTP
             301                                                  350
     humu    SPERFFMPLY KGCSGDFKKW VGAPFTGSSL ELGPWSPEVP STLEVYSCHP
  mousemu    TPESFFQPLY REHSGNFKKW VNTPFTASSI ELVPQSSTTT SAL.....HL
humil2rbc    DPSKFFSQLS SEHGGDVQKW LSSPFPSSSF SPGGLAPEIS PLEVLERDKV
             351                                                  400
     humu    PRSPAKRLQL TELQEPA..E LVESDGVPKP SFW...PTAQ NSGGSAYSEE
  mousemu    SLYPAKEKKF PGLPGLE..E QLECDGMSEP GHWCIIPLAA GQAVSAYSEE
humil2rbc    TQLLLQQDKV PEPASLSSNH SLTSCFTNQG YFFFHLPDAL EIEACQVYFT
             401                                                  450
     humu    RDRPYGLVSI DTVTVLDAEG PC...TWPCS CEDDGYPALD LDAGLEPSPG
  mousemu    RDRPYGLVSI DTVTVGDAEG LC...VWPCS CEDDGYPAMN LDAGRESGPN
humil2rbc    YD.PYSEEDP DEGVAGAPTG SSPQPLQPLS GEDDAYCTF. ........PS
             451                                                  500
     humu    LEDPLLDAGT TVLSCGCVSA GSPGLGGPLG SLLDRLKPPL AD..GEDWAG
  mousemu    SEDLLLVTDP AFLSCGCVSG SGLRLGGSPG SLLDRLRLSF AK..EGDWTA
humil2rbc    RDDLLLFS.P SLL..GGPSP PSTAPGGS.G AGEERMPPSL QERVPRDWDP
             501                                                  550
     humu    GLPWGGRSPG GVSESEAGSP LAGLDMDTFD SGFVGSDCSS PVECDFTSPG
  mousemu    DPTWRTGSPG GGSESEAGSP .PGLDMDTFD SGFAGSDCGS PVET......
humil2rbc    Q.PLGPPTPG VPDLVDFQPP P...ELVLRE AGEEVPDAG. PRE.GVSFPW
             551                                      588
     humu    DEGPPRSYLR QWVVIPPPLS SPGPQAS*~~ ~~~~~~~~
  mousemu    DEGPPRSYLR QWVVRTPPPV DSGAQSS~~~ ~~~~~~~~
humil2rbc    SRPPGQGEFR ALNARLPLNT DAYLSLQELQ GQDPTHLV
```

Fig. 5

Fig. 6
Signaling through MU-1
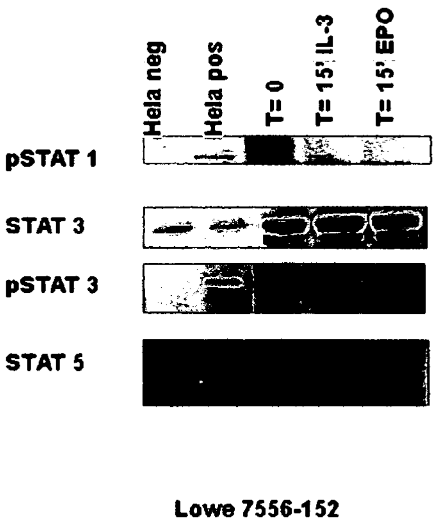
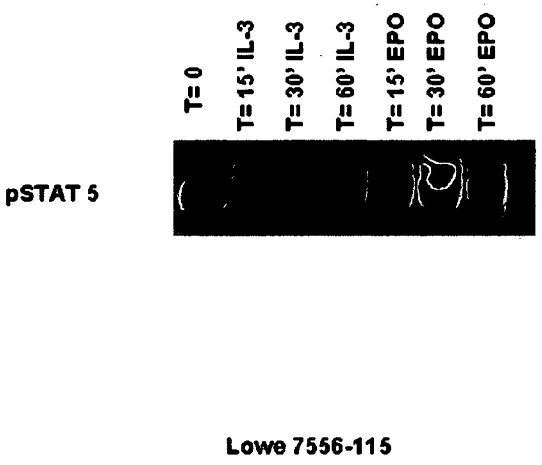

Fig. 7A atg aaa ttc tta gtc aac gtt gcc ctt gtt ttt atg gtc gtg tac att 48
Met Lys Phe Leu Val Asn Val Ala Leu Val Phe Met Val Val Tyr Ile
1 5 10 15 tct tac atc tat gcc ggc agc gga cac cac cat cat cac cac ggt agc 96
Ser Tyr Ile Tyr Ala Gly Ser Gly His His His His His His Gly Ser
20 25 30 ggc gac tat aaa gac gat gac gat aag ggt tcc gga tgc ccc gac ctc 144
Gly Asp Tyr Lys Asp Asp Asp Asp Lys Gly Ser Gly Cys Pro Asp Leu
35 40 45 gtc tgc tac acc gat tac ctc cag acg gtc atc tgc atc ctg gaa atg 192
Val Cys Tyr Thr Asp Tyr Leu Gln Thr Val Ile Cys Ile Leu Glu Met
50 55 60 tgg aac ctc cac ccc agc acg ctc acc ctt acc tgg caa gac cag tat 240
Trp Asn Leu His Pro Ser Thr Leu Thr Leu Thr Trp Gln Asp Gln Tyr
65 70 75 80 gaa gag ctg aag gac gag gcc acc tcc tgc agc ctc cac agg tcg gcc 288
Glu Glu Leu Lys Asp Glu Ala Thr Ser Cys Ser Leu His Arg Ser Ala
85 90 95 cac aat gcc acg cat gcc acc tac acc tgc cac atg gat gta ttc cac 336
His Asn Ala Thr His Ala Thr Tyr Thr Cys His Met Asp Val Phe His
100 105 110 ttc atg gcc gac gac att ttc agt gtc aac atc aca gac cag tct ggc 384
Phe Met Ala Asp Asp Ile Phe Ser Val Asn Ile Thr Asp Gln Ser Gly
115 120 125 aac tac tcc cag gag tgt ggc agc ttt ctc ctg gct gag agc atc aag 432
Asn Tyr Ser Gln Glu Cys Gly Ser Phe Leu Leu Ala Glu Ser Ile Lys
130 135 140 ccg gct ccc cct ttc aac gtg act gtg acc ttc tca gga cag tat aat 480
Pro Ala Pro Pro Phe Asn Val Thr Val Thr Phe Ser Gly Gln Tyr Asn
145 150 155 160 atc tcc tgg cgc tca gat tac gaa gac cct gcc ttc tac atg ctg aag 528
Ile Ser Trp Arg Ser Asp Tyr Glu Asp Pro Ala Phe Tyr Met Leu Lys
165 170 175 ggc aag ctt cag tat gag ctg cag tac agg aac cgg gga gac ccc tgg 576
Gly Lys Leu Gln Tyr Glu Leu Gln Tyr Arg Asn Arg Gly Asp Pro Trp
180 185 190 gct gtg agt ccg agg aga aag ctg atc tca gtg gac tca aga agt gtc 624
Ala Val Ser Pro Arg Arg Lys Leu Ile Ser Val Asp Ser Arg Ser Val
195 200 205 tcc ctc ctc ccc ctg gag ttc cgc aaa gac tcg agc tat gag ctg cag 672
Ser Leu Leu Pro Leu Glu Phe Arg Lys Asp Ser Ser Tyr Glu Leu Gln
210 215 220

Fig. 7B

```
gtg cgg gca ggg ccc atg cct ggc tcc tcc tac cag ggg acc tgg agt      720
Val Arg Ala Gly Pro Met Pro Gly Ser Ser Tyr Gln Gly Thr Trp Ser
225                 230                 235                 240

gaa tgg agt gac ccg gtc atc ttt cag acc cag tca gag gag tta aag      768
Glu Trp Ser Asp Pro Val Ile Phe Gln Thr Gln Ser Glu Glu Leu Lys
                245                 250                 255

gaa ggc tgg aac taa tga                                              786
Glu Gly Trp Asn
            260
```

Fig. 8A

```
gcggccgcac cacc atg ccg cgt ggc tgg gcc gcc ccc ttg ctc ctg ctg     50
                Met Pro Arg Gly Trp Ala Ala Pro Leu Leu Leu Leu
                1               5                   10

ctg ctc cag gga ggc tgg ggc tgc ccc gac ctc gtc tgc tac acc gat     98
Leu Leu Gln Gly Gly Trp Gly Cys Pro Asp Leu Val Cys Tyr Thr Asp
        15                  20                  25

tac ctc cag acg gtc atc tgc atc ctg gaa atg tgg aac ctc cac ccc    146
Tyr Leu Gln Thr Val Ile Cys Ile Leu Glu Met Trp Asn Leu His Pro
    30                  35                  40

agc acg ctc acc ctt acc tgg caa gac cag tat gaa gag ctg aag gac    194
Ser Thr Leu Thr Leu Thr Trp Gln Asp Gln Tyr Glu Glu Leu Lys Asp
45                  50                  55                  60

gag gcc acc tcc tgc agc ctc cac agg tcg gcc cac aat gcc acg cat    242
Glu Ala Thr Ser Cys Ser Leu His Arg Ser Ala His Asn Ala Thr His
                65                  70                  75

gcc acc tac acc tgc cac atg gat gta ttc cac ttc atg gcc gac gac    290
Ala Thr Tyr Thr Cys His Met Asp Val Phe His Phe Met Ala Asp Asp
            80                  85                  90

att ttc agt gtc aac atc aca gac cag tct ggc aac tac tcc cag gag    338
Ile Phe Ser Val Asn Ile Thr Asp Gln Ser Gly Asn Tyr Ser Gln Glu
        95                  100                 105

tgt ggc agc ttt ctc ctg gct gag agc atc aag ccg gct ccc cct ttc    386
Cys Gly Ser Phe Leu Leu Ala Glu Ser Ile Lys Pro Ala Pro Pro Phe
    110                 115                 120

aac gtg act gtg acc ttc tca gga cag tat aat atc tcc tgg cgc tca    434
Asn Val Thr Val Thr Phe Ser Gly Gln Tyr Asn Ile Ser Trp Arg Ser
125                 130                 135                 140

gat tac gaa gac cct gcc ttc tac atg ctg aag ggc aag ctt cag tat    482
Asp Tyr Glu Asp Pro Ala Phe Tyr Met Leu Lys Gly Lys Leu Gln Tyr
                145                 150                 155

gag ctg cag tac agg aac cgg gga gac ccc tgg gct gtg agt ccg agg    530
Glu Leu Gln Tyr Arg Asn Arg Gly Asp Pro Trp Ala Val Ser Pro Arg
            160                 165                 170

aga aag ctg atc tca gtg gac tca aga agt gtc tcc ctc ctc ccc ctg    578
Arg Lys Leu Ile Ser Val Asp Ser Arg Ser Val Ser Leu Leu Pro Leu
        175                 180                 185

gag ttc cgc aaa gac tcg agc tat gag ctg cag gtg cgg gca ggg ccc    626
Glu Phe Arg Lys Asp Ser Ser Tyr Glu Leu Gln Val Arg Ala Gly Pro
    190                 195                 200

atg cct ggc tcc tcc tac cag ggg acc tgg agt gaa tgg agt gac ccg    674
Met Pro Gly Ser Ser Tyr Gln Gly Thr Trp Ser Glu Trp Ser Asp Pro
205                 210                 215                 220
```

Fig. 8B

```
gtc atc ttt cag acc cag tca gag gag tta aag gaa ggc tgg aac ggc   722
Val Ile Phe Gln Thr Gln Ser Glu Glu Leu Lys Glu Gly Trp Asn Gly
                225                 230                 235

tcc ggc tct aga gac aaa act cac aca tgc cca ccg tgc cca gca cct   770
Ser Gly Ser Arg Asp Lys Thr His Thr Cys Pro Pro Cys Pro Ala Pro
            240                 245                 250

gaa ctc ctg ggg gga ccg tca gtc ttc ctc ttc ccc cca aaa ccc aag   818
Glu Leu Leu Gly Gly Pro Ser Val Phe Leu Phe Pro Pro Lys Pro Lys
        255                 260                 265

gac acc ctc atg atc tcc cgg acc cct gag gtc aca tgc gtg gtg gtg   866
Asp Thr Leu Met Ile Ser Arg Thr Pro Glu Val Thr Cys Val Val Val
    270                 275                 280

gac gtg agc cac gaa gac cct gag gtc aag ttc aac tgg tac gtg gac   914
Asp Val Ser His Glu Asp Pro Glu Val Lys Phe Asn Trp Tyr Val Asp
285                 290                 295                 300

ggc gtg gag gtg cat aat gcc aag aca aag ccg cgg gag gag cag tac   962
Gly Val Glu Val His Asn Ala Lys Thr Lys Pro Arg Glu Glu Gln Tyr
                305                 310                 315

aac agc acg tac cgt gtg gtc agc gtc ctc acc gtc ctg cac cag gac   1010
Asn Ser Thr Tyr Arg Val Val Ser Val Leu Thr Val Leu His Gln Asp
            320                 325                 330

tgg ctg aat ggc aag gag tac aag tgc aag gtc tcc aac aaa gcc ctc   1058
Trp Leu Asn Gly Lys Glu Tyr Lys Cys Lys Val Ser Asn Lys Ala Leu
        335                 340                 345

cca gtc ccc atc gag aaa acc atc tcc aaa gcc aaa ggg cag ccc cga   1106
Pro Val Pro Ile Glu Lys Thr Ile Ser Lys Ala Lys Gly Gln Pro Arg
    350                 355                 360

gaa cca cag gtg tac acc ctg ccc cca tcc cgg gag gag atg acc aag   1154
Glu Pro Gln Val Tyr Thr Leu Pro Pro Ser Arg Glu Glu Met Thr Lys
365                 370                 375                 380

aac cag gtc agc ctg acc tgc ctg gtc aaa ggc ttc tat ccc agc gac   1202
Asn Gln Val Ser Leu Thr Cys Leu Val Lys Gly Phe Tyr Pro Ser Asp
                385                 390                 395

atc gcc gtg gag tgg gag agc aat ggg cag ccg gag aac aac tac aag   1250
Ile Ala Val Glu Trp Glu Ser Asn Gly Gln Pro Glu Asn Asn Tyr Lys
            400                 405                 410

acc acg cct ccc gtg ctg gac tcc gac ggc tcc ttc ttc ctc tat agc   1298
Thr Thr Pro Pro Val Leu Asp Ser Asp Gly Ser Phe Phe Leu Tyr Ser
        415                 420                 425

aag ctc acc gtg gac aag agc agg tgg cag cag ggg aac gtc ttc tca   1346
Lys Leu Thr Val Asp Lys Ser Arg Trp Gln Gln Gly Asn Val Phe Ser
    430                 435                 440
```

Fig. 8C

```
tgc tcc gtg atg cat gag gct ctg cac aac cac tac acg cag aag agc      1394
Cys Ser Val Met His Glu Ala Leu His Asn His Tyr Thr Gln Lys Ser
445                 450                 455                 460

ctc tcc ctg tcc ccg ggt aaa tgagtgaatt c                             1426
Leu Ser Leu Ser Pro Gly
                465
```

Fig. 9A

```
gcggccgcac cacc atg ccg cgt ggc tgg gcc gcc ccc ttg ctc ctg ctg     50
                Met Pro Arg Gly Trp Ala Ala Pro Leu Leu Leu Leu
                1               5                   10

ctg ctc cag gga ggc tgg ggc tgc ccc gac ctc gtc tgc tac acc gat     98
Leu Leu Gln Gly Gly Trp Gly Cys Pro Asp Leu Val Cys Tyr Thr Asp
        15                  20                  25

tac ctc cag acg gtc atc tgc atc ctg gaa atg tgg aac ctc cac ccc    146
Tyr Leu Gln Thr Val Ile Cys Ile Leu Glu Met Trp Asn Leu His Pro
    30                  35                  40

agc acg ctc acc ctt acc tgg caa gac cag tat gaa gag ctg aag gac    194
Ser Thr Leu Thr Leu Thr Trp Gln Asp Gln Tyr Glu Glu Leu Lys Asp
45                  50                  55                  60

gag gcc acc tcc tgc agc ctc cac agg tcg gcc cac aat gcc acg cat    242
Glu Ala Thr Ser Cys Ser Leu His Arg Ser Ala His Asn Ala Thr His
                65                  70                  75

gcc acc tac acc tgc cac atg gat gta ttc cac ttc atg gcc gac gac    290
Ala Thr Tyr Thr Cys His Met Asp Val Phe His Phe Met Ala Asp Asp
            80                  85                  90

att ttc agt gtc aac atc aca gac cag tct ggc aac tac tcc cag gag    338
Ile Phe Ser Val Asn Ile Thr Asp Gln Ser Gly Asn Tyr Ser Gln Glu
        95                  100                 105

tgt ggc agc ttt ctc ctg gct gag agc atc aag ccg gct ccc cct ttc    386
Cys Gly Ser Phe Leu Leu Ala Glu Ser Ile Lys Pro Ala Pro Pro Phe
    110                 115                 120

aac gtg act gtg acc ttc tca gga cag tat aat atc tcc tgg cgc tca    434
Asn Val Thr Val Thr Phe Ser Gly Gln Tyr Asn Ile Ser Trp Arg Ser
125                 130                 135                 140

gat tac gaa gac cct gcc ttc tac atg ctg aag ggc aag ctt cag tat    482
Asp Tyr Glu Asp Pro Ala Phe Tyr Met Leu Lys Gly Lys Leu Gln Tyr
                145                 150                 155

gag ctg cag tac agg aac cgg gga gac ccc tgg gct gtg agt ccg agg    530
Glu Leu Gln Tyr Arg Asn Arg Gly Asp Pro Trp Ala Val Ser Pro Arg
            160                 165                 170

aga aag ctg atc tca gtg gac tca aga agt gtc tcc ctc ctc ccc ctg    578
Arg Lys Leu Ile Ser Val Asp Ser Arg Ser Val Ser Leu Leu Pro Leu
        175                 180                 185

gag ttc cgc aaa gac tcg agc tat gag ctg cag gtg cgg gca ggg ccc    626
Glu Phe Arg Lys Asp Ser Ser Tyr Glu Leu Gln Val Arg Ala Gly Pro
    190                 195                 200

atg cct ggc tcc tcc tac cag ggg acc tgg agt gaa tgg agt gac ccg    674
Met Pro Gly Ser Ser Tyr Gln Gly Thr Trp Ser Glu Trp Ser Asp Pro
205                 210                 215                 220
```

Fig. 9B

```
gtc atc ttt cag acc cag tca gag gag tta aag gaa ggc tgg aac ggc     722
Val Ile Phe Gln Thr Gln Ser Glu Glu Leu Lys Glu Gly Trp Asn Gly
                225                 230                 235

tcc ggc tct aga gac aaa act cac aca tgc cca ccg tgc cca gca cct     770
Ser Gly Ser Arg Asp Lys Thr His Thr Cys Pro Pro Cys Pro Ala Pro
            240                 245                 250

gaa ctc ctg ggg gga ccg tca gtc ttc ctc ttc ccc cca aaa ccc aag     818
Glu Leu Leu Gly Gly Pro Ser Val Phe Leu Phe Pro Pro Lys Pro Lys
        255                 260                 265

gac acc ctc atg atc tcc cgg acc cct gag gtc aca tgc gtg gtg gtg     866
Asp Thr Leu Met Ile Ser Arg Thr Pro Glu Val Thr Cys Val Val Val
    270                 275                 280

gac gtg agc cac gaa gac cct gag gtc aag ttc aac tgg tac gtg gac     914
Asp Val Ser His Glu Asp Pro Glu Val Lys Phe Asn Trp Tyr Val Asp
285                 290                 295                 300

ggc gtg gag gtg cat aat gcc aag aca aag ccg cgg gag gag cag tac     962
Gly Val Glu Val His Asn Ala Lys Thr Lys Pro Arg Glu Glu Gln Tyr
                305                 310                 315

aac agc acg tac cgt gtg gtc agc gtc ctc acc gtc ctg cac cag gac    1010
Asn Ser Thr Tyr Arg Val Val Ser Val Leu Thr Val Leu His Gln Asp
            320                 325                 330

tgg ctg aat ggc aag gag tac aag tgc aag gtc tcc aac aaa gcc ctc    1068
Trp Leu Asn Gly Lys Glu Tyr Lys Cys Lys Val Ser Asn Lys Ala Leu
        335                 340                 345

cca gtc ccc atc gag aaa acc atc tcc aaa gcc aaa ggg cag ccc cga    1106
Pro Val Pro Ile Glu Lys Thr Ile Ser Lys Ala Lys Gly Gln Pro Arg
    350                 355                 360

gaa cca cag gtg tac acc ctg ccc cca tcc cgg gag gag atg acc aag    1154
Glu Pro Gln Val Tyr Thr Leu Pro Pro Ser Arg Glu Glu Met Thr Lys
365                 370                 375                 380

aac cag gtc agc ctg acc tgc ctg gtc aaa ggc ttc tat ccc agc gac    1202
Asn Gln Val Ser Leu Thr Cys Leu Val Lys Gly Phe Tyr Pro Ser Asp
                385                 390                 395

atc gcc gtg gag tgg gag agc aat ggg cag ccg gag aac aac tac aag    1250
Ile Ala Val Glu Trp Glu Ser Asn Gly Gln Pro Glu Asn Asn Tyr Lys
            400                 405                 410

acc acg cct ccc gtg ctg gac tcc gac ggc tcc ttc ttc ctc tat agc    1298
Thr Thr Pro Pro Val Leu Asp Ser Asp Gly Ser Phe Phe Leu Tyr Ser
        415                 420                 425

aag ctc acc gtg gac aag agc agg tgg cag cag ggg aac gtc ttc tca    1346
Lys Leu Thr Val Asp Lys Ser Arg Trp Gln Gln Gly Asn Val Phe Ser
    430                 435                 440
```

Fig. 9C

```
tgc tcc gtg atg cat gag gct ctg cac aac cac tac acg cag aag agc      1394
Cys Ser Val Met His Glu Ala Leu His Asn His Tyr Thr Gln Lys Ser
445                 450                 455                 460

ctc tcc ctg tcc ccg ggt aaa tca gga atg gca tca atg aca gga ggt      1442
Leu Ser Leu Ser Pro Gly Lys Ser Gly Met Ala Ser Met Thr Gly Gly
                465                 470                 475

caa caa atg ggt tct gga tct cat cat cat cat cat cat tct gga ggt      1490
Gln Gln Met Gly Ser Gly Ser His His His His His His Ser Gly Gly
            480                 485                 490

tgagaattc
                                                                     1499
```

Fig. 10A

```
gcggccgcac cacc atg ccg cgt ggc tgg gcc gcc ccc ttg ctc ctg ctg      50
                Met Pro Arg Gly Trp Ala Ala Pro Leu Leu Leu Leu
                1               5                   10

ctg ctc cag gga ggc tgg ggc tgc ccc gac ctc gtc tgc tac acc gat      98
Leu Leu Gln Gly Gly Trp Gly Cys Pro Asp Leu Val Cys Tyr Thr Asp
        15                  20                  25

tac ctc cag acg gtc atc tgc atc ctg gaa atg tgg aac ctc cac ccc     146
Tyr Leu Gln Thr Val Ile Cys Ile Leu Glu Met Trp Asn Leu His Pro
    30                  35                  40

agc acg ctc acc ctt acc tgg caa gac cag tat gaa gag ctg aag gac     194
Ser Thr Leu Thr Leu Thr Trp Gln Asp Gln Tyr Glu Glu Leu Lys Asp
45                  50                  55                  60

gag gcc acc tcc tgc agc ctc cac agg tcg gcc cac aat gcc acg cat     242
Glu Ala Thr Ser Cys Ser Leu His Arg Ser Ala His Asn Ala Thr His
                65                  70                  75

gcc acc tac acc tgc cac atg gat gta ttc cac ttc atg gcc gac gac     290
Ala Thr Tyr Thr Cys His Met Asp Val Phe His Phe Met Ala Asp Asp
            80                  85                  90

att ttc agt gtc aac atc aca gac cag tct ggc aac tac tcc cag gag     338
Ile Phe Ser Val Asn Ile Thr Asp Gln Ser Gly Asn Tyr Ser Gln Glu
        95                  100                 105

tgt ggc agc ttt ctc ctg gct gag agc atc aag ccg gct ccc cct ttc     386
Cys Gly Ser Phe Leu Leu Ala Glu Ser Ile Lys Pro Ala Pro Pro Phe
    110                 115                 120

aac gtg act gtg acc ttc tca gga cag tat aat atc tcc tgg cgc tca     434
Asn Val Thr Val Thr Phe Ser Gly Gln Tyr Asn Ile Ser Trp Arg Ser
125                 130                 135                 140

gat tac gaa gac cct gcc ttc tac atg ctg aag ggc aag ctt cag tat     482
Asp Tyr Glu Asp Pro Ala Phe Tyr Met Leu Lys Gly Lys Leu Gln Tyr
                145                 150                 155

gag ctg cag tac agg aac cgg gga gac ccc tgg gct gtg agt ccg agg     530
Glu Leu Gln Tyr Arg Asn Arg Gly Asp Pro Trp Ala Val Ser Pro Arg
            160                 165                 170

aga aag ctg atc tca gtg gac tca aga agt gtc tcc ctc ctc ccc ctg     578
Arg Lys Leu Ile Ser Val Asp Ser Arg Ser Val Ser Leu Leu Pro Leu
        175                 180                 185

gag ttc cgc aaa gac tcg agc tat gag ctg cag gtg cgg gca ggg ccc     626
Glu Phe Arg Lys Asp Ser Ser Tyr Glu Leu Gln Val Arg Ala Gly Pro
    190                 195                 200

atg cct ggc tcc tcc tac cag ggg acc tgg agt gaa tgg agt gac ccg     674
Met Pro Gly Ser Ser Tyr Gln Gly Thr Trp Ser Glu Trp Ser Asp Pro
205                 210                 215                 220
```

Fig. 10B

```
gtc atc ttt cag acc cag tca gag gag tta aag gaa ggc tgg aac ggc     722
Val Ile Phe Gln Thr Gln Ser Glu Glu Leu Lys Glu Gly Trp Asn Gly
                225                 230                 235

tcc ggc tct aga gac aaa act cac aca tgc cca ccg tgc cca gca cct     770
Ser Gly Ser Arg Asp Lys Thr His Thr Cys Pro Pro Cys Pro Ala Pro
            240                 245                 250

gaa gcc ctg ggg gca ccg tca gtc ttc ctc ttc ccc cca aaa ccc aag     818
Glu Ala Leu Gly Ala Pro Ser Val Phe Leu Phe Pro Pro Lys Pro Lys
        255                 260                 265

gac acc ctc atg atc tcc cgg acc cct gag gtc aca tgc gtg gtg gtg     866
Asp Thr Leu Met Ile Ser Arg Thr Pro Glu Val Thr Cys Val Val Val
    270                 275                 280

gac gtg agc cac gaa gac cct gag gtc aag ttc aac tgg tac gtg gac     914
Asp Val Ser His Glu Asp Pro Glu Val Lys Phe Asn Trp Tyr Val Asp
285                 290                 295                 300

ggc gtg gag gtg cat aat gcc aag aca aag ccg cgg gag gag cag tac     962
Gly Val Glu Val His Asn Ala Lys Thr Lys Pro Arg Glu Glu Gln Tyr
                305                 310                 315

aac agc acg tac cgt gtg gtc agc gtc ctc acc gtc ctg cac cag gac    1010
Asn Ser Thr Tyr Arg Val Val Ser Val Leu Thr Val Leu His Gln Asp
            320                 325                 330

tgg ctg aat ggc aag gag tac aag tgc aag gtc tcc aac aaa gcc ctc    1058
Trp Leu Asn Gly Lys Glu Tyr Lys Cys Lys Val Ser Asn Lys Ala Leu
        335                 340                 345

cca gcc ccc atc gag aaa acc atc tcc aaa gcc aaa ggg cag ccc cga    1106
Pro Ala Pro Ile Glu Lys Thr Ile Ser Lys Ala Lys Gly Gln Pro Arg
    350                 355                 360

gaa cca cag gtg tac acc ctg ccc cca tcc cgg gag gag atg acc aag    1154
Glu Pro Gln Val Tyr Thr Leu Pro Pro Ser Arg Glu Glu Met Thr Lys
365                 370                 375                 380

aac cag gtc agc ctg acc tgc ctg gtc aaa ggc ttc tat ccc agc gac    1202
Asn Gln Val Ser Leu Thr Cys Leu Val Lys Gly Phe Tyr Pro Ser Asp
                385                 390                 395

atc gcc gtg gag tgg gag agc aat ggg cag ccg gag aac aac tac aag    1250
Ile Ala Val Glu Trp Glu Ser Asn Gly Gln Pro Glu Asn Asn Tyr Lys
            400                 405                 410

acc acg cct ccc gtg ctg gac tcc gac ggc tcc ttc ttc ctc tat agc    1298
Thr Thr Pro Pro Val Leu Asp Ser Asp Gly Ser Phe Phe Leu Tyr Ser
        415                 420                 425

aag ctc acc gtg gac aag agc agg tgg cag cag ggg aac gtc ttc tca    1346
Lys Leu Thr Val Asp Lys Ser Arg Trp Gln Gln Gly Asn Val Phe Ser
    430                 435                 440
```

Fig. 10C

```
tgc tcc gtg atg cat gag gct ctg cac aac cac tac acg cag aag agc      1394
Cys Ser Val Met His Glu Ala Leu His Asn His Tyr Thr Gln Lys Ser
445                 450                 455                 460

ctc tcc ctg tcc ccg ggt aaa tgagtgaatt c                             1426
Leu Ser Leu Ser Pro Gly Lys
                465
```

Fig. 11A

```
atg ccg cgt ggc tgg gcc gcc ccc ttg ctc ctg ctg ctg ctc cag gga      48
Met Pro Arg Gly Trp Ala Ala Pro Leu Leu Leu Leu Leu Leu Gln Gly
1               5                   10                  15

ggc tgg ggc tgc ccc gac ctc gtc tgc tac acc gat tac ctc cag acg      96
Gly Trp Gly Cys Pro Asp Leu Val Cys Tyr Thr Asp Tyr Leu Gln Thr
            20                  25                  30

gtc atc tgc atc ctg gaa atg tgg aac ctc cac ccc agc acg ctc acc      144
Val Ile Cys Ile Leu Glu Met Trp Asn Leu His Pro Ser Thr Leu Thr
        35                  40                  45

ctt acc tgg caa gac cag tat gaa gag ctg aag gac gag gcc acc tcc      192
Leu Thr Trp Gln Asp Gln Tyr Glu Glu Leu Lys Asp Glu Ala Thr Ser
    50                  55                  60

tgc agc ctc cac agg tcg gcc cac aat gcc acg cat gcc acc tac acc      240
Cys Ser Leu His Arg Ser Ala His Asn Ala Thr His Ala Thr Tyr Thr
65                  70                  75                  80

tgc cac atg gat gta ttc cac ttc atg gcc gac gac att ttc agt gtc      288
Cys His Met Asp Val Phe His Phe Met Ala Asp Asp Ile Phe Ser Val
                85                  90                  95

aac atc aca gac cag tct ggc aac tac tcc cag gag tgt ggc agc ttt      336
Asn Ile Thr Asp Gln Ser Gly Asn Tyr Ser Gln Glu Cys Gly Ser Phe
            100                 105                 110

ctc ctg gct gag agc atc aag ccg gct ccc cct ttc aac gtg act gtg      384
Leu Leu Ala Glu Ser Ile Lys Pro Ala Pro Pro Phe Asn Val Thr Val
        115                 120                 125

acc ttc tca gga cag tat aat atc tcc tgg cgc tca gat tac gaa gac      432
Thr Phe Ser Gly Gln Tyr Asn Ile Ser Trp Arg Ser Asp Tyr Glu Asp
    130                 135                 140

cct gcc ttc tac atg ctg aag ggc aag ctt cag tat gag ctg cag tac      480
Pro Ala Phe Tyr Met Leu Lys Gly Lys Leu Gln Tyr Glu Leu Gln Tyr
145                 150                 155                 160

agg aac cgg gga gac ccc tgg gct gtg agt ccg agg aga aag ctg atc      528
Arg Asn Arg Gly Asp Pro Trp Ala Val Ser Pro Arg Arg Lys Leu Ile
                165                 170                 175

tca gtg gac tca aga agt gtc tcc ctc ctc ccc ctg gag ttc cgc aaa      576
Ser Val Asp Ser Arg Ser Val Ser Leu Leu Pro Leu Glu Phe Arg Lys
            180                 185                 190

gac tcg agc tat gag ctg cag gtg cgg gca ggg ccc atg cct ggc tcc      624
Asp Ser Ser Tyr Glu Leu Gln Val Arg Ala Gly Pro Met Pro Gly Ser
        195                 200                 205

tcc tac cag ggg acc tgg agt gaa tgg agt gac ccg gtc atc ttt cag      672
Ser Tyr Gln Gly Thr Trp Ser Glu Trp Ser Asp Pro Val Ile Phe Gln
    210                 215                 220
```

Fig. 11B

```
acc cag tca gag gag tta aag gaa ggc tgg aac aaa acc gaa acc tcc      720
Thr Gln Ser Glu Glu Leu Lys Glu Gly Trp Asn Lys Thr Glu Thr Ser
225                 230                 235                 240

cag gtt gct ccg gca taa tga                                          741
Gln Val Ala Pro Ala
                245
```

Fig. 12A

```
atg ccg cgt ggc tgg gcc gcc ccc ttg ctc ctg ctg ctg ctc cag gga      48
Met Pro Arg Gly Trp Ala Ala Pro Leu Leu Leu Leu Leu Leu Gln Gly
1               5                   10                  15

ggc tgg ggc tgc ccc gac ctc gtc tgc tac acc gat tac ctc cag acg      96
Gly Trp Gly Cys Pro Asp Leu Val Cys Tyr Thr Asp Tyr Leu Gln Thr
        20                      25                  30

gtc atc tgc atc ctg gaa atg tgg aac ctc cac ccc agc acg ctc acc     144
Val Ile Cys Ile Leu Glu Met Trp Asn Leu His Pro Ser Thr Leu Thr
        35                  40                  45

ctt acc tgg caa gac cag tat gaa gag ctg aag gac gag gcc acc tcc     192
Leu Thr Trp Gln Asp Gln Tyr Glu Glu Leu Lys Asp Glu Ala Thr Ser
    50                  55                  60

tgc agc ctc cac agg tcg gcc cac aat gcc acg cat gcc acc tac acc     240
Cys Ser Leu His Arg Ser Ala His Asn Ala Thr His Ala Thr Tyr Thr
65                  70                  75                  80

tgc cac atg gat gta ttc cac ttc atg gcc gac gac att ttc agt gtc     288
Cys His Met Asp Val Phe His Phe Met Ala Asp Asp Ile Phe Ser Val
                85                  90                  95

aac atc aca gac cag tct ggc aac tac tcc cag gag tgt ggc agc ttt     336
Asn Ile Thr Asp Gln Ser Gly Asn Tyr Ser Gln Glu Cys Gly Ser Phe
            100                 105                 110

ctc ctg gct gag agc atc aag ccg gct ccc cct ttc aac gtg act gtg     384
Leu Leu Ala Glu Ser Ile Lys Pro Ala Pro Pro Phe Asn Val Thr Val
        115                 120                 125

acc ttc tca gga cag tat aat atc tcc tgg cgc tca gat tac gaa gac     432
Thr Phe Ser Gly Gln Tyr Asn Ile Ser Trp Arg Ser Asp Tyr Glu Asp
    130                 135                 140

cct gcc ttc tac atg ctg aag ggc aag ctt cag tat gag ctg cag tac     480
Pro Ala Phe Tyr Met Leu Lys Gly Lys Leu Gln Tyr Glu Leu Gln Tyr
145                 150                 155                 160

agg aac cgg gga gac ccc tgg gct gtg agt ccg agg aga aag ctg atc     528
Arg Asn Arg Gly Asp Pro Trp Ala Val Ser Pro Arg Arg Lys Leu Ile
                165                 170                 175

tca gtg gac tca aga agt gtc tcc ctc ctc ccc ctg gag ttc cgc aaa     576
Ser Val Asp Ser Arg Ser Val Ser Leu Leu Pro Leu Glu Phe Arg Lys
            180                 185                 190

gac tcg agc tat gag ctg cag gtg cgg gca ggg ccc atg cct ggc tcc     624
Asp Ser Ser Tyr Glu Leu Gln Val Arg Ala Gly Pro Met Pro Gly Ser
        195                 200                 205

tcc tac cag ggg acc tgg agt gaa tgg agt gac ccg gtc atc ttt cag     672
Ser Tyr Gln Gly Thr Trp Ser Glu Trp Ser Asp Pro Val Ile Phe Gln
    210                 215                 220
```

Fig. 12B

```
acc cag tca gag gag tta aag gaa ggc tgg aac gat gac gat gac aag
Thr Gln Ser Glu Glu Leu Lys Glu Gly Trp Asn Asp Asp Asp Asp Lys
225                 230                 235                 240

ggc tcc ggc gac aaa act cac aca tgc cca ccg tgc cca gca cct gaa
Gly Ser Gly Asp Lys Thr His Thr Cys Pro Pro Cys Pro Ala Pro Glu
                245                 250                 255

gcc ctg ggg gca ccg tca gtc ttc ctc ttc ccc cca aaa ccc aag gac
Ala Leu Gly Ala Pro Ser Val Phe Leu Phe Pro Pro Lys Pro Lys Asp
            260                 265                 270

acc ctc atg atc tcc cgg acc cct gag gtc aca tgc gtg gtg gtg gac
Thr Leu Met Ile Ser Arg Thr Pro Glu Val Thr Cys Val Val Val Asp
        275                 280                 285

gtg agc cac gaa gac cct gag gtc aag ttc aac tgg tac gtg gac ggc
Val Ser His Glu Asp Pro Glu Val Lys Phe Asn Trp Tyr Val Asp Gly
    290                 295                 300

gtg gag gtg cat aat gcc aag aca aag ccg cgg gag gag cag tac aac
Val Glu Val His Asn Ala Lys Thr Lys Pro Arg Glu Glu Gln Tyr Asn
305                 310                 315                 320

agc acg tac cgt gtg gtc agc gtc ctc acc gtc ctg cac cag gac tgg
Ser Thr Tyr Arg Val Val Ser Val Leu Thr Val Leu His Gln Asp Trp
                325                 330                 335

ctg aat ggc aag gag tac aag tgc aag gtc tcc aac aaa gcc ctc cca
Leu Asn Gly Lys Glu Tyr Lys Cys Lys Val Ser Asn Lys Ala Leu Pro
            340                 345                 350

gcc ccc atc gag aaa acc atc tcc aaa gcc aaa ggg cag ccc cga gaa
Ala Pro Ile Glu Lys Thr Ile Ser Lys Ala Lys Gly Gln Pro Arg Glu
        355                 360                 365

cca cag gtg tac acc ctg ccc cca tcc cgg gag gag atg acc aag aac
Pro Gln Val Tyr Thr Leu Pro Pro Ser Arg Glu Glu Met Thr Lys Asn
    370                 375                 380

cag gtc agc ctg acc tgc ctg gtc aaa ggc ttc tat ccc agc gac atc
Gln Val Ser Leu Thr Cys Leu Val Lys Gly Phe Tyr Pro Ser Asp Ile
385                 390                 395                 400

gcc gtg gag tgg gag agc aat ggg cag ccg gag aac aac tac aag acc
Ala Val Glu Trp Glu Ser Asn Gly Gln Pro Glu Asn Asn Tyr Lys Thr
                405                 410                 415

acg cct ccc gtg ctg gac tcc gac ggc tcc ttc ttc ctc tat agc aag
Thr Pro Pro Val Leu Asp Ser Asp Gly Ser Phe Phe Leu Tyr Ser Lys
            420                 425                 430

ctc acc gtg gac aag agc agg tgg cag cag ggg aac gtc ttc tca tgc
Leu Thr Val Asp Lys Ser Arg Trp Gln Gln Gly Asn Val Phe Ser Cys
        435                 440                 445
```

Fig. 12C

```
tcc gtg atg cat gag gct ctg cac aac cac tac acg cag aag agc ctc      1392
Ser Val Met His Glu Ala Leu His Asn His Tyr Thr Gln Lys Ser Leu
    450                 455                 460

tcc ctg tcc ccg ggt aaa tga                                          1413
Ser Leu Ser Pro Gly Lys
465                 470
```

Fig. 13A

```
atg ccc cgg ggc cca gtg gct gcc tta ctc ctg ctg att ctc cat gga      48
Met Pro Arg Gly Pro Val Ala Ala Leu Leu Leu Leu Ile Leu His Gly
1               5                   10                  15

gct tgg agc tgc ctg gac ctc act tgc tac act gac tac ctc tgg acc      96
Ala Trp Ser Cys Leu Asp Leu Thr Cys Tyr Thr Asp Tyr Leu Trp Thr
            20                  25                  30

atc acc tgt gtc ctg gag aca cgg agc ccc aac ccc agc ata ctc agt      144
Ile Thr Cys Val Leu Glu Thr Arg Ser Pro Asn Pro Ser Ile Leu Ser
        35                  40                  45

ctc acc tgg caa gat gaa tat gag gaa ctt cag gac caa gag acc ttc      192
Leu Thr Trp Gln Asp Glu Tyr Glu Glu Leu Gln Asp Gln Glu Thr Phe
    50                  55                  60

tgc agc cta cac agg tct ggc cac aac acc aca cat ata tgg tac acg      240
Cys Ser Leu His Arg Ser Gly His Asn Thr Thr His Ile Trp Tyr Thr
65                  70                  75                  80

tgc cat atg cgc ttg tct caa ttc ctg tcc gat gaa gtt ttc att gtc      288
Cys His Met Arg Leu Ser Gln Phe Leu Ser Asp Glu Val Phe Ile Val
                85                  90                  95

aat gtg acg gac cag tct ggc aac aac tcc caa gag tgt ggc agc ttt      336
Asn Val Thr Asp Gln Ser Gly Asn Asn Ser Gln Glu Cys Gly Ser Phe
            100                 105                 110

gtc ctg gct gag agc atc aaa cca gct ccc ccc ttg aac gtg act gtg      384
Val Leu Ala Glu Ser Ile Lys Pro Ala Pro Pro Leu Asn Val Thr Val
        115                 120                 125

gcc ttc tca gga cgc tat gat atc tcc tgg gac tca gct tat gac gaa      432
Ala Phe Ser Gly Arg Tyr Asp Ile Ser Trp Asp Ser Ala Tyr Asp Glu
    130                 135                 140

ccc tcc aac tac gtg ctg agg ggc aag cta caa tat gag ctg cag tat      480
Pro Ser Asn Tyr Val Leu Arg Gly Lys Leu Gln Tyr Glu Leu Gln Tyr
145                 150                 155                 160

cgg aac ctc aga gac ccc tat gct gtg agg ccg gtg acc aag ctg atc      528
Arg Asn Leu Arg Asp Pro Tyr Ala Val Arg Pro Val Thr Lys Leu Ile
                165                 170                 175

tca gtg gac tca aga aac gtc tct ctt ctc cct gaa gag ttc cac aaa      576
Ser Val Asp Ser Arg Asn Val Ser Leu Leu Pro Glu Glu Phe His Lys
            180                 185                 190

gat tct agc tac cag ctg cag gtg cgg gca gcg cct cag cca ggc act      624
Asp Ser Ser Tyr Gln Leu Gln Val Arg Ala Ala Pro Gln Pro Gly Thr
        195                 200                 205

tca ttc agg ggg acc tgg agt gag tgg agt gac ccc gtc atc ttt cag      672
Ser Phe Arg Gly Thr Trp Ser Glu Trp Ser Asp Pro Val Ile Phe Gln
    210                 215                 220
```

Fig. 13B

```
acc cag gct ggg gag ccc gag gca ggc tgg gac ggc tcc ggc tct aga        720
Thr Gln Ala Gly Glu Pro Glu Ala Gly Trp Asp Gly Ser Gly Ser Arg
225                 230                 235                 240

gagccccgcg gaccgacaat caagccctgt cctccatgca aatgcccagg taagtcacta      780

gaccagagct ccactcccgg gagaatggta agtgctataa acatccctgc actagaggat      840

aagccatgta cagatccatt tccatctctc ctcatcagca cctaacctcg agggtggacc      900

atccgtcttc atcttccctc caaagatcaa ggatgtactc atgatctccc tgagccccat      960

agtcacatgt gtggtggtgg atgtgagcga ggatgaccca gatgtccaga tcagctggtt     1020

tgtgaacaac gtggaagtac acacagctca gacacaaacc catagagagg attacaacag     1080

tactctccgg gtggtcagtg ccctccccat ccagcaccag gactggatga gtggcaaggc     1140

tttcgcatgc gccgtcaaca acaaagacct cccagcgccc atcgagagaa ccatctcaaa     1200

acccaaaggt gagagctgca gcctgactgc atgggggctg ggatgggcat aaggataaag     1260

gtctgtgtgg acagccttct gcttcagcca tgacctttgt gtatgtttct accctcacag     1320

ggtcagtaag agctccacag gtatatgtct tgcctccacc agaagaagag atgactaaga     1380

aacaggtcac tctgacctgc atggtcacag acttcatgcc tgaagacatt tacgtggagt     1440

ggaccaacaa cgggaaaaca gagctaaact acaagaacac tgaaccagtc ctggactctg     1500

atggttctta cttcatgtac agcaagctga gagtggaaaa gaagaactgg gtggaaagaa     1560

atagctactc ctgttcagtg gtccacgagg gtctgcacaa tcaccacacg actaagagct     1620

tctcccggac tccgggtaaa tgagctcagc acccacaaaa ctctcaggtc caaagagaca     1680

cccacactca tctccatgct tcccttgtat aaataaagca cccagcaatg cctgggacca     1740

tgtaatagga attc                                                       1754
```

Fig. 14A

```
ctgcaggtcg acaccacc atg ccc cgg ggc cca gtg gct gcc tta ctc ctg      51
                    Met Pro Arg Gly Pro Val Ala Ala Leu Leu Leu
                    1               5                   10

ctg att ctc cat gga gct tgg agc tgc ctg gac ctc act tgc tac act      99
Leu Ile Leu His Gly Ala Trp Ser Cys Leu Asp Leu Thr Cys Tyr Thr
            15                  20                  25

gac tac ctc tgg acc atc acc tgt gtc ctg gag aca cgg agc ccc aac     147
Asp Tyr Leu Trp Thr Ile Thr Cys Val Leu Glu Thr Arg Ser Pro Asn
        30                  35                  40

ccc agc ata ctc agt ctc acc tgg caa gat gaa tat gag gaa ctt cag     195
Pro Ser Ile Leu Ser Leu Thr Trp Gln Asp Glu Tyr Glu Glu Leu Gln
    45                  50                  55

gac caa gag acc ttc tgc agc cta cac agg tct ggc cac aac acc aca     243
Asp Gln Glu Thr Phe Cys Ser Leu His Arg Ser Gly His Asn Thr Thr
60                  65                  70                  75

cat ata tgg tac acg tgc cat atg cgc ttg tct caa ttc ctg tcc gat     291
His Ile Trp Tyr Thr Cys His Met Arg Leu Ser Gln Phe Leu Ser Asp
                80                  85                  90

gaa gtt ttc att gtc aat gtg acg gac cag tct ggc aac aac tcc caa     339
Glu Val Phe Ile Val Asn Val Thr Asp Gln Ser Gly Asn Asn Ser Gln
            95                  100                 105

gag tgt ggc agc ttt gtc ctg gct gag agc atc aaa cca gct ccc ccc     387
Glu Cys Gly Ser Phe Val Leu Ala Glu Ser Ile Lys Pro Ala Pro Pro
        110                 115                 120

ttg aac gtg act gtg gcc ttc tca gga cgc tat gat atc tcc tgg gac     435
Leu Asn Val Thr Val Ala Phe Ser Gly Arg Tyr Asp Ile Ser Trp Asp
    125                 130                 135

tca gct tat gac gaa ccc tcc aac tac gtg ctg agg ggc aag cta caa     483
Ser Ala Tyr Asp Glu Pro Ser Asn Tyr Val Leu Arg Gly Lys Leu Gln
140                 145                 150                 155

tat gag ctg cag tat cgg aac ctc aga gac ccc tat gct gtg agg ccg     531
Tyr Glu Leu Gln Tyr Arg Asn Leu Arg Asp Pro Tyr Ala Val Arg Pro
                160                 165                 170

gtg acc aag ctg atc tca gtg gac tca aga aac gtc tct ctt ctc cct     579
Val Thr Lys Leu Ile Ser Val Asp Ser Arg Asn Val Ser Leu Leu Pro
            175                 180                 185

gaa gag ttc cac aaa gat tct agc tac cag ctg cag gtg cgg gca gcg     627
Glu Glu Phe His Lys Asp Ser Ser Tyr Gln Leu Gln Val Arg Ala Ala
        190                 195                 200

cct cag cca ggc act tca ttc agg ggg acc tgg agt gag tgg agt gac     675
Pro Gln Pro Gly Thr Ser Phe Arg Gly Thr Trp Ser Glu Trp Ser Asp
    205                 210                 215
```

Fig. 14B

```
ccc gtc atc ttt cag acc cag gct ggg gag ccc gag gca ggc tgg gac        723
Pro Val Ile Phe Gln Thr Gln Ala Gly Glu Pro Glu Ala Gly Trp Asp
220                 225                 230                 235

ggc agc gga cac cac cat cat cac cac ggt agc ggc gac tat aaa gac        771
Gly Ser Gly His His His His His His Gly Ser Gly Asp Tyr Lys Asp
                240                 245                 250

gat gac gat aag tagtgagaat tc                                          795
Asp Asp Asp Lys
            255
```

Fig. 15A

```
atg aaa ttc tta gtc aac gtt gcc ctt gtt ttt atg gtc gtg tac att      48
Met Lys Phe Leu Val Asn Val Ala Leu Val Phe Met Val Val Tyr Ile
1               5                   10                  15

tct tac atc tat gcc ggc agc gga cac cac cat cat cac cac ggt agc      96
Ser Tyr Ile Tyr Ala Gly Ser Gly His His His His His His Gly Ser
            20                  25                  30

ggc gac tat aaa gac gat gac gat aag ggt tcc gga tgc ctg gac ctc     144
Gly Asp Tyr Lys Asp Asp Asp Asp Lys Gly Ser Gly Cys Leu Asp Leu
        35                  40                  45

act tgc tac act gac tac ctc tgg acc atc acc tgt gtc ctg gag aca     192
Thr Cys Tyr Thr Asp Tyr Leu Trp Thr Ile Thr Cys Val Leu Glu Thr
    50                  55                  60

cgg agc ccc aac ccc agc ata ctc agt ctc acc tgg caa gat gaa tat     240
Arg Ser Pro Asn Pro Ser Ile Leu Ser Leu Thr Trp Gln Asp Glu Tyr
65                  70                  75                  80

gag gaa ctt cag gac caa gag acc ttc tgc agc cta cac agg tct ggc     288
Glu Glu Leu Gln Asp Gln Glu Thr Phe Cys Ser Leu His Arg Ser Gly
                85                  90                  95

cac aac acc aca cat ata tgg tac acg tgc cat atg cgc ttg tct caa     336
His Asn Thr Thr His Ile Trp Tyr Thr Cys His Met Arg Leu Ser Gln
            100                 105                 110

ttc ctg tcc gat gaa gtt ttc att gtc aat gtg acg gac cag tct ggc     384
Phe Leu Ser Asp Glu Val Phe Ile Val Asn Val Thr Asp Gln Ser Gly
        115                 120                 125

aac aac tcc caa gag tgt ggc agc ttt gtc ctg gct gag agc atc aaa     432
Asn Asn Ser Gln Glu Cys Gly Ser Phe Val Leu Ala Glu Ser Ile Lys
    130                 135                 140

cca gct ccc ccc ttg aac gtg act gtg gcc ttc tca gga cgc tat gat     480
Pro Ala Pro Pro Leu Asn Val Thr Val Ala Phe Ser Gly Arg Tyr Asp
145                 150                 155                 160

atc tcc tgg gac tca gct tat gac gaa ccc tcc aac tac gtg ctg agg     528
Ile Ser Trp Asp Ser Ala Tyr Asp Glu Pro Ser Asn Tyr Val Leu Arg
                165                 170                 175

ggc aag cta caa tat gag ctg cag tat cgg aac ctc aga gac ccc tat     576
Gly Lys Leu Gln Tyr Glu Leu Gln Tyr Arg Asn Leu Arg Asp Pro Tyr
            180                 185                 190

gct gtg agg ccg gtg acc aag ctg atc tca gtg gac tca aga aac gtc     624
Ala Val Arg Pro Val Thr Lys Leu Ile Ser Val Asp Ser Arg Asn Val
        195                 200                 205

tct ctt ctc cct gaa gag ttc cac aaa gat tct agc tac cag ctg cag     672
Ser Leu Leu Pro Glu Glu Phe His Lys Asp Ser Ser Tyr Gln Leu Gln
    210                 215                 220
```

Fig. 15B

```
gtg cgg gca gcg cct cag cca ggc act tca ttc agg ggg acc tgg agt      720
Val Arg Ala Ala Pro Gln Pro Gly Thr Ser Phe Arg Gly Thr Trp Ser
225                 230                 235                 240

gag tgg agt gac ccc gtc atc ttt cag acc cag gct ggg gag ccc gag      768
Glu Trp Ser Asp Pro Val Ile Phe Gln Thr Gln Ala Gly Glu Pro Glu
                245                 250                 255

gca ggc tgg gac tagtgagaat tc                                        792
Ala Gly Trp Asp
            260
```

Fig. 17 (continued)
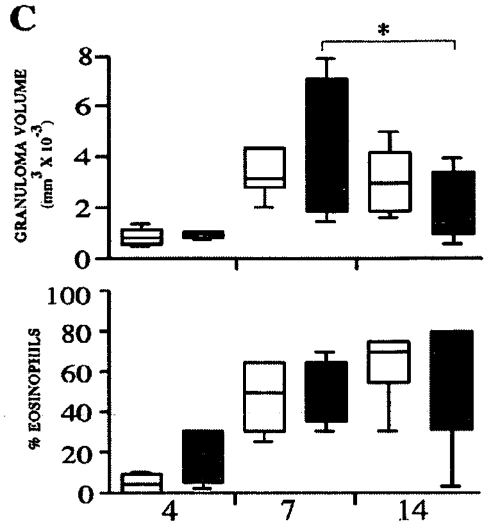
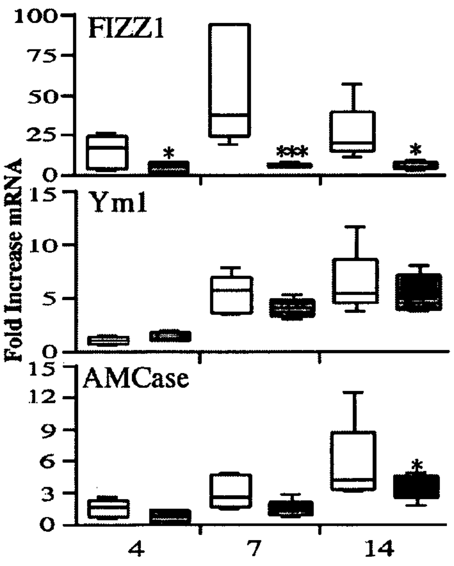

Fig. 19 (continued)
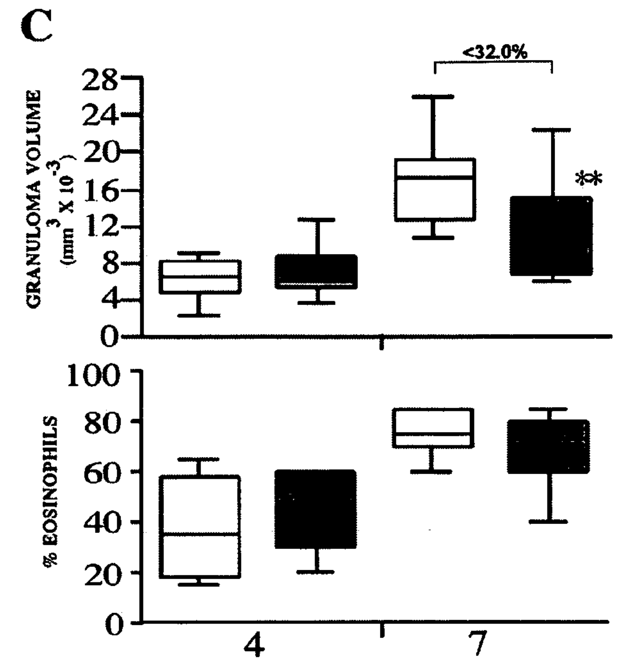
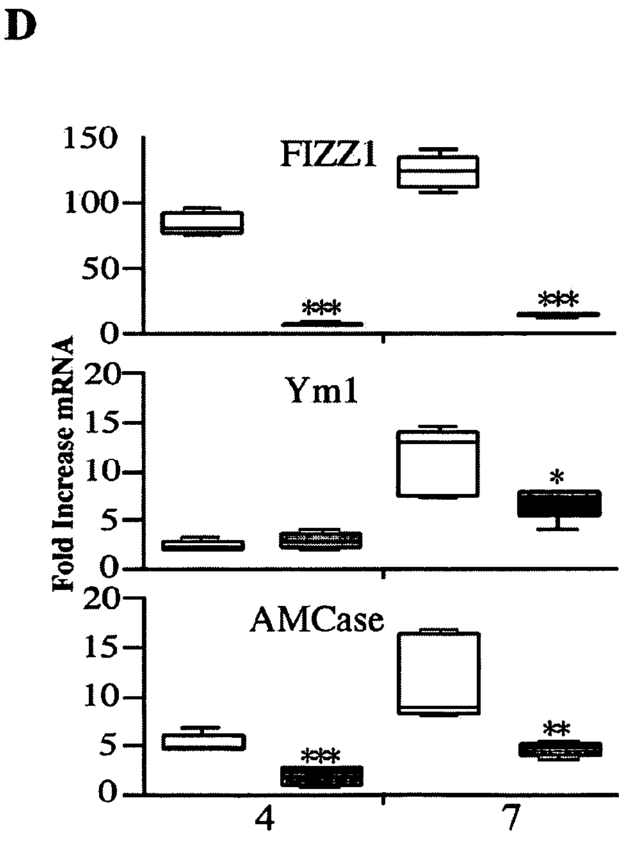

Fig. 20 (continued)
C
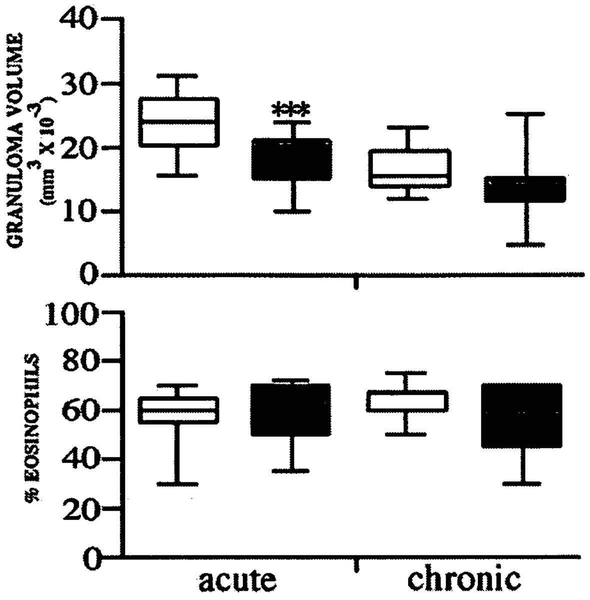
D
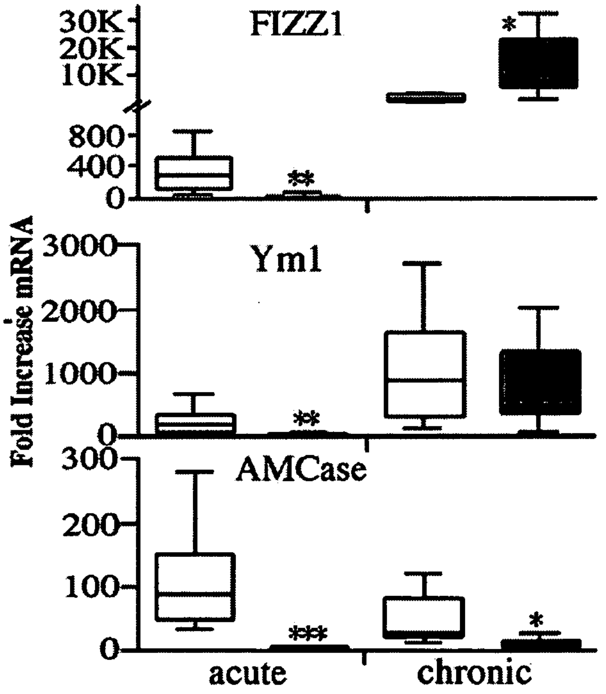

A

| Week postinfection | Group | Worm Pairs | Total Worms | Eggs/worm pair (in thousands) |
|---|---|---|---|---|
| 9 | WT (*n*=29) | 6.53± 0.63 | 15.53± 1.55 | 7.29 ±0.49 |
| | KO (*n*=26) | 5.00± 0.70 | 12.30± 1.74 | 9.63 ±1.16 |
| 12 | WT (*n*=19) | 3.74± 0.60 | 10.44± 2.08 | 14.75 ±1.91 |
| | KO (*n*=19) | 4.05± 0.62 | 9.89± 1.77 | 14.50 ±1.95 |

METHODS FOR TREATING AND PREVENTING FIBROSIS

RELATED APPLICATIONS

This application claims the benefit of priority to U.S. Provisional Patent Application No. 60/671,374, filed Apr. 14, 2005, which is hereby incorporated by reference herein in its entirety.

BACKGROUND OF THE INVENTION

1. Field the Invention

The present invention relates to methods for treating and preventing fibrosis and fibrosis-associated conditions.

2. Background Art

Injury to any organ typically leads to a physiological response involving platelet-induced hemostasis, followed by an influx of inflammatory cells and activated fibroblasts. Cytokines produced by these cell types drive the formation of new extracellular matrix and blood vessels, which collectively form granulation tissue. The formation of fibrous tissue is part of the normal beneficial process of healing following injury; fibrosis, however, is a condition characterized by an abnormal accumulation of a collagen matrix following injury or inflammation that alters the structure and function of various tissues. Progressive fibrosis in the kidney, liver, lung, heart, bone, bone marrow, and skin is a major cause of, or contributor to, death.

Many of the diseases associated with the proliferation of fibrous tissue are chronic and often debilitating and include, for example, skin diseases such as scleroderma. Some, including pulmonary fibrosis, may be fatal, due in part to the fact that the current treatments have significant side effects and are generally not effective in slowing or halting the progression of fibrosis. There is, accordingly, a continuing need for new anti-fibrotic agents.

The IL-21 receptor (IL-21R) is a newly discovered member of the class I cytokine receptor family (Parrish-Novak et al. (2000) *Nature* 408:57-63; Ozaki et al. (2000) *Proc. Natl. Acad. Sci. U.S.A.* 97:11439-44). The IL-21 receptor shows significant sequence and structural homology with the IL-4 receptor alpha (IL-4Rα) chain and is adjacent to the IL-4Rα in the human and mouse genomes, while its ligand, IL-21, shares significant homology with the cytokines IL-2, IL4, and IL-15 (Sivakumar et al. (2004) *Immunology* 112:177-82; Habib et al. (2003) *J. Allergy Clin. Immunol.* 112:1033-45). IL-21 and IL-21R are thus newly described members of the gamma chain (γc)-dependent cytokine network because of their homology with cytokines and receptors that require the γc for functional signaling (Vosshenrich and Di Santo (2001) *Curr. Biol.* 11:R175-77). Because all members of the yc network exhibit important and unique roles in host immunity, there has been growing interest in dissecting the novel functions of the IL-21R during antigen-triggered immune responses in vivo.

Initial studies examining the function of IL-21 showed that NK cell expansion is antagonized, whereas antigen-specific T cell immunity is promoted by IL-21, including anti-tumor immunity (Ma et al. (2003) *J. Immunol.* 171:608-15; Kishida et al. (2003) *Mol. Ther.* 8:552-58; Di Carlo et al. (2004) *J. Immunol.* 172:1540-47), findings that suggest that IL-21 serves as a bridge between innate and adaptive immune responses (Collins et al. (2003) *Immunol. Res.* 28:131-40). IL-21 also regulates B cell and $CD8^+$ T cell function in vivo (Ozaki et al. (2002) *Science* 298:1630-34; Suto et al. (2002) *Blood* 100:4565-73; Mehta et al. (2003) *J. Immunol.* 170: 4111-18; Pene et al. (2004) *J. Immunol.* 172:5154-57; Jin et al. (2004) *J. Immunol.* 173:657-65; Zeng et al. (2005) *J. Exp. Med.* 201:139-48). Additional studies suggest that IL-21 is a $T_H2$ cytokine that can inhibit the differentiation of naïve $T_H$ cells into IFN-γ-secreting $T_H1$ cells (Wurster et al. (2002) *J. Exp. Med.* 196:969-77). Indeed, exogenous treatment with IL-21 potently inhibited IFN-γ production without affecting other $T_H1/T_H2$-associated cytokines, suggesting that the repression of IFN-γ by IL-21 is highly specific. Thus, by virtue of its ability to suppress the development of $T_H1$ cells, it was hypothesized that IL-21 might promote $T_H2$ responses (Wurster et al., supra). Nevertheless, the involvement of the IL-21R signaling pathway in $T_H2$ response development was not previously investigated in any $T_H2$-dependent disorder.

In schistosomiasis, $T_H2$ cytokines play an indispensable role in the pathogenesis of the disease (Wynn (2004) *Nat. Rev. Immunol.* 4:583-594; Pearce and MacDonald (2002) *Nat. Rev. Immunol.* 2:499-511). Indeed, IL4/IL-13-, IL-4Rα-, and Stat6-deficient mice all show significantly impaired granuloma formation and liver fibrosis following infection with *S. mansoni* (Chiaramonte et al. (1999) *J. Clin. Invest.* 104:777-85; Kaplan et al. (1998) *J. Immunol.* 160:1850-56; Jankovic et al. (1999) *J. Immunol.* 163:337-42; Fallon et al. (2000) *J. Immunol.* 164:2585-91). Given the recent classification of IL-21 as a $T_H2$ cytokine (Wurster et al. (2002), supra; Mehta et al. (2005). *Proc. Natl. Acad. Sci. U.S.A.* 102:2016-21), the striking similarities between the IL-4 and IL-21 receptors (Sivakumar et al., supra; Habib et al., supra), and the critical role of the related IL-4Rα/Stat6-signaling pathway in this disease as well as in other $T_H2$ cytokine-driven inflammatory disorders (Wynn (2003) *Annu. Rev. Immunol.* 21:425-56), an important question evolving from these studies was whether IL-21R signaling plays a significant role in the initiation and/or maintenance of $T_H2$ immunity.

SUMMARY OF THE INVENTION

The present invention provides methods of treating, ameliorating or preventing fibrosis or a fibrosis-associated disorder, as well as methods of screening for compounds and compositions useful in those methods. The invention also provides methods of diagnosing, prognosing, and monitoring the progress (e.g., the course of treatment) of fibrosis and/or fibrosis-associated conditions. These methods are related to measuring and/or modulating the level of IL-21 and/or IL-21R (i.e., the level of activity of IL-21 and/or IL-21R, the level of expression of IL-21 and/or IL-21R (e.g., the level of IL-21 and/or IL-21R gene products), and/or the level of interaction of IL-21 with IL-21R). The invention further provides antagonists of IL-21 or IL-21R for the treatment of fibrosis and/or fibrosis-associated conditions.

In one embodiment, the invention provides a method for treating, ameliorating, or preventing fibrosis or a fibrosis-associated disorder in a subject (e.g., a human) comprising administering to the subject a therapeutically effective amount of an agent that reduces the level of IL-21 and/or IL-21R in the subject. In a further embodiment, the agent is an IL-21/IL-21R antagonist selected from the group consisting of an anti-IL-21R antibody, an anti-IL-21 antibody, an antigen-binding fragment of an anti-IL-21R antibody, an antigen-binding fragment of an anti-IL-21 antibody, and a soluble fragment of an IL-21R. In another further embodiment, the agent is a soluble fragment of an IL-21R, and the soluble fragment of the IL-21R comprises an amino acid sequence that is at least 90% identical to an amino acid sequence selected from the group consisting of amino acids 1-538 of SEQ ID NO:2, amino acids 20-538 of SEQ ID NO:2, amino acids 1-235 of SEQ ID NO:2, amino acids 20-235 of SEQ ID NO:2, amino acids 1-236 of SEQ ID NO: 2, amino acids 20-236 of SEQ ID NO:2, amino acids 1-529 of SEQ ID NO:5, amino acids 20-529 of SEQ ID NO:5, amino acids 1-236 of SEQ ID NO:5, and amino acid 20-236 of SEQ ID NO:5. In another embodiment, the soluble fragment of the IL-21R binds to an IL-21 polypeptide.

In another embodiment, the agent is a soluble fragment of an IL-21R, and the soluble fragment of the IL-21R comprises an amino acid sequence that is substantially identical to the amino acid sequence set forth in SEQ ID NO:11, SEQ ID NO:13, SEQ ID NO:15, SEQ ID NO:17, SEQ ID NO:19, SEQ ID NO:21, SEQ ID NO:23, SEQ ID NO:25, or SEQ ID NO:27. In another embodiment, the amino acid sequence of the soluble fragment of the IL-21R comprises an amino acid sequence that is substantially identical to the amino acid sequence set forth in SEQ ID NO:11 or SEQ ID NO:13. In another embodiment, the agent is a soluble fragment of an IL-21R, and the soluble fragment of the IL-21R is encoded by a nucleotide sequence that is substantially identical to the nucleic acid sequence set forth in SEQ ID NO:10, SEQ ID NO:12, SEQ ID NO:14, SEQ ID NO:16, SEQ ID NO:18, SEQ ID NO:20, SEQ ID NO:22, SEQ ID NO:24, or SEQ ID NO:26. In another embodiment, the soluble fragment of the IL-21R is encoded by a nucleotide sequence that is substantially identical to the nucleic acid sequence set forth in SEQ ID NO:12 or SEQ ID NO:16.

In another embodiment, the agent is a soluble fragment of an IL-21R, and the soluble fragment of the IL-21R comprises an extracellular domain of IL-21R and an immunoglobulin Fc fragment. In a further embodiment, the amino acid sequence of the extracellular domain of the IL-21R comprises an amino acid sequence that is at least 90% identical to amino acids 1-235 of SEQ ID NO:2 or amino acids 20-235 of SEQ ID NO:2. In another embodiment, the immunoglobulin Fc fragment has an altered function. In another further embodiment, the immunoglobulin Fc fragment has the amino acid sequence of amino acids 244-467 of SEQ ID NO:17.

In another embodiment, the fibrosis or fibrosis-associated disorder affects the liver, epidermis, endodermis, muscle, tendon, cartilage, heart, pancreas, lung, uterus, nervous system, testis, ovary, adrenal gland, artery, vein, colon, small intestine, biliary tract, or stomach. In a further embodiment, the fibrosis or fibrosis-associated disorder is interstitial lung fibrosis. In another embodiment, the fibrosis or fibrosis-associated disorder is the result of an infection with schistosoma. In another embodiment, the fibrosis or fibrosis-associated disorder is the result of wound healing. In a further embodiment, the wound healing results from a surgical incision.

In another embodiment, the invention further comprises administering to the subject at least one additional therapeutic agent. In another embodiment, the at least one additional therapeutic agent is selected from the group consisting of cytokine inhibitors, growth factor inhibitors, immunosuppressants, anti-inflammatory agents, metabolic inhibitors, enzyme inhibitors, cytotoxic agents, and cytostatic agents. In a further embodiment, the at least one additional therapeutic agent is selected from the group consisting of TNF antagonists, anti-TNF agents, IL-12 antagonists, IL-15 antagonists, IL-17 antagonists, IL-18 antagonists, IL-22 antagonists, T cell-depleting agents, B cell-depleting agents, cyclosporin, FK506, CCI-779, etanercept, infliximab, rituximab, adalimumab, prednisolone, azathioprine, gold, sulphasalazine, hydroxychloroquine, minocycline, anakinra, abatacept, methotrexate, leflunomide, rapamycin, rapamycin analogs, Cox-2 inhibitors, cPLA2 inhibitors, NSAIDs, p38 inhibitors, antagonists of B7.1, B7.2, ICOSL, ICOS and/or CD28, and agonists of CTLA4.

In another embodiment, the invention provides a method for identifying a compound for treating, ameliorating or preventing fibrosis or a fibrosis-associated disorder in a subject, comprising: (a) measuring the level of IL-21 and/or IL-21R in a cell or sample of interest; (b) contacting the cell or sample of interest with a compound; and (c) measuring the level of IL-21 and/or IL-21R in the cell or sample of interest following contact with the compound, wherein a lower level of IL-21 and/or IL-21R in the contacted cell or sample of interest, in comparison to the level of IL-21 and/or IL-21R in a noncontacted cell or sample of interest, identifies the compound as a compound useful for treating, ameliorating, or preventing fibrosis or a fibrosis-associated condition in a subject.

In another embodiment, the invention provides a method for identifying a compound for treating, ameliorating or preventing fibrosis or a fibrosis-associated disorder in a subject, comprising: (a) measuring the level of IL-21 and/or IL-21R in a cell or sample of interest; (b) contacting the cell or sample of interest with a compound; (c) measuring the level of IL-21 and/or IL-21R in the cell or sample of interest following contact with the compound; and (d) comparing the level of IL-21 and/or IL-21R in the contacted cell or sample of interest with a reference level of IL-21 and/or IL-21R, wherein a lower level of IL-21 and/or IL-21R in the contacted cell or sample of interest, in comparison to the reference level of IL-21 and/or IL-21R, identifies the compound as a compound useful for treating, ameliorating, or preventing fibrosis or a fibrosis-associated condition in a subject.

In another embodiment, the invention provides a method for monitoring the progress of fibrosis or a fibrosis-associated condition in a subject, comprising: (a) measuring the level of IL-21 and/or IL-21R in a cell or sample of interest from the subject at a first time point; and (b) measuring the level of IL-21 and/or IL-21R in a cell or sample of interest from the subject at a second time point, wherein a lower level of IL-21 and/or IL-21R in the cell or sample of interest from the subject at the second time point, in comparison to the level of IL-21 and/or IL-21R in the cell or sample of interest from the subject at the first time point, provides an indication that the fibrosis or fibrosis-associated condition has decreased in severity.

In another embodiment, the invention provides a method for prognosing fibrosis or a fibrosis-associated condition in a subject, comprising: (a) measuring the level of IL-21 and/or IL-21R in a cell or sample of interest from the subject at a first time point; and (b) measuring the level of IL-21 and/or IL-21R in a cell or sample of interest from the subject at a second time point, wherein a lower level of IL-21 and/or IL-21R in the cell or sample of interest from the subject at the second time point, in comparison to the level of IL-21 and/or IL-21R in the cell or sample of interest from the subject at the first time point, indicates a decreased likelihood that the subject will develop fibrosis or the fibrosis-associated condition or a decreased likelihood that the fibrosis or fibrosis-associate condition will worsen in the subject.

In another embodiment, the invention provides a method for prognosing fibrosis or a fibrosis-associated condition in a subject, comprising: (a) measuring the level of IL-21 and/or IL-21R in a cell or sample of interest from the subject; and (b) comparing the level of IL-21 and/or IL-21R in the cell or sample of interest from the subject to a reference level of IL-21 and/or IL-21R, wherein a lower level of IL-21 and/or IL-21R in the cell or sample of interest from the subject, in comparison to the reference level of IL-21 and/or IL-21R, indicates a decreased likelihood that the subject will develop fibrosis or the fibrosis-associated condition or a decreased likelihood that the fibrosis or fibrosis-associate condition will worsen in the subject.

In another embodiment, the invention provides a method for diagnosing fibrosis or a fibrosis-associated condition in a subject, comprising: (a) measuring the level of IL-21 and/or IL-21R in a cell or sample of interest from the subject, and (b) comparing the level of IL-21 and/or IL-21R in the cell or sample of interest from the subject with a reference level of IL-21 and/or IL-21R, wherein a higher level of IL-21 and/or IL-21R in the cell or sample of interest from the subject, in comparison to the reference level of IL-21 and/or IL-21R, indicates the presence of fibrosis or the fibrosis-associated condition in the subject.

BRIEF DESCRIPTION OF THE DRAWINGS

FIG. 1 depicts the full-length cDNA sequence of murine IL-2 1R/MU-1. The nucleotide sequence corresponds to nucleotides 1-2628 of SEQ ID NO:4. FIG. 1A depicts the cDNA sequence of murine IL-21R/MU-1 from nucleotide 1 to 1450, and FIG. 1B depicts the cDNA sequence of murine IL-21R/MU-1 from nucleotide 1451 to 2628.

FIGS. 2A and 2B depict the amino acid sequences of murine and human IL-21R/MU-1. FIG. 2A depicts the amino acid sequence of murine IL-21R/MU-1 (corresponding to the amino acids 1-529 of SEQ ID NO:5). There is a leader sequence (predicted by SPScan with a score of 10.1) at amino acids 1-19 (boldface type). A predicted transmembrane domain (underlined) is found at amino acids 237-253 of SEQ ID NO:5. Predicted signaling motifs include the "Box 1" motif at amino acids 265-274 and the "Box 2" motif at amino acids 311-324 (bold and underlined). Six tyrosines are located at amino acid positions 281, 319, 361, 369, 397, and 510, of SEQ ID NO:5. The WSXWS motif (SEQ ID NO:3) is located at amino acid residues 214-218 (in large, boldface type). Potential Stat docking sites include amino acids 393-398 and amino acids 510-513 of SEQ ID NO:5. FIG. 2B depicts the amino acid sequence of human IL-21R/MU-1 (corresponding to SEQ ID NO:2). The location of the predicted signal sequence (about amino acids 1-19 of SEQ ID NO:2); WSXWS motif (about amino acids 214-218 of SEQ ID NO:2); and transmembrane domain (about amino acids 236-252 (or 236-253, or 236-254) of SEQ ID NO:2 (underlined)) are indicated. Potential JAK binding sites, Box 1 and 2 signaling motifs, and Stat docking sites are indicated by labeled arrows.

FIG. 3 depicts the GAP comparison of human and murine IL-21R/MU-1 cDNA sequences (corresponding to nucleic acids 1 -1909, 1960-2050, and 2151-2665 of SEQ ID NO:1 and nucleic acids 151-2628 of SEQ ID NO:4, respectively). huMU-1=human IL-21R/MU-1, murMU-1=murine IL-21R/MU-1. Gap Parameters: Gap Weight=50; Average Match=10.000; Length Weight=3; Average Mismatch=0.000; Percent Identity=66.116. FIG. 3A is a comparison of nucleotides 1-721 of human IL-21R/MU-1 of SEQ ID NO:1 to nucleotides 151-892 of mouse IL-21R/MU-1 of SEQ ID NO:4; FIG. 3B is a comparison of nucleotides 722-1509 of human IL-21R/MU-1 of SEQ ID NO:1 to nucleotides 893-1674 of mouse IL-21R/MU-1 of SEQ ID NO:4; FIG. 3C is a comparison of nucleotides 1510-2404 of human IL-21R/MU-1 of SEQ ID NO:1, wherein nucleic acids 1910-1959 and 2051-2150 of SEQ ID NO: 1 have been removed for the purposes of the alignment, to nucleotides 1675-2368 of mouse IL-21R/MU-1 of SEQ ID NO:4; and FIG. 3D is a comparison of nucleotides 2405- 2665 of human IL-21R/MU-1 of SEQ ID NO:1 to nucleotides 2369-2628 of mouse IL-21R/MU-1 of SEQ ID NO:4.

FIG. 4 depicts a GAP comparison of human IL-21R/MU-1 protein (corresponding to amino acids of SEQ ID NO:2) and murine IL-21R/MU-1 protein (corresponding to amino acids of SEQ ID NO:5). The alignment was generated by BLOSUM62 amino acid substitution matrix (Henikoff and Henikoff (1992) *Proc. Natl. Acad. Sci. US.A.* 89:10915-19). Gap parameters=Gap Weight: 8; Average Match=2.912; Length Weight=2; Average Mismatch=−2.003; Percent Identity=65.267.

FIG. 5 depicts a multiple sequence alignment of the amino acids of human IL-21R/MU-1 (corresponding to SEQ ID NO:2), murine IL-21R/MU-1 (corresponding to SEQ ID NO:5), and human IL-2 beta chain (GENBANK® Accession No. M26062, corresponding to SEQ ID NO: 35). Leader and transmembrane domains are underlined. Conserved cytokine receptor module motifs are indicated by boldface type. Potential signaling regions are indicated by underlining and boldface type.

FIG. 6 depicts signaling through IL-21R/MU-1. IL-21R/MU-1 phosphorylates Stat 5 in Clone E7 EPO IL-21R/MU-1 chimera expressing cells stimulated with EPO. Treatment of controls or chimeric BAF-3 cells with IL-3 resulted in phosphorylation of Stat 3, but not Stat 1 or 5.

FIGS. 7A-7B depict an alignment of the nucleotide and amino acid sequences of mature human IL-21R fused at the amino terminal to a honeybee leader sequence and $His_6$ and Flag tags. The nucleotide and amino acid sequences of the fusion protein depicted in FIGS. 7A-7B are set forth in SEQ ID NO:10 and SEQ ID NO:11, respectively. The amino acid sequences of the mature human IL-21R fragment and the honeybee leader/His tags fragment of the fusion protein correspond to amino acids 20-235 of SEQ ID NO:2 and amino acids 144 of SEQ ID NO:11, respectively.

FIGS. 8A-8C depict an alignment of the nucleotide and amino acid sequences of human IL-21R extracellular domain fused at the C-terminus via a linker to human immunoglobulin G1 (IgG1) Fc sequence. The nucleotide and amino acid sequences of the fusion protein depicted in FIGS. 8A-8C are set forth in SEQ ID NO:12 and SEQ ID NO:13, respectively. The amino acid sequences of the human IL-21R extracellular domain, the linker, and the human immunoglobulin G1 (IgG1) Fc sequence correspond to amino acids 1-235 of SEQ ID NO:2, amino acids 236-243 of SEQ ID NO:13, and amino acids 244-467 of SEQ ID NO:13, respectively.

FIGS. 9A-9C depict an alignment of the nucleotide and amino acid sequences of human IL-21R extracellular domain fused at the C-terminus via a linker to human immunoglobulin G1 (IgG1) Fc sequence and $His_6$ sequence tag. The nucleotide and amino acid sequences of the fusion protein depicted in FIGS. 9A-9C are set forth in SEQ ID NO:14 and SEQ ID NO:15, respectively. The amino acid sequences of the human IL-21R extracellular domain, the linker, the human immunoglobulin G1 (IgG1) Fc sequence, and the HiS6 sequence tag correspond to amino acids 1-235 of SEQ ID NO:2, amino acids 236-243 of SEQ ID NO:15, amino acids 244-467 of SEQ ID NO:15, and amino acids 468-492 of SEQ ID NO:15, respectively.

FIGS. 10A-10C depict an alignment of the nucleotide and amino acid sequences of human IL-21R extracellular domain fused at the C-terminus via a linker to human immunoglobulin G1 (IgG1) Fc-mutated sequence. The human Fc sequence has been mutated at residues 254 and 257 from the wild-type sequence to reduce Fc-receptor binding. The nucleotide and amino acid sequences of the fusion protein depicted in FIGS.

10A-10C are set forth in SEQ ID NO:16 and SEQ ID NO:17, respectively. The amino acid sequences of the human IL-21R extracellular domain, the linker, and the human immunoglobulin G1 (IgG1) Fc-mutated sequence correspond to amino acids 1-235 of SEQ ID NO:2, amino acids 236-243 of SEQ ID NO:17, and amino acids 244-467 of SEQ ID NO:17, respectively.

FIGS. 11A-11B depict an alignment of the nucleotide and amino acid sequences of human IL-21R extracellular domain fused at the C-terminus to a rhodopsin sequence tag. The nucleotide and amino acid sequences of the fusion protein are set forth in SEQ ID NO:18 and SEQ ID NO:19, respectively. The amino acid sequence of the human IL-21R extracellular domain corresponds to amino acids 1-235 of SEQ ID NO:2.

FIGS. 12A-12C depict an alignment of the nucleotide and amino acid sequences of human IL-21R extracellular domain fused at the C-terminus to an EK cleavage site and mutated IgG1 Fc region. The nucleotide and amino acid sequences of the fusion protein depicted in FIGS. 12A-12C are set forth in SEQ ID NO:20 and SEQ ID NO:21, respectively. The amino acid sequences of the human IL-21R extracellular domain, and the EK cleavage site/mutated IgG1 Fc region correspond to amino acids 1-235 of SEQ ID NO:2 and amino acids 236-470 of SEQ ID NO:21, respectively.

FIGS. 13A-13B depict an alignment of the nucleotide and amino acid sequences of murine IL-21R extracellular domain fused at the C-terminus to mouse immunoglobulin G2a (IgG2a). The nucleotide and amino acid sequences are set forth in SEQ ID NO:22 and SEQ ID NO:23, respectively.

FIGS. 14A-14B depict an alignment of the nucleotide and amino acid sequences of murine IL-21R extracellular domain fused at the C-terminus to Flag and $His_6$ sequence tags. The nucleotide and amino acid sequences are set forth in SEQ ID NO:24 and SEQ ID NO:25, respectively.

FIGS. 15A-15B depict an alignment of the nucleotide and amino acid sequences of (honeybee leader) murine IL-21R extracellular domain fused at the N-terminus to Flag and $His_6$ sequence tags. The nucleotide and amino acid sequences are set forth in SEQ ID NO:26 and SEQ ID NO:27, respectively.

Figure 2B:
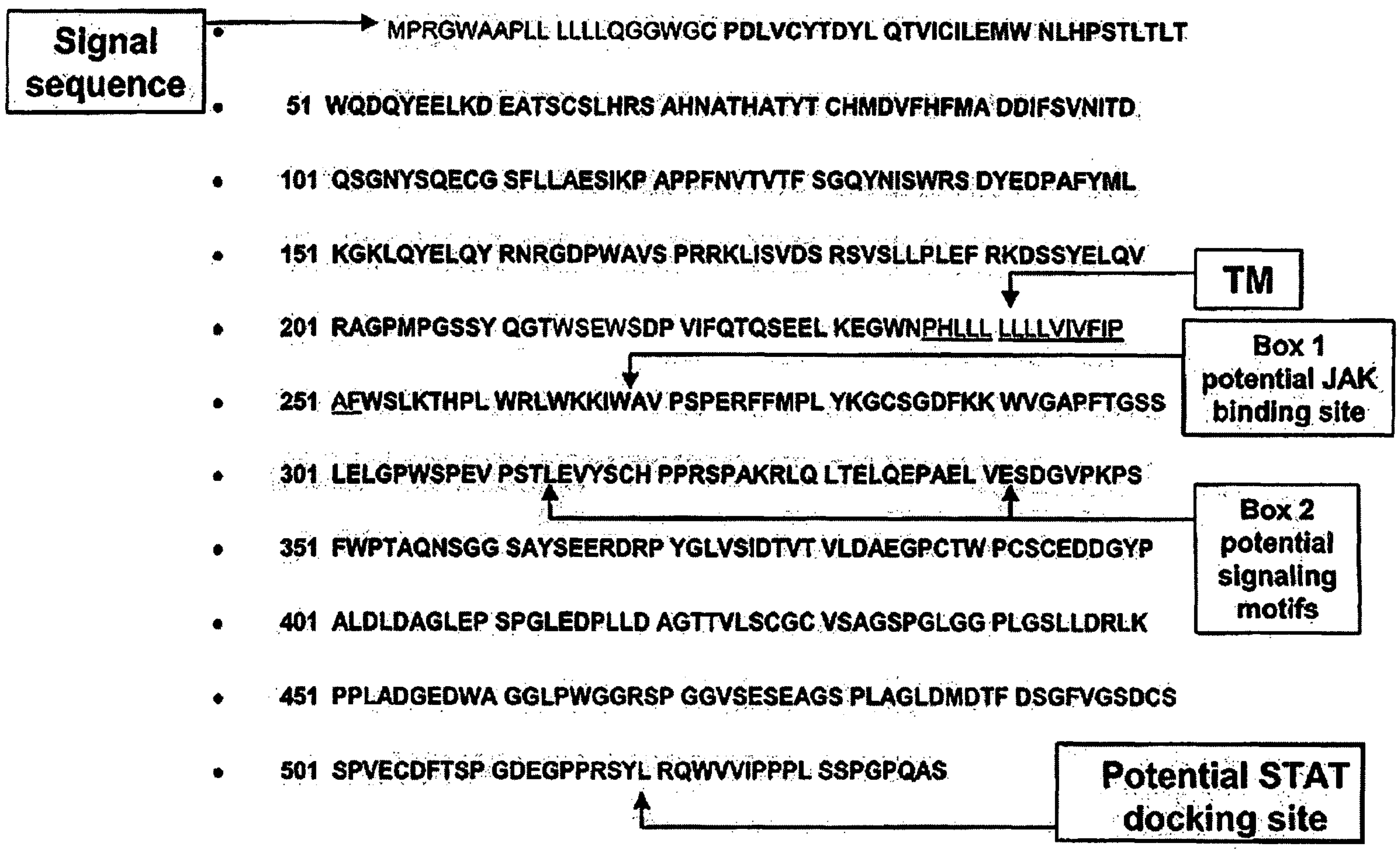
Figure 16:
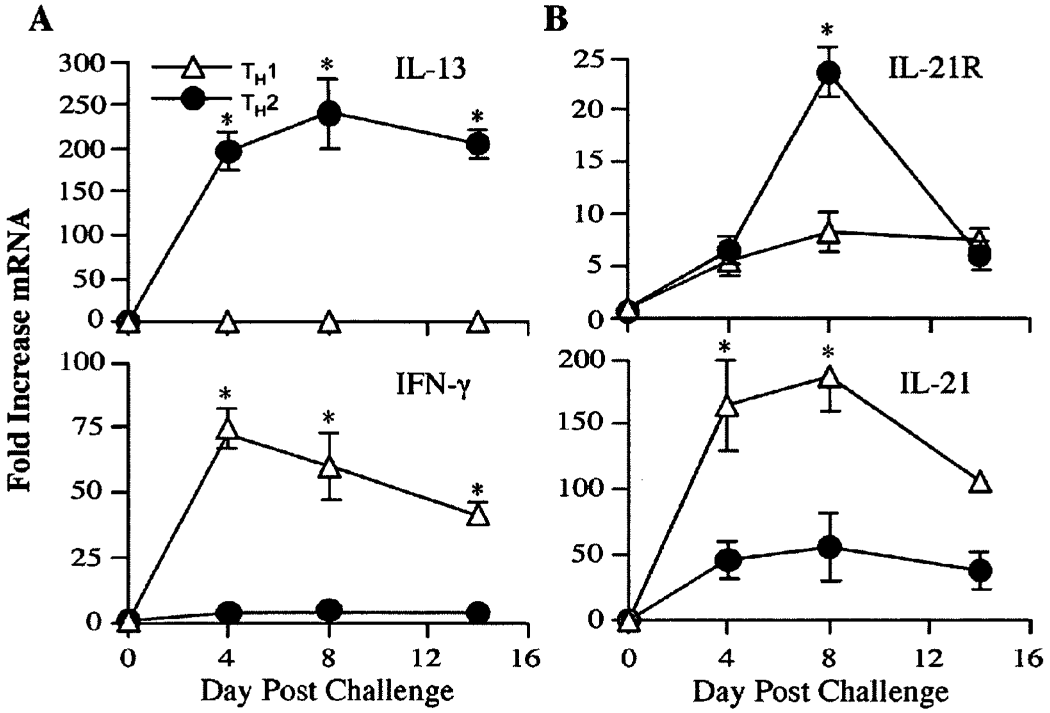

FIG. 16 shows IL-21 and IL-21R expression profiles during highly polarized type-1 and type-2 immune responses. Groups of five IL-10/IL-4 KO (TH1, Δ) and IL-10/IL-12 KO (TH2, ●) mice were sensitized i.p. with *S. mansoni* eggs and challenged i.v. 14 days later. Lung RNA specimens were prepared individually for real-time RT-PCR analysis of IL-13 and IFN-γ (FIG. 16A) and IL-21R and IL-21 (FIG. 16B). The means±SEM in gene expression were expressed as fold-increases over unchallenged WT controls after normalization to HPRT. Asterisks denote significant differences between groups at the given time point, * p<0.05.

Figure 17:
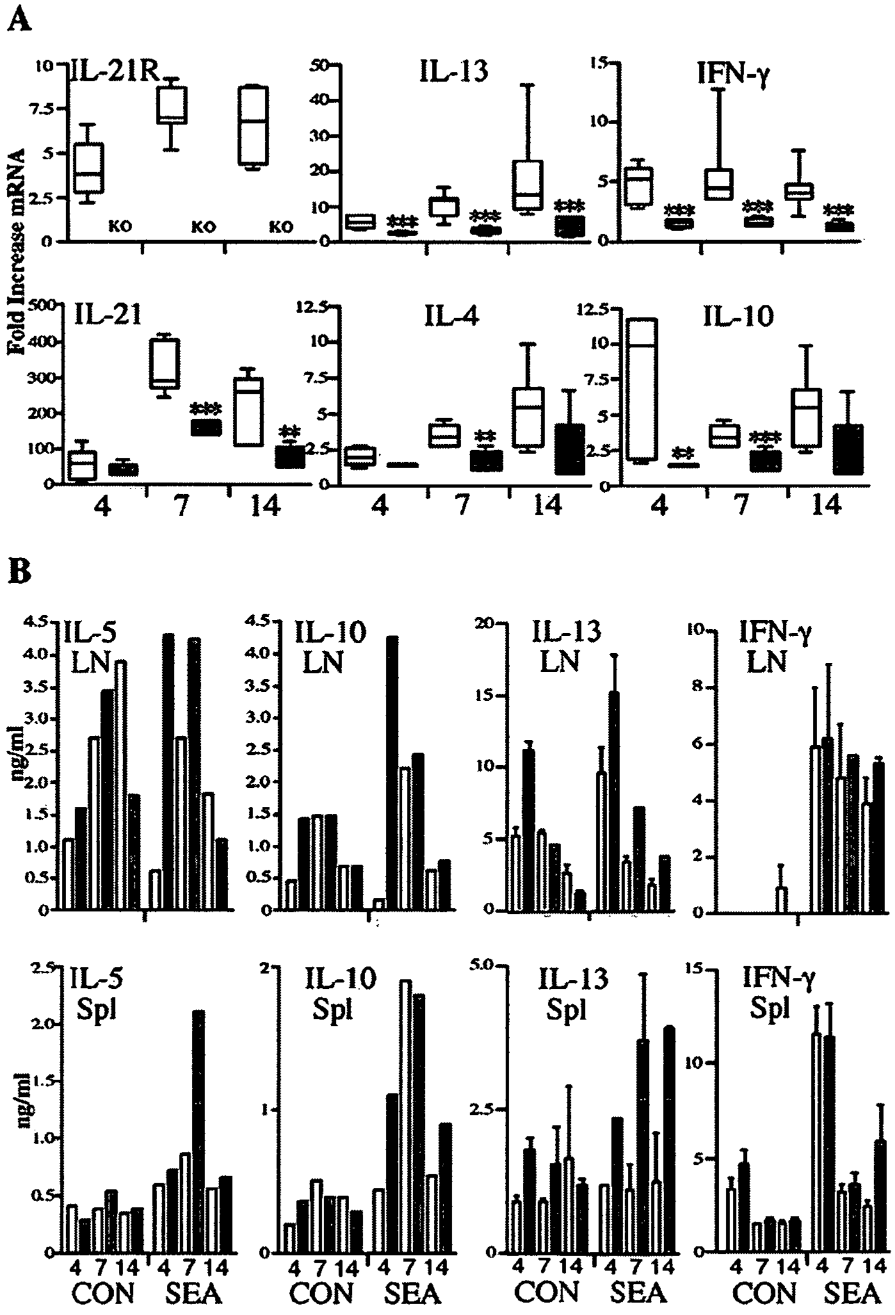

FIG. 17 shows that type-2 cytokine production is reduced in the lungs of schistosome egg-challenged IL-21R$^{-/-}$ mice. Groups of naïve WT (open bars) and IL-21R$^{-/-}$ mice (filled bars) were i.v. challenged with live *S. mansoni* eggs and sacrificed on days 4, 7, and 14 post-challenge. (A) RNA was prepared from lung tissues and analyzed individually (N=5 per group/time point) by real-time RT-PCR. Results are shown as box-and-whisker plots with five-number summary bars showing the median, the quartiles, and the smallest and greatest percentiles in the distribution; bars (from bottom to top) indicate the 10th, 25th, 50th, 75th, and 90th percentiles, respectively, of the tested samples. The asterisks denote significant differences from wild-type values at the given time point, * p<0.05,  p<0.01, * p<0.001. (B) Spleens (Spl) and lung-associated lymph nodes (LN) were each pooled (2 separate groups, 3-4 mice per group) and single cell suspensions were assayed for IL-5, IL-10, IL-13, and IFN-γ after a 72-h incubation in the presence of Con A (CON, 1 μg/ml) or soluble egg antigen (SEA, 20 μg/ml). Cytokines were below the level of detection in unstimulated cultures. (C) Granuloma size (volume, mm$^3$×10$^{-3}$) and the percentage of eosinophils in granulomas were quantified microscopically. (D) Real-time PCR analysis of $T_H2$-regulated inflammatory genes in granulomatous lung tissue. All data are representative of at least 2 separate experiments.

Figure 18:
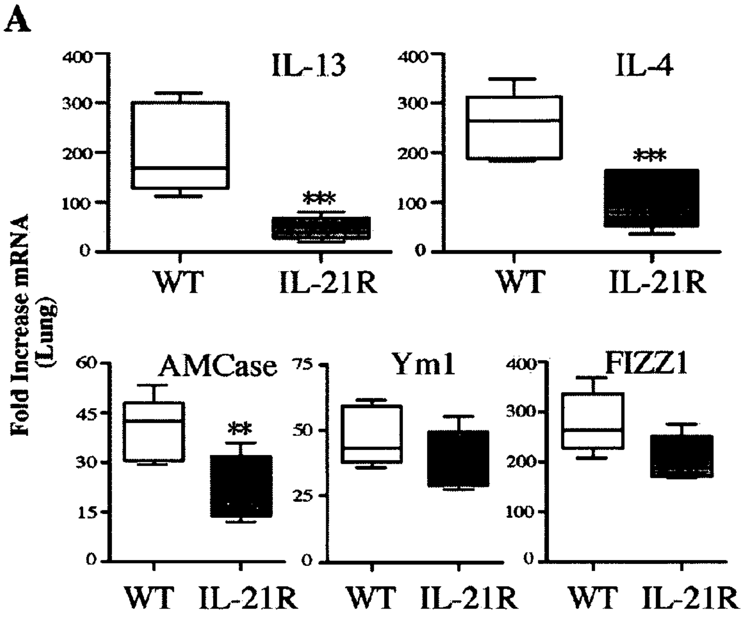
Figure 18:
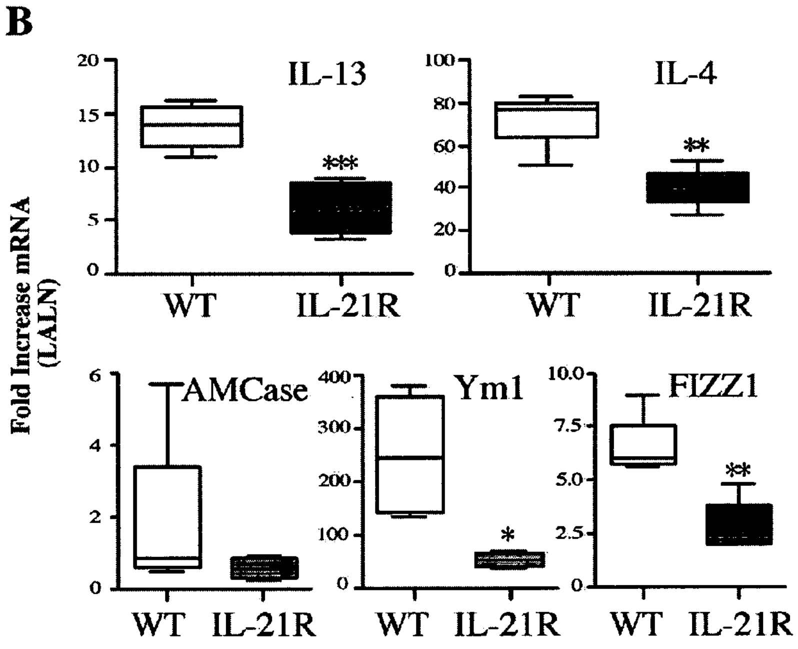

FIG. 18 shows that the type-2 response is impaired in *N. brasiliensis*-infected IL-21R$^{-/-}$ mice. Lungs (A) and lung-associated lymph nodes (LALN) (B) were removed on day 7 from individual *N. brasiliensis*-infected and untreated C57BL/6 or IL-21R$^{-/-}$ mice (5/treatment group). RNA was isolated and cDNA was generated as described in the legend to FIG. 17. mRNA was analyzed individually for IL-13, IL-4, AMCase, Ym1, and FIZZ1 by real-time quantitative PCR. Fold changes are based on comparisons of infected mice to naive animals.

Figure 19:
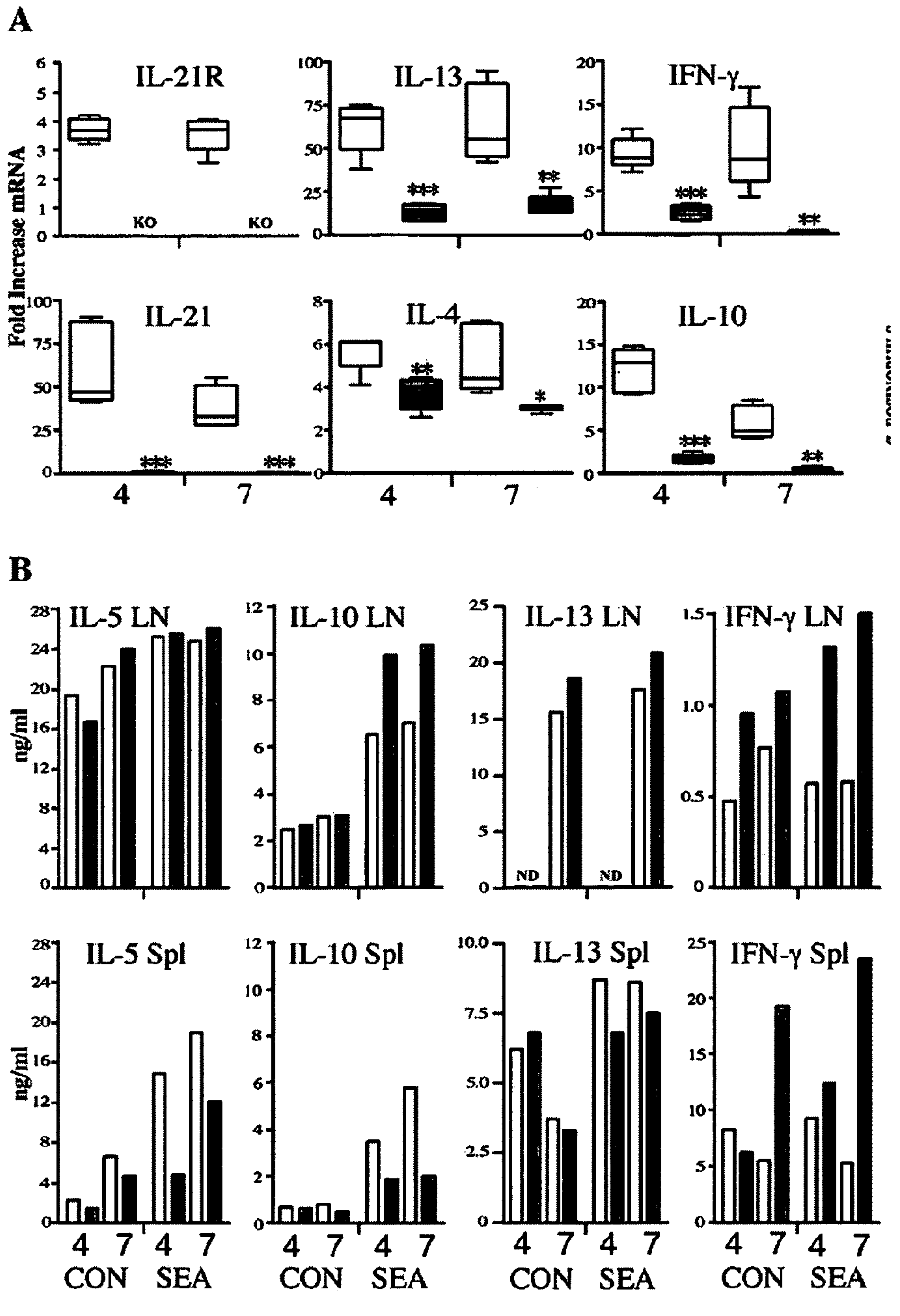

FIG. 19 shows that type-2 cytokine-driven inflammation is reduced in IL-21R$^{-/-}$ mice. WT (open bars) and IL-21R$^{-/-}$ mice (filled bars) were sensitized i.p. with eggs, challenged i.v. two weeks later with live *S. mansoni* eggs and then sacrificed on days 4 and 7 post-challenge. (A) RNA was prepared from lung tissues and analyzed individually (N=5 per group/time point) by real-time RT-PCR as described above in the legend to FIG. 17. (B) Spleens (Spl) and lung-associated lymph nodes (LN) were assayed for IL-5, IL-10, IL-13, and IFN-γ following antigen (SEA) or mitogen stimulation (CON). (C) Granuloma size (mm$^3$×10$^{-3}$) and the percentage of eosinophils in granulomas were quantified microscopically in WT (mice per group: N=10, day 4; N=15, day 7) and IL-21R$^{-/-}$ mice (N=11, day 4; N=16, day 7). (D) Real-time PCR analysis of $T_H2$ inflammatory genes in granulomatous lung tissue (N=5 per group/time point). The asterisks denote significant differences from wild-type values at the given time point, * p<0.05,  p<0.01, * p<0.001. Data shown are the combined results of 3 separate experiments.

Figure 20:
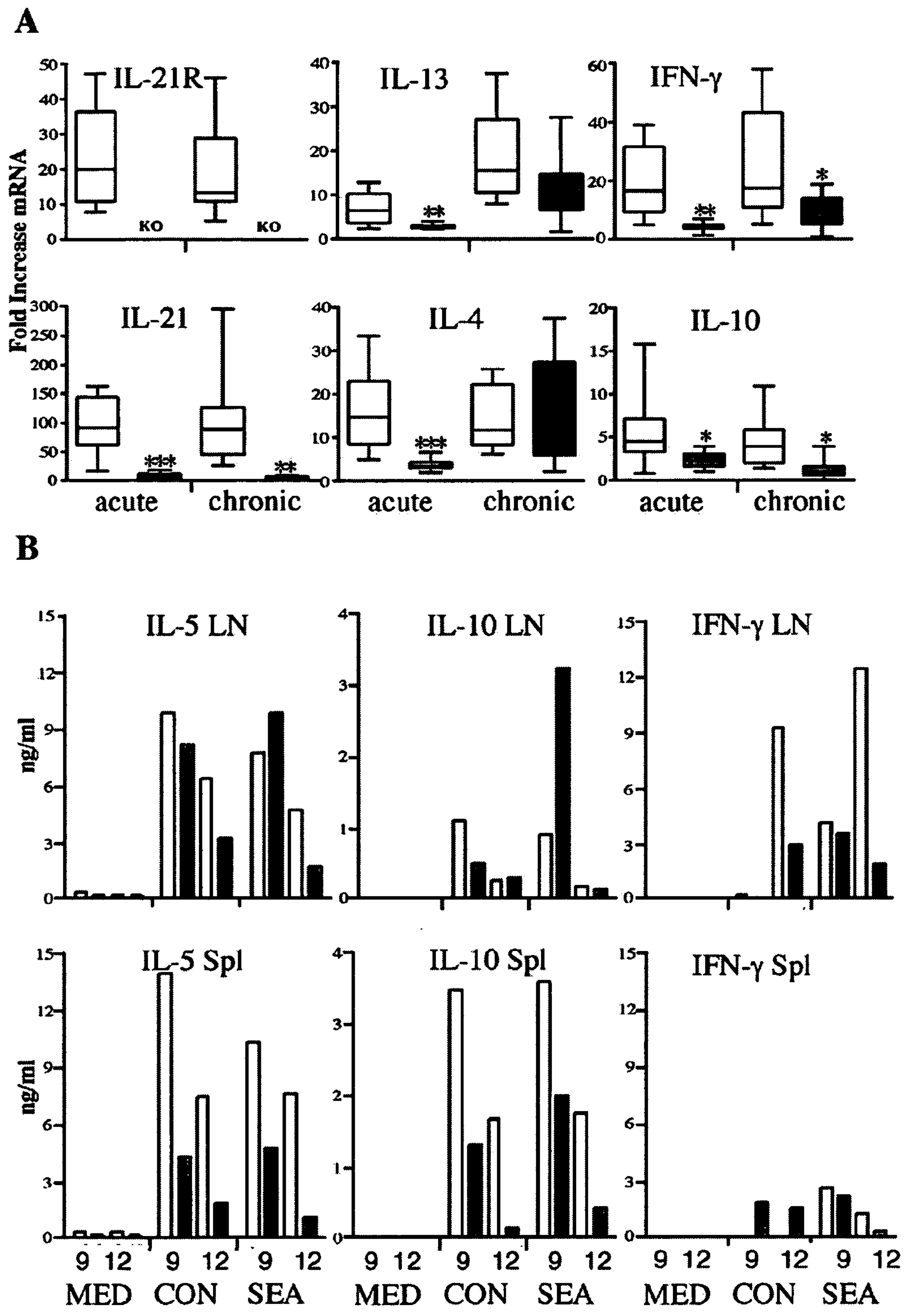

FIG. 20 shows that chronic liver disease following percutaneous *S. mansoni* infection is reduced in the absence of IL-21R. WT (open bars) and IL-21R$^{-/-}$ mice (filled bars) were infected with 25-30 *S. mansoni* cercariae. All animals were sacrificed at week 9 (acute) or week 12 (chronic) post-infection. (A) RNA was isolated from liver tissues and analyzed individually (N=8-10 per group/time point) by real-time RT-PCR as described above in the legend to FIG. 17. (B) Spleens (Spl) and mesenteric lymph nodes (LN) were pooled in groups of 2-4 mice and single cell suspensions were assayed for IL-5, IL-10, and IFN-γ. The data shown are the averages of three separate pooled groups. (C) Granuloma size (mm$^3$×10$^{-3}$) and the percentage of eosinophils in granulomas were evaluated microscopically in WT mice (mice per group: N=30 for week 9, N=17 for week 12) and IL-21R$^{-/-}$ mice (mice per group: N=27 for week 9, N=19 for week 12). (D) Real-time PCR analysis of Th2 inflammatory genes in granulomatous liver tissue (N=8-10 per group/time point). Data shown are the combined results of 3 separate experiments conducted on week 9 and two performed on week 12. The asterisks denote significant differences from wild-type values at the given time point, * p<0.05,  p<0.01, * p<0.001.

Figure 21:
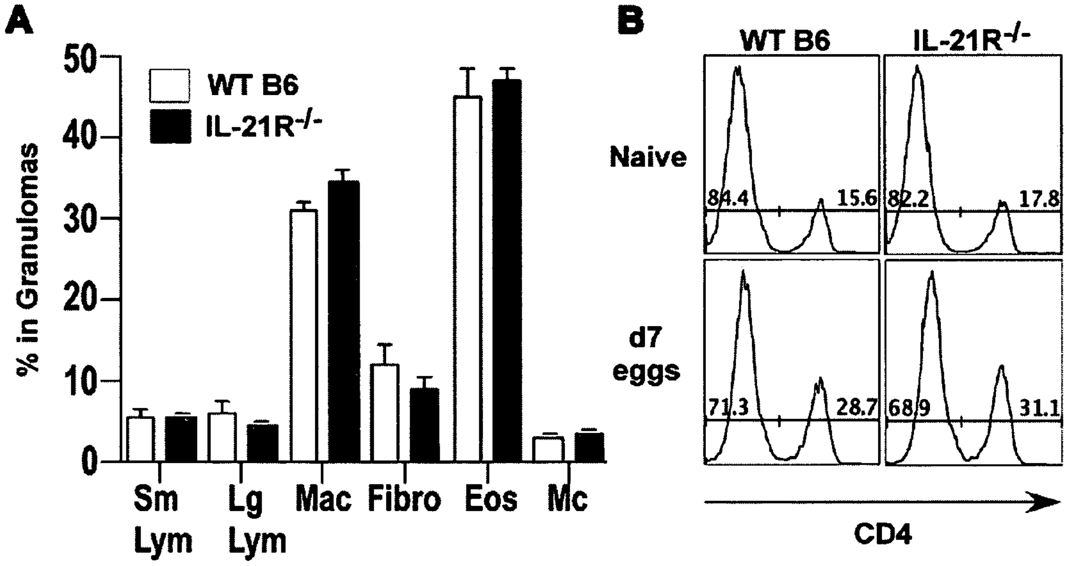

FIG. 21 shows that the cellular composition of granulomas is unchanged by IL-21R deficiency. (A) The cellular composition of granulomas was evaluated in the livers of 9 week infected WT (N=10) and IL-21R$^{-/-}$ (N=9) mice. The average±SEM of small lymphocytes (Sm Lym), large lymphocytes (Lg Lym), macrophages (Mac), Fibroblasts (Fibro), Eosinophils (Eos), and Mast Cells (Mc) are shown. (B) Lymphocytes were isolated from the perfused lungs of naïve WT and IL-21R$^{-/-}$ mice (top panels) and on day 7 following i.v. challenge with 5000 *S. mansoni* eggs (bottom panels). The numbers in the histograms indicate the percentages of CD4$^{-}$ and CD4$^{+}$ T cells among total lung lymphocytes.

Figure 22:
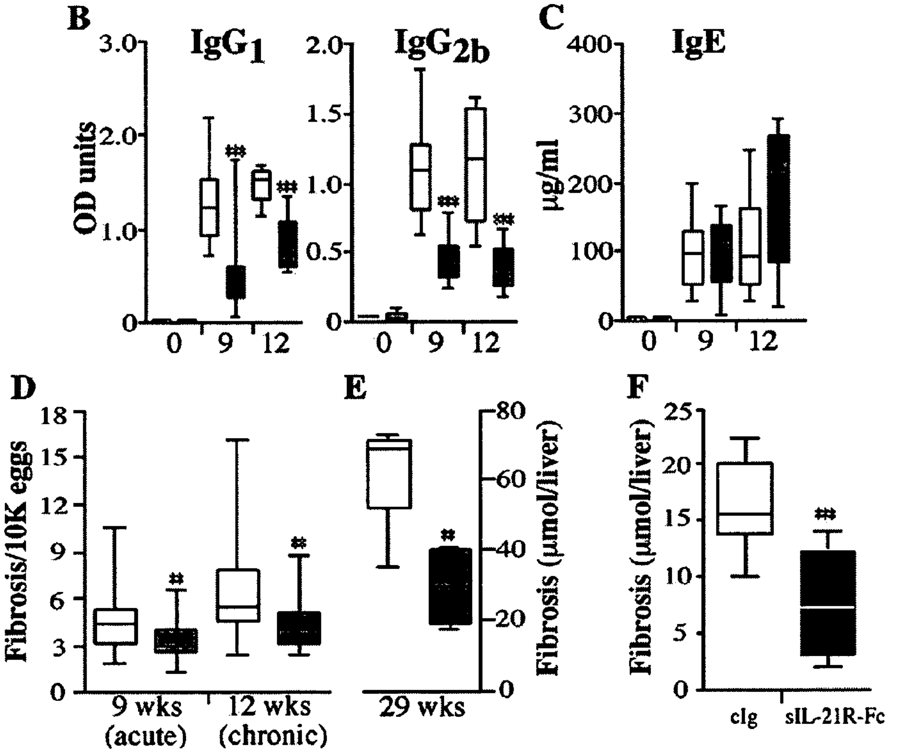

FIG. 22 shows that IL-21R-deficiency significantly slows the progression of $T_H2$ cytokine-dependent fibrosis. WT (open bars) and IL-21R$^{-/-}$ mice (filled bars) were infected with *S. mansoni* cercariae. Animals were sacrificed at 9 (acute), 12 (chronic) (panels A-D) or 29 weeks (late chronic) (panel E) post-infection. (A) The average worm pairs, total worms and eggs/worm pair in thousands±SE are shown for each group. No difference in infection intensity was noted in any experiment (n=number of mice). (B) Mice were bled at the time of sacrifice and SEA isotype-specific Ab titers were determined by ELISA. (C) Total serum IgE values in μg/ml. (D-F) Fibrosis was assessed by the amount of hydroxyproline in micromoles detected in the liver per 10,000 eggs (panel D) or in total liver (panels E and F). In panel F, infected WT C57BL/6 mice were treated with either an IgG2a control antibody (cIg—open bar) or with sIL-21R-Fc (filled bar) for 6 weeks. The asterisks denote significant differences from wild-type values at the given time point, * $p<0.05$,  $p<0.01$, * $p<0.001$.

Figure 23:
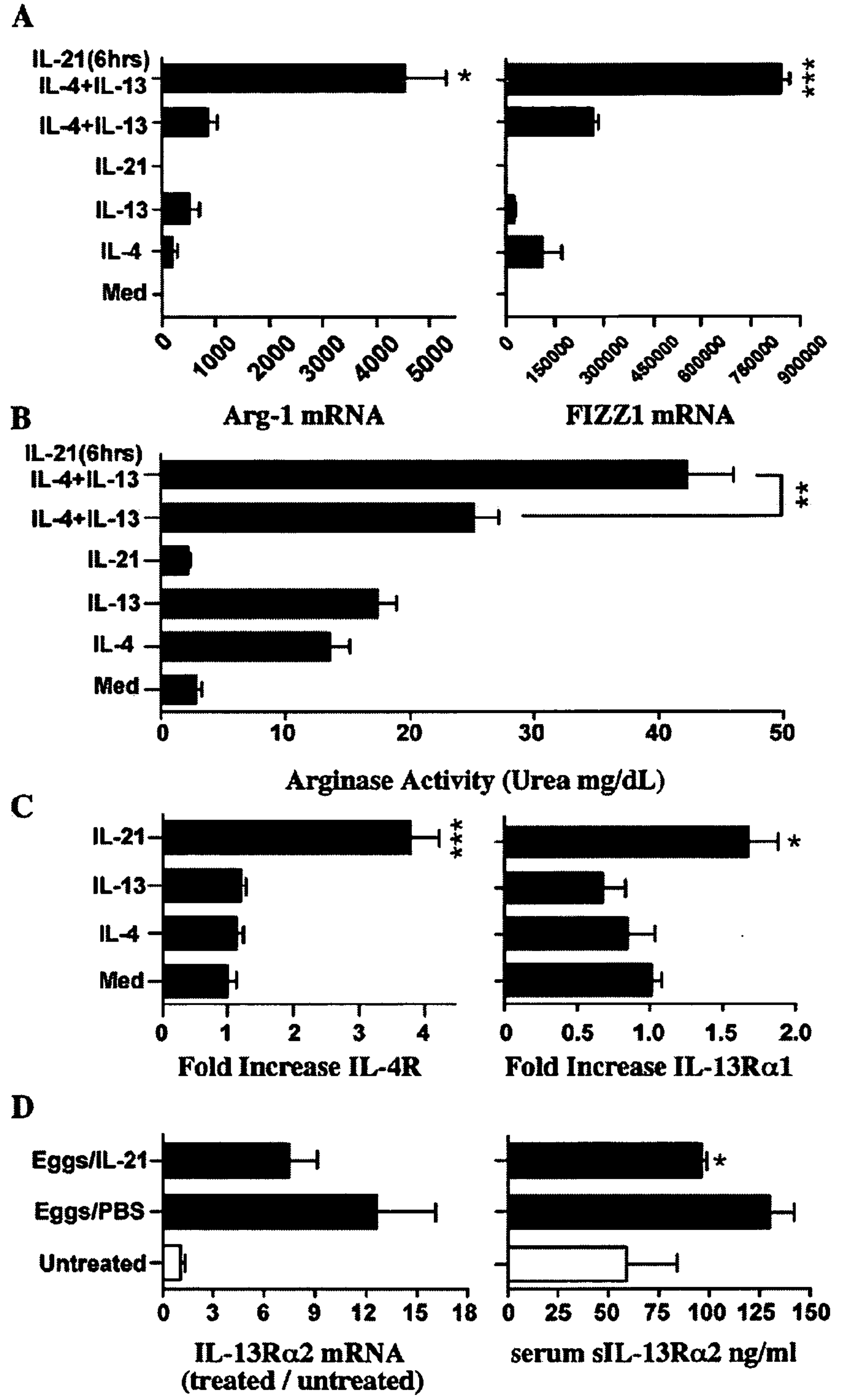

FIG. 23 shows that IL-21 signaling promotes alternative macrophage activation by modulating IL-13 receptor expression. Bone marrow-derived macrophages were treated with various combinations of IL-4 (20 ng/ml), IL-13 (20 ng/ml), and IL-21 (20 ng/ml) overnight. Macrophages treated with IL-4, IL-13, and IL-21 were pretreated with IL-21 for 6 hours prior to administration of IL-4 and IL-13. Cells were lysed 20 hr later and RNA was analyzed individually by real-time RT-PCR. (A) The ability of IL-21 to promote alternative macrophage activation was assessed by measuring Arg-1 and FIZZ1 gene expression. (B) Arginase activity was quantified in cell lysates by measuring the conversion of L-arginine to urea (mg/dL±SEM, triplicate measurements) (C) Expression of IL-4Rα and IL-13Rα1 mRNA was evaluated by real-time PCR. IL-13Rα2 mRNA was nearly undetectable in all conditions (not shown). The data shown in panels A, B, and C are representative of 3 separate experiments. (D) Naïve C57BL/6 mice were challenged intravenously with 5000 live *S. mansoni* eggs and treated with PBS or rIL-21 (2 μg/dose) every other day from day 1 through day 6. Animals (5 per group) were sacrificed on day 7 and lung IL-13Rα2 mRNA levels were assayed by real-time PCR and expressed as fold-increase over untreated controls (open bar). Mice were also bled at the time of sacrifice and the amount of sIL-13Rα2 in individual serum samples was assayed by ELISA. The asterisks denote significant differences, * $p<0.05$,  $p<0.01$, * $p<0.001$.

Figure 24:
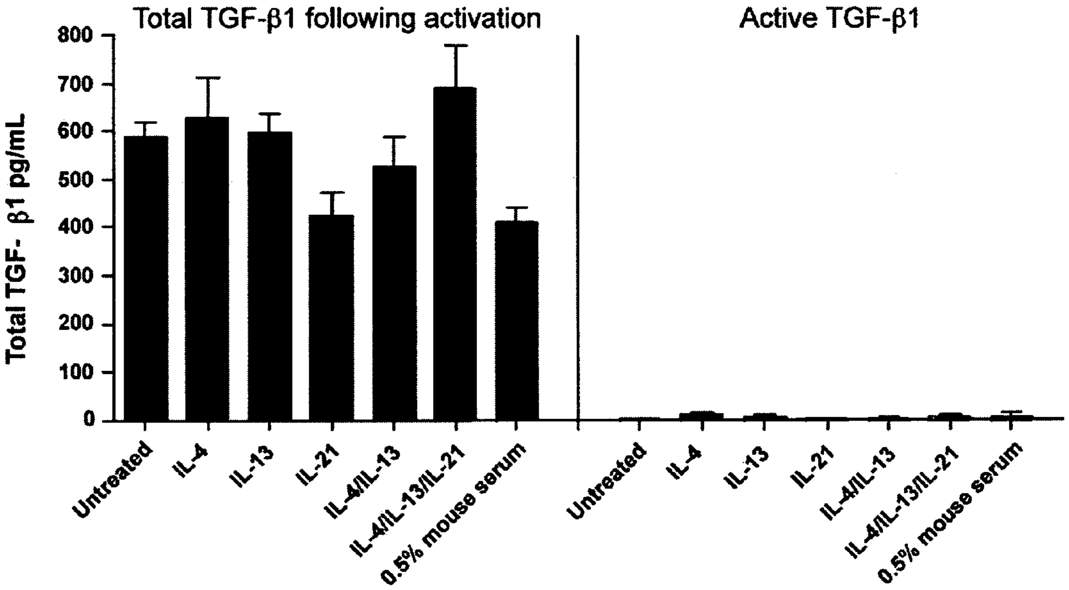

FIG. 24 shows that alternatively activated macrophages do not produce significant quantities of active TGF-β1. The right panel shows active TGF-β1 following macrophage activation, while the left panel shows total TGF-β1 levels following macrophage activation. Bone marrow-derived macrophages were treated with various combinations of IL-4 (20 ng/ml), IL-13 (20 ng/ml), and IL-21 (20 ng/ml) overnight. Macrophages treated with IL-4, IL-13, and IL-21 were pretreated with IL-21 for 6 hours prior to administration of IL-4 and IL-13. 20 hours post-activation, supernatants were assayed for total and active TGF-β1 by ELISA. High levels of total TGF-β1 were detected in all groups (e.g., compare left panel "IL-4" with "Untreated") except for cells treated with IL-21 alone (compare left panel "IL-21" with "Untreated"). Although total TGF-β1 expression was high, active TGF-β1 was minimal in all groups (right panel). The data shown are representative of 3 separate experiments producing similar results.

DETAILED DISCRIPTION OF THE INVENTION

To examine the role of the IL-21/IL-21R signaling pathway in the pathogenesis of fibrosis, immune responses were compared in mice lacking a functional IL-21R (IL-21R$^{-/-}$) and in wild type mice using various models of lung and liver inflammation. In one model, live schistosome eggs were injected intravenously into naïve or antigen-sensitized animals to study primary and secondary granulomatous inflammation in the lung. In another model, mice were infected percutaneously with *S. mansoni* cercariae and the development of egg-induced inflammation and fibrosis was observed in the liver. In another model, mice were infected with *N. brasiliensis*. Using these models, the influence of the IL-21R on type-2 cytokine-driven pathology in acute and chronic disease settings was studied. The results demonstrate an important role for the IL-21R in the generation of polarized type-2 responses in vivo, particularly in type-2 cytokine-mediated inflammation and fibrosis.

The present invention therefore provides methods for treating, ameliorating, or preventing fibrosis or fibrosis-associated disorders in a subject (e.g., a human, e.g., a human patient) using an agent(s) that reduces the level of IL-21 and/or IL-21R (e.g., the level of expression of IL-21 and/or IL-21R (e.g., the level of IL-21 and/or IL-21R gene products (i.e., protein and/or mRNA)), the level of activity of IL-21 and/or IL-21R, the level of interaction of IL-21 with IL-21R, etc.) relative to an untreated control (e.g., a control subject afflicted with fibrosis or a fibrosis-associated condition, a control subject not afflicted with fibrosis or a fibrosis-associated condition) or relative to an appropriate reference level. In relation to identifying an agent(s) that reduces the level of IL-21 and/or IL-21R, measuring "the level of IL-21 and/or IL-21R" includes, but is not limited to, (1) measuring the level of expression of IL-21 and/or IL-21R (e.g., measuring the level of IL-21 and/or IL-21R gene products (e.g., protein and/or its corresponding mRNA)); (2) measuring the level of activity of IL-21 and/or IL-21R; and (3) measuring the level of interaction of IL-21 with IL-21R (e.g., in a cell or sample of interest, e.g., from a subject (e.g., a human patient, a control subject)). As described in further detail herein, exemplary agents useful to treat, ameliorate, and/or prevent fibrosis or fibrosis-associated conditions or disorders include anti-IL-21R antibodies, antigen-binding fragments of anti-IL-21R antibodies, anti-IL-21 antibodies, antigen-binding fragments of anti-IL-21 antibodies, and soluble fragments of IL-21R polypeptides. The invention further provides methods for monitoring the course of treatment of fibrosis or a fibrosis-associated disorder, diagnosing and prognosing the same, and screening for compounds useful to treat fibrosis or a fibrosis-associated disorder.

As used herein, "IL-21" or "IL-21R" means any polypeptide that is substantially identical to the naturally occurring IL-21 or IL-21 receptor protein, respectively. The nucleotide and amino acid sequences encoding human interleukin-21 (IL-21) and its receptor (IL-21R) are described, for example, in WO 00/53761, WO 01/85792, Parrish-Novak et al. (2000) *Nature* 408:57-63, and Ozaki et al. (2000) *Proc. Natl. Acad. Sci. U.S.A.* 97:11439-44. Desirably, the IL-21 polypeptide binds IL-21R or the IL-21R polypeptide binds IL-21, and upon interaction there is an increase in the signaling activity of the IL-21/IL-21R pathway by at least 5%, 10%, 20%, 30%, 40%, 50%, 60%, 70%, 80%, 90%, or more than 100% above control levels, as measured by any standard method. IL-21R is also known as "MU-1," "NILR," and "zalpha11."

An agent that decreases the level of IL-21 and/or IL-21R encompasses any agent that decreases the signaling activity of the IL-21/IL-21R pathway, the level of activity of IL-21 and/or IL-21R, the level of expression of IL-21 and/or IL-21R, and/or the level of interaction of IL-21 and IL-21R by at least 5%, 10%, 20%, 30%, 40%, 50%, 60%, 70%, 80%, 90%, or 100%. Optionally, the decrease in levels of IL-21 and/or IL-21R is assessed by measuring the level of reduction in fibrosis. An agent that decreases the level of interaction of IL-21 with IL-21R encompasses any agent that decreases the interaction of IL-21 with IL-21R by at least 5%, 10%, 20%, 30%, 40%, 50%, 60%, 70%, 80%, 90%, or 100%. These aforementioned agents that decrease the level of activity or expression of IL-21 and/or IL-21R and/or decrease the level of interaction of IL-21 with IL-21R (i.e., agents that decrease the level of IL-21 and/or IL-21R) may be referred to herein as "antagonists" of IL-21 and/or IL-21R.

An "IL-21 gene" or "IL-21R gene" is defined as a nucleic acid that encodes an IL-21 or IL-21R polypeptide, respectively.

"Fibrosis" is defined as any pathological condition resulting from an overproduction or aberrant production of fibrous tissue. Fibrosis may occur in any organ including, for example, kidney, lung, liver, skin, central nervous system, bone, bone marrow, cardiovascular system, an endocrine organ or the gastrointestinal system. By "fibrosis-associated condition" is meant any condition that is related to fibrosis. Thus, fibrosis-associated conditions may be caused by, be concomitant with, or cause fibrosis.

Decreasing the level of activity of IL-21 and/or IL-21R may refer to a reduction in the level or biological activity of IL-21 relative to the level or biological activity of IL-21 and/or IL-21R in an untreated control or reference sample (e.g., a reference level). Such level or activity may be decreased by at least 10%, 20%, 30%, 40%, 50%, 60%, 70%, 80%, 90%, or 100%. A decrease in the activity of IL-21 and/or IL-21R may also be associated with a reduction in type-2 ("Th2") cytokine expression and/or function, which may include a modulation in, e.g., IL-4, IL-13, AMCase, Ym1, and Fizz1/RELMα-levels and activity.

Decreasing the level of interaction of IL-21 with IL-21R may refer to a decrease in the interaction in a treated cell or sample relative to the level of interaction of IL-21 with IL-21R in an untreated control or reference sample. Such level of interaction may be decreased by at least 10%, 20%, 30%, 40%, 50%, 60%, 70%, 80%, 90%, or 100%. The level of interaction may be assessed by several well-known molecular biology techniques, e.g., ELISA and Western blotting.

Decreasing the level IL-21 and/or IL-21R gene products refers to a decrease in the mRNA and/or protein expression level in a treated cell or sample relative to the gene or protein expression level of IL-21 and/or IL-21R in an untreated control or reference sample. Such expression may be decreased by at least 10%, 20%, 30%, 40%, 50%, 60%, 70%, 80%, 90%, or 100%. The level of expression may be assessed by a number of well-known molecular biology techniques, e.g., Northern blotting or Western blotting.

By "treating or ameliorating fibrosis" is meant decreasing the level of fibrosis relative to an untreated control, as measured by any standard method. A reduction in fibrosis may also be measured by a reduction in any symptom associated with fibrosis or a fibrosis-associated condition. The examples disclosed herein provide exemplary methods of determining whether the level of fibrosis is decreased relative to a control.

By "treating or ameliorating a fibrosis-associated condition (or disorder)" is meant decreasing such condition before or after it has occurred. As compared with an equivalent untreated control, such reduction or degree of prevention is at least 5%, 10%, 20%, 40%, 50%, 60%, 80%, 90%, 95%, or 100% as measured by any standard technique. A subject who is being treated for a fibrosis-associated condition is one who a medical practitioner has diagnosed as having such a condition. Diagnosis may be by any suitable means. A subject in whom the development of a fibrosis-associated condition is being prevented may or may not have received such a diagnosis. One in the art will understand that these subjects (e.g., patients) may have been subjected to standard tests for diagnosing fibrosis-associated conditions or may have been identified, without examination, as one at high risk due to the presence of one or more risk factors. The examples disclosed herein provide exemplary methods of determining whether the level of a fibrosis-associated disorder is decreased relative to a control.

"Preventing" refers to delaying the onset of a fibrosis or a fibrosis-associated condition, or prohibiting the onset of fibrosis or a fibrosis-associated condition in a subject likely to develop such a condition.

By "an effective amount" is meant an amount of a compound, alone or in a combination, required to treat, ameliorate, reduce or prevent fibrosis or a fibrosis-associated condition in a mammal. The effective amount of active compound(s) varies depending upon the route of administration, age, body weight, and general health of the subject. Ultimately, the attending physician or veterinarian will decide the appropriate amount and dosage regimen.

By "substantially identical," when referring to a protein or polypeptide, is meant a protein or polypeptide exhibiting at least 75%, but preferably 85%, more preferably 90%, most preferably 95%, or even 99% identity to a reference amino acid sequence, e.g., SEQ ID NO:2, SEQ ID NO:5, and fusion proteins such as those set forth in SEQ ID NOs:11, 13, 15, 17, 19, 21, 23, 25 and 27. For proteins or polypeptides, the length of comparison sequences will generally be at least 20 amino acids, preferably at least 30 amino acids, more preferably at least 40 amino acids, and most preferably 50 amino acids or the full-length protein or polypeptide. Nucleic acids that encode such "substantially identical" proteins or polypeptides constitute examples of "substantially identical" nucleic acids. It is recognized that, due to the redundancy of the genetic code, several nucleic acids may encode a given protein or polypeptide; such nucleic acids are within the scope of the invention if they encode a polypeptide that is "substantially identical" to a reference polypeptide.

The nucleic acids related to the present invention may comprise DNA or RNA and may be wholly or partially synthetic. Reference to a nucleotide sequence as set forth herein encompasses a DNA molecule with the specified sequence (or a complement thereof), and encompasses an RNA molecule with the specified sequence in which U is substituted for T, unless context requires otherwise.

The isolated polynucleotides related to the present invention may be used as hybridization probes and primers to identify and isolate nucleic acids having sequences identical to or similar to those encoding the disclosed polynucleotides. Hybridization methods for identifying and isolating nucleic acids include polymerase chain reaction (PCR), Southern hybridization, in situ hybridization and Northern hybridization, and are well known to those skilled in the art.

Hybridization reactions may be performed under conditions of different stringency. The stringency of a hybridization reaction includes the difficulty with which any two nucleic acid molecules will hybridize to one another. Preferably, each hybridizing polynucleotide hybridizes to its corresponding polynucleotide under reduced stringency conditions, more preferably stringent conditions, and most preferably highly stringent conditions. Examples of stringency conditions are shown in Table 1 below: highly stringent conditions are those that are at least as stringent as, for example, conditions A-F; stringent conditions are at least as stringent as, for example, conditions G-L; and reduced stringency conditions are at least as stringent as, for example, conditions M-R.

TABLE 1

Stringency Conditions

| Stringency Condition | Polynucleotide Hybrid | Hybrid Length (bp)[1] | Hybridization Temperature and Buffer[2] | Wash Temperature and Buffer[2] |
|---|---|---|---|---|
| A | DNA:DNA | >50 | 65° C.; 1xSSC -or-<br>42° C.; 1xSSC, 50% formamide | 65° C.; 0.3xSSC |
| B | DNA:DNA | <50 | $T_B$*; 1xSSC | $T_B$*; 1xSSC |
| C | DNA:RNA | >50 | 67° C.; 1xSSC -or-<br>45° C.; 1xSSC, 50% formamide | 67° C.; 0.3xSSC |
| D | DNA:RNA | <50 | $T_D$*; 1xSSC | $T_D$*; 1xSSC |
| E | RNA:RNA | >50 | 70° C.; 1xSSC -or-<br>50° C.; 1xSSC, 50% formamide | 70° C.; 0.3xSSC |
| F | RNA:RNA | <50 | $T_F$*; 1xSSC | $T_F$*; 1xSSC |
| G | DNA:DNA | >50 | 65° C.; 4xSSC -or-<br>42° C.; 4xSSC, 50% formamide | 65° C.; 1xSSC |
| H | DNA:DNA | <50 | $T_H$*; 4xSSC | $T_H$*; 4xSSC |
| I | DNA:RNA | >50 | 67° C.; 4xSSC -or-<br>45° C.; 4xSSC, 50% formamide | 67° C.; 1xSSC |
| J | DNA:RNA | <50 | $T_J$*; 4xSSC | $T_J$*; 4xSSC |
| K | RNA:RNA | >50 | 70° C.; 4xSSC -or-<br>50° C.; 4xSSC, 50% formamide | 67° C.; 1xSSC |
| L | RNA:RNA | <50 | $T_L$*; 2xSSC | $T_L$*; 2xSSC |
| M | DNA:DNA | >50 | 50° C.; 4xSSC -or-<br>40° C.; 6xSSC, 50% formamide | 50° C.; 2xSSC |
| N | DNA:DNA | <50 | $T_N$*; 6xSSC | $T_N$*; 6xSSC |
| O | DNA:RNA | >50 | 55° C.; 4xSSC -or-<br>42° C.; 6xSSC, 50% formamide | 55° C.; 2xSSC |
| P | DNA:RNA | <50 | $T_P$*; 6xSSC | $T_P$*; 6xSSC |
| Q | RNA:RNA | >50 | 60° C.; 4xSSC -or-<br>45° C.; 6xSSC, 50% formamide | 60° C.; 2xSSC |
| R | RNA:RNA | <50 | $T_R$*; 4xSSC | $T_R$*; 4xSSC |

[1]The hybrid length is that anticipated for the hybridized region(s) of the hybridizing polynucleotides. When hybridizing a polynucleotide to a target polynucleotide of unknown sequence, the hybrid length is assumed tobe that of the hybridizing polynucleotide. When polynucleotides of known sequence are hybridized, thehybrid length can be determined by aligning the sequences of the polynucleotides and identifying the region or regions of optimal sequence complementarity.

[2]SSPE (1xSSPE is 0.15M NaCl, 10 mM $NaH_2PO_4$, and 1.25 mM EDTA, pH 7.4) can be substituted for SSC (1xSSC is 0.15M NaCl and 15 mM sodium citrate) in the hybridization and wash buffers; washes are performed for 15 minutes after hybridization is complete.

$T_B$*–$T_R$*: The hybridization temperature for hybrids anticipated to be less than 50 base pairs in length should be 5–10° C. less than the melting temperature ($T_m$) of the hybrid, where $T_m$ is determined according to thefollowing equations. For hybrids less than 18 base pairs in length, $T_m$(° C.) = 2(# of A + T bases) + 4(# of G + C bases). For hybrids between 18 and 49 base pairs in length, $T_m$(° C.) = 81.5 + 16.6($\log_{10}Na^+$) + 0.41(% G + C) − (600/N), where N is the number of bases in the hybrid, and $Na^+$ is the concentration of sodium ions in the hybridization buffer ($Na^+$ for 1xSSC = 0.165M).

Additional examples of stringency conditions for polynucleotide hybridization are provided in Sambrook, J., E. F. Fritsch, and T. Maniatis, 1989, Molecular Cloning: A Laboratory Manual, Cold Spring HarborLaboratory Press, Cold Spring Harbor, NY, chapters 9 and 11, and Current Protocols in Molecular Biology, 1995, F. M. Ausubel et al., eds., John Wiley & Sons, Inc., sections 2.10 and 6.3–6.4, incorporated herein byreference.

The isolated polynucleotides related to the present invention may be used as hybridization probes and primers to identify and isolate DNA having sequences encoding allelic variants of the disclosed polynucleotides. Allelic variants are naturally occurring alternative forms of the disclosed polynucleotides that encode polypeptides that are identical to or have significant similarity to the polypeptides encoded by the disclosed polynucleotides. Preferably, allelic variants have at least 90% sequence identity (more preferably, at least 95% identity; most preferably, at least 99% identity) with the disclosed polynucleotides. Alternatively, significant similarity exists when the nucleic acid segments will hybridize under selective hybridization conditions (e.g., highly stringent hybridization conditions) to the disclosed polynucleotides.

The isolated polynucleotides related to the present invention may also be used as hybridization probes and primers to identify and isolate DNAs having sequences encoding polypeptides homologous to the disclosed polynucleotides. These homologs are polynucleotides and polypeptides isolated from a different species than that of the disclosed polypeptides and polynucleotides, or within the same species, but with significant sequence similarity to the disclosed polynucleotides and polypeptides. Preferably, polynucleotide homologs have at least 50% sequence identity (more preferably, at least 75% identity; most preferably, at least 90% identity) with the disclosed polynucleotides, whereas polypeptide homologs have at least 30% sequence identity (more preferably, at least 45% identity; most preferably, at least 60% identity) with the disclosed polypeptides. Preferably, homologs of the disclosed polynucleotides and polypeptides are those isolated from mammalian species.

Calculations of "homology" or "sequence identity" between two sequences are performed by means well known to those of skill in the art. For example, one general means for calculating sequence identity is described as follows. The sequences are aligned for optimal comparison purposes (e.g., gaps can be introduced in one or both of a first and a second amino acid or nucleic acid sequence for optimal alignment and nonhomologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent sequence identity between two sequences may be accomplished using a mathematical algorithm. In a preferred embodiment, the percent identity between two amino acid sequences is determined using the Needleman and Wunsch ((1970) *J. Mol. Biol.* 48:444-53) algorithm, which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. One preferred set of parameters is a Blossum 62 scoring matrix with a gap penalty of 12, a gap extend penalty of 4, and a frameshift gap penalty of 5. The percent identity between two amino acid or nucleotide sequences can also be determined using the algorithm of Meyers and Miller ((1989) *CABIOS* 4:11 -17), which has been incorporated into the ALIGN program (version 2.0), using a PAM120 weight residue table, a gap length penalty of 12 and a gap penalty of 4.

"Substantially pure" is defined as a nucleic acid, polypeptide, or other molecule that has been separated from the components that naturally accompany it, e.g., genetic material, associated proteins, membranes, and cell debris. Typically, a polypeptide is substantially pure if it is at least 60%, 70%, 80%, 90%, 95%, or even 99%, by weight, free from the proteins and naturally occurring organic molecules with which it naturally associates. For example, a substantially pure polypeptide may be obtained by extraction from a natural source, by expression of a recombinant nucleic acid in a cell that does not normally express that protein, or by chemical synthesis.

The term "isolated DNA" is defined as DNA that is relatively or substantially free of the genes and other DNA sequences that flank the DNA in the naturally occurring genome of the organism from which the given DNA is derived. Thus, the term "isolated DNA" encompasses, for example, cDNA, cloned genomic DNA, and synthetic DNA.

"IL-21 fusion" polypeptide or protein, or "IL-21R fusion" polypeptide or protein is defined as all or part of an IL-21 or IL-21R amino acid sequence, e.g., the IL-21R extracellular fragment from amino acids 1-235 of SEQ ID NO:2, linked to a second, heterologous amino acid sequence. In one embodiment, the second, heterologous amino acid sequence is a tag sequence. Common tag sequences include myc tags, his tags, flag tags, etc. In another embodiment of the invention, the second, heterologous amino acid sequence is an immunoglobulin sequence, e.g., an Fc fragment. Such fusion proteins and polypeptides, which are described in greater detail herein, are encoded by nucleic acid sequences referred to as "IL-21 fusion genes" or "IL-21R fusion genes."

In the screening methods a "compound" refers to a chemical, whether naturally occurring or artificially derived. Such compounds may include, for example, peptides, polypeptides, synthetic organic molecules, naturally occurring organic molecules, nucleic acid molecules, peptide nucleic acid molecules, and components and derivatives thereof. For example, a useful compound according to the present invention reduces binding of IL-21 to IL-21R.

Antagonists of IL-21 and IL-21R for use in treating, ameliorating, or preventing fibrosis or a fibrosis-associated condition may also consist of small molecules. The term "small molecule" refers to compounds that are not macromolecules (see, e.g., Karp (2000) *Bioinformatics Ontology* 16:269-85; Verkman (2004) *AJP-Cell Physiol.* 286:465-74). Thus, small molecules are often considered those compounds that are, e.g., less than one thousand daltons (e.g., Voet and Voet, Biochemistry, $2^{nd}$ ed., ed. N. Rose, Wiley and Sons, N.Y., 14 (1995)). For example, Davis et al. (2005) *Proc. Natl. Acad. Sci. USA* 102:5981-86, use the phrase small molecule to indicate folates, methotrexate, and neuropeptides, while Halpin and Harbury (2004) *PLos Biology* 2:1022-30, use the phrase to indicate small molecule gene products, e.g., DNAs, RNAs and peptides. Examples of natural and synthesized small molecules include, but are not limited to, cholesterols, neurotransmitters, siRNAs, and various chemicals listed in numerous commercially available small molecule databases, e.g., FCD (Fine Chemicals Database), SMID (Small Molecule Interaction Database), ChEBI (Chemical Entities of Biological Interest), and CSD (Cambridge Structural Database) (see, e.g., Alfarano et al. (2005) *Nuc. Acids Res. Database Issue* 33:D416-24).

The term "pharmaceutical composition" means any composition that contains at least one therapeutically or biologically active agent and is suitable for administration to a subject. Any of these formulations can be prepared by well-known and accepted methods of the art. See, for example, *Remington: The Science and Practice of Pharmacy,* $21^{st}$ Ed., (ed. A.R. Gennaro), Lippincott Williams & Wilkins, Baltimore, Md. (2005).

The present invention provides significant advantages over standard therapies for treatment and prevention of fibrosis-associated conditions. As described herein, administration of a therapeutic agent that reduces the level of activity or expression of IL-21 and/or IL-21R or decreases the interactions between IL-21 and IL-21R (i.e., reduces the level of IL-21 and/or IL-21R activity) results in amelioration, reduction or prevention of fibrosis and fibrosis-associated conditions. In addition, the compound screening methods, provided by this invention, allow one to identify novel therapeutics that modify the injury process, rather than merely mitigating the symptoms.

Fibrotic Disorders

The generation of granulation tissue is a carefully orchestrated process in which the expression of protease inhibitors and extracellular matrix proteins is upregulated and the expression of proteases is reduced, leading to the accumulation of extracellular matrix. Abnormal accumulation of fibrous materials, however, may ultimately lead to organ failure (e.g., Border et al. (1994) *New Engl. J. Med.* 331:1286-92). The development of fibrotic conditions, whether induced or spontaneous, is caused at least in part by the stimulation of fibroblast activity. The influx of inflammatory cells and activated fibroblasts into the injured organ depends on the ability of these cell types to interact with the interstitial matrix, which contains primarily collagens. Exemplary tissues that may be affected by fibrosis include the kidney, lung, liver, skin, central nervous system, bone, bone marrow, tissues of the cardiovascular system, endocrine organs, and tissues of the gastrointestinal system.

The methods and compositions of the present invention are useful for any fibrosis or fibrosis-associated condition affecting any tissue including, for example, fibrosis of an internal organ, a cutaneous or dermal fibrosing disorder, and fibrotic conditions of the eye. Fibrosis of internal organs (e.g., liver, lung, kidney, heart blood vessels, gastrointestinal tract) occurs in disorders such as pulmonary fibrosis, idiopathic fibrosis, autoimmune fibrosis, myelofibrosis, liver cirrhosis, veno-occlusive disease, mesangial proliferative glomerulonephritis, crescentic glomerulonephritis, diabetic nephropathy, renal interstitial fibrosis, renal fibrosis in subjects receiving cyclosporin, allograft rejection, HIV associated nephropathy. Other fibrosis-associated disorders include systemic sclerosis, eosinophilia-myalgia syndrome, and fibrosis-associated CNS disorders such as intraocular fibrosis. Dermal fibrosing disorders include, for example, scleroderma, morphea, keloids, hypertrophic scars, familial cutaneous collagenoma, and connective tissue nevi of the collagen type. Fibrotic conditions of the eye include conditions such as diabetic retinopathy, post-surgical scarring (for example, after glaucoma filtering surgery and after crossed-eyes (strabismus) surgery), and proliferative vitreoretinopathy. Additional fibrotic conditions that may be treated by the methods of the present invention may result, for example, from rheumatoid arthritis, diseases associated with prolonged joint pain and deteriorated joints; progressive systemic sclerosis, polymyositis, dermatomyositis, eosinophilic fascitis, morphea, Raynaud's syndrome, and nasal polyposis. As described herein, an IL-21/IL-21R pathway antagonist may be administered to treat or prevent fibrosis and fibrosis-associated disorders, or to ameliorate one or more of the symptoms associated with these disorders.

IL-21 or IL-21R Antagonists (IL-21/IL-21R Antagonists)

The IL-21 antagonists or IL-21R antagonists of the invention interact with IL-21 or IL-21R (e.g., mammalian IL-21 or IL-21R such as human, bovine, rat, mouse, horse, or dog), respectively, and reduce the level of IL-21 and/or IL-21R, e.g., reduce one or more biological activities associated with IL-21 and/or IL-21R. When this interaction involves direct binding, antagonists bind to IL-21 or IL-21R with high affinity (e.g., with an affinity constant of at least about $10^7$ $M^{-1}$, preferably about $10^8$ $M^{-1}$, and more preferably, about $10^9$ $M^{-1}$ to $10^{10}$ $M^{-1}$ or stronger).

The level of IL-21 and/or IL-21R is desirably reduced by 10%, 20%, 30%, 40%, 50%, 60%, 70%, 80%, 90%, or even 100%. An antagonist may, for example, reduce the activity of IL-21R by neutralizing IL-21. An antagonist may be a fusion protein that includes a fragment of an IL-21R fused to a non-IL-21R fragment such as an immunoglobulin Fc region, e.g., the fusion proteins set forth in SEQ ID NOs: 11, 13, 15, 17, 19, 21, 23, 25 and 27. Other exemplary antagonists are anti-IL-21R or anti-IL-21 antibodies or antigen-binding fragments thereof, soluble forms of IL-21R, peptides, inhibitory polynucleotides (e.g., siRNAs, SNPs, and aptamers) and small molecules.

In one embodiment, the IL-21/IL-21R antagonist is an anti-IL-21R or anti-IL-21 antibody, or an antigen-binding fragment thereof. In a further embodiment, the antibody is a neutralizing antibody. If desired, the antibody may be a monoclonal or single-specificity antibody that binds to IL-21 or IL-21R or an antigen-binding fragment thereof (e.g., an Fab, $F(ab')_2$, Fv or a single chain Fv fragment). The antibody may be human, humanized, chimeric, or in vitro-generated antibody to IL-21 or IL-21R polypeptide.

Alternatively, the IL-21 antagonist or IL-21R antagonist may be a full length (e.g., a mutated sequence) or a fragment of an IL-21 polypeptide or an IL-21R polypeptide (e.g., human). Exemplary antagonists include, for example, an inhibitory IL-21 receptor-binding domain of an IL-21 polypeptide (e.g., human) or the extracellular domain of murine or human IL-21R. The IL-21 antagonist may have an amino acid sequence that is substantially identical to (e.g., having at least 85%, 90%, 95%, 98%, 99% sequence identity with) the naturally occurring IL-21R (e.g., SEQ ID NO:2 (human) or SEQ ID NO:5 (murine)) or a fragment thereof (see Table 2). Alternatively, the antagonist may have an amino acid sequence encoded by a nucleotide sequence that is substantially identical to the naturally occurring mammalian IL-21R or a fragment thereof (e.g., SEQ ID NO: 1 (human) or SEQ ID NO:4 (murine)) or by a nucleotide sequence that hybridizes to one of the foregoing nucleotide sequences under stringent conditions, e.g., highly stringent conditions (see Table 1).

TABLE 2

Summary of Sequences

| Designation | Description |
|---|---|
| SEQ ID NO: 1 | Nucleic acid sequence of human IL-21R cDNA |
| SEQ ID NO: 2 | Amino acid sequence of human IL-21R |
| SEQ ID NO: 3 | Amino acid sequence of conserved WSXWS motif |
| SEQ ID NO: 4 | Nucleic acid sequence of mouse IL-21R cDNA |
| SEQ ID NO: 5 | Amino acid sequence of mouse IL-21R |
| SEQ ID NO: 6 | Amino acid sequence of Fc fragment |
| SEQ ID NO: 7 | Nucleic acid (cDNA) sequence of human IL-21 |
| SEQ ID NO: 8 | Amino acid sequence of human IL-21 |
| SEQ ID NO: 9 | Peptide signal sequence |
| SEQ ID NO: 10 | Nucleic acid (cDNA) sequences of human IL-21R monomer fused to a honeybee leader sequence and amino terminal $His_6$ and Flag tags |
| SEQ ID NO: 11 | Amino acid sequence of human IL-21R monomer (20–235) fused to a honeybee leader sequence and amino terminal $His_6$ and Flag tags |
| SEQ ID NO: 12 | Nucleic acid (cDNA) sequence of human IL-21R extracellular domain (1–235) fused to an IgG fragment |
| SEQ ID NO: 13 | Amino acid sequence of human IL-21R extracellular domain (1–235) fused to an IgG fragment |
| SEQ ID NO: 14 | Nucleic acid (cDNA) sequence of human IL-21R extracellular domain (1–235) fused to an IgG fragment and a $His_6$ tag |
| SEQ ID NO: 15 | Amino acid sequence of human IL-21R extracellular domain (1–235) fused to an IgG fragment and a $His_6$ tag |

TABLE 2-continued

| Summary of Sequences | |
|---|---|
| Designation | Description |
| SEQ ID NO: 16 | Nucleic acid (cDNA) sequence of human IL-21R extracellular domain (1–235) fused to an IgG fragment mutated at residues 254 and 257 |
| SEQ ID NO: 17 | Amino acid sequence of human IL-21R extracellular domain (1–235) fused to an IgG fragment mutated at residues 254 and 257 |
| SEQ ID NO: 18 | Nucleic acid (cDNA) sequence of human IL-21R monomer fused to a Rhodopsin tag |
| SEQ ID NO: 19 | Amino acid sequence of human IL-21R monomer (20–235) fused to a Rhodopsin tag |
| SEQ ID NO: 20 | Nucleic acid (cDNA) sequence of human IL-21R extracellular domain (1–235) fused to EK cleavage sites and an IgG1 fragment with a mutated Fc region |
| SEQ ID NO: 21 | Amino acid sequence of human IL-21R extracellular domain (1–235) fused to EK cleavage sites and an IgG1 fragment with a mutated Fc region |
| SEQ ID NO: 22 | Nucleic acid sequence of mouse IL-21R extracellular domain fused to a mouse genomic IgG2a fragment |
| SEQ ID NO: 23 | Amino acid sequence of mouse IL-21R extracellular domain fused to a mouse genomic IgG2a fragment |
| SEQ ID NO: 24 | Nucleic acid (genomic) sequence of mouse IL-21R extracellular domain fused to Flag and $His_6$ tags |
| SEQ ID NO: 25 | Amino acid sequence of mouse IL-21R extracellular domain fused to fused to Flag and $His_6$ tags |
| SEQ ID NO: 26 | Nucleic acid sequence of mouse IL-21R extracellular domain fused to a honeybee leader sequence and amino terminal Flag and $His_6$ tags |
| SEQ ID NO: 27 | Amino acid sequence of mouse IL-21R extracellular domain fused to a honeybee leader sequence and amino terminal Flag and $His_6$ tags |
| SEQ ID NO: 28 | Sense primer for mouse IL-21 |
| SEQ ID NO: 29 | Antisense primer for mouse IL-21 |
| SEQ ID NO: 30 | Sense primer for mouse IL-21R |
| SEQ ID NO: 31 | Antisense primer for mouse IL-21R |
| SEQ ID NO: 32 | Sense primer for mouse IFN-γ |
| SEQ ID NO: 33 | Antisense primer for mouse IFN-γ |
| SEQ ID NO: 34 | Peptide Linker (Ser-Gly-Gly-Gly-Gly)$_y$, wherein “y” is 1, 2, 3, 4, 5, 6, 7, or 8 |
| SEQ ID NO: 35 | Human IL-2 beta chain |

Optionally, the IL-21R polypeptide may be a soluble polypeptide incapable of membrane anchoring. Such soluble polypeptides include, for example, IL-21R polypeptides that lack a sufficient portion of their membrane spanning domain or are modified such that the membrane spanning domain is nonfunctional. For example, the IL-21R polypeptide may be a soluble fragment of an IL-21R (e.g., a fragment of an IL-21R containing the extracellular domain of murine or human IL-21R, including an amino acid sequence from about amino acids 1-235, 1-236, 20-235, or 20-236 of SEQ ID NO:2 (human), or from about amino acids 1-236, or 20-236 of SEQ ID NO:5 (murine)). Exemplary IL-21 antagonists may have an amino acid sequence that is substantially identical to amino acids 20-538 of SEQ ID NO:2 (mature human IL-21R), amino acids 1-235 of SEQ ID NO:2 (extracellular domain of human IL-21R), amino acids 1-236 of SEQ ID NO:2, amino acids 20-235 of SEQ ID NO:2, amino acids 20-236 of SEQ ID NO:2, amino acids 1-236 of SEQ ID NO:5, or amino acids 20-236 of SEQ ID NO:5.

An IL-21 antagonist of the invention may also be encoded by nucleic acids that hybridize to the nucleotide sequence set forth in SEQ ID NO: 1, SEQ ID NO:4, SEQ ID NO:10, SEQ ID NO:12, SEQ ID NO:14, SEQ ID NO: 16, SEQ ID NO: 18, SEQ ID NO:20, SEQ ID NO:22, SEQ ID NO:24, or SEQ ID NO:26, under highly stringent conditions, e.g., as set forth in Table 1. Isolated polynucleotides which encode IL-21R proteins or fusion proteins, but which differ from the nucleotide sequence set forth in SEQ ID NOs:1, 4, 10, 12, 14, 16, 18, 20, 22, 24, or 26, by virtue of the degeneracy of the genetic code, are also encompassed by the present invention. Variations in the nucleotide sequence as set forth in SEQ ID NOs:1, 4, 10, 12, 14, 16, 18, 20, 22, 24, or 26, which are caused by point mutations or by induced modifications, are also included in the invention.

If desired, a soluble IL-21R polypeptide may include, or be fused to, a second moiety such as a polypeptide (e.g., an immunoglobulin chain, a GST, Lex-A or MBP polypeptide sequence). For example, a fusion protein may include a fragment of an IL-21R polypeptide, which is capable of binding IL-21, such as a soluble fragment of an IL-21R (e.g., a fragment containing the extracellular domain of murine or human IL-21R such as amino acids 1-235, 1-236, 20-235 or 20-236 of SEQ ID NO:2 (human), or amino acids 1-236 or 20-236 of SEQ ID NO:5 (murine)) fused to a second moiety (e.g., an immunoglobulin chain, an Fc fragment, a heavy chain constant regions of various immunoglobulin isotypes, including IgG1, IgG2, IgG3, IgG4, IgM, IgA1, IgA2, IgD, and IgE).

Desirably, the IL-21 antagonist of the invention reduces at least one biological activity associated with the naturally occurring IL-21R, including, for example, the ability to interact with or bind to an IL-21 polypeptide, the ability to associate with signal transduction molecules such as γc or JAK1, the ability to stimulate phosphorylation and/or activation of stat proteins (e.g., Stat 5 and/or Stat 3), and the ability to modulate (e.g., stimulate or decrease) proliferation, differentiation, effector cell function, cytolytic activity, cytokine secretion, and/or survival of immune cells such as T cells (CD8+ and CD4+ T cells, including Th1 and Th2 cells), NK cells, B cells, macrophages, and megakaryocytes.

According to the present invention, an IL-21 polypeptide is a cytokine showing sequence homology to IL-2, IL-4 and IL-15 (Parrish-Novak et al. (2000) Nature 408:57-63). Despite low sequence homology among interleukin cytokines, cytokines share a common secondary motif, i.e., a "four-helix-bundle" structure that is representative of the family. IL-21 is expressed primarily in activated CD4+T cells, and has been reported to have effects on NK, B and T cells (Parrish-Novak et al. (2000) supra; Kasaian et al. (2002) Immunity 16:559-69). IL-21 binds to IL-21R (also referred to as "MU-1," "NILR," and "zalpha11"). Upon IL-21 binding, activation of IL-21R leads to Stat5 and/or Stat3 signaling (Ozaki et al. (2000) supra).

The amino acid sequences of IL-21 polypeptides are publicly known. For example, the nucleotide sequence and amino acid sequence of a human IL-21 is available at GenBank Acc. No. NM_021803. The disclosed human IL-21 nucleotide sequence is presented below:

```
                                                        (SEQ ID NO:7)
  1 gctgaagtga aaacgagacc aaggtctagc tctactgttg gtacttatga gatccagtcc

 61 tggcaacatg gagaggattg tcatctgtct gatggtcatc ttcttgggga cactggtcca

121 caaatcaagc tcccaaggtc aagatcgcca catgattaga atgcgtcaac ttatagatat

181 tgttgatcag ctgaaaaatt atgtgaatga cttggtccct gaatttctgc cagctccaga

241 agatgtagag acaaactgtg agtggtcagc tttttcctgc tttcagaagg cccaactaaa

301 gtcagcaaat acaggaaaca atgaaaggat aatcaatgta tcaattaaaa agctgaagag

361 gaaaccacct tccacaaatg cagggagaag acagaaacac agactaacat gcccttcatg

421 tgattcttat gagaaaaaac cacccaaaga attcctagaa agattcaaat cacttctcca

481 aaagatgatt catcagcatc tgtcctctag aacacacgga agtgaagatt cctgaggatc

541 taacttgcag ttggacacta tgttacatac tctaatatag tagtgaaagt catttctttg

601 tattccaagt ggaggag
```

The amino acid sequence of the disclosed human IL-21 polypeptide is presented below:

```
                                                        (SEQ ID NO:8)
MRSSPGNMERIVICLMVIFLGTLVHKSSSQGQDRHMIRMRQLIDIVDQLK

NYVNDLVPEFLPAPEDVETNCEWSAFSCFQKAQLKSANTGNNERIINVSI

KKLKRKPPSTNAGRRQKHRLTCPSCDSYEKKPPKEFLERFKSLLQKMIHQ

HLSSRTHGSEDS
```

Thus, an IL-21 polypeptide refers to a protein that is capable of interacting with or binding to IL-21R and having one of the following features: (i) an amino acid sequence substantially identical to a naturally occurring mammalian IL-21 or a fragment thereof (e.g., SEQ ID NO: 8 (human)); (ii) an amino acid sequence which is encoded by a nucleotide sequence that is substantially identical to a naturally occurring mammalian IL-21 nucleotide sequence or a fragment thereof (e.g., SEQ ID NO:7 (human) or a fragment thereof); (iii) an amino acid sequence encoded by a nucleotide sequence degenerate to a naturally occurring IL-21 nucleotide sequence or a fragment thereof, e.g., SEQ ID NO:7 (human) or a fragment thereof; or (iv) a nucleotide sequence that hybridizes to one of the foregoing nucleotide sequence sequences under stringent conditions.

In all foregoing aspects of the invention, the IL-21 or IL-21R polypeptides may be provided as a variant polypeptide having a mutation in the naturally occurring IL-21 or IL-21R sequence (wild type) that results in higher affinity (relative to the nonmutated sequence) binding to IL-21R or IL-21, respectively. Such mutations may be useful, for example, to increase resistance to proteolysis (relative to the nonmutated sequence). Some amino acid sequences in the disclosed sequences can be varied without significantly modifying IL-21 or IL-21R structure or function. In general, it is possible to replace residues that form IL-21 or IL-21R protein tertiary structure, provided that residues that perform a similar function are used. In other instances, the type of residue may be completely irrelevant if an alteration occurs in a noncritical area. Thus, the invention further includes IL-21 and IL-21R variants that show substantial IL-21-type biological activity. Such variants include deletions, insertions, inversions, repeats, and type substitutions (for example, substituting one hydrophilic residue for another, but not a strongly hydrophilic residue for a strongly hydrophobic residue). Small changes or "neutral" amino acid substitutions will often have little impact on protein function. (Taylor (1986) J. Theor. Biol. 119:205-18). Conservative substitutions may include, but are not limited to, replacements among the aliphatic amino acids, substitutions between amide residues, exchanges of basic residues, and replacements among the aromatic residues. Further guidance concerning which amino acid change is likely to be phenotypically silent (i.e., is unlikely to significantly affect function) can be found in Bowie et al. (1990) Science 247:1306-10 and Zvelebil et al. (1987) J. Mol. Biol. 195:957-61.

Optionally, the IL-21 or IL-21R antagonist is a fusion protein containing the IL-21 or IL-21R polypeptides or fragments thereof described herein fused to a second moiety such as an immunoglobulin chain, e.g., an Fc fragment, an epitope (tag) sequence, e.g., GST or myc, and additional well-known sequences such as Lex-A, or MBP polypeptide sequence. If desired, the fusion protein may include a fragment of an IL-21R polypeptide that is capable of binding IL-21, such as a soluble fragment of an IL-21R (e.g., a fragment of an IL-21R containing the extracellular domain of murine or human IL-21R from about amino acids 1-235, 1-236, 20-235, or 20-236 of SEQ ID NO:2 (human), or from about amino acids 1-236, or 20-236 of SEQ ID NO:5 (murine) or a fragment identical to, or substantially identical to, a polypeptide encoded by SEQ ID NOs: 1 or 4) fused to a second moiety (e.g., an immunoglobulin chain, an Fc fragment, a heavy chain constant region(s) of the various isotypes, including:

IgG1, IgG2, IgG3, IgG4, IgM, IgA1, IgA2, IgD, and IgE). Alternatively, the human Fc sequence has been mutated at one or more amino acids (e.g., mutated at residues 254 and 257 of SEQ ID NO: 16) in the naturally occurring sequence to reduce Fc receptor binding. In other embodiments, the fusion protein may include the extracellular domain of murine IL-21R (from about amino acids 1-236, or 20-235 of SEQ ID NO:5 (murine)) fused to a murine immunoglobulin Fc chain (including, but not limited to, murine IgG, e.g., murine IgG2a or a mutated form of murine IgG2a).

Examples of antagonistic fusion proteins that may be used in the methods of the invention are shown in FIGS. 7-15. The fusion protein may include an amino acid sequence substantially identical to SEQ ID NO:11, SEQ ID NO:13, SEQ ID NO:15, SEQ ID NO:17, SEQ ID NO:19, SEQ ID NO:21, SEQ ID NO:23, SEQ ID NO:25, or SEQ ID NO:27 or an amino acid sequence encoded by a nucleotide sequence that is substantially identical to SEQ ID NOs:10, 12, 14, 16, 18, 20, 22, 24, or 26. One exemplary fusion protein contains the human IL-21R extracellular domain (e.g., amino acids 1-235 of SEQ ID NO:2) fused at the C-terminus via a linker (corresponding to amino acids 236-243 of SEQ ID NO:17) to human immunoglobulin G1 (IgG1) Fc mutated sequence (corresponding to amino acids 244-467 of SEQ ID NO:17). The human Fc sequence has been mutated at residues 254 and 257 from the wild type sequence to reduce Fc receptor binding. The nucleotide and amino acid sequences are shown as SEQ ID NO:16 and SEQ ID NO:17, respectively.

The second polypeptide is preferably soluble. Optionally, the second polypeptide enhances the half-life, (e.g., the serum half-life) of the linked polypeptide. If desired, the second polypeptide includes a sequence that facilitates association of the fusion polypeptide with a second IL-21R or IL-21 polypeptide. The second polypeptide may include at least a region of an immunoglobulin polypeptide. Immunoglobulin fusions polypeptides are known in the art and are described in, e.g., U.S. Pat. Nos. 5,225,538; 5,428,130; 5,514,582; 5,714,147; and 5,455,165.

Optionally, the second polypeptide is a full-length immunoglobulin polypeptide or a fragment thereof (e.g., a heavy chain, light chain, Fab, $Fab_2$, Fv, or Fc).

In one example, the second polypeptide has less effector function that the effector function of an Fc region of a wild-type immunoglobulin heavy chain. Fc effector function includes for example, Fc receptor binding, complement fixation and T cell-depleting activity (see, for example, U.S. Pat. No. 6,136,310). Methods for assaying T cell-depleting activity, Fc effector function, and antibody stability are known in the art. In one embodiment, the second polypeptide has low or no affinity for the Fc receptor. In an alternative embodiment, the second polypeptide has low or no affinity for complement protein C1q.

A preferred second polypeptide sequence includes the amino acid sequence of SEQ ID NO:6. This sequence includes an Fc region. Underlined amino acids are those that differ from the amino acids found in the corresponding positions of the wild-type immunoglobulin sequence:

```
                                         (SEQ ID NO:6)
HTCPPCPAPEALGAPSVFLFPPKPKDTLMISRTPEVTCVVVDVSHEDPEV

KFNWYVDGVEVHNAKTKPREEQYNSTYRVVSVLTVLHQDWLNGKEYKCKV

SNKALPVPIEKTISKAKGQPREPQVYTLPPSREEMTKNQVSLTCLVKGFY

PSDIAVEWESNGQPENNYKTTPPVLDSDGSFFLYSKLTVDKSRWQQGNVF

SCSVMHEALHNHYTQKSLSLSPGK
```

Fusion proteins may additionally include a linker sequence(s) joining the first moiety to the second moiety. For example, the fusion protein may include a peptide linker of about 4 to 20 amino acids, more preferably 5 to 10 amino acids in length, and most preferably about 8 amino acids in length. The amino acids in the peptide linker may include, e.g., Gly, Ser, Asn, Thr and Ala. Thus, a peptide linker may consist of a Gly-Ser element. In other embodiments, the fusion protein includes a peptide linker having the formula $(Ser-Gly-Gly-Gly-Gly)_y$ (SEQ ID NO:34), wherein "y" is 1, 2, 3, 4, 5, 6, 7, or 8.

In other embodiments, additional amino acid sequences can be added to the N-or C-terminus of the fusion protein to facilitate expression, detection and/or isolation or purification. For example, an IL-21/IL-21R fusion protein may be linked to one or more additional moieties, e.g., GST (i.e., glutathione S-transferase), His, FLAG, or myc tags. For example, the fusion protein may additionally include a GST peptide in which the fusion protein sequences are fused to the C-terminus of the GST sequences. Such fusion proteins facilitate the purification or identification of the IL-21R/MU-1 fusion protein. In other embodiments, additional amino acid sequences may be added to the N— or C-terminus of the fusion protein to facilitate expression, steric flexibility, detection, and/or isolation or purification.

The fusion protein may also include a heterologous signal sequence at its N-terminus. For example, the native IL-21R signal sequence may be removed and replaced with a signal sequence from another protein. In certain host cells (e.g., mammalian host cells), expression and/or secretion of IL-21R may be increased using a heterologous signal sequence. A signal peptide that can be included in the fusion protein is MPLLLLLLLLPSPLHP (SEQ ID NO:9). If desired, one or more amino acids can additionally be inserted between the first polypeptide moiety comprising the IL-21R/MU-1 moiety and the second polypeptide moiety.

The IL-21/IL-21R antagonists described herein may be derivatized or linked to another functional molecule, e.g., another peptide or protein (e.g., an Fab' fragment). For example, the fusion protein or an antibody, or antigen-binding portion, can be functionally linked (e.g., by chemical coupling, genetic fusion, noncovalent association or otherwise) to one or more other molecular entities, such as an antibody (e.g., a bispecific or a multispecific antibody), toxins, radioisotopes, cytotoxic or cytostatic agents, among others.

A chimeric or fusion protein of the invention may be produced by standard recombinant DNA techniques. For example, DNA fragments coding for the different polypeptide sequences are ligated together in-frame in accordance with conventional techniques, e.g., by employing blunt-ended or sticky-ended termini for ligation, restriction enzyme digestion to create appropriate termini, filling-in of sticky ends as appropriate, alkaline phosphatase treatment to avoid undesirable ligation, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al., supra). Moreover, many expression vectors that encode a fusion moiety (e.g., an Fc region of an immunoglobulin heavy chain) are commercially available. An IL-21R/MU-1 or IL-21 encoding nucleic acid can be cloned into such an expression vector such that the fusion moiety is linked in-frame to the immunoglobulin protein. In some embodiments, IL-21R/MU-1 or IL-21 fusion polypeptides exist as oligomers, such as dimers or trimers. An IL-21R/MU-1 or IL-21 monomer, and/or nucleic acids encoding an IL-21RIMU-1 or IL-21, can be constructed using methods known in the art.

Production of Nucleic Acids

The isolated polynucleotides of the invention may be operably linked to an expression control sequence, such as the pMT2 or pED expression vectors disclosed in Kaufman et al. (1991) *Nuc. Acids Res.* 19:4485-90, in order to produce the IL-21R or IL-21 polypeptides (including fragments and fusions thereof) recombinantly. Many suitable expression control sequences are known in the art. General methods of expressing recombinant proteins are also known and are exemplified in Kaufinan (1990) *Meth. Enzym.* 185:537-66. As defined herein "operably linked" means enzymatically or chemically ligated to form a covalent bond between the isolated polynucleotide of the invention and the expression control sequence in such a way that the IL-21R or IL-21 polypeptide is expressed by a host cell that has been transformed (transfected) with the ligated polynucleotide/expression control sequence.

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., nonepisomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression constructs of the invention may carry additional sequences, such as regulatory sequences (i.e., sequences that regulate either vector replication, e.g., origins of replication, transcription of the nucleic acid sequence encoding the polypeptide (or peptide) of interest, or expression of the encoded polypeptide), tag sequences such as histidine, and selectable marker genes. The term "regulatory sequence" is intended to include promoters, enhancers and any other expression control elements (e.g., polyadenylation signals, transcription splice sites) that control transcription, replication or translation. Such regulatory sequences are described, for example, in Goeddel, *Gene Expression Technology: Methods in Enzymology*, Academic Press, San Diego, Calif. (1990). It will be appreciated by those skilled in the art that the design of the expression vector, including the selection of regulatory sequences, will depend on various factors, including choice of the host cell and the level of protein expression desired. Preferred regulatory sequences for expression of proteins in mammalian host cells include viral elements that direct high levels of protein expression, such as promoters and/or enhancers derived from the FF-1 a promoter and BGH poly A, cytomegalovirus (CMV) (e.g., the CMV promoter/enhancer), Simian virus 40 (SV40) (e.g., the SV40 promoter/enhancer), adenovirus (e.g., the adenovirus major late promoter (AdMLP)), and polyoma. Viral regulatory elements, and sequences thereof, are described in, e.g., U.S. Pat. Nos. 5,168,062; 4,510,245; and 4,968,615.

The recombinant expression vectors of the invention may carry additional sequences, such as sequences that regulate replication of the vector in host cells (e.g., origins of replication and terminator sequences) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance of the host cell transfected or transformed with the selectable marker to compounds such as G418 (geneticin), hygromycin or methotrexate. Preferred selectable marker genes include the dihydrofolate reductase (DHFR) gene (for use in dhf$^-$ host cells with methotrexate selection/amplification), the neo gene (for G418 selection), and genes conferring tetracycline and/or ampicillin resistance to bacteria.

Suitable vectors, containing appropriate regulatory sequences, including promoter sequences, terminator sequences, polyadenylation sequences, enhancer sequences, marker genes and other sequences as appropriate, may be either chosen or constructed. Inducible expression of proteins, achieved by using vectors with inducible promoter sequences, such as tetracycline-inducible vectors, e.g., pTet-On™ and pTet-Off™ (Clontech, Palo Alto, Calif.), may also be used in the disclosed method. For further details regarding expression vectors, see, for example, Sambrook et al., supra. Many known techniques and protocols for manipulation of nucleic acids, for example, in preparation of nucleic acid constructs, mutagenesis, sequencing, introduction of DNA into cells, gene expression, and analysis of proteins, are also described in detail in Sambrook et al., supra.

A number of types of cells may act as suitable host cells for expression of the IL-21R/MU-1 or IL-21 or fusion protein thereof. Any cell type capable of expressing functional IL-21R/MU-1 or IL-21 protein or fusion thereof may be used. Suitable mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK, C3HIOT1/2,Rat2, BaF3, 32D, FDCP-1, PC12, Mlx or C2C12 cells.

The IL-21R or IL-21 polypeptide or fusion protein thereof may also be produced by operably linking the isolated polynucleotide of the invention to suitable control sequences in one or more insect expression vectors, and employing an insect expression system. Materials and methods for baculovirus/Sf9 expression systems are commercially available in kit form (e.g., the MAXBAC® kit, Invitrogen, Carlsbad, Calif.). Soluble forms of the polypeptides described herein may also be produced in insect cells using appropriate isolated polynucleotides as described above.

Alternatively, the IL-21R or IL-21 polypeptide or fusion protein thereof may be produced in lower eukaryotes such as yeast, or in prokaryotes such as bacteria. Suitable yeast strains include *Saccharomyces cerevisiae, Schizosaccharomyces pombe, Kluyveromyces strains, Candida*, or any yeast strain capable of expressing heterologous proteins. Suitable bacterial strains include *Escherichia coli, Bacillus subtilis, Salmonella typhimurium*, or any bacterial strain capable of expressing heterologous proteins. Expression in bacteria may result in formation of inclusion bodies incorporating the recombinant protein. Thus, refolding of the recombinant protein may be required in order to produce active or more active material. Several methods for obtaining correctly folded heterologous proteins from bacterial inclusion bodies are known in the art. These methods generally involve solubilizing the protein from the inclusion bodies, then denaturing the protein completely using a chaotropic agent. When cysteine residues are present in the primary amino acid sequence of the protein, it is often necessary to accomplish the refolding in an environment that allows correct formation of disulfide bonds (a redox system). General methods of refolding are disclosed in Kohno (1990) *Meth. Enzym.* 185:187-95, EP 0433225, and U.S. Pat. No.5,399,677.

A protein of the invention (or a fragment or fusion thereof) may also be expressed as a product of transgenic animals, e.g., as a component of the milk of transgenic cows, goats, pigs, or sheep which are characterized by somatic or germ cells containing a polynucleotide sequence, e.g., encoding the IL-21R or IL-21 or fusion protein thereof. Accordingly, the protein may be prepared by growing a culture transformed host cells under culture conditions necessary to express the desired protein. The resulting expressed protein may then be purified from the culture medium or cell extracts. Soluble forms of the protein may be purified from conditioned media. Membrane-bound forms of IL-21R protein of the invention can be purified by preparing a total membrane fraction from the expressing cell and extracting the membranes with a nonionic detergent such as TRITON® X-100 (EMD Biosciences, San Diego, Calif.).

The polypeptides described herein may be purified using methods known to those skilled in the art. For example, the protein of the invention may be concentrated using a commercially available protein concentration filter, for example, by using an AMICON® or PELLICON® ultrafiltration unit (Millipore, Billerica, Mass.). Following the concentration step, the concentrate may be applied to a purification matrix such as a gel filtration medium. Alternatively, an anion exchange resin may be employed, for example, a matrix or substrate having pendant diethylaminoethyl (DEAE) or polyethyleneimine (PEI) groups. The matrices may be acrylamide, agarose, dextran, cellulose or other types commonly employed in protein purification. Alternatively, a cation exchange step may be employed. Suitable cation exchangers include various insoluble matrices comprising sulfopropyl or carboxymethyl groups. Sulfopropyl groups are preferred (e.g., S-SEPHAROSE® columns, Sigma-Aldrich, St. Louis, Mo.). The purification of the IL-21R/MU-1 protein or fusion protein from culture supernatant may also include one or more column steps over such affinity resins such as concanavalin A-agarose, AF-HEPARIN650, heparin-TOYOPEARL® or Cibacron blue 3GA SEPHAROSE® (Tosoh Biosciences, San Francisco, Calif.); or by hydrophobic interaction chromatography using such resins as phenyl ether, butyl ether, or propyl ether; or by immunoaffinity chromatography. Finally, one or more reverse-phase high performance liquid chromatography (RP-HPLC) steps employing hydrophobic RP-HPLC media, e.g., silica gel having pendant methyl or other aliphatic groups, can be employed to further purify the IL-21R/MU-1 or IL-21 protein. Affinity columns including antibodies to the protein of the invention may also be used in purification in accordance with known methods. Some or all of the foregoing purification steps, in various combinations or with other known methods, may also be employed to provide a substantially purified isolated recombinant protein. Preferably, the isolated protein is purified so that it is substantially free of other mammalian proteins.

Production of Antibodies

The IL-21 or IL-21R polypeptides of the invention may be used to immunize animals to obtain polyclonal and monoclonal antibodies that specifically react with the IL-21 or IL-21R and regulate the expression or activity of IL-21 and/or IL-21R, or regulate the level of interaction of IL-21 with IL-21R. Such antibodies may be obtained, for example, using the entire IL-21R or fragments thereof as immunogens. The peptide immunogens may additionally contain a cysteine residue at the carboxyl terminus and be conjugated to a hapten such as keyhole limpet hemocyanin (KLH). Additional peptide immunogens may be generated by replacing tyrosine residues with sulfated tyrosine residues. Methods for synthesizing such peptides are known in the art, for example, as in Merrifield (1963) *J. Amer. Chem. Soc.* 85: 2149-54 and Krstenansky and Mao (1987) *FEBS Lett.* 211:10-16.

Human monoclonal antibodies (mAbs) directed against IL-21 or IL-21R may be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., WO 91/00906, WO 91/10741, WO 92/03918, WO 92/03917, Lonberg et al. (1994) *Nature* 368:856-59, Green et al. (1994) *Nat. Genet.* 7:13-21, Morrison et al. (1994) *Proc. Natl. Acad. Sci. U.S.A.* 81:6851-55, and Tuaillon et al. (1993) *Proc. Natl. Acad. Sci. U.S.A.* 90:3720-24).

Monoclonal antibodies may also be generated by other methods known to those skilled in the art of recombinant DNA technology. One exemplary method, referred to as the "combinatorial antibody display" method, has been developed to identify and isolate antibody fragments having a particular antigen specificity, and can be utilized to produce monoclonal antibodies (for descriptions of combinatorial antibody display see, e.g., Sastry et al. (1989) *Proc. Natl. Acad. Sci. US.A.* 86:5728-32; Huse et al. (1989) Science 246:1275-81; and Orlandi et al. (1989) *Proc. Natl. Acad. Sci. US.A.* 86:3833-37). After immunizing an animal with an immunogen as described above, the antibody repertoire of the resulting B cell pool is cloned. The DNA sequence of the variable regions of a diverse population of immunoglobulin molecules may be obtained using a mixture of oligomer primers and PCR. For instance, mixed oligonucleotide primers corresponding to the 5' leader (signal peptide) sequences and/or framework 1 (FR1) sequences, as well as primer to a conserved 3' constant region primer may be used for PCR amplification of the heavy and light chain variable regions from a number of murine antibodies (Larrick et al. (1991) *BioTechniques* 11: 152-56). A similar strategy may also been used to amplify human heavy and light chain variable regions from human antibodies (Larrick et al. (1991) *Methods: Companion to Methods in Enzymology* 2:106-10).

Chimeric antibodies, including chimeric immunoglobulin chains, may also be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see PCT/US86/02269; EP 184,187; EP 171,496; EP 173,494; WO 86/01533; U.S. Pat. No. 4,816,567; EP 125,023; Better et al. (1988) *Science* 240:1041-43; Liu et al. (1987) *Proc. Natl. Acad. Sci. U.S.A.* 84:3439-43; Liu et al. (1987) *J. Immunol.* 139:3521-26; Sun et al. (1987) *Proc. Natl. Acad. Sci. US.A.* 84:214-18; Nishimura et al. (1987) *Canc. Res.* 47:999-1005; Wood et al. (1985) *Nature* 314:446-49; and Shaw et al. (1988) *J. Natl. Cancer Inst.* 80:1553-59).

If desired, an antibody or an immunoglobulin chain may be humanized by methods known in the art. Humanized antibodies, including humanized immunoglobulin chains, may be generated by replacing sequences of the Fv variable region that are not directly involved in antigen binding with equivalent sequences from human Fv variable regions. General methods for generating humanized antibodies are provided by Morrison (1985) *Science* 229:1202-07; Oi et al. (1986) *BioTechniques* 4:214-21; and U.S. Pat. Nos. 5,585,089, 5,693,761 and 5,693,762, all of which are hereby incorporated by reference in their entireties. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a predetermined target. The recombinant DNA encoding the humanized antibody, or fragment thereof, may then be cloned into an appropriate expression vector.

Humanized or CDR-grafted antibody molecules or immunoglobulins may be produced by CDR grafting or CDR substitution, wherein one, two, or all CDRs of an immunoglobulin chain can be replaced. See e.g., U.S. Pat. No. 5,225,539; Jones et al. (1986) *Nature* 321:552-25; Verhoeyan et al. (1988) *Science* 239:1534-36; and Beidler et al. (1988) *J. Immunol.* 141:4053-60, all of which are hereby incorporated by reference in their entireties. U.S. Pat. No. 5,225,539 describes a CDR-grafting method that may be used to prepare humanized antibodies of the present invention (see also, GB 2188638A). All of the CDRs of a particular human antibody may be replaced with at least a portion of a nonhuman CDR, or only some of the CDRs may be replaced with nonhuman CDRs. It is only necessary to replace the number of CDRs required for binding of the humanized antibody to a predetermined antigen.

Monoclonal, chimeric and humanized antibodies, which have been modified by, e.g., deleting, adding, or substituting other portions of the antibody, e.g., the constant region, are also within the scope of the invention. For example, an antibody may be modified as follows: (i) by deleting the constant region; (ii) by replacing the constant region with another constant region, e.g., a constant region meant to increase half-life, stability or affinity of the antibody, or a constant region from another species or antibody class; or (iii) by modifying one or more amino acids in the constant region to alter, for example, the number of glycosylation sites, effector cell function, Fc receptor (FcR) binding, complement fixation, among others.

Methods for altering an antibody constant region are known in the art. Antibodies with altered function (e.g., altered affinity for an effector ligand, such as FcR on a cell, or the C1 component of complement) may be produced by replacing at least one amino acid residue in the constant portion of the antibody with a different residue (see, e.g., EP 388,151 A1, U.S. Pat. Nos. 5,624,821 and 5,648,260, all of which are hereby incorporated by reference in their entireties). Similar types of alterations may also be applied to murine immunoglobulins and immunoglobulins from other species. For example, it is possible to alter the affinity of an Fc region of an antibody (e.g., an IgG, such as a human IgG) for an FcR (e.g., Fc gamma R1) or for C1q binding by replacing the specified residue(s) with a residue(s) having an appropriate functionality on its side chain, or by introducing a charged functional group, such as glutamate or aspartate, or perhaps an aromatic nonpolar residue such as phenylalanine, tyrosine, tryptophan or alanine (see, e.g., U.S. Pat. No. 5,624,821).

Human antibodies to IL-21 and/or IL-21R may additionally be produced using transgenic nonhuman animals that are modified so as to produce fully human antibodies rather than the animal's endogenous antibodies in response to challenge by an antigen. See, e.g., PCT publication WO 94/02602. The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. One embodiment of such a nonhuman animal is a mouse, and is termed the XENOMOUSE™ as disclosed in PCT publications WO 96/33735 and WO 96/34096. This animal produces B cells that secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv molecules.

Other protein-binding molecules may also be employed to modulate the activity of IL-21 and/or IL-21R. Such protein-binding molecules include small modular immunopharmaceutical (SMIP™) drugs (Trubion Pharmaceuticals, Seattle, Wash.). SMIPs are single-chain polypeptides composed of a binding domain for a cognate structure such as an antigen, a counterreceptor or the like, a hinge-region polypeptide having either one or no cysteine residues, and immunoglobulin CH2 and CH3 domains (see also www.trubion.com). SMIPs and their uses and applications are disclosed in, e.g., U.S. Published Patent Appln. Nos. 2003/0118592, 2003/0133939, 2004/0058445, 2005/0136049, 2005/0175614, 2005/0180970, 2005/0186216, 2005/0202012, 2005/0202023, 2005/0202028, 2005/0202534, and 2005/0238646, and related patent family members thereof, all of which are hereby incorporated by reference herein in their entireties.

As discussed herein, neutralizing or nonneutralizing antibodies (preferably monoclonal antibodies) binding to IL-21R or IL-21 or a fusion protein thereof may be useful in the treatment of immune conditions such as fibrosis and fibrosis-associated conditions.

Accordingly, the present invention further provides for compositions comprising an antibody that specifically reacts with an IL-21 or IL-21R or a fusion protein thereof.

Screening Assays

The IL-21R or IL-21 polypeptides or fusion proteins of the invention may also be used to screen for agents that are capable of binding to IL-21 or IL-21R, and regulating the level of IL-21 and/or IL-21R, e.g., the level of activity of IL-21 and/or IL-2 IR, the level of expression of IL-21 and/or IL-21R (e.g., the level of IL-21 and/or IL-21R gene products), and/or the level of interaction between IL-21 and IL-21R. Binding assays using a protein of the invention, or a binding partner thereof, which may be free or immobilized to a support, are well known in the art. Purified cell-based or protein-based (cell-free) screening assays may be used to identify binding partners and/or ligands (natural or synthetic, e.g., test compounds) to IL-21R or IL-21 polypeptides or fusion proteins of the invention. For example, IL-21R may be immobilized in purified form on a carrier and binding of potential ligands to IL-21R may be measured.

Methods for Diagnosing, Prognosing, and Monitoring the Progress of Fibrosis and Fibrosis-Associated Disorders, Related to IL-21

The present invention provides methods for diagnosing, prognosing, and monitoring the progress (e.g., monitoring the course of treatment) of disorders, i.e., fibrosis or fibrosis-associated conditions or disorders, related to IL-21 and/or IL-21R by, e.g., detecting and/or measuring the level of IL-21 and/or IL-21R, wherein the phrase "level of IL-21 and/or IL-21R" and equivalents thereof includes, but is not limited to, (1) the level of expression of IL-21 and/or IL-21R gene products (e.g., the level of IL-21 and/or IL-21R protein and/or mRNA in a cell or sample of interest); (2) the level of activity of IL-21 protein and/or IL-21R protein (e.g., Th2 cytokine expression and/or function in a cell or sample of interest); and (3) the level of interaction of IL-21 with IL-21R (e.g., in a cell or sample of interest). For example, the invention provides methods of diagnosing, prognosing and monitoring, e.g., by detecting the upregulation or downregulation of IL-21 and/or IL-21R gene products and/or activity, and/or by measuring the interaction of IL-21 with IL-21R, etc. (including but not limited to the use of such methods in human subjects). IL-21 and/or IL-21R levels may also be measured in a reference cell or sample of interest to produce or obtain a reference level of IL-21 and/or IL-21R, or such reference level may be obtained through other methods, or may be generally known, by one of skill in the art. These methods may be performed by, e.g., utilizing prepackaged diagnostic kits comprising at least one of the group comprising an IL-21 or IL-21R polynucleotide (or fragments thereof); an IL-21 or IL-21R polypeptide (or fragments and/or fusion proteins thereof); an antibody to an IL-21 or IL-21R polypeptide (or derivatives thereof, or antigen-binding fragments thereof); or modulators of IL-21 or IL-21R polynucleotides and/or polypeptides as described herein, which may be conveniently used, for example, in a clinical setting.

"Diagnostic" or "diagnosing" means identifying the presence or absence of a pathologic condition. Diagnostic methods include, but are not limited to, detecting upregulation of the level of IL-21 and/or IL-21R by determining a test amount of the gene products (e.g., RNA, cDNA, or polypeptide, including fragments thereof) of IL-21 and/or IL-21R, by measuring the activity of IL-21 and/or IL-21R, and/or by measuring the level of interaction of IL-21 with IL-21R, in a biological sample from a subject (human or nonhuman mammal), and comparing the test amount with, e.g., a normal amount or range (e.g., an amount or range from an individual(s) known not to suffer from disorders related to IL-21, or from an individual known not to suffer from fibrosis or a fibrosis-associated condition). Although a particular diagnostic method may not provide a definitive diagnosis of disorders related to IL-21, it suffices if the method provides a positive indication that aids in diagnosis.

The present invention also provides methods for prognosing such disorders by detecting, for example, the upregulation of levels of IL-21 and/or IL-21R, e.g., by detecting upregulation of IL-21 and/or IL-21R gene products and/or activity, and/or by measuring the level of interaction of IL-21 with IL-21R, etc. "Prognostic" or "prognosing" means predicting the probable development and/or severity of a pathologic condition. Prognostic methods include determining the test amount of a gene product of IL-21 and/or IL-21R in a biological sample from a subject, and comparing the test amount to a prognostic amount or range (i.e., an amount or range from individuals with varying severities of disorders, i.e., fibrosis and/or a fibrosis-associated condition, e.g., related to IL-21) for the level of IL-21 and/or IL-21R. Various amounts related to the level of IL-21 and/or IL-21R in a test sample are consistent with certain prognoses for disorders, e.g., fibrosis or fibrosis-associated conditions or disorders, related to IL-21 and/or IL-21R. The detection of an amount of IL-21 and/or IL-21R level at a particular prognostic level provides a prognosis for the subject.

The present invention also provides methods for monitoring the progress or course of such disorders related to IL-21 by detecting, for example, the upregulation of IL-21 and/or IL-21R levels, e.g., by detecting upregulation of IL-21 and/or IL-21R gene products, activity, and/or the interaction of IL-21 with IL-21R. Monitoring methods include determining the test amounts of a gene product of IL-21 in biological samples taken from a subject at a first and second time, and comparing the amounts. A change in amount of an IL-21 and/or IL-21R gene product between the first and second times indicates a change in the course of an IL-21 -related disorder, with a decrease in amount indicating remission of such disorders, and an increase in amount indicating progression of such disorders. Such monitoring assays are also useful for evaluating the efficacy of a particular therapeutic intervention in patients being treated for fibrosis or a fibrosis-associated disorder.

Measuring the Level of IL-21 and/or IL-21R

The level of IL-21 and/or IL-21R (e.g., the level of IL-21 and/or IL-21 gene products, activity, and/or interaction) in methods of the invention (e.g., methods for screening for and/or identifying a compound for treating, ameliorating, or preventing fibrosis or a fibrosis-associated condition, methods of diagnosing, prognosing, and/or monitoring the progress of fibrosis or a fibrosis-associated condition, and methods of treating, ameliorating, or preventing fibrosis or a fibrosis-associated condition) outlined herein may be measured in a variety of biological samples, including bodily fluids (e.g., whole blood, plasma, and urine), cells (e.g., whole cells, cell fractions, and cell extracts), and other tissues. Biological samples also include sections of tissue, such as biopsies and frozen sections taken for histological purposes. Preferred biological samples include blood, plasma, lymph, tissue biopsies, urine, CSF (cerebrospinal fluid), synovial fluid, and BAL (bronchoalveolar lavage). It will be appreciated that analysis of a biological sample need not necessarily require removal of cells or tissue from the subject. For example, appropriately labeled agents that bind IL-21 and/or IL-21R gene products (e.g., antibodies, nucleic acids) may be administered to a subject and visualized (when bound to the target) using standard imaging technology (e.g., CAT, NMR (MRI), and PET).

In the methods of treating, ameliorating, or preventing fibrosis or a fibrosis-associated disorder, in the methods for identifying a compound for treating, ameliorating or preventing fibrosis or a fibrosis-associated disorder in a subject, and in the diagnostic, prognostic, and monitoring assays and methods of the present invention, the level of IL-21 and/or IL-21R is detected and measured to yield a test amount. The test amount is then compared with, e.g., a normal amount or range. For example, an amount above (e.g., a higher level) the normal amount or range is a positive sign in the diagnosis of disorders related to IL-21.

Normal amounts or baseline levels of IL-21 and/or IL-21R may be determined for any particular sample type and population. Generally, baseline (normal) levels of IL-21 and/or IL-21R are determined by measuring respective levels of IL-21 and/or IL-21R in a biological sample type from normal (i.e., healthy) subjects. Alternatively, normal levels of IL-21 and/or IL-21R may be determined by measuring the amount in healthy cells or tissues taken from the same subject from which the diseased (or possibly diseased) test cells or tissues were taken. The level of IL-21 and/or IL-21R (either the normal amount or the test amount) may be determined or expressed on a per cell, per total protein, or per volume basis. To determine the cell amount of a sample, one can measure the level of a constitutively expressed gene product or other gene product expressed at known levels in cells of the type from which the biological sample was taken.

It will be appreciated that the assay methods of the present invention do not necessarily require measurement of absolute values for the level of IL-21 and/or IL-21R because relative values are sufficient for many applications of these methods. It will also be appreciated that in addition to the quantity or abundance of IL-21 and/or IL-21R levels, variant or abnormal IL-21 and/or IL-21R levels or their expression patterns (e.g., mutated transcripts, truncated polypeptides) may be identified by comparison to normal levels and expression patterns.

Whether the level of a particular gene or protein in two samples is increased (i.e., higher) or reduced (i.e., lower), e.g., significantly above or significantly below a given level, respectively, depends on the gene itself and, inter alia, its variability in expression, activity, and/or interaction with a ligand between different individuals or different samples. It is within the skill in the art to determine whether IL-21 and/or IL-21R levels are significantly similar or different among samples. Factors such as genetic variation between individuals, species, organs, tissues, or cells may be taken into consideration (when and where necessary) for determining whether the level of IL-21 and/or IL-21R between two samples is increased or reduced. As a result of the natural heterogeneity in IL-21 and/or IL-21R levels between individuals, species, organs, tissues, or cells, phrases such as "significantly above" or "significantly below" cannot be defined as a precise percentage or value, but rather can be ascertained by one skilled in the art upon practicing the invention. Particular methods of detection and measurement of IL-21 and/or IL-21R gene products, activity, and interaction are described herein.

Assays for Measuring IL-21 and/or IL-21R Gene Products

The methods of the present invention involve detecting and quantifying the level of IL-21 and/or IL-21R, e.g., the level of the gene products of IL-21 and/or IL-21R, the level of activity of IL-21 and/or IL-21R, and/or the level of interaction of IL-21 with IL-21R, in biological samples. IL-21 and IL-21R gene products include mRNAs and polypeptides, and both can be measured using methods well known to those skilled in the art.

For example, mRNA can be directly detected and quantified using hybridization-based assays, such as Northern hybridization, in situ hybridization, dot and slot blots, and oligonucleotide arrays. Hybridization-based assays refer to assays in which a probe nucleic acid is hybridized to a target nucleic acid. In some formats, the target, the probe, or both are immobilized. The immobilized nucleic acid may be DNA, RNA, or another oligonucleotide or polynucleotide, and may comprise naturally or nonnaturally occurring nucleotides, nucleotide analogs, or backbones. Methods of selecting nucleic acid probe sequences for use in the present invention (e.g., based on the nucleic acid sequence of IL-21) are well known in the art.

Alternatively, MRNA may be amplified before detection and quantitation. Such amplification-based assays are well known in the art and include polymerase chain reaction (PCR), reverse-transcription-PCR (RT-PCR), PCR-enzyme-linked inimunosorbent assay (PCR-ELISA), and ligase chain reaction (LCR). Primers and probes for producing and detecting amplified IL-21 gene products (e.g., mRNA or cDNA) may be readily designed and produced without undue experimentation by those of skill in the art based on the nucleic acid sequences of IL-21 and/or IL-21R. Amplified IL-21 and/or IL-21R gene products may be directly analyzed, for example, by gel electrophoresis; by hybridization to a probe nucleic acid; by sequencing; by detection of a fluorescent, phosphorescent, or radioactive signal; or by any of a variety of well-known methods. In addition, methods are known to those of skill in the art for increasing the signal produced by amplification of target nucleic acid sequences. One of skill in the art will recognize that, whichever amplification method is used, a variety of quantitative methods known in the art (e.g., quantitative PCR) may be used if quantitation of gene products is desired.

An IL-21 and/or IL-21R polypeptide (or fragments thereof) may be detected using various well-known immunological assays employing the respective anti-IL-21 and/or IL-21R antibodies that may be generated as described herein. Immunological assays refer to assays that utilize an antibody (e.g., polyclonal, monoclonal, chimeric, humanized, scFv, and/or fragments thereof) that specifically binds to, e.g., an IL-21 polypeptide (or a fragment thereof). Such well-known immunological assays suitable for the practice of the present invention include ELISA, radioimmunoassay (RIA), immunoprecipitation, immunofluorescence, fluorescence-activated cell sorting (FACS), and Western blotting. The ordinarily skilled artisan will also recognize that an IL-21 polypeptide may also be detected using a labeled IL-21R polypeptide(s). One of skill in the art will understand that the aforementioned methods may be applied to disorders related to IL-21, especially fibrosis or a fibrosis-associated condition.

Assays for Measuring the Activity of IL-21 and/or IL-21R

The activity of IL-21/IL-21R (e.g., in response to IL-21/IL-21R antagonists as modulators of cytokine production and cell proliferation/differentiation) can be tested using any one of a number of routine factor-dependent cell proliferation assays for cell lines including, without limitation, 32D, DA2, DAIG, T10, B9, B9/11, BaF3, MC9/G, M+(preB M+), 2E8, RB5, DA1, 123, Ti 165, HT2, CTLL2, TF-1, Mo7e and CMK.

Assays for T cell or thymocyte proliferation are described, for example, in *Current Protocols in Immunology*, Coligan et al. (eds.) Greene Pub. Assoc. & Wiley-Interscience, NY, N.Y. (1991) (Chapter 3, "In Vitro assays for Mouse Lymphocyte Function" and Chapter 7, "Immunologic studies in Humans"); Takai et al. (1986) *J. Immunol.* 137:3494-500; Bertagnolli et al. (1990) *J. Immunol.* 145:1706-12; Bertagnolli et al. (1991) *Cell. Immunol.* 133:32741; Bertagnolli et al. (1992) *J. Immunol.* 149:3778-83; Bowman et al. (1994) *J. Immunol.* 152:1756-61. Assays for cytokine production and/or proliferation of spleen cells, lymph node cells or thymocytes are described, for example, in "Polyclonal T cell stimulation" Kruisbeek and Shevach in *Current Protocols in Immunology*, Vol. 1 Coligan et al. (eds.) pp.3.12.1-14, John Wiley and Sons, Toronto (1994); and "Measurement of mouse and human Interferon gamma" Schreiber, R. D. in *Current Protocols in Immunology*, Vol. 1 Coligan et al. (eds.) pp. 6.8.1-8, John Wiley and Sons, Toronto (1994).

Assays for proliferation and differentiation of hematopoietic and lymphopoietic cells are described in, for example, "Measurement of Human and Murine Interleukin 2 and Interleukin 4" Bottomly et al. in *Current Protocols in Immunology*, Vol. 1 Coligan et al. (eds.) pp. 6.3.1-12, John Wiley and Sons, Toronto (1991); deVries et al. (1991) *J. Exp. Med.* 173:1205-11; Moreau et al. (1988) *Nature* 336:690-92; Greenberger et al. (1983) *Proc. Natl. Acad. Sci. USA.* 80:2931-38; "Measurement of mouse and human interleukin 6" Nordan, R. in *Current Protocols in Immunology*, Vol. 1

Coligan et al. (eds.) pp. 6.6.1-5, John Wiley and Sons, Toronto (1991); Smith et al. (1986) *Proc. Natl. Acad. Sci. US.A.* 83:1857-61; "Measurement of human Interleukin 11" Bennett et al. in *Current Protocols in Immunology*, Vol. 1 Coligan et al. (eds.) p. 6.15.1, John Wiley and Sons, Toronto (1991); "Measurement of mouse and human Interleukin 9" Ciarletta et al. in *Current Protocols in Immunology*, Vol. 1. Coligan et al. (eds.) p. 6.13.1, John Wiley and Sons, Toronto (1991).

Assays for T cell clone responses to antigens (which will identify, among others, proteins that affect APC-T cell interactions as well as direct T cell effects by measuring proliferation and cytokine production) include, for example, those described in: *Current Protocols in Immunology*, Coligan et al. (eds.) Greene Pub. Assoc. and Wiley-Interscience, NY, N.Y. (1 991) (Chapter 3, "In Vitro assays for Mouse Lymphocyte Function"; Chapter 6, "Cytokines and their cellular receptors"; Chapter 7, "Immunologic studies in Humans"); Weinberger et al. (1980) *Proc. Natl. Acad. Sci. U.S.A.* 77:6091-95; Weinberger et al. (1981) *Eur. J. Immunol.* 11:405-11; Takai et al. (1986) *J. Immunol.* 137:3494-500; Takai et al. (1988) *J. Immunol.* 140:508-12.

Assays for Measuring the Interaction of IL-21 with IL-21R

Methods for detecting and/or measuring the level of interaction of IL-21 with IL-21R are well known in the art. For example, such interactions between a cytokine and its receptor may be detected and/or measured with, but not limited to, such techniques as ELISA, Western blotting, immunoprecipitation, Biacore analysis, etc.

Pharmaceutical Compositions

In one aspect, the invention features a method of treating, ameliorating, or preventing an IL-21 -related disorder, i.e., fibrosis or a fibrosis-associated condition. The method may comprise contacting a population of cells with (e.g., by administering to a subject suffering from or at risk for fibrosis or a fibrosis-associated disorder) an agent that reduces the level of IL 21 and/or IL 21R activity in the subject, e.g., an IL-21/IL-21R antagonist (e.g., an anti-IL-21R antibody, an anti-IL-21 antibody, an antigen-binding fragment of an anti-IL-21R antibody, an antigen-binding fragment of an anti-IL-21 antibody, and a soluble fragment of an IL-21R (e.g., an amino acid sequence that is at least 90% identical to an amino acid sequence selected from the group consisting of amino acids 1-538 of SEQ ID NO:2, amino acids 20-538 of SEQ ID NO:2, amino acids 1-235 of SEQ ID NO:2, amino acids 20-235 of SEQ ID NO:2, amino acids 1-236 of SEQ ID NO: 2, amino acids 20-236 of SEQ ID NO:2, amino acids 1-529 of SEQ ID NO:5, amino acids 20-529 of SEQ ID NO:5, amino acids 1-236 of SEQ ID NO:5, and amino acid 20-236 of SEQ ID NO:5)) in an amount sufficient to inhibit the activity of IL-21 in the cell or population.

IL-21/IL-21R antagonists for treating fibrosis or a fibrosis-associated condition may be used as a pharmaceutical composition when combined with a pharmaceutically acceptable carrier. Such a composition may contain, in addition to the IL-21 /IL-2 IR-antagonists and carrier, various diluents, fillers, salts, buffers, stabilizers, solubilizers, and other materials well known in the art. The term "pharmaceutically acceptable" means a nontoxic material that does not interfere with the effectiveness of the biological activity of the active ingredient(s). The characteristics of the carrier will depend on the route of administration, and are generally well known in the art.

The pharmaceutical composition of the invention may be in the form of a liposome in which an IL-21/IL-21R-antagonist(s) is combined with, in addition to other pharmaceutically acceptable carriers, amphipathic agents such as lipids which exist in aggregated form as micelles, insoluble monolayers, liquid crystals, or lamellar layers which exist in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, e.g., in U.S. Pat. Nos. 4,235,871,4,501,728, 4,837,028, and 4,737,323, all of which are incorporated herein by reference in their entireties.

As used herein, the term "therapeutically effective amount" means the total amount of each active component of the pharmaceutical composition or method that is sufficient to show a meaningful subject benefit, e.g., amelioration or reduction of symptoms of, prevention of, healing of, or increase in rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of an IL-21/IL-21R antagonist is administered to a subject, e.g., a mammal (e.g., a human). An IL-21/IL-21R antagonist(s) may be administered in accordance with the method of the invention either alone or in combination with other therapies as described in more detail herein. When coadministered with one or more agents, an IL-21 and/or IL-21R antagonist may be administered either simultaneously with the second agent, or sequentially. If administered sequentially, the attending physician will decide on the appropriate sequence of administering an IL-21/IL-21R antagonist in combination with other agents.

Administration of an IL-21/IL-21R antagonist used in a pharmaceutical composition of the present invention or to practice a method of the present invention may be carried out in a variety of conventional ways, such as oral ingestion, inhalation, or cutaneous, subcutaneous, or intravenous injection. Intravenous administration to the subject is sometimes preferred. When a therapeutically effective amount of an IL-21/IL-21R agonist or antagonist is administered orally, the binding agent will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% binding agent, and preferably from about 25 to 90% binding agent. When administered in liquid form, a liquid carrier such as water, petroleum, oils of animal or plant origin such as peanut oil (albeit keeping in mind the frequency of peanut allergies in the population), mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of the binding agent, and preferably from about 1 to 50% of the binding agent.

When a therapeutically effective amount of an IL-21/IL-21R antagonist is administered by intravenous, cutaneous or subcutaneous injection, the binding agent will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to a binding agent, an isotonic vehicle such as sodium chloride injection, Ringer's injection, dextrose injection, dextrose and sodium chloride injection, lactated Ringer's injection, or other vehicle as known in the art. The pharmaceutical composition of the present invention may also contain stabilizers, preservatives, buffers, antioxidants, or other additive known to those of skill in the art.

The amount of an IL-21/IL-21R antagonist in the pharmaceutical composition of the present invention will depend upon the nature and severity of the condition being treated, and on the nature of prior treatments that the subject has undergone. Ultimately, the attending physician will decide the amount of binding agent with which to treat each individual subject. Initially, the attending physician will administer low doses of binding agent and observe the subject's response. Larger doses of binding agent may be administered until the optimal therapeutic effect is obtained for the subject, and at that point the dosage is not generally increased further. It is contemplated that the various pharmaceutical compositions used to practice the method of the present invention should contain about 0.1 μg to about 100 mg IL-21/IL-21R antagonist per kg body weight.

The duration of intravenous therapy using the pharmaceutical composition of the present invention will vary, depending on the severity of the disease being treated and the condition and potential idiosyncratic response of each individual subject. It is contemplated that the duration of each application of an IL-21/IL-21R antagonist may be in the range of 12 to 24 hours of continuous i.v. administration. Also contemplated is subcutaneous (s.c.) therapy using a pharmaceutical composition of the present invention. These therapies can be administered daily, weekly, or, more preferably, biweekly, or monthly. It is also contemplated that where the IL-21 /IL-21R antagonist is a small molecule (e.g., for oral delivery), the therapies may be administered daily, twice a day, three times a day, etc. Ultimately the attending physician will decide on the appropriate duration of i.v. or s.c. therapy, or therapy with a small molecule, and the timing of administration of the therapy using the pharmaceutical composition of the present invention.

The polynucleotide and proteins of the present invention are expected to exhibit one or more of the uses or biological activities (including those associated with assays cited herein) identified below. Uses or activities described for proteins, antibodies, or polynucleotides of the present invention may be provided by administration or use of such proteins, or antibodies, or by administration or use of polynucleotides encoding such proteins or antibodies (such as, for example, in gene therapies or vectors suitable for introduction of DNA).

Combination Therapy

In one embodiment, a pharmaceutical composition comprising at least one IL-21R/IL-21 antagonist, e.g., an IL-21R/IL-21 antibody, and at least one therapeutic agent is administered in combination therapy. Such therapy is useful for treating pathological conditions or disorders, such as immune and/or inflammatory disorders. The term "in combination" in this context means that the antagonist composition and the therapeutic agent are given substantially contemporaneously, either simultaneously or sequentially. If given sequentially, at the onset of administration of the second compound, the first of the two compounds may still be detectable at effective concentrations at the site of treatment.

For example, the combination therapy can include at least one IL-21R/IL-21 antagonist coformulated with, and/or coadministered with, at least one additional therapeutic agent. Additional agents may include at least one cytokine inhibitor, growth factor inhibitor, immunosuppressant, anti-inflammatory agent, metabolic inhibitor, enzyme inhibitor, cytotoxic agent, or cytostatic agent, as described in more detail below. Such combination therapies may advantageously utilize lower dosages of the administered therapeutic agents, thus avoiding possible toxicities or complications associated with the various monotherapies. Moreover, the therapeutic agents disclosed herein act on pathways that differ from the IL-21L-21R pathway, and thus are expected to enhance and/or synergize with the effects of the IL-21R/IL-21 antagonists.

Therapeutic agents used in combination with IL-21R/IL-21 antagonists may be those agents that interfere at different stages in the autoimmune and subsequent inflammatory response. In one embodiment, at least one IL-21R/IL-21 antagonist described herein may be coformulated with, and/or coadministered with, at least one cytokine and/or growth factor antagonist. The cytokine and/or growth factor antagonists may include soluble receptors, peptide inhibitors, small molecules, ligand fusions, antibodies (that bind cytokines or growth factors or their receptors or other cell surface molecules), and "anti-inflammatory cytokines" and agonists thereof.

Nonlimiting examples of the agents that can be used in combination with the IL-21R/IL-21 antagonists described herein, include, but are not limited to, antagonists of at least one interleukin (e.g., IL-1, IL-2, IL-6, IL-7, IL-8, IL-12, IL-13, IL-1 5, IL-16, IL-1 7, IL-1 8, and IL-22); cytokine (e.g., TNFα, LT, EMAP-II, and GM-CSF); or growth factor (e.g., FGF and PDGF). The agents may also include, but are not limited to, antagonists of at least one receptor for an interleukin, cytokine, and growth factor. IL-21R/IL-21 antagonists can also be combined with inhibitors of, e.g., antibodies to, cell surface molecules such as CD2, CD3, CD4, CD8, CD20 (e.g., the CD20 inhibitor rituximab (RITUXAN®)), CD25, CD28, CD30, CD40, CD45, CD69, CD80 (B7.1), CD86 (B7.2), CD90, or their ligands, including CD154 (gp39 or CD40L), or LFA-1/ICAM-1 and VLA-4VCAM-I (Yusuf-Makagiansar et al. (2002) *Med. Res. Rev.* 22:146-67). Other compounds that can be used in combination with IL-2IR/IL-21 antagonists described herein may include antagonists of the receptors for IL-1, IL-1 2, TNFα, IL-15, IL-17, IL-18 and IL-22.

Examples of agents useful in combination therapies with an IL-21R/IL-21 antagonist include IL-12 antagonists (such as antibodies that bind IL-12 (see e.g., WO 00/56772); IL-12 receptor inhibitors (such as antibodies to the IL-12 receptor); and soluble IL-12 receptor and fragments thereof. Examples of IL-15 antagonists include antibodies against IL-15 or its receptor, soluble fragments of the IL-15 receptor, and IL-15-binding proteins. Examples of IL-18 antagonists include antibodies to IL-18, soluble fragments of the IL-18 receptor, and IL-18 binding proteins (IL-18BP, Mallat et al. (2001) *Circ. Res.* 89:E4145). Examples of IL-1 antagonists include interleukin-l-converting enzyme (ICE) inhibitors (such as Vx740), IL-1 antagonists (e.g., IL-1RA (anakinra (KINERET™), Amgen)), sIL-1RII (Immunex), and anti-IL-1 receptor antibodies.

Examples of TNF antagonists include antibodies to TNF (e.g., human TNFα), such as D2E7 (human anti-TNFα antibody, U.S. Pat. No. 6,258,562, HUMIRATM, Abbott Labs); CDP-571/CDP-870/BAY-10-3356 (humanized anti-TNFα antibodies, Celltech/Pharmacia); cA2 (chimeric anti-TNFα antibody, REMICADE™, Centocor); and anti-TNF antibody fragments (e.g., CPD870). Other examples include soluble TNF receptor (e.g., human p55 or p75) fragments and derivatives, such as p55 kdTNFR-IgG (55 kD TNF receptor-IgG fusion protein, LENERCEP™) and 75 kdTNFR-IgG (75 kD TNF receptor-IgG fusion protein, ENBREL™ (etanercept-Immunex)). See, e.g., van der Poll et al. (1997) *Blood.* 89:3727-34; Mori et al. (1996) *J. Immunol.* 157:3178-82. Further examples include enzyme antagonists (e.g., TNFα converting enzyme inhibitors (TACE) such as alpha-sulfonyl hydroxamic acid derivative (WO 01/55112) or N-hydroxy-formamide inhibitors (GW 3333, −005, or −022, GlaxoSmithKline) and TNF-bp/s-TNFR (soluble TNF binding protein, see, e.g., Lantz et al. (1991) *J Clin Invest.* 88:2026-31; Kapadia et al. (1995) *Amer. J. Physiol. Heart Circ. Phys.* 268:H517-25). TNF antagonists may be soluble TNF receptor (e.g., human p55 or p75) fragments and derivatives, such as 75 kdTNFR-IgG; and TNFα converting enzyme (TACE) inhibitors.

In other embodiments, the IL-21R/IL-21 antagonists described herein can be administered in combination with at least one of the following: IL-13 antagonists, such as soluble IL-13 receptors and/or anti-IL-13 antibodies; and IL-2 antagonists, such as IL-2 fusion proteins (e.g., DAB 486-IL-2 and/or DAB 389-IL-2 made by Seragen, see e.g., Sewell et al. (1993) *Arthritis Rheum.* 36:1223-33) and anti-IL-2R antibodies (e.g., anti-Tac (humanized antibody, Protein Design Labs, see Junghans et al. (1990) *Cancer Res.* 50:1495-502). Another combination includes IL-21R/IL-21 antagonists in combination with nondepleting anti-CD4 inhibitors such as IDEC-CE9.1/SB 210396 (anti-CD4 antibody, GlaxoSmithKline). Yet other combinations include IL-21R/IL-21 antagonists with CD80 (B7.1) and CD86 (B7.2) costimulatory pathway antagonists (such as antibodies, soluble receptors, or antagonistic ligands); P-selectin glycoprotein ligand (PSGL) and PSGL-1 inhibitors (such as antibodies to PSGL and/or PSGL-1 and small molecule inhibitors); T cell-and B cell-depleting agents (such as anti-CD4 or anti-CD22 antibodies), and anti-inflammatory cytokines and agonists thereof (e.g., antibodies). The anti-inflammatory cytokines may include IL-4 (e.g., Schering-Plough Biopharma); IL-10 (e.g., SCH 52000, recombinant IL-10, Schering-Plough Biopharma); IL-11; IL-13; and TGFβ or agonists thereof (e.g., agonist antibodies).

In other embodiments, at least one IL-21R/IL-21 antagonist can be coformulated with, and/or coadministered with, at least one anti-inflammatory drug, immunosuppressant, metabolic inhibitor, and enzymatic inhibitor. Nonlimiting examples of the drugs or inhibitors that can be used in combination with the IL-21R/IL-21 antagonists described herein, include, but are not limited to, at least one of: nonsteroidal anti-inflammatory drugs (NSAIDS) (including, but not limited to, aspirin, salsalate, diflunisal, ibuprofen, ketoprofen, nabumetone, piroxicam, naproxen, diclofenac, indomethacin, sulindac, tolmetin, etodolac, ketorolac, oxaprozin, tenidap, meloxicam, piroxicam, aceclofenac, tolmetin, tiaprofenic acid, nimesulide, etc.); sulfasalazine; corticosteroids (such as prednisolone); cytokine suppressive anti-inflammatory drugs (CSAID); inhibitors of nucleotide biosynthesis (such as inhibitors of purine biosynthesis (e.g., folate antagonist such as methotrexate)); and inhibitors of pyrimidine biosynthesis, e.g., a dihydroorotate dehydrogenase (DHODH) inhibitor such as leflunomide (see, e.g., Kraan et al. (2004) *Ann. Rheum. Dis.* 63:1056-61). Therapeutic agents for use in combination with IL-21/IL-21R antagonists may include one or more NSAIDs, CSAIDs, DHODH inhibitors (such as leflunomide), and folate antagonists (such as methotrexate).

Examples of additional agents that may be used in combination with IL-21 /IL-21R antagonists include at least one of: corticosteroid (oral, inhaled and local injection); immunosuppressant (such as cyclosporin and tacrolimus (FK-506)); an mTOR inhibitor (such as sirolimus (rapamycin) or a rapamycin analog and/or derivative, e.g., ester rapamycin derivative such as CCI-779 (see, e.g., Elit (2002) *Curr. Opin. Investig. Drugs* 3:1249-53; Huang et al. (2002) *Curtr. Opin. Investig. Drugs* 3:295-304)); an agent which interferes with the signaling of proinflammatory cytokines such as TNFα and IL-1 (e.g., an IRAK, NIK, IKK, p38 or MAP kinase inhibitor); TPL-2, Mk-2 and NFKb inhibitors; COX-2 inhibitors (e.g., celecoxib, rofecoxib, etc., and variants thereof); phosphodiesterase inhibitors (such as Rolipram); phospholipase inhibitors (e.g., an inhibitor of cytosolic phospholipase 2 (cPLA2) such as trifluoromethyl ketone analogs (U.S. Pat. No. 6,350,892)); inhibitors of vascular endothelial cell growth factor (VEGF); inhibitors of the VEGF receptor; inhibitors of angiogenesis; RAGE and soluble RAGE; estrogen receptor beta (ERB) agonists, ERB-NFκb antagonists; interferon-β (for example, IFNβ-1a and IFNβ-1b); copaxone; and corticosteroids.

Other useful therapeutic agents that may be combined with an IL-21R/IL-21 antagonist include: budenoside; epidermal growth factor; aminosalicylates; 6-mercaptopurine; azathioprine; metronidazole; lipoxygenase inhibitors; mesalamine; olsalazine; balsalazide; antioxidants; thromboxane inhibitors; growth factors; elastase inhibitors; pyridinyl-imidazole compounds; glucuronide-or dextran-conjugated prodrugs of prednisolone; dexamethasone or budesonide; ICAM-1 anfisense phosphorothioate oligodeoxynucleotides (ISIS 2302; Isis Pharmaceuticals, Inc.); soluble complement receptor I (TP10; T Cell Sciences, Inc.); slow-release mesalazine; antagonists of platelet activating factor (PAF); ciprofloxacin; lignocaine; cyclosporin A; hydroxychloroquine (PLAQUENIL™); minocycline (MINOCIN™); and anakinra (KINERET™).

Choosing a particular therapeutic agent for administration in combination with an IL-21/IL-21R antagonist of the invention will largely depend on factors such as the particular subject, the desired target, and chosen length of treatment. Such decisions are well within the skill and knowledge of one skilled in the art.

Additional examples of therapeutic agents that can be combined with an IL-21R/IL-21 antagonist include one or more of: 6-mercaptopurines (6-MP); azathioprine; sulphasalazine; mesalazine; olsalazine; chloroquine, hydroxychloroquine (PLAQUENIL®); pencillamine; aurothiomalate (intramuscular and oral); azathioprine; colchicine; beta-2 adrenoreceptor agonists (salbutamol, terbutaline, salmeterol); xanthines (theophylline, aminophylline); cromoglycate; nedocromil; ketotifen; ipratropium and oxitropium; mycophenolate mofetil; adenosine agonists; antithrombotic agents; complement inhibitors; and adrenergic agents.

In one embodiment, an IL-21R/IL-21 antagonist can be used in combination with one or more antibodies directed at other targets involved in regulating immune responses. Nonlimiting examples of agents for treating or preventing immune responses with which an IL-21R/IL-21 antagonist of the invention can be combined include the following: antibodies against other cell surface molecules, including but not limited to CD25 (interleukin-2 receptor-a), CD11a (LFA-1), CD54 (ICAM-1), CD4, CD45, CD28, CTLA4, ICOSL, ICOS, CD80 (B7.1), and/or CD86 (B7.2). In yet another embodiment, an IL-21R/IL-21 antagonist is used in combination with one or more general immunosuppressive agents, such as cyclosporine A or FK506. In another embodiment, an IL-21/IL-21R antagonist is used in combination with a CTLA4 agonist, e.g., (e.g., CTLA4 Ig-abatacept (ORENCIA®)).

The entire contents of all references, patents, and published patent applications cited throughout this application are hereby incorporated by reference herein.

EXAMPLES

The following Examples provide illustrative embodiments of the invention and do not in any way limit the invention. One of ordinary skill in the art will recognize that numerous other embodiments are encompassed within the scope of the invention.

Example 1

Materials and Methods

Example 1.1

Mice, Parasite Infections and Antigen Preparation

Female or male C57BL/6, C57BL/6/Ai-IL-10KO/IL-4KO mice and C57BL/6Ai-IL-10KO/IL-12KO were obtained from Taconic Farms (Germantown, N.Y.) (Hoffmann et al. (1999) *J. Immunol.* 163:927-938). Breeding pairs of IL-21R$^{-/-}$ mice on a C57BL/6 background were obtained from a breeding colony housed at Harvard School of Public Health (Boston, Mass.) (Kasaian et al. (2002) *Immunity* 16:559-69). All mice were housed under specific pathogen-free conditions at the National Institutes of Health in an American Association for the Accreditation of Laboratory Animal Care-approved facility. The NLAID animal care and use committee approved all experimental procedures. *S. mansoni* eggs were extracted from the livers of infected mice (Biomedical Research Institute, Rockville, Md.) as previously described (Wynn et al. (1995) *Nature* 376:594-96). For the induction of synchronous primary pulmonary granulomas, mice were given 5,000 eggs intravenously (i.v.). For the induction of secondary granulomas, mice were sensitized intraperitoneally (i.p.) with 5000 live eggs, and then challenged with 5,000 live eggs i.v. (Wynn et al. (1994) *J. Exp. Med.* 179:551-61). In the infection experiments, mice were infected percutaneously via the tail with 25-30 cercariae of a Puerto-Rican Strain of *S. mansoni* (NMRI) that were obtained from infected Biomphalaria glabrata snails (Biomedical Research Institute, Rockville, Md.). Soluble egg antigen (SEA) and soluble worm antigenic preparations (SWAP) were from purified and homogenized from *S. mansoni* eggs and adult parasites as previously described (Cheever et al. (1994) *J. Immunol.* 153:753-59). All animals underwent perfusion at the time of sacrifice so that worm and tissue egg burdens could be determined, as described elsewhere (id.). *Nippostrongylus brasiliensis* larvae (L3) were prepared as previously described (Katona et al. (1983) *J. Immunol.* 130: 350-56). Mice were inoculated through s.c. injection of 500 L3. On day seven post-inoculation, lung tissue and mediastinal lymph nodes were collected for cytokine analysis.

Example 1.2

Histopathology and Fibrosis

The sizes of pulmonary and hepatic granulomas were determined on histological sections that were stained with Wright's Giemsa stain (Histopath of America, Clinton, Md.). Around 30 granulomas per mouse were included in all analyses. A skilled pathologist evaluated the percentages of eosinophils, mast cells and other types of cells in the same sections. The number of schistosome eggs in the liver and the gut and the collagen content of the liver, as measured by hydroxyproline levels, were determined as previously described (Cheever et al., supra). Specifically, hepatic collagen was measured as hydroxyproline by the technique of Bergman and Loxley (Bergman and Loxley (1963) *Analytical Biochem.* 35:1961-65) after hydrolysis of a 200-mg portion of liver in 5 ml of 6N HCI at 110° C. for 18 h. The increase in hepatic hydroxyproline was positively related to egg numbers in all experiments and hepatic collagen is reported as the increase above normal liver collagen in micromoles per 10,000 eggs; (infected liver collagen—normal liver collagen)/liver eggs$\times10^{-4}$ or micromoles per worm pair. At late chronic time points, fibrosis is reported as total liver collagen per liver. The same individual scored all histological features and had no knowledge of the experimental design.

Example 1.3

FACS Analysis

Whole lungs were harvested and placed in RPMI. Tissues were disrupted by straining through a 70-micron nylon mesh (BD Falcon, San Diego, Calif.). The single cell suspensions were washed and RBCs were lysed by incubation with ACK lysis solution for 3 min. Lung lymphocytes were labeled with PE-Cy5 labeled anti-CD4 along with Fc Block (both antibodies from BD Pharmingen, San Diego, CA) in FACS buffer for 15 min at 4° C. After washing, the cells were analyzed on a FACS Calibur using FLOWJO™ software (Treestar, Inc., Ashland, Oreg.).

Example 1.4

IL-21 Blocking Experiments with sIL-21R-Fc

C57BL/6 (10/group) mice were infected percutaneously via the tail with 30-35 *S. mansoni* cercariae. Beginning on week 6 post-infection, mice were treated with either mIL-21R-Fc (Wyeth Research) or Anti-E. tenella murine IgG2a control antibody (Wyeth Research). Each mouse received one 200 μg dose via i.p. injection 3×/week for a total of 5 weeks. Mice were sacrificed 12 weeks post-infection and hepatic fibrosis was measured by hydroxyproline assay.

Example 1.5

Lymphocyte Culture and Cytokine Detection Using the Enzyme-linked Immunosorbent Assay (ELISA)

Spleen and mesenteric lymph nodes (infection model) or lung-associated lymph nodes (pulmonary model) were removed aseptically and single cell suspensions were prepared as previously described (Hesse et al. (2000) *Am. J. Pathol.* 157:945-55). Cultures were incubated at 37° C. in a humidified atmosphere of 5% $CO_2$. Cells were stimulated with SEA (20 μg/ml), SWAP (50 μg/ml), concanavalin A (Con A; 1 μg/ml), or medium alone. Supernatant fluids were harvested at 72 hours and assayed for cytokine production. IFN-γ, IL-5 and IL-10 were measured by sandwich ELISA using paired antibodies (BD Pharmingen, San Diego, Calif.) as previously described (id.). Cytokine levels were calculated with standard curves constructed using recombinant murine cytokines (BD Pharmingen, San Diego, Calif.). IL-13 levels were measured using murine IL-13 ELISA kits (R&D Systems, Minneapolis, Minn.) according to the manufacturer's protocol. TGF-β1 levels were quantified using mouse TGF- PL DUOSET® ELISA development system (R&D Systems, Minneapolis, Minn.) according to manufacture's protocol. To avoid bovine-derived TGF-β1 contamination, cells were washed 3× in PBS and cultured in media containing 0.5% mouse serum.

Example 1.6

Isolation and Purification and Real-Time Polymerase Chain Reaction

Total RNA was extracted from lung and liver tissue samples placed individually in 1 ml TRIZOL™ reagent (Invitrogen, Carlsbad, Calif.). The sample was homogenized using a tissue polytron (Omni International Inc., Marietta, Ga.) and total RNA was extracted according to the recommendations of the manufacturer and further purified using RNEASY™ Mini Kit from Qiagen (Qiagen Sciences, Germantown, Md.). Individual sample RNA (1 μg) was reverse-transcribed using SUPERSCRIPT II™ (Invitrogen, Carlsbad, Calif.) and a mixture of oligo (dT) and random primers. Real-time polymerase chain reaction (RT-PCR) was performed on an ABI PRISMTM 7900 sequence detection system (Applied Biosystems, Foster City, Calif.). Relative quantities of mRNA for several genes was determined using SYBR™ Green PCR Master Mix (Applied Biosystems, Foster City, Calif.) and by the comparative threshold cycle method as described by Applied Biosystems for the ABI PRISM™ 7700/7900 sequence detection systems (Applied Biosystems, Foster City, Calif.). In this method, mRNA levels for each sample were normalized to hypoxanthine guanine phosphoribosyl transferase mRNA levels and then expressed as a relative increase or decrease compared with levels in uninfected controls. Primers were designed using PRIMER EXPRESS™ software (Applied Biosystems, Foster City, Calif.). Primers for IL-13, IL-4, IL-10, HPRT (Hesse et al. (2001) *J. Immunol.* 167:6533-44), IL-13Rα2 (Chiaramonte et al. (2003) *J. Exp. Med.* 197:687-701), Ym1, FIZZ1 and acidic chitinase (AMCase) (Sandler et al., supra) were published previously, and include:

```
IL-21
                                        (SEQ ID NO:28)
5' GCCAG ATCGC CTCCT GATTA 3' (sense);

                                        (SEQ ID NO:29)
5' CATGC TCACA GTGCC CCTTT 3' (antisense);

IL-21R
                                        (SEQ ID NO:30)
5' CTCCC CCCTT GAACG TGACT 3' (sense);

                                        (SEQ ID NO:31)
5' TTGCC CCTCA GCACG TAGTT 3' (antisense);

IFN-γ
                                        (SEQ ID NO:32)
5' AGAGC CAGAT TATCT CTTTC TACCT CAG 3' (sense);

                                        (SEQ ID NO:33)
5' CCTTT TTCGC CTTGC TGTTG 3' (antisense).
```

Example 1.7

Serum Antibody Isotype Analysis and Bone Marrow-Derived Macrophages

Total IgE was measured using the BD OPTEIA™ mouse IgE ELISA Set (BD Biosciences Pharmingen, San Diego, Calif.) according to the manufacturer's protocol. SEA-specific IgGI and IgG2b isotype-specific antibody (Ab) titers were evaluated by indirect ELISA. IMMULON™ 4 plates (Thermo Labsystems Inc., Beverly Mass.) were coated with 10 μg/ml SEA (100 μl/well) diluted in PBS, and serum samples were analyzed using serial two-fold dilutions. Biotin-Rabbit Anti-mouse IgG 1 (Zymed, San Francisco, Calif.) was used at a 1:1000 dilution. This was followed by peroxidase-labeled streptavidin (KPL, Gaithersburg, Md.) substrate enzyme at a 1:1000 dilution. Second-step horseradish peroxidase-conjugated rabbit anti-mouse IgG2b (Zymed, San Francisco, Calif.) Ab was used at a 1:1000 dilution. The absorbance in the wells was read at 405 mn using a VMAX™ Kinetic Microplate Reader (Molecular Devices) after adding 100 μl one-component ABTS Peroxidase Substrate (KPL, Gaithersburg, Md.).

Bone marrow was recovered from female C57BL/6 mice and cultured in Petri dishes (100×15 mm) containing supplemented DMEM media (L929-conditioned medium) for a period of 6 days. After six days, cells were harvested and seeded at a concentration of $0.5\times10^6$ cells/well in 24 well plates containing supplemented DMEM media (10% FBS, 2 mM L-glutamine, 100 U/mL penicillin, and 100 μg/mL streptomycin). Cells were stimulated with IL-4, IL-13, and IL-21 (R&D, Minneapolis, Minn.) for a period of 20 hours. In some assays, cells were pretreated with IL-21. Cells were lysed and RNA was purified using the RNA Cleanup procedure with the RNEASY™ kits (Qiagen Sciences, Germantown, Md.).

Example 1.8

Arginase Activity Assay

Bone marrow-derived macrophages were plated at $6\times10^5$ per well in 96 well tissue culture plates and stimulated with combinations of IL-4, IL-13, and IL-21. IL-21 was added 6 hours prior to IL-4 or IL-13 stimulation. Following stimulation, cells were washed with PBS and lysed with 0.1% Triton X-100 containing protease inhibitor (Roche, Nutley, N.J.). Lysates were transferred into a 96 well PCR plate and incubated with 10 mM $MnCl_2$ and 50 mM Tris HCl (pH 7.5) to activate enzyme for 10 min at 55° C. After enzyme activation, 25 μl of lysate was removed and added to 25 μl 1 M arginine (pH 9.7) in a new PCR plate and incubated for 20 hours at 37° C. 5 μl of each sample was added in duplicate to a 96 well ELISA plate along with 5 μl of each standard, diluted in the same assay conditions, starting at 100 mg/dL. The urea determination reagent from QUANTICHROM™ Urea Assay Kit (BioAssay Systems, Hayward, Calif.) was used according to the manufacture's protocol.

Example 1.9

Statistics

Hepatic fibrosis (adjusted for egg number) decreases with increasing intensity of infection (worm pairs). Therefore, these variables were compared by analysis of covariance, using the logarithm of total liver eggs as the covariate and the logarithm of hydroxyproline content per egg. Variables that did not change with infection intensity were compared by one-way ANOVA or Student's t test (Cheever et al., supra). Changes in cytokine MRNA expression and granuloma size were evaluated using ANOVA. Differences were considered significant when $p<0.05$*, $p<0.01$ , or $p<0.001$ *.

Example 2

Regulation of IL-21 and IL-21R during Type-1-and Type-2-Polarized Responses

To investigate the regulation and function of the IL-21 receptor in vivo, several different experimental systems of $T_H2$-dependent inflammation were examined, including models of pulmonary and hepatic inflammation, as well as an experimental model of nematode infection (Pearce et al., supra; Wynn et al. (1994), supra). In each case, the immune responses of wild type (WT) animals were compared with IL-21R-deficient mice (Hoffinan et al., supra; Kasaian et al. (2002), supra).

In comparison to IL-21 (Wurster et al. (2002), supra; Mehta et al. (2004) Immunol. Rev. 202:84-95), little is known about the regulation and function of the IL-21 receptor. To determine whether IL-21 and its receptor are regulated during a pathological $T_H2$ response in vivo, the *S. mansoni* model of granuloma formation was used. In this model, $T_H2$ cytokines are known to play a prominent role in lesion formation (Pearce and MacDonald, supra). Initial studies were designed to determine whether IL-21 and IL-21R mRNA expression were linked with polarized $T_H2$ cytokine responses in vivo. This was achieved by using mice that develop highly exaggerated $T_H1$ (IL-$4^{-/-}$/IL-$10^{-/-}$) or $T_H^2$ (IL-$12^{-/-}$IL-$10^{-/-}$) cytokine responses following exposure to *S. mansoni* eggs. In IL-$4^{-/-}$/IL-$10^{-/-}$ "$T_H1$" mice, IFN-γ mRNA expression increased in the lung 75-fold over baseline by day 4 post-challenge and remained approximately 50-fold above background through day 14 (FIG. 16A). IL-13 MRNA was not detectable in these mice at any time point, confirming the establishment of a highly polarized $T_H1$ inflammatory response. In contrast, the IL-$12^{-/-}$/IL-$10^{-/-}$ "$T_H2$" mice displayed a 200 to 250-fold increase in IL-13 mRNA at all time points post-challenge, with little to no change in IFN-γ. In contrast to the $T_H1$/$T_H2$ cytokines, which displayed a highly polarized pattern of expression, IL-21 was not associated with a polarized phenotype (FIG. 16B). In both groups, IL-21 mRNA levels increased at least 50-fold over baseline following challenge with schistosome eggs, although the increase observed in the $T_H1$ -polarized mice was on average 3-to 4-fold greater than the $T_H^2$ polarized animals (FIG. 16B; lower panel). IL-21R was also not specifically associated with a $T_H1$ or $T_H2$ immune response. However, in contrast to IL-21, which was more pronounced in $T_H1$ skewed animals, the maximal response for the IL-21R was observed in the $T_H2$-polarized mice (FIG. 16B; upper panel).

Example 3

Type-2 Cytokine Production is Reduced in the Lungs of IL-21R-deficient Mice During a Primary Response to Schistosome Eggs Given the significant elevation in IL-21R expression in mice challenged with schistosome eggs (FIG. 16), the next series of experiments examined whether IL-21R signaling was influencing the development of the $T_H2$ response. In these experiments, naïve WT and IL-$21R^{-/-}$ mice were injected intravenously with live schistosome eggs and the production of $T_H2$ cytokines and $T_H2$-regulated genes were monitored in the lung, spleen, and draining lymph nodes over the following 14 days. In WT mice, IL-21R mRNA expression increased rapidly following egg exposure and remained elevated through day 14 (FIG. 17A). IL-21 showed a similar profile with peak expression occurring on day 7 and then declining slightly thereafter. Notably, there was a consistent and highly significant decrease in IL-21 expression on days 7 and 14 in the IL-$21R^{-/-}$ mice, suggesting that IL-21R was positively influencing the expression of its own ligand. Consistent with previous observations (Wynn et al. (1993) *J. Immunol.* 151:143040; Vella and Pearce (1992) *J. Immunol.* 148:2283-88), expression of the $T_H2$-associated cytokines IL-4 and IL-13 rose gradually in the granulomatous tissues of WT mice, with 5-to 15-fold increases detectable by day 14. In contrast, there was a marked and significant decrease in IL-4 and IL-13 mRNA expression in the IL-$21R^{-/-}$ tissues. Although little change in IFN-γ and IL-10 mRNA was detected in WT mice between day 4 and 14 post-challenge, production of IFN-γ and IL-10 also decreased slightly in the IL-$21R^{-/-}$ animals. Thus, the reduced $T_H2$ response observed in the IL-$21R^{-/-}$ mice was not associated with increased $T_H^1$ cytokine production. The decrease in $T_H2$ cytokines was also specific to the granulomatous tissues, since significant $T_H2$ cytokine production was observed in lymph node and splenocyte cultures following in vitro stimulation with soluble egg antigen (SEA) or mitogen (FIG. 17B). In fact, SEA consistently stimulated stronger IL-5, IL-10, and IL-13 responses in the lymph node cultures prepared from IL-$21R^{-/-}$ mice. Nevertheless, consistent with the reduced $T_H2$ response in the lung, a more rapid resolution of granuloma formation was observed in the IL-$21R^{-/-}$ animals (FIG. 17C). In addition, there was a marked decrease in several genes associated with Stat6-activation or "alternatively-activated macrophages" (AAMø) (Nair et al. (2005) *Infect. Immun.* 73:385-94; Zhu et al. (2004) *Science* 304:1678-82; Chiaramonte et al. (2003), supra; Gordon, S. (2003) *Nat. Rev. Immunol.* 3:23-35), providing further evidence of an overall reduction in the $T_H2$ effector response in IL-$21R^{-/-}$ mice (FIG. 17D).

Example 4

TH2Response is Reduced in IL-$21R^{-/-}$ Mice Following *N. brasiliensis* Infection To determine if the reduced $T_H2$ effector response was specific to S. mansoni pulmonary granuloma formation, WT and IL-$21R^{-/-}$ mice were infected with the intestinal nematode *N. brasiliensis*. Infection is established by inoculating third stage larvae (L3) under the skin. As the parasites mature, they migrate from the site of inoculation and enter the lungs via the circulatory system. Once inside the lungs, the parasites trigger a vigorous and highly polarized $T_H2$ response (Urban et al. (1993) *J. Immunol.* 151:7086-94), which was confirmed by analyzing the expression of several $T_H2$-associated genes in the lung (FIG. 18A) and lung-associated lymph nodes (FIG. 18B). The lungs and lymph nodes of WT mice displayed marked increases in IL-4, IL-13, AMCase, FIZZ1/RELM1α, and Ym1 mRNA expression following *N. brasiliensis* infection (FIG. 18A and 18B). However, in agreement with the pulmonary granuloma model, significantly reduced levels of IL-4, IL-13, and AMCase were observed, as well as slightly reduced levels ofYm1 and FIZZ1 mRNA in the lungs of the IL-$21R^{-/-}$ mice (FIG. 18A). The draining lymph nodes displayed a similar reduction, although the decreases in Ym1 and FIZZ1 were more significant in the lymph nodes (FIG. 18B). The only other major difference between the two tissues was the AMCase mRNA response, which appeared to be restricted to the lung. Together, these data confirm an important role for the IL-21R in $T_H2$ response development in vivo. Notably however, despite developing a markedly attenuated $T_H2$ response, the *N. brasiliensis* infected IL-21R$^{-/-}$ mice displayed no significant delay in adult worm expulsion (not shown).

Example 5

Type-2 Cytokine-Driven Inflammation is Diminished in the Lungs of IL-21R$^{-/-}$ Mice The next series of experiments were designed to determine whether the IL-21R modulates the development of secondary $T_H2$ responses. For these experiments, WT and IL-21R$^{-/-}$ mice were sensitized with *S. mansoni* eggs and challenged intravenously 2 weeks later. As expected, the sensitized mice developed a robust granulomatous response that was 4-to 5-times greater (FIG. 19C) than the primary challenge animals (FIG. 17C). As observed in the primary model, there was a significant increase in IL-21 and IL-21R mRNA in the lungs following egg exposure, although the IL-21 response peaked much earlier during the secondary challenge. IL-21R was only modestly increased when compared with IL-21 although it remained significantly elevated at both time points, while IL-21 mRNA levels declined after reaching a peak on day 4 (FIG. 19A). Thus, there was evidence of tighter regulation of the ligand in the tissues. There was also a remarkable decrease in IL-21 expression in the IL-21R$^{-/-}$ mice, confirming a potent feedback mechanism between the receptor and its ligand. Among the TH2-associated cytokines, IL-13 was the most robust response, displaying a 50-to 100-fold increase over baseline in WT mice. However, it was reduced to 10-to 20-fold above background in the IL-21R$^{-/-}$ mice, demonstrating that the IL-21R is required for maximum development of the secondary TH2 response. Again, the reduction in $T_H2$ cytokine expression in IL-21R$^{-/-}$ mice was not accompanied by a significant increase in IFN-γ. In fact, IFN-γ mRNA expression decreased in the lungs of the IL-21R$^{-/-}$ mice. Nevertheless, the knockouts displayed a modest but consistent increase in IFN-γ production in the lymph nodes and spleen, suggesting a greater inhibition of the $T_H2$ cytokines overall (FIG. 19B). Consistent with the primary egg challenge model, the reduction in $T_H2$ and $T_H1$ cytokine production was more pronounced in the granulomatous tissues (FIG. 19A), although the SEA-induced $T_H2$ response was also partially reduced in the spleen (FIG. 19B). The significant reduction in secondary granulomatous inflammation was consistent with the development of a weaker $T_H2$ response in the lung (FIG. 19C). In addition, there was a marked decrease in FIZZ1, Ym1, and AMCase expression (FIG. 19D), further confirming a significant impairment of secondary $T_H2$ effector responses in the IL-21R$^{-/-}$ mice.

Example 6

IgG Antibodies, Granuloma Formation, and Type-2 Cytokines Are Substantially Reduced in Infected IL-2 I R-deficient Mice Next, to determine if IL-21 signaling is required for the maintenance of a chronic $T_H2$-dominated response, animals were exposed percutaneously to *S. mansoni* cercariae, and their pathological reactions and immune responses at both acute and chronic time points post-infection were analyzed. As observed in the pulmonary granuloma studies, there was a marked upregulation in IL-21R and IL-21 mRNA expression in the livers of infected WT mice. In contrast, IL-21 mRNA was almost undetectable in the IL-21R$^{-/-}$ mice even after chronic infection (FIG. 20A). At the acute stage post-infection, the IL-21R$^{-/-}$ mice also manifested a marked reduction in $T_H2$ cytokine mRNA expression (FIG. 20A). However, the changes were again restricted to the granulomatous tissues because the lymph node and splenocyte responses of both groups were similar following in vitro stimulation with parasite antigens (FIG. 20B). The only consistent difference noted in the in vitro assays was a 2-to 3-fold decrease in IL-5 and IL-10 production in the splenocyte cultures. The IL-21R$^{-/-}$ mice also developed significantly smaller granulomas at the acute stage post-infection (FIG. 20C), which was consistent with the reduced IL-4 and IL-13 mRNA responses in the liver (FIG. 20A). However, this was not accompanied by any obvious change in the percentage of eosinophils in the granulomas (FIG. 20C). A more detailed microscopic analysis of the lesions confirmed that there was no detectable change in the overall composition of the granulomas (FIG. 21A). Experiments were also undertaken to determine whether IL-21R-deficiency was specifically affecting the recruitment of CD4$^+$ T cells to the granulomatous tissues. To address this issue, the pulmonary granuloma model was used in order to synchronize the recruitment of inflammatory cells. However, consistent with the microscopic evaluations of liver granulomas (FIG. 21A), the percentage of CD4$^+$ T cells in the lungs was similar in WT and IL-21R$^{-/-}$ mice both before and after egg exposure (FIG. 21B). Thus, changes in CD4$^+$ T cell recruitment or expansion are unlikely to explain the decreased Th1/Th2 cytokine responses observed in the tissues. Instead, they appear to result from a more general reduction in the overall inflammatory response. Importantly, both groups effectively dowmodulated their granulomatous responses by week 12 post-infection (Pearce and MacDonald, supra). Consequently, there was no significant difference in granuloma size at the chronic time point (FIG. 20C). Minimal impairment in the $T_H2$ cytokine response was observed in the chronically infected knockout mice (FIG. 20A). The marked reduction in FIZZ1 and Ym1 observed at the acute stage had also diminished in the chronically infected IL-21R$^{-/-}$ animals (FIG. 20D). Nevertheless, expression of AMCase remained remarkably low on week 12, suggesting a sustained diminution of at least a subset of the $T_H2$-driven responses in chronically infected IL-21R$^{-/-}$ mice.

The IL-21R$^{-/-}$ mice were also examined for changes in serum antibody levels (FIG. 22). Consistent with their suppressed cytokine responses (FIG. 20A), the IL-21R$^{-/-}$ mice displayed a marked reduction in parasite specific $IgG_1$ (TH2-associated antibody) and IgG2b ($T_H1$-associated antibody) titers, which was maintained at the chronic time point (FIG. 22B). Interestingly however, this was not accompanied by any significant change in IgE (FIG. 22C), suggesting a selective impairment in only a subset of serum antibody isotypes. Exogenous IL-21 has been shown to inhibit IgE production (Suto et al. (2002) *Blood* 100:4565-73), which may explain the slight elevation of IgE in the chronically infected IL-21R$^{-/-}$ mice. Importantly, the overall reduction in type-2 responsiveness in the IL-21R$^{-/-}$ mice was not attributed to differences in parasite burden since similar numbers of eggs and paired adult parasites were found in the tissues of both groups at all time points (FIG. 22A).

Example 7

IL-21R-deficiency Slows the Progression of Hepatic Fibrosis

Because $T_H2$ cytokines are believed to play a major role in tissue fibrogenesis (Wynn (2004), supra), the development and progression of hepatic fibrosis in S. mansoni-infected IL-21R$^{-/-}$ mice was next examined. Liver hydroxyproline levels were assayed at various time points post-infection as a direct measure of tissue collagen content. As expected, marked hepatic fibrosis was observed in the infected WT mice (FIG. 22D). In contrast, the IL-21R$^{-/-}$ displayed significantly less fibrosis at both the acute and chronic time points. Notably, by week 29 post-infection the IL-21R$^{-/-}$ mice exhibited more than a 50% decrease in total liver collagen content compared to WT mice (FIG. 22E), thus confirming an important and indispensable role for the IL-21R in the progression of $T_H$2-dependent fibrosis.

Experiments were undertaken to examine whether an IL-21 inhibitor could slow the progression of fibrosis in infected WT mice. For these experiments, groups of C57BL/6 mice were treated with sIL-21R-Fc or control protein for a total of 5 weeks, starting on week 6 post-infection, around the time when eggs are first detected in the liver. Although both groups had similar worm and tissue egg burdens (data not shown), mice receiving the IL-21 blocker displayed over a 50% reduction in hepatic fibrosis at the termination of the experiment (FIG. 22F). IL-4 and IL-13 mRNA expression also decreased in the liver, and granuloma size was reduced approximately 15% (data not shown). Thus, these data compliment the experiments performed with IL-21R$^{-/-}$ mice.

Example 8

IL-21 Signaling Promotes the Development of Alternatively Activated Macrophages Because Arg-1, FIZZ1, and TGF-β1 have been linked with the development of fibrosis, and the expression of several TH2/Stat6-regulated genes were reduced in the diseased tissues of IL-21R$^{-/-}$ mice (FIGS. 17-20) (see also, Gordon, supra; Nair et al., supra), experiments were undertaken to determine whether Arg-1, FIZZ1, and TGF-β1 were directly modulated in macrophages following stimulation with IL-21. Arg-1 and FIZZ1 are also well-known markers of alternatively activated macrophages (AAMø) (Gordon, supra). For these studies, bone marrow-derived macrophage cultures (BMMø) were generated and then stimulated with various combinations of IL-4, IL-13, and IL-21. As expected, IL-4 and IL-13 both increased Arg-1 and FIZZ1 mRNA expression, with an additive effect observed when the two stimuli were used in combination (FIG. 23A). Notably however, although IL-21 had no effect on either gene when used alone, cultures that were pretreated with IL-21 displayed highly significant increases in Arg-1 and FIZZ1 mRNA expression when subsequently stimulated with IL-4 and IL-13 (FIG. 23A). The same combination also significantly increased the function of arginase in the cells (FIG. 23B). In contrast, IL-21 had no effect on the levels of total or active TGF-β1 in the culture supernatants (FIG. 24). Unexpectedly, IL-21 treatment alone significantly increased the expression IL-4Rα and IL-13Rα1 (FIG. 23C). In contrast, IL-4 and IL-13 had no effect when used alone (FIG. 23C) and there was no additional effect when the three stimuli were used in combination (not shown).

Because the IL-13Ra2 can also influence IL-13-dependent signaling (Chiaramonte et al. (2003), supra; Mentink-Kane et al. *Proc. Natl. Acad. Sci. U.S.A.* 101:586-90; Wood et al. (2003) *J. Exp. Med.* 197:703-09), experiments were undertaken to examine whether IL-21 was regulating the production of the IL-13Rα2. Not surprisingly, because the IL-13Rα2 is primarily produced by nonhematopoietic cells like fibroblasts and smooth muscle (Chiaramonte et al. (2003), supra; Jakubzick et al. (2003) *Am. J. Pathol.* 162: 1475-86; Zheng et al. (2003) *J. Allergy Clin. Immunol.* 111: 720-28; Morimoto et al. (2006) *J. Immunol.* 176:34248), there was no evidence of decoy receptor regulation in the BMMø cultures (data not shown). However, when the regulation of the decoy receptor in vivo was examined, IL-21 downregulated IL-13Rα2 mRNA expression in the lungs of i.v. egg-challenged mice and significantly decreased the levels of the soluble IL-13Rα2 in their serum (FIG. 23D). When viewed together, these data suggest that IL-21 contributes to the development of alternatively activated macrophages by upregulating the type-2 IL-4 receptor (signaling receptor) in macrophages and by simultaneously decreasing the levels of the soluble IL-13Rα2 (decoy receptor) in the serum. Both mechanisms likely contributed to the increased activation of Arg-1 and FIZZ1 in the IL-4/IL-13-stimulated macrophages. As such, they provide an additional mechanistic explanation for the impaired $T_H$2 responses and $T_H$2-dependent fibrosis in the helminth-infected IL-21R$^{-/-}$ mice.

Example 9

Discussion

IL-21 was recently characterized as a $T_H$2 cytokine that can inhibit the differentiation of naïve $T_H$ cells into IFN-γ-producing $T_H$1 cells (Wurster et al. (2002), supra). Because the immune response in schistosomiasis evolves from an early IFN-γ to a sustained and dominant $T_H$2 response (Pearce and MacDonald, supra), the influence of IL-21R signaling on the development of helminth-induced $T_H$2 responses was examined. Infection of WT mice with *S. mansoni* increased IL-21 and IL-21R expression in the liver, confirming an association of IL-21 signaling with helminth-induced type-2 immunity. However, in the lung, schistosome eggs induced significant IL-21 expression during both $T_H$1 and $T_H^2$ polarized responses. In fact, IL-21 expression increased most when mice were polarized to a $T_H$1 response. These data suggested that IL-21 exhibits a less restricted pattern of expression than that of the other $T_H$2-associated cytokines. The receptor for IL-21 also failed to display a $T_H1/T_H2$-specific pattern. However, the IL-21 receptor was induced nearly 4-fold more in the lungs of $T_H^2$ versus $T_H$1 polarized mice, which provided one of the first indications that IL-21R signaling might be involved in the regulation of $T_H$2-mediated inflammation.

To determine whether type-2 effector responses were compromised in the absence of the IL-21R, the expression of several genes that are induced preferentially under $T_H$2-polarizing conditions was examined. These genes included AMCase, Ym1, and FIZZ1, all of which are thought to play important and nonredundant roles in the regulation of $T_H$2-mediated inflammation (Zhu et al., supra; Chiaramonte et al. (2003), supra; Nair et al., supra; Mentink-Kane et al., supra; Guo et al. (2000) *J. Biol. Chem.* 275:8032-37). Although some variation was observed during a primary, secondary, or chronic immune response, in each case the IL-21R$^{-/-}$ mice displayed highly significant decreases in these $T_H$2-associated genes. Ym1 and AMCase are members of a family of proteins that share homology with chitinases of lower organisms (Nair et al., supra). Although their exact function in host immune reactions remains uncertain, they are thought to play important roles in eosinophil chemotaxis, tissue remodeling and fibrosis. Indeed, a recent study showed that AMCase neutralization could ameliorate allergen-driven inflammation and airway hyperresponsiveness, thus confirming the participation of mammalian chitinases in $T_H$2 immunity (Zhu et al, supra). FIZZ1 is also associated with tissue fibrogenesis (Mentink-Kane et al., supra; Liu et al. (2004) *J. Immunol.* 173:3425-31). Consequently, a major function of the IL-21R may be to regulate the mechanisms of wound healing and fibrosis. Therefore, in addition to its participation in helminth-induced immune responses, the IL-21R may be involved in the regulation of a variety of $T_H2$-mediated inflammatory disorders.

In schistosomiasis, IL-21R-deficiency had a profound effect on the progression of the disease. Although infection intensities were the same in WT and IL-21R$^{-/-}$ mice, the egg-induced inflammatory response decreased significantly in the absence of the IL-21R. There was also a marked reduction in secondary granuloma formation and a faster resolution of primary granulomas in the lung. Together, these data illustrate an indispensable role for the IL-21R in granulomatous inflammation. Previous studies showed that IL-4 and IL-13 are essential for lesion formation (Pearce and MacDonald; supra), thus the IL-21R is believed to be either directly or indirectly affecting the activity of these cytokines. These studies suggested that IL-21 was not acting alone since extremely high levels of IL-21 were observed in IL-4/IL-10 double knockout mice, yet granuloma formation was almost completely ablated in these $T_H2$-deficient animals (Hoffmann et al. (2000) *J. Immunol.* 164:6406-16; Sandler et al. (2003) *J. Immunol.* 171:3655-67). Thus, IL-21 appears to collaborate with IL-4 and IL-13 to induce a maximal response. The data disclosed herein show there is no detectable change in the cellular composition of the granulomas in IL-21R$^{-/-}$ mice and no specific impairment in CD4$^+$ T cell recruitment. Together, these findings suggested that the IL-21R regulates the development of parasite-induced pathology by modulating the overall intensity of the $T_H2$ effector response.

IL-21 is not thought to regulate IL-4-induced $T_H2$ cell differentiation directly (Suto et al., supra; Wurster et al. (2002), supra). Instead, it was hypothesized in a recent paper that IL-21 might amplify $T_H2$-driven responses by downregulating the expansion of IFN-γ-producing $T_H1$ cells (Wurster et al. (2002), supra). As such, it is theorized that the IFN-γ response in schistosome-infected mice might increase in the absence of the IL-21 receptor. Although a small increase was observed in lung-associated lymph nodes in vitro, IFN-γ production was consistently reduced in the granulomatous tissues. Thus, the studies did not show that endogenous IL-21R played a substantial role in the inhibition of IFN-γ production during helminth infection. However, the IL-21R$^{-/-}$ mice simultaneously generated weaker $T_H1$ and $T_H2$ cytokine responses in the tissues. The significant reduction in IgG2b ($T_H1$-associated) and $IgG_1$ ($T_H2$-associated) antibody titers at all times post-infection supports this conclusion. Th2 cytokines were also decreased at the mRNA level in both the lungs and lymph nodes following *N. brasiliensis* infection. Indeed, all of the direct ex vivo data confirmed a marked reduction in $T_{H2}$ cytokine expression and function within the affected tissues. Nevertheless, there was no consistent reduction in $T_H2$ cytokine production by isolated lymphocytes following antigen restimulation, which suggests the IL-21R$^{-/-}$ mice are capable of generating significant $T_H2$ responses, at least in vitro. Thus, the data disclosed herein suggest the IL-21R is selectively augmenting $T_H2$ responses in the tissues. In addition to promoting the $T_H2$ response, the IL-21R also increased IL-21 production. Thus, the IL-21R appears to operate in an autocrine fashion to drive $T_H2$ cytokine expression and type-2 effector functions in vivo.

To further elucidate the mechanisms involved, experiments were undertaken to determine whether IL-21 was directly modulating macrophage function, because the in vivo data showed a marked reduction in several genes that have been associated with the "alternatively-activated" phenotype (Gordon, supra; Mantovani et al. (2005) *Immunity* 23:344-46). Macrophages and fibroblasts exhibiting an alternatively activated phenotype are major cellular constituents of schistosome granulomas and functional studies suggested they are critically involved in the progression of the disease (Hesse et al.(2001), supra). Indeed, an important study by Brombacher et al. showed that mice that are completely deficient in alternatively activated macrophages develop lethal egg-induced pathology following infection with *S. mansoni* (Herbert et al. (2004) *Immunity* 20:623-35). In addition, because macrophage-derived TGF-β1 has been implicated in the mechanism of IL-13-mediated fibrosis (Lee et al. (2001) *J. Exp. Med.* 194: 809-21; Fichtner-Feigl et al. (2006) *Nat. Med.* 12:99-106), experiments were undertaken to determine whether IL-21 was modulating TGF-β1 production in macrophages. To investigate these issues, Arg-1 and FIZZ1 mRNA, arginase activity, and TGF-β1 protein responses were measured in bone marrow-derived macrophages following stimulation with various combinations of IL-21, IL-4, and IL-13. Arg-1 and FIZZI are IL-4Rα/Stat6-dependent genes (Liu et al., supra; Hesse et al. (2001), supra; Munder et al. (1998) *J. Immunol.* 160:5347-54); therefore, they serve as functional markers of alternative macrophage activation. Importantly, the findings suggested that when macrophages were exposed to IL-21, they became much more sensitive to the Arg-1-and FIZZ1-inducing activities of IL-4 and IL-13. Arginase activity assessed by the production of urea also increased significantly, confirming IL-21 as an important stimulus for the development of highly functional alternatively activated macrophages. In contrast, IL-21 had no effect on the production of TGF-β1 by macrophages. Thus, the pro-fibrotic cytokine TGF-β1 does appear to be involved, which is consistent with previous studies that have investigated the role of TGF-β1 in schistosomiasis (Kaviratne et al. (2004) *J. Immunol.* 173: 4020-29). Instead, IL-21 significantly increased IL-4Rα and IL-13Ral expression in BMMøs and decreased the production of the soluble IL-13 decoy receptor in vivo, which likely explains their heightened sensitivity to IL-4 and IL-13. As such, these data compliment the in vivo studies with IL-21R$^{-/-}$ mice and suggest that an important function of IL-21R signaling is to enhance the development of AAMø, which have been implicated in the mechanism of fibrosis (Hesse et al. (2001), supra; Hesse et al. (2000), supra). Moreover, because AAMøhave been shown to amplify CD4$^+$ $T_H2$ cell differentiation (Bonecchi et al. (1998) *Blood* 92:2668-71), these data may also explain the overall reduction in helminth-induced $T_H2$ activity in the IL-21R$^{-/-}$ mice.

In human schistosomiasis, the development of fibrotic liver pathology is the principle cause of chronic morbidity and mortality (Pearce and MacDonald, supra; Wynn et al. (2004) *Immunol. Rev.* 201:156-67). Because the $T_H2$ cytokine response is known to play an important role in collagen deposition (Wynn et al. (2004), supra), a final series of experiments examined the influence of the IL-21R on the progression of hepatic fibrosis. Notably, development of fibrosis decreased significantly in the IL-21R$^{-/-}$ mice, with the knockout animals displaying over a 50% reduction in hepatic fibrosis by week 29 post-infection. Importantly, similar findings were also generated when infected WT mice were treated with sIL-21R-Fc. Thus, the IL-21 receptor was revealed as a potential new target for anti-fibrotic therapy. In conclusion, these studies illustrate an essential role for the IL-21R in the progression of $T_H2$ cytokine-mediated disease. As such, the IL-21R should be added to list of important receptors that regulate type-2 immunity and macrophage polarization.

Example 10

Prophetic Treatments

A nonlimiting set of prophetic treatment examples follows.

A subject diagnosed with liver cirrhosis is administered an IL-21R fusion protein to reduce the accumulation of fibrotic tissue in the liver. The IL-21R fusion protein includes amino acids 1-235 of SEQ ID NO:2 fused at its C-terminus via a linker (corresponding to amino acids 236-243 of SEQ ID NO:17) to a human immunoglobulin G1 (IgG1) Fc-mutated sequence (corresponding to amino acids 244-467 of SEQ ID NO: 17).

A subject diagnosed with an infection with schistosoma is administered a soluble IL-21R fragment to reduce the accumulation of fibrotic tissue. The fragment contains amino acids 20-538 of SEQ ID NO:2.

Following surgery, a subject is administered an IL-21R antibody to reduce the accumulation of fibrosis due to surgical incision during the wound healing process.

A subject diagnosed with liver cirrhosis is administered an IL-21 antibody to reduce the accumulation of fibrotic tissue in the liver.

What is claimed is:

1. A method for treating or ameliorating fibrosis or a fibrosis-associated disorder in a subject comprising administering to the subject a therapeutically effective amount of an agent that reduces the level of IL-21 and/or IL-21R in the subject, wherein the agent is an IL-21/IL-21R antagonist selected from the group consisting of an anti-IL-21R antibody, an anti-IL-21 antibody, an antigen-binding fragment of an anti-IL-21R antibody, and an antigen-binding fragment of an anti-IL-21 antibody.

2. The method of claim 1, wherein the fibrosis or fibrosis-associated disorder affects the liver, epidermis, endodermis, muscle, tendon, cartilage, heart, pancreas, lung, uterus, nervous system, testis, ovary, adrenal gland, artery, vein, colon, small intestine, biliary tract, or stomach.

3. The method of claim 2, wherein the fibrosis or fibrosis-associated disorder affects the liver, epidermis, endodermis, or lung.

4. The method of claim 3, wherein the fibrosis or fibrosis-associated disorder is interstitial lung fibrosis.

5. The method of claim 2, wherein the fibrosis or fibrosis-associated disorder is the result of an infection with schistosoma.

6. The method of claim 1, wherein the fibrosis or fibrosis-associated disorder is the result of wound healing.

7. The method of claim 6, wherein the wound healing results from a surgical incision.

8. The method of claim 1, wherein the subject is a human.

* * * * *

UNITED STATES PATENT AND TRADEMARK OFFICE

CERTIFICATE OF CORRECTION

PATENT NO. : 7,910,105 B2
APPLICATION NO. : 11/402885
DATED : March 22, 2011
INVENTOR(S) : Deborah A. Young et al.

It is certified that error appears in the above-identified patent and that said Letters Patent is hereby corrected as shown below:

TITLE PG, ITEM [56] REFERENCES CITED:

Foreign Patent Documents, “WO WO2004/083249 9/2004” should be deleted; and “WO WO2004083249 * 9/2004” should read --WO WO 2004/083249 *9/2004--.

TITLE PG, ITEM [56] REFERENCES CITED:

Other Publications, “under Distler et al.” “Arthirtis” should read --Arthritis--.

COLUMN 1:

Line 52, “yc” should read --γc--.

COLUMN 4:

Line 58, “fibrosis-associate” should read --fibrosis-associated--.

COLUMN 5:

Line 21, “IL-Z 1R/MU-1.” should read --IL-21R/MU-1.--.

COLUMN 13:

Line 47, “byreference.” should read --by reference.--.

Signed and Sealed this
Tenth Day of January, 2012

David J. Kappos
*Director of the United States Patent and Trademark Office*

COLUMN 19

TABLE 2-continued

At SEQ ID NO:18, “monomer” should read --extracellular domain (1-235)--; and
At SEQ ID NO:19, “monomer (20-235)” should read --extracellular domain (1-235)--.

COLUMN 20:

Line 63, “yc” should read --γc--.

COLUMN 27:

Line 18, “a culture transformed” should read --transformed--.

COLUMN 32:

Line 17, “IL-21  -related” should read --IL-21-related--.

COLUMN 34:

Line 39, “Ti165,” should read --T1165,--; and
Line 47, “133:32741;” should read --133:327-41;--.

COLUMN 35:

Line 15, “(1  991)” should read --(1991)--.

COLUMN 38:

Line 28, “IL-1  5,” should read --IL-15,--; and “IL-1  7, IL-1  8,” should read --IL-17, IL-18,--;
Line 42, “IL-1  2,” should read --IL-12,--; and
Line 61, “HUMIRATM,” should read --HUMIRA™,--.

COLUMN 39:

Line 1, “LENERCEP™)” should read --LENERCEPT™)--.

COLUMN 40:

Line 9, “NFKb” should read --NFκb--.

COLUMN 41:

Line 31, “NLAID” should read --NIAID--.

COLUMN 45:

Line 43, "$T_H{}^2$" should read --$T_H2$--.

COLUMN 46:

Line 6, "151:143040;" should read --151:1430-40;--;
Line 16, "$T_H{}^1$" should read --$T_H1$--;
Line 38, "TH2Response" should read --$T_H2$ Response--; and
Line 42, "S. mansoni" should be italicized.

COLUMN 47:

Line 9, "were" should read --was--;
Line 27, "TH2-associated" should read --$T_H2$-associated--;
Line 32, "TH2" should read --$T_H2$--; and
Line 55, "IL-2 1 R-deficient" should read --IL-21R-deficient--.

COLUMN 48:

Line 66, "S. mansoni" should be italicized.

COLUMN 49:

Line 58, "IL-13Ra2" should read --IL–13Rα2--.

COLUMN 50:

Line 1, "176:34248" should read --176:342-48--;
Line 34, "$T_H{}^2$" should read --$T_H2$--; and
Line 41, "$T_H{}^2$" should read --$T_H2$--.

COLUMN 51:

Line 44, "IgG2b" should read --$IgG_{2b}$--;
Line 46, "Th2" should read --$T_H2$--; and
Line 50, "$T_{H2}$" should read --$T_H2$--.

COLUMN 52:

Line 49, "AAMρhave" should read --AAMρ have--.

SEQUENCE LISTING

```
<160> NUMBER OF SEQ ID NOS: 35

<210> SEQ ID NO 1
<211> LENGTH: 2665
<212> TYPE: DNA
<213> ORGANISM: Homo sapiens
<220> FEATURE:
<221> NAME/KEY: CDS
<222> LOCATION: (236)..(1849)

<400> SEQUENCE: 1

gtcgactgga ggcccagctg cccgtcatca gagtgacagg tcttatgaca gcctgattgg      60

tgactcgggc tgggtgtgga ttctcacccc aggcctctgc ctgctttctc agaccctcat     120

ctgtcacccc cacgctgaac ccagctgcca cccccagaag cccatcagac tgcccccagc     180

acacggaatg gatttctgag aaagaagccg aaacagaagg cccgtgggag tcagc atg      238
                                                             Met
                                                             1

ccg cgt ggc tgg gcc gcc ccc ttg ctc ctg ctg ctg ctc cag gga ggc      286
Pro Arg Gly Trp Ala Ala Pro Leu Leu Leu Leu Leu Leu Gln Gly Gly
            5                   10                  15

tgg ggc tgc ccc gac ctc gtc tgc tac acc gat tac ctc cag acg gtc      334
Trp Gly Cys Pro Asp Leu Val Cys Tyr Thr Asp Tyr Leu Gln Thr Val
        20                  25                  30

atc tgc atc ctg gaa atg tgg aac ctc cac ccc agc acg ctc acc ctt      382
Ile Cys Ile Leu Glu Met Trp Asn Leu His Pro Ser Thr Leu Thr Leu
    35                  40                  45

acc tgg caa gac cag tat gaa gag ctg aag gac gag gcc acc tcc tgc      430
Thr Trp Gln Asp Gln Tyr Glu Glu Leu Lys Asp Glu Ala Thr Ser Cys
50                  55                  60                  65

agc ctc cac agg tcg gcc cac aat gcc acg cat gcc acc tac acc tgc      478
Ser Leu His Arg Ser Ala His Asn Ala Thr His Ala Thr Tyr Thr Cys
                70                  75                  80

cac atg gat gta ttc cac ttc atg gcc gac gac att ttc agt gtc aac      526
His Met Asp Val Phe His Phe Met Ala Asp Asp Ile Phe Ser Val Asn
            85                  90                  95

atc aca gac cag tct ggc aac tac tcc cag gag tgt ggc agc ttt ctc      574
Ile Thr Asp Gln Ser Gly Asn Tyr Ser Gln Glu Cys Gly Ser Phe Leu
        100                 105                 110

ctg gct gag agc atc aag ccg gct ccc cct ttc aac gtg act gtg acc      622
Leu Ala Glu Ser Ile Lys Pro Ala Pro Pro Phe Asn Val Thr Val Thr
    115                 120                 125

ttc tca gga cag tat aat atc tcc tgg cgc tca gat tac gaa gac cct      670
Phe Ser Gly Gln Tyr Asn Ile Ser Trp Arg Ser Asp Tyr Glu Asp Pro
130                 135                 140                 145

gcc ttc tac atg ctg aag ggc aag ctt cag tat gag ctg cag tac agg      718
Ala Phe Tyr Met Leu Lys Gly Lys Leu Gln Tyr Glu Leu Gln Tyr Arg
                150                 155                 160

aac cgg gga gac ccc tgg gct gtg agt ccg agg aga aag ctg atc tca      766
Asn Arg Gly Asp Pro Trp Ala Val Ser Pro Arg Arg Lys Leu Ile Ser
            165                 170                 175
```

```
gtg gac tca aga agt gtc tcc ctc ctc ccc ctg gag ttc cgc aaa gac      814
Val Asp Ser Arg Ser Val Ser Leu Leu Pro Leu Glu Phe Arg Lys Asp
        180                 185                 190

tcg agc tat gag ctg cag gtg cgg gca ggg ccc atg cct ggc tcc tcc      862
Ser Ser Tyr Glu Leu Gln Val Arg Ala Gly Pro Met Pro Gly Ser Ser
    195                 200                 205

tac cag ggg acc tgg agt gaa tgg agt gac ccg gtc atc ttt cag acc      910
Tyr Gln Gly Thr Trp Ser Glu Trp Ser Asp Pro Val Ile Phe Gln Thr
210                 215                 220                 225

cag tca gag gag tta aag gaa ggc tgg aac cct cac ctg ctg ctt ctc      958
Gln Ser Glu Glu Leu Lys Glu Gly Trp Asn Pro His Leu Leu Leu Leu
                230                 235                 240

ctc ctg ctt gtc ata gtc ttc att cct gcc ttc tgg agc ctg aag acc     1006
Leu Leu Leu Val Ile Val Phe Ile Pro Ala Phe Trp Ser Leu Lys Thr
            245                 250                 255

cat cca ttg tgg agg cta tgg aag aag ata tgg gcc gtc ccc agc cct     1054
His Pro Leu Trp Arg Leu Trp Lys Lys Ile Trp Ala Val Pro Ser Pro
        260                 265                 270

gag cgg ttc ttc atg ccc ctg tac aag ggc tgc agc gga gac ttc aag     1102
Glu Arg Phe Phe Met Pro Leu Tyr Lys Gly Cys Ser Gly Asp Phe Lys
    275                 280                 285

aaa tgg gtg ggt gca ccc ttc act ggc tcc agc ctg gag ctg gga ccc     1150
Lys Trp Val Gly Ala Pro Phe Thr Gly Ser Ser Leu Glu Leu Gly Pro
290                 295                 300                 305

tgg agc cca gag gtg ccc tcc acc ctg gag gtg tac agc tgc cac cca     1198
Trp Ser Pro Glu Val Pro Ser Thr Leu Glu Val Tyr Ser Cys His Pro
                310                 315                 320

cca cgg agc ccg gcc aag agg ctg cag ctc acg gag cta caa gaa cca     1246
Pro Arg Ser Pro Ala Lys Arg Leu Gln Leu Thr Glu Leu Gln Glu Pro
            325                 330                 335

gca gag ctg gtg gag tct gac ggt gtg ccc aag ccc agc ttc tgg ccg     1294
Ala Glu Leu Val Glu Ser Asp Gly Val Pro Lys Pro Ser Phe Trp Pro
        340                 345                 350

aca gcc cag aac tcg ggg ggc tca gct tac agt gag gag agg gat cgg     1342
Thr Ala Gln Asn Ser Gly Gly Ser Ala Tyr Ser Glu Glu Arg Asp Arg
    355                 360                 365

cca tac ggc ctg gtg tcc att gac aca gtg act gtg cta gat gca gag     1390
Pro Tyr Gly Leu Val Ser Ile Asp Thr Val Thr Val Leu Asp Ala Glu
370                 375                 380                 385

ggg cca tgc acc tgg ccc tgc agc tgt gag gat gac ggc tac cca gcc     1438
Gly Pro Cys Thr Trp Pro Cys Ser Cys Glu Asp Asp Gly Tyr Pro Ala
                390                 395                 400

ctg gac ctg gat gct ggc ctg gag ccc agc cca ggc cta gag gac cca     1486
Leu Asp Leu Asp Ala Gly Leu Glu Pro Ser Pro Gly Leu Glu Asp Pro
            405                 410                 415

ctc ttg gat gca ggg acc aca gtc ctg tcc tgt ggc tgt gtc tca gct     1534
Leu Leu Asp Ala Gly Thr Thr Val Leu Ser Cys Gly Cys Val Ser Ala
        420                 425                 430

ggc agc cct ggg cta gga ggg ccc ctg gga agc ctc ctg gac aga cta     1582
Gly Ser Pro Gly Leu Gly Gly Pro Leu Gly Ser Leu Leu Asp Arg Leu
    435                 440                 445

aag cca ccc ctt gca gat ggg gag gac tgg gct ggg gga ctg ccc tgg     1630
Lys Pro Pro Leu Ala Asp Gly Glu Asp Trp Ala Gly Gly Leu Pro Trp
450                 455                 460                 465

ggt ggc cgg tca cct gga ggg gtc tca gag agt gag gcg ggc tca ccc     1678
Gly Gly Arg Ser Pro Gly Gly Val Ser Glu Ser Glu Ala Gly Ser Pro
                470                 475                 480

ctg gcc ggc ctg gat atg gac acg ttt gac agt ggc ttt gtg ggc tct     1726
Leu Ala Gly Leu Asp Met Asp Thr Phe Asp Ser Gly Phe Val Gly Ser
            485                 490                 495
```

```
gac tgc agc agc cct gtg gag tgt gac ttc acc agc ccc ggg gac gaa      1774
Asp Cys Ser Ser Pro Val Glu Cys Asp Phe Thr Ser Pro Gly Asp Glu
        500                 505                 510

gga ccc ccc cgg agc tac ctc cgc cag tgg gtg gtc att cct ccg cca      1822
Gly Pro Pro Arg Ser Tyr Leu Arg Gln Trp Val Val Ile Pro Pro Pro
    515                 520                 525

ctt tcg agc cct gga ccc cag gcc agc taatgaggct gactggatgt            1869
Leu Ser Ser Pro Gly Pro Gln Ala Ser
530                 535

ccagagctgg ccaggccact gggccctgag ccagagacaa ggtcacctgg gctgtgatgt   1929

gaagacacct gcagcctttg gtctcctgga tgggcctttg agcctgatgt ttacagtgtc   1989

tgtgtgtgtg tgtgcatatg tgtgtgtgtg catatgcatg tgtgtgtgtg tgtgtgtctt   2049

aggtgcgcag tggcatgtcc acgtgtgtgt gtgattgcac gtgcctgtgg gcctgggata   2109

atgcccatgg tactccatgc attcacctgc cctgtgcatg tctggactca cggagctcac   2169

ccatgtgcac aagtgtgcac agtaaacgtg tttgtggtca acagatgaca acagccgtcc   2229

tccctcctag ggtcttgtgt tgcaagttgg tccacagcat ctccggggct ttgtgggatc   2289

agggcattgc ctgtgactga ggcggagccc agccctccag cgtctgcctc caggagctgc   2349

aagaagtcca tattgttcct tatcacctgc caacaggaag cgaaagggga tggagtgagc   2409

ccatggtgac ctcgggaatg gcaatttttt gggcggcccc tggacgaagg tctgaatccc   2469

gactctgata ccttctggct gtgctacctg agccaagtcg cctcccctct ctgggctaga   2529

gtttccttat ccagacagtg ggaaggcat gacacacctg gggaaattg gcgatgtcac    2589

ccgtgtacgg tacgcagccc agagcagacc ctcaataaac gtcagcttcc ttcaaaaaaa   2649

aaaaaaaaaa tctaga                                                    2665
```

```
<210> SEQ ID NO 2
<211> LENGTH: 538
<212> TYPE: PRT
<213> ORGANISM: Homo sapiens

<400> SEQUENCE: 2

Met Pro Arg Gly Trp Ala Ala Pro Leu Leu Leu Leu Leu Leu Gln Gly
1               5                   10                  15

Gly Trp Gly Cys Pro Asp Leu Val Cys Tyr Thr Asp Tyr Leu Gln Thr
            20                  25                  30

Val Ile Cys Ile Leu Glu Met Trp Asn Leu His Pro Ser Thr Leu Thr
        35                  40                  45

Leu Thr Trp Gln Asp Gln Tyr Glu Glu Leu Lys Asp Glu Ala Thr Ser
    50                  55                  60

Cys Ser Leu His Arg Ser Ala His Asn Ala Thr His Ala Thr Tyr Thr
65                  70                  75                  80

Cys His Met Asp Val Phe His Phe Met Ala Asp Asp Ile Phe Ser Val
                85                  90                  95

Asn Ile Thr Asp Gln Ser Gly Asn Tyr Ser Gln Glu Cys Gly Ser Phe
            100                 105                 110

Leu Leu Ala Glu Ser Ile Lys Pro Ala Pro Pro Phe Asn Val Thr Val
        115                 120                 125

Thr Phe Ser Gly Gln Tyr Asn Ile Ser Trp Arg Ser Asp Tyr Glu Asp
    130                 135                 140

Pro Ala Phe Tyr Met Leu Lys Gly Lys Leu Gln Tyr Glu Leu Gln Tyr
145                 150                 155                 160

Arg Asn Arg Gly Asp Pro Trp Ala Val Ser Pro Arg Arg Lys Leu Ile
                165                 170                 175
```

```
Ser Val Asp Ser Arg Ser Val Ser Leu Leu Pro Leu Glu Phe Arg Lys
            180                 185                 190

Asp Ser Ser Tyr Glu Leu Gln Val Arg Ala Gly Pro Met Pro Gly Ser
        195                 200                 205

Ser Tyr Gln Gly Thr Trp Ser Glu Trp Ser Asp Pro Val Ile Phe Gln
    210                 215                 220

Thr Gln Ser Glu Glu Leu Lys Glu Gly Trp Asn Pro His Leu Leu Leu
225                 230                 235                 240

Leu Leu Leu Leu Val Ile Val Phe Ile Pro Ala Phe Trp Ser Leu Lys
                245                 250                 255

Thr His Pro Leu Trp Arg Leu Trp Lys Lys Ile Trp Ala Val Pro Ser
            260                 265                 270

Pro Glu Arg Phe Phe Met Pro Leu Tyr Lys Gly Cys Ser Gly Asp Phe
        275                 280                 285

Lys Lys Trp Val Gly Ala Pro Phe Thr Gly Ser Ser Leu Glu Leu Gly
    290                 295                 300

Pro Trp Ser Pro Glu Val Pro Ser Thr Leu Glu Val Tyr Ser Cys His
305                 310                 315                 320

Pro Pro Arg Ser Pro Ala Lys Arg Leu Gln Leu Thr Glu Leu Gln Glu
                325                 330                 335

Pro Ala Glu Leu Val Glu Ser Asp Gly Val Pro Lys Pro Ser Phe Trp
            340                 345                 350

Pro Thr Ala Gln Asn Ser Gly Gly Ser Ala Tyr Ser Glu Glu Arg Asp
        355                 360                 365

Arg Pro Tyr Gly Leu Val Ser Ile Asp Thr Val Thr Val Leu Asp Ala
    370                 375                 380

Glu Gly Pro Cys Thr Trp Pro Cys Ser Cys Glu Asp Asp Gly Tyr Pro
385                 390                 395                 400

Ala Leu Asp Leu Asp Ala Gly Leu Glu Pro Ser Pro Gly Leu Glu Asp
                405                 410                 415

Pro Leu Leu Asp Ala Gly Thr Thr Val Leu Ser Cys Gly Cys Val Ser
            420                 425                 430

Ala Gly Ser Pro Gly Leu Gly Gly Pro Leu Gly Ser Leu Leu Asp Arg
        435                 440                 445

Leu Lys Pro Pro Leu Ala Asp Gly Glu Asp Trp Ala Gly Gly Leu Pro
    450                 455                 460

Trp Gly Gly Arg Ser Pro Gly Gly Val Ser Glu Ser Glu Ala Gly Ser
465                 470                 475                 480

Pro Leu Ala Gly Leu Asp Met Asp Thr Phe Asp Ser Gly Phe Val Gly
                485                 490                 495

Ser Asp Cys Ser Ser Pro Val Glu Cys Asp Phe Thr Ser Pro Gly Asp
            500                 505                 510

Glu Gly Pro Pro Arg Ser Tyr Leu Arg Gln Trp Val Val Ile Pro Pro
        515                 520                 525

Pro Leu Ser Ser Pro Gly Pro Gln Ala Ser
    530                 535

<210> SEQ ID NO 3
<211> LENGTH: 5
<212> TYPE: PRT
<213> ORGANISM: Unknown
<220> FEATURE:
<223> OTHER INFORMATION: Chemokine receptor conserved motif
<220> FEATURE:
<221> NAME/KEY: misc_feature
<222> LOCATION: (3)..(3)
```

<223> OTHER INFORMATION: Xaa can be any naturally occurring amino acid

<400> SEQUENCE: 3

```
Trp Ser Xaa Trp Ser
1               5
```

<210> SEQ ID NO 4
<211> LENGTH: 2628
<212> TYPE: DNA
<213> ORGANISM: Mus musculus
<220> FEATURE:
<221> NAME/KEY: CDS
<222> LOCATION: (407)..(1993)

<400> SEQUENCE: 4

```
gtcgacgcgg cggtaccagc tgtctgccca cttctcctgt ggtgtgcctc acggtcactt      60

gcttgtctga ccgcaagtct gcccatccct ggggcagcca actggcctca gcccgtgccc     120

caggcgtgcc ctgtctctgt ctggctgccc cagccctact gtcttcctct gtgtaggctc     180

tgcccagatg cccggctggt cctcagcctc aggactatct cagcagtgac tcccctgatt     240

ctggacttgc acctgactga actcctgccc acctcaaacc ttcacctccc accaccacca     300

ctccgagtcc cgctgtgact cccacgccca ggagaccacc caagtgcccc agcctaaaga     360

atggctttct gagaaagacc ctgaaggagt aggtctggga cacagc atg ccc cgg        415
                                                   Met Pro Arg
                                                   1

ggc cca gtg gct gcc tta ctc ctg ctg att ctc cat gga gct tgg agc       463
Gly Pro Val Ala Ala Leu Leu Leu Leu Ile Leu His Gly Ala Trp Ser
    5                   10                  15

tgc ctg gac ctc act tgc tac act gac tac ctc tgg acc atc acc tgt       511
Cys Leu Asp Leu Thr Cys Tyr Thr Asp Tyr Leu Trp Thr Ile Thr Cys
20                  25                  30                  35

gtc ctg gag aca cgg agc ccc aac ccc agc ata ctc agt ctc acc tgg       559
Val Leu Glu Thr Arg Ser Pro Asn Pro Ser Ile Leu Ser Leu Thr Trp
                40                  45                  50

caa gat gaa tat gag gaa ctt cag gac caa gag acc ttc tgc agc cta       607
Gln Asp Glu Tyr Glu Glu Leu Gln Asp Gln Glu Thr Phe Cys Ser Leu
            55                  60                  65

cac agg tct ggc cac aac acc aca cat ata tgg tac acg tgc cat atg       655
His Arg Ser Gly His Asn Thr Thr His Ile Trp Tyr Thr Cys His Met
        70                  75                  80

cgc ttg tct caa ttc ctg tcc gat gaa gtt ttc att gtc aat gtg acg       703
Arg Leu Ser Gln Phe Leu Ser Asp Glu Val Phe Ile Val Asn Val Thr
    85                  90                  95

gac cag tct ggc aac aac tcc caa gag tgt ggc agc ttt gtc ctg gct       751
Asp Gln Ser Gly Asn Asn Ser Gln Glu Cys Gly Ser Phe Val Leu Ala
100                 105                 110                 115

gag agc atc aaa cca gct ccc ccc ttg aac gtg act gtg gcc ttc tca       799
Glu Ser Ile Lys Pro Ala Pro Pro Leu Asn Val Thr Val Ala Phe Ser
                120                 125                 130

gga cgc tat gat atc tcc tgg gac tca gct tat gac gaa ccc tcc aac       847
Gly Arg Tyr Asp Ile Ser Trp Asp Ser Ala Tyr Asp Glu Pro Ser Asn
            135                 140                 145

tac gtg ctg agg ggc aag cta caa tat gag ctg cag tat cgg aac ctc       895
Tyr Val Leu Arg Gly Lys Leu Gln Tyr Glu Leu Gln Tyr Arg Asn Leu
        150                 155                 160

aga gac ccc tat gct gtg agg ccg gtg acc aag ctg atc tca gtg gac       943
Arg Asp Pro Tyr Ala Val Arg Pro Val Thr Lys Leu Ile Ser Val Asp
    165                 170                 175

tca aga aac gtc tct ctt ctc cct gaa gag ttc cac aaa gat tct agc       991
Ser Arg Asn Val Ser Leu Leu Pro Glu Glu Phe His Lys Asp Ser Ser
```

-continued

```
180                 185                 190                 195

tac cag ctg cag gtg cgg gca gcg cct cag cca ggc act tca ttc agg      1039
Tyr Gln Leu Gln Val Arg Ala Ala Pro Gln Pro Gly Thr Ser Phe Arg
                200                 205                 210

ggg acc tgg agt gag tgg agt gac ccc gtc atc ttt cag acc cag gct      1087
Gly Thr Trp Ser Glu Trp Ser Asp Pro Val Ile Phe Gln Thr Gln Ala
            215                 220                 225

ggg gag ccc gag gca ggc tgg gac cct cac atg ctg ctg ctc ctg gct      1135
Gly Glu Pro Glu Ala Gly Trp Asp Pro His Met Leu Leu Leu Leu Ala
        230                 235                 240

gtc ttg atc att gtc ctg gtt ttc atg ggt ctg aag atc cac ctg cct      1183
Val Leu Ile Ile Val Leu Val Phe Met Gly Leu Lys Ile His Leu Pro
    245                 250                 255

tgg agg cta tgg aaa aag ata tgg gca cca gtg ccc acc cct gag agt      1231
Trp Arg Leu Trp Lys Lys Ile Trp Ala Pro Val Pro Thr Pro Glu Ser
260                 265                 270                 275

ttc ttc cag ccc ctg tac agg gag cac agc ggg aac ttc aag aaa tgg      1279
Phe Phe Gln Pro Leu Tyr Arg Glu His Ser Gly Asn Phe Lys Lys Trp
                280                 285                 290

gtt aat acc cct ttc acg gcc tcc agc ata gag ttg gtg cca cag agt      1327
Val Asn Thr Pro Phe Thr Ala Ser Ser Ile Glu Leu Val Pro Gln Ser
            295                 300                 305

tcc aca aca aca tca gcc tta cat ctg tca ttg tat cca gcc aag gag      1375
Ser Thr Thr Thr Ser Ala Leu His Leu Ser Leu Tyr Pro Ala Lys Glu
        310                 315                 320

aag aag ttc ccg ggg ctg ccg ggt ctg gaa gag caa ctg gag tgt gat      1423
Lys Lys Phe Pro Gly Leu Pro Gly Leu Glu Glu Gln Leu Glu Cys Asp
    325                 330                 335

gga atg tct gag cct ggt cac tgg tgc ata atc ccc ttg gca gct ggc      1471
Gly Met Ser Glu Pro Gly His Trp Cys Ile Ile Pro Leu Ala Ala Gly
340                 345                 350                 355

caa gcg gtc tca gcc tac agt gag gag aga gac cgg cca tat ggt ctg      1519
Gln Ala Val Ser Ala Tyr Ser Glu Glu Arg Asp Arg Pro Tyr Gly Leu
                360                 365                 370

gtg tcc att gac aca gtg act gtg gga gat gca gag ggc ctg tgt gtc      1567
Val Ser Ile Asp Thr Val Thr Val Gly Asp Ala Glu Gly Leu Cys Val
            375                 380                 385

tgg ccc tgt agc tgt gag gat gat ggc tat cca gcc atg aac ctg gat      1615
Trp Pro Cys Ser Cys Glu Asp Asp Gly Tyr Pro Ala Met Asn Leu Asp
        390                 395                 400

gct ggc cga gag tct ggc cct aat tca gag gat ctg ctc ttg gtc aca      1663
Ala Gly Arg Glu Ser Gly Pro Asn Ser Glu Asp Leu Leu Leu Val Thr
    405                 410                 415

gac cct gct ttt ctg tct tgc ggc tgt gtc tca ggt agt ggt ctc agg      1711
Asp Pro Ala Phe Leu Ser Cys Gly Cys Val Ser Gly Ser Gly Leu Arg
420                 425                 430                 435

ctt gga ggc tcc cca ggc agc cta ctg gac agg ttg agg ctg tca ttt      1759
Leu Gly Gly Ser Pro Gly Ser Leu Leu Asp Arg Leu Arg Leu Ser Phe
                440                 445                 450

gca aag gaa ggg gac tgg aca gca gac cca acc tgg aga act ggg tcc      1807
Ala Lys Glu Gly Asp Trp Thr Ala Asp Pro Thr Trp Arg Thr Gly Ser
            455                 460                 465

cca gga ggg ggc tct gag agt gaa gca ggt tcc ccc cct ggt ctg gac      1855
Pro Gly Gly Gly Ser Glu Ser Glu Ala Gly Ser Pro Pro Gly Leu Asp
        470                 475                 480

atg gac aca ttt gac agt ggc ttt gca ggt tca gac tgt ggc agc ccc      1903
Met Asp Thr Phe Asp Ser Gly Phe Ala Gly Ser Asp Cys Gly Ser Pro
    485                 490                 495

gtg gag act gat gaa gga ccc cct cga agc tat ctc cgc cag tgg gtg      1951
Val Glu Thr Asp Glu Gly Pro Pro Arg Ser Tyr Leu Arg Gln Trp Val
```

```
500                 505                 510                 515

gtc agg acc cct cca cct gtg gac agt gga gcc cag agc agc             1993
Val Arg Thr Pro Pro Pro Val Asp Ser Gly Ala Gln Ser Ser
                520                 525

tagcatataa taaccagcta tagtgagaag aggcctctga gcctggcatt tacagtgtga   2053

acatgtaggg gtgtgtgtgt gtgtgtgtgt gtgtgtgtgt gtgtgtgtgt gtgtgtgtgt   2113

gtgtgtgtgt cttgggttgt gtgttagcac atccatgttg ggatttggtc tgttgctatg   2173

tattgtaatg ctaaattctc tacccaaagt tctaggccta cgagtgaatt ctcatgttta   2233

caaacttgct gtgtaaacct tgttccttaa tttaatacca ttggttaaat aaaattggct   2293

gcaaccaatt actggaggga ttagaggtag ggggcttttg agttacctgt ttggagatgg   2353

agaaggagag aggagagacc aagaggagaa ggaggaagga gaggagagga gaggagagga   2413

gaggagagga gaggagagga gaggagagga gaggagaggc tgccgtgagg ggagagggac   2473

catgagcctg tggccaggag aaacagcaag tatctggggt acactggtga ggaggtggcc   2533

aggccagcag ttagaagagt agattagggg tgacctccag tatttgtcaa agccaattaa   2593

aataacaaaa aaaaaaaaaa agcggccgct ctaga                               2628


<210> SEQ ID NO 5
<211> LENGTH: 529
<212> TYPE: PRT
<213> ORGANISM: Mus musculus

<400> SEQUENCE: 5

Met Pro Arg Gly Pro Val Ala Ala Leu Leu Leu Leu Ile Leu His Gly
1               5                   10                  15

Ala Trp Ser Cys Leu Asp Leu Thr Cys Tyr Thr Asp Tyr Leu Trp Thr
            20                  25                  30

Ile Thr Cys Val Leu Glu Thr Arg Ser Pro Asn Pro Ser Ile Leu Ser
        35                  40                  45

Leu Thr Trp Gln Asp Glu Tyr Glu Glu Leu Gln Asp Gln Glu Thr Phe
    50                  55                  60

Cys Ser Leu His Arg Ser Gly His Asn Thr Thr His Ile Trp Tyr Thr
65                  70                  75                  80

Cys His Met Arg Leu Ser Gln Phe Leu Ser Asp Glu Val Phe Ile Val
                85                  90                  95

Asn Val Thr Asp Gln Ser Gly Asn Asn Ser Gln Glu Cys Gly Ser Phe
            100                 105                 110

Val Leu Ala Glu Ser Ile Lys Pro Ala Pro Pro Leu Asn Val Thr Val
        115                 120                 125

Ala Phe Ser Gly Arg Tyr Asp Ile Ser Trp Asp Ser Ala Tyr Asp Glu
    130                 135                 140

Pro Ser Asn Tyr Val Leu Arg Gly Lys Leu Gln Tyr Glu Leu Gln Tyr
145                 150                 155                 160

Arg Asn Leu Arg Asp Pro Tyr Ala Val Arg Pro Val Thr Lys Leu Ile
                165                 170                 175

Ser Val Asp Ser Arg Asn Val Ser Leu Leu Pro Glu Glu Phe His Lys
            180                 185                 190

Asp Ser Ser Tyr Gln Leu Gln Val Arg Ala Ala Pro Gln Pro Gly Thr
        195                 200                 205

Ser Phe Arg Gly Thr Trp Ser Glu Trp Ser Asp Pro Val Ile Phe Gln
    210                 215                 220

Thr Gln Ala Gly Glu Pro Glu Ala Gly Trp Asp Pro His Met Leu Leu
225                 230                 235                 240
```

```
Leu Leu Ala Val Leu Ile Ile Val Leu Val Phe Met Gly Leu Lys Ile
                245                 250                 255

His Leu Pro Trp Arg Leu Trp Lys Lys Ile Trp Ala Pro Val Pro Thr
            260                 265                 270

Pro Glu Ser Phe Phe Gln Pro Leu Tyr Arg Glu His Ser Gly Asn Phe
        275                 280                 285

Lys Lys Trp Val Asn Thr Pro Phe Thr Ala Ser Ser Ile Glu Leu Val
    290                 295                 300

Pro Gln Ser Ser Thr Thr Thr Ser Ala Leu His Leu Ser Leu Tyr Pro
305                 310                 315                 320

Ala Lys Glu Lys Lys Phe Pro Gly Leu Pro Gly Leu Glu Glu Gln Leu
                325                 330                 335

Glu Cys Asp Gly Met Ser Glu Pro Gly His Trp Cys Ile Ile Pro Leu
            340                 345                 350

Ala Ala Gly Gln Ala Val Ser Ala Tyr Ser Glu Glu Arg Asp Arg Pro
        355                 360                 365

Tyr Gly Leu Val Ser Ile Asp Thr Val Thr Val Gly Asp Ala Glu Gly
    370                 375                 380

Leu Cys Val Trp Pro Cys Ser Cys Glu Asp Asp Gly Tyr Pro Ala Met
385                 390                 395                 400

Asn Leu Asp Ala Gly Arg Glu Ser Gly Pro Asn Ser Glu Asp Leu Leu
                405                 410                 415

Leu Val Thr Asp Pro Ala Phe Leu Ser Cys Gly Cys Val Ser Gly Ser
            420                 425                 430

Gly Leu Arg Leu Gly Gly Ser Pro Gly Ser Leu Leu Asp Arg Leu Arg
        435                 440                 445

Leu Ser Phe Ala Lys Glu Gly Asp Trp Thr Ala Asp Pro Thr Trp Arg
    450                 455                 460

Thr Gly Ser Pro Gly Gly Gly Ser Glu Ser Glu Ala Gly Ser Pro Pro
465                 470                 475                 480

Gly Leu Asp Met Asp Thr Phe Asp Ser Gly Phe Ala Gly Ser Asp Cys
                485                 490                 495

Gly Ser Pro Val Glu Thr Asp Glu Gly Pro Pro Arg Ser Tyr Leu Arg
            500                 505                 510

Gln Trp Val Val Arg Thr Pro Pro Pro Val Asp Ser Gly Ala Gln Ser
        515                 520                 525

Ser
```

<210> SEQ ID NO 6
<211> LENGTH: 224
<212> TYPE: PRT
<213> ORGANISM: Unknown
<220> FEATURE:
<223> OTHER INFORMATION: Immunoglobulin Fc Fragment

<400> SEQUENCE: 6

```
His Thr Cys Pro Pro Cys Pro Ala Pro Glu Ala Leu Gly Ala Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
```

-continued

```
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Val Pro Ile Glu Lys Thr
            100                 105                 110

Ile Ser Lys Ala Lys Gly Gln Pro Arg Glu Pro Gln Val Tyr Thr Leu
        115                 120                 125

Pro Pro Ser Arg Glu Glu Met Thr Lys Asn Gln Val Ser Leu Thr Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly Lys
    210                 215                 220


<210> SEQ ID NO 7
<211> LENGTH: 617
<212> TYPE: DNA
<213> ORGANISM: Homo sapiens
<220> FEATURE:
<221> NAME/KEY: CDS
<222> LOCATION: (47)..(532)

<400> SEQUENCE: 7

gctgaagtga aaacgagacc aaggtctagc tctactgttg gtactt atg aga tcc        55
                                                   Met Arg Ser
                                                   1

agt cct ggc aac atg gag agg att gtc atc tgt ctg atg gtc atc ttc      103
Ser Pro Gly Asn Met Glu Arg Ile Val Ile Cys Leu Met Val Ile Phe
    5                   10                  15

ttg ggg aca ctg gtc cac aaa tca agc tcc caa ggt caa gat cgc cac      151
Leu Gly Thr Leu Val His Lys Ser Ser Ser Gln Gly Gln Asp Arg His
20                  25                  30                  35

atg att aga atg cgt caa ctt ata gat att gtt gat cag ctg aaa aat      199
Met Ile Arg Met Arg Gln Leu Ile Asp Ile Val Asp Gln Leu Lys Asn
                40                  45                  50

tat gtg aat gac ttg gtc cct gaa ttt ctg cca gct cca gaa gat gta      247
Tyr Val Asn Asp Leu Val Pro Glu Phe Leu Pro Ala Pro Glu Asp Val
            55                  60                  65

gag aca aac tgt gag tgg tca gct ttt tcc tgc ttt cag aag gcc caa      295
Glu Thr Asn Cys Glu Trp Ser Ala Phe Ser Cys Phe Gln Lys Ala Gln
        70                  75                  80

cta aag tca gca aat aca gga aac aat gaa agg ata atc aat gta tca      343
Leu Lys Ser Ala Asn Thr Gly Asn Asn Glu Arg Ile Ile Asn Val Ser
    85                  90                  95

att aaa aag ctg aag agg aaa cca cct tcc aca aat gca ggg aga aga      391
Ile Lys Lys Leu Lys Arg Lys Pro Pro Ser Thr Asn Ala Gly Arg Arg
100                 105                 110                 115

cag aaa cac aga cta aca tgc cct tca tgt gat tct tat gag aaa aaa      439
Gln Lys His Arg Leu Thr Cys Pro Ser Cys Asp Ser Tyr Glu Lys Lys
                120                 125                 130

cca ccc aaa gaa ttc cta gaa aga ttc aaa tca ctt ctc caa aag atg      487
Pro Pro Lys Glu Phe Leu Glu Arg Phe Lys Ser Leu Leu Gln Lys Met
            135                 140                 145
```

```
att cat cag cat ctg tcc tct aga aca cac gga agt gaa gat tcc          532
Ile His Gln His Leu Ser Ser Arg Thr His Gly Ser Glu Asp Ser
        150                 155                 160

tgaggatcta acttgcagtt ggacactatg ttacatactc taatatagta gtgaaagtca    592

tttctttgta ttccaagtgg aggag                                          617


<210> SEQ ID NO 8
<211> LENGTH: 162
<212> TYPE: PRT
<213> ORGANISM: Homo sapiens

<400> SEQUENCE: 8

Met Arg Ser Ser Pro Gly Asn Met Glu Arg Ile Val Ile Cys Leu Met
1               5                   10                  15

Val Ile Phe Leu Gly Thr Leu Val His Lys Ser Ser Ser Gln Gly Gln
            20                  25                  30

Asp Arg His Met Ile Arg Met Arg Gln Leu Ile Asp Ile Val Asp Gln
        35                  40                  45

Leu Lys Asn Tyr Val Asn Asp Leu Val Pro Glu Phe Leu Pro Ala Pro
    50                  55                  60

Glu Asp Val Glu Thr Asn Cys Glu Trp Ser Ala Phe Ser Cys Phe Gln
65                  70                  75                  80

Lys Ala Gln Leu Lys Ser Ala Asn Thr Gly Asn Asn Glu Arg Ile Ile
                85                  90                  95

Asn Val Ser Ile Lys Lys Leu Lys Arg Lys Pro Pro Ser Thr Asn Ala
            100                 105                 110

Gly Arg Arg Gln Lys His Arg Leu Thr Cys Pro Ser Cys Asp Ser Tyr
        115                 120                 125

Glu Lys Lys Pro Pro Lys Glu Phe Leu Glu Arg Phe Lys Ser Leu Leu
    130                 135                 140

Gln Lys Met Ile His Gln His Leu Ser Ser Arg Thr His Gly Ser Glu
145                 150                 155                 160

Asp Ser


<210> SEQ ID NO 9
<211> LENGTH: 16
<212> TYPE: PRT
<213> ORGANISM: Apis mellifera

<400> SEQUENCE: 9

Met Pro Leu Leu Leu Leu Leu Leu Leu Leu Pro Ser Pro Leu His Pro
1               5                   10                  15


<210> SEQ ID NO 10
<211> LENGTH: 786
<212> TYPE: DNA
<213> ORGANISM: Homo sapiens
<220> FEATURE:
<221> NAME/KEY: CDS
<222> LOCATION: (1)..(780)

<400> SEQUENCE: 10

atg aaa ttc tta gtc aac gtt gcc ctt gtt ttt atg gtc gtg tac att       48
Met Lys Phe Leu Val Asn Val Ala Leu Val Phe Met Val Val Tyr Ile
1               5                   10                  15

tct tac atc tat gcc ggc agc gga cac cac cat cat cac cac ggt agc       96
Ser Tyr Ile Tyr Ala Gly Ser Gly His His His His His His Gly Ser
            20                  25                  30

ggc gac tat aaa gac gat gac gat aag ggt tcc gga tgc ccc gac ctc      144
Gly Asp Tyr Lys Asp Asp Asp Asp Lys Gly Ser Gly Cys Pro Asp Leu
```

-continued

```
        35                  40                  45

gtc tgc tac acc gat tac ctc cag acg gtc atc tgc atc ctg gaa atg       192
Val Cys Tyr Thr Asp Tyr Leu Gln Thr Val Ile Cys Ile Leu Glu Met
    50                  55                  60

tgg aac ctc cac ccc agc acg ctc acc ctt acc tgg caa gac cag tat       240
Trp Asn Leu His Pro Ser Thr Leu Thr Leu Thr Trp Gln Asp Gln Tyr
65                  70                  75                  80

gaa gag ctg aag gac gag gcc acc tcc tgc agc ctc cac agg tcg gcc       288
Glu Glu Leu Lys Asp Glu Ala Thr Ser Cys Ser Leu His Arg Ser Ala
                85                  90                  95

cac aat gcc acg cat gcc acc tac acc tgc cac atg gat gta ttc cac       336
His Asn Ala Thr His Ala Thr Tyr Thr Cys His Met Asp Val Phe His
            100                 105                 110

ttc atg gcc gac gac att ttc agt gtc aac atc aca gac cag tct ggc       384
Phe Met Ala Asp Asp Ile Phe Ser Val Asn Ile Thr Asp Gln Ser Gly
        115                 120                 125

aac tac tcc cag gag tgt ggc agc ttt ctc ctg gct gag agc atc aag       432
Asn Tyr Ser Gln Glu Cys Gly Ser Phe Leu Leu Ala Glu Ser Ile Lys
    130                 135                 140

ccg gct ccc cct ttc aac gtg act gtg acc ttc tca gga cag tat aat       480
Pro Ala Pro Pro Phe Asn Val Thr Val Thr Phe Ser Gly Gln Tyr Asn
145                 150                 155                 160

atc tcc tgg cgc tca gat tac gaa gac cct gcc ttc tac atg ctg aag       528
Ile Ser Trp Arg Ser Asp Tyr Glu Asp Pro Ala Phe Tyr Met Leu Lys
                165                 170                 175

ggc aag ctt cag tat gag ctg cag tac agg aac cgg gga gac ccc tgg       576
Gly Lys Leu Gln Tyr Glu Leu Gln Tyr Arg Asn Arg Gly Asp Pro Trp
            180                 185                 190

gct gtg agt ccg agg aga aag ctg atc tca gtg gac tca aga agt gtc       624
Ala Val Ser Pro Arg Arg Lys Leu Ile Ser Val Asp Ser Arg Ser Val
        195                 200                 205

tcc ctc ctc ccc ctg gag ttc cgc aaa gac tcg agc tat gag ctg cag       672
Ser Leu Leu Pro Leu Glu Phe Arg Lys Asp Ser Ser Tyr Glu Leu Gln
    210                 215                 220

gtg cgg gca ggg ccc atg cct ggc tcc tcc tac cag ggg acc tgg agt       720
Val Arg Ala Gly Pro Met Pro Gly Ser Ser Tyr Gln Gly Thr Trp Ser
225                 230                 235                 240

gaa tgg agt gac ccg gtc atc ttt cag acc cag tca gag gag tta aag       768
Glu Trp Ser Asp Pro Val Ile Phe Gln Thr Gln Ser Glu Glu Leu Lys
                245                 250                 255

gaa ggc tgg aac taatga                                                786
Glu Gly Trp Asn
            260


<210> SEQ ID NO 11
<211> LENGTH: 260
<212> TYPE: PRT
<213> ORGANISM: Homo sapiens

<400> SEQUENCE: 11

Met Lys Phe Leu Val Asn Val Ala Leu Val Phe Met Val Val Tyr Ile
1               5                   10                  15

Ser Tyr Ile Tyr Ala Gly Ser Gly His His His His His His Gly Ser
            20                  25                  30

Gly Asp Tyr Lys Asp Asp Asp Asp Lys Gly Ser Gly Cys Pro Asp Leu
        35                  40                  45

Val Cys Tyr Thr Asp Tyr Leu Gln Thr Val Ile Cys Ile Leu Glu Met
    50                  55                  60

Trp Asn Leu His Pro Ser Thr Leu Thr Leu Thr Trp Gln Asp Gln Tyr
65                  70                  75                  80
```

```
Glu Glu Leu Lys Asp Glu Ala Thr Ser Cys Ser Leu His Arg Ser Ala
                85                  90                  95

His Asn Ala Thr His Ala Thr Tyr Thr Cys His Met Asp Val Phe His
            100                 105                 110

Phe Met Ala Asp Asp Ile Phe Ser Val Asn Ile Thr Asp Gln Ser Gly
        115                 120                 125

Asn Tyr Ser Gln Glu Cys Gly Ser Phe Leu Leu Ala Glu Ser Ile Lys
    130                 135                 140

Pro Ala Pro Pro Phe Asn Val Thr Val Thr Phe Ser Gly Gln Tyr Asn
145                 150                 155                 160

Ile Ser Trp Arg Ser Asp Tyr Glu Asp Pro Ala Phe Tyr Met Leu Lys
                165                 170                 175

Gly Lys Leu Gln Tyr Glu Leu Gln Tyr Arg Asn Arg Gly Asp Pro Trp
            180                 185                 190

Ala Val Ser Pro Arg Arg Lys Leu Ile Ser Val Asp Ser Arg Ser Val
        195                 200                 205

Ser Leu Leu Pro Leu Glu Phe Arg Lys Asp Ser Ser Tyr Glu Leu Gln
    210                 215                 220

Val Arg Ala Gly Pro Met Pro Gly Ser Ser Tyr Gln Gly Thr Trp Ser
225                 230                 235                 240

Glu Trp Ser Asp Pro Val Ile Phe Gln Thr Gln Ser Glu Glu Leu Lys
                245                 250                 255

Glu Gly Trp Asn
            260


<210> SEQ ID NO 12
<211> LENGTH: 1472
<212> TYPE: DNA
<213> ORGANISM: Homo sapiens
<220> FEATURE:
<221> NAME/KEY: CDS
<222> LOCATION: (15)..(1415)

<400> SEQUENCE: 12

gcggccgcac cacc atg ccg cgt ggc tgg gcc gcc ccc ttg ctc ctg ctg      50
                Met Pro Arg Gly Trp Ala Ala Pro Leu Leu Leu Leu
                1               5                   10

ctg ctc cag gga ggc tgg ggc tgc ccc gac ctc gtc tgc tac acc gat      98
Leu Leu Gln Gly Gly Trp Gly Cys Pro Asp Leu Val Cys Tyr Thr Asp
        15                  20                  25

tac ctc cag acg gtc atc tgc atc ctg gaa atg tgg aac ctc cac ccc     146
Tyr Leu Gln Thr Val Ile Cys Ile Leu Glu Met Trp Asn Leu His Pro
    30                  35                  40

agc acg ctc acc ctt acc tgg caa gac cag tat gaa gag ctg aag gac     194
Ser Thr Leu Thr Leu Thr Trp Gln Asp Gln Tyr Glu Glu Leu Lys Asp
45                  50                  55                  60

gag gcc acc tcc tgc agc ctc cac agg tcg gcc cac aat gcc acg cat     242
Glu Ala Thr Ser Cys Ser Leu His Arg Ser Ala His Asn Ala Thr His
                65                  70                  75

gcc acc tac acc tgc cac atg gat gta ttc cac ttc atg gcc gac gac     290
Ala Thr Tyr Thr Cys His Met Asp Val Phe His Phe Met Ala Asp Asp
            80                  85                  90

att ttc agt gtc aac atc aca gac cag tct ggc aac tac tcc cag gag     338
Ile Phe Ser Val Asn Ile Thr Asp Gln Ser Gly Asn Tyr Ser Gln Glu
        95                  100                 105

tgt ggc agc ttt ctc ctg gct gag agc atc aag ccg gct ccc cct ttc     386
Cys Gly Ser Phe Leu Leu Ala Glu Ser Ile Lys Pro Ala Pro Pro Phe
    110                 115                 120
```

-continued

```
aac gtg act gtg acc ttc tca gga cag tat aat atc tcc tgg cgc tca       434
Asn Val Thr Val Thr Phe Ser Gly Gln Tyr Asn Ile Ser Trp Arg Ser
125                 130                 135                 140

gat tac gaa gac cct gcc ttc tac atg ctg aag ggc aag ctt cag tat       482
Asp Tyr Glu Asp Pro Ala Phe Tyr Met Leu Lys Gly Lys Leu Gln Tyr
                145                 150                 155

gag ctg cag tac agg aac cgg gga gac ccc tgg gct gtg agt ccg agg       530
Glu Leu Gln Tyr Arg Asn Arg Gly Asp Pro Trp Ala Val Ser Pro Arg
            160                 165                 170

aga aag ctg atc tca gtg gac tca aga agt gtc tcc ctc ctc ccc ctg       578
Arg Lys Leu Ile Ser Val Asp Ser Arg Ser Val Ser Leu Leu Pro Leu
        175                 180                 185

gag ttc cgc aaa gac tcg agc tat gag ctg cag gtg cgg gca ggg ccc       626
Glu Phe Arg Lys Asp Ser Ser Tyr Glu Leu Gln Val Arg Ala Gly Pro
    190                 195                 200

atg cct ggc tcc tcc tac cag ggg acc tgg agt gaa tgg agt gac ccg       674
Met Pro Gly Ser Ser Tyr Gln Gly Thr Trp Ser Glu Trp Ser Asp Pro
205                 210                 215                 220

gtc atc ttt cag acc cag tca gag gag tta aag gaa ggc tgg aac ggc       722
Val Ile Phe Gln Thr Gln Ser Glu Glu Leu Lys Glu Gly Trp Asn Gly
                225                 230                 235

tcc ggc tct aga gac aaa act cac aca tgc cca ccg tgc cca gca cct       770
Ser Gly Ser Arg Asp Lys Thr His Thr Cys Pro Pro Cys Pro Ala Pro
            240                 245                 250

gaa ctc ctg ggg gga ccg tca gtc ttc ctc ttc ccc cca aaa ccc aag       818
Glu Leu Leu Gly Gly Pro Ser Val Phe Leu Phe Pro Pro Lys Pro Lys
        255                 260                 265

gac acc ctc atg atc tcc cgg acc cct gag gtc aca tgc gtg gtg gtg       866
Asp Thr Leu Met Ile Ser Arg Thr Pro Glu Val Thr Cys Val Val Val
    270                 275                 280

gac gtg agc cac gaa gac cct gag gtc aag ttc aac tgg tac gtg gac       914
Asp Val Ser His Glu Asp Pro Glu Val Lys Phe Asn Trp Tyr Val Asp
285                 290                 295                 300

ggc gtg gag gtg cat aat gcc aag aca aag ccg cgg gag gag cag tac       962
Gly Val Glu Val His Asn Ala Lys Thr Lys Pro Arg Glu Glu Gln Tyr
                305                 310                 315

aac agc acg tac cgt gtg gtc agc gtc ctc acc gtc ctg cac cag gac      1010
Asn Ser Thr Tyr Arg Val Val Ser Val Leu Thr Val Leu His Gln Asp
            320                 325                 330

tgg ctg aat ggc aag gag tac aag tgc aag gtc tcc aac aaa gcc ctc      1058
Trp Leu Asn Gly Lys Glu Tyr Lys Cys Lys Val Ser Asn Lys Ala Leu
        335                 340                 345

cca gtc ccc atc gag aaa acc atc tcc aaa gcc aaa ggg cag ccc cga      1106
Pro Val Pro Ile Glu Lys Thr Ile Ser Lys Ala Lys Gly Gln Pro Arg
    350                 355                 360

gaa cca cag gtg tac acc ctg ccc cca tcc cgg gag gag atg acc aag      1154
Glu Pro Gln Val Tyr Thr Leu Pro Pro Ser Arg Glu Glu Met Thr Lys
365                 370                 375                 380

aac cag gtc agc ctg acc tgc ctg gtc aaa ggc ttc tat ccc agc gac      1202
Asn Gln Val Ser Leu Thr Cys Leu Val Lys Gly Phe Tyr Pro Ser Asp
                385                 390                 395

atc gcc gtg gag tgg gag agc aat ggg cag ccg gag aac aac tac aag      1250
Ile Ala Val Glu Trp Glu Ser Asn Gly Gln Pro Glu Asn Asn Tyr Lys
            400                 405                 410

acc acg cct ccc gtg ctg gac tcc gac ggc tcc ttc ttc ctc tat agc      1298
Thr Thr Pro Pro Val Leu Asp Ser Asp Gly Ser Phe Phe Leu Tyr Ser
        415                 420                 425

aag ctc acc gtg gac aag agc agg tgg cag cag ggg aac gtc ttc tca      1346
Lys Leu Thr Val Asp Lys Ser Arg Trp Gln Gln Gly Asn Val Phe Ser
    430                 435                 440
```

-continued

```
tgc tcc gtg atg cat gag gct ctg cac aac cac tac acg cag aag agc      1394
Cys Ser Val Met His Glu Ala Leu His Asn His Tyr Thr Gln Lys Ser
445                 450                 455                 460

ctc tcc ctg tcc ccg ggt aaa tgagtgaatt cacacgcaga agagcctctc        1445
Leu Ser Leu Ser Pro Gly Lys
                465

cctgtccccg ggtaaatgag tgaattc                                        1472


<210> SEQ ID NO 13
<211> LENGTH: 467
<212> TYPE: PRT
<213> ORGANISM: Homo sapiens

<400> SEQUENCE: 13

Met Pro Arg Gly Trp Ala Ala Pro Leu Leu Leu Leu Leu Leu Gln Gly
1               5                   10                  15

Gly Trp Gly Cys Pro Asp Leu Val Cys Tyr Thr Asp Tyr Leu Gln Thr
            20                  25                  30

Val Ile Cys Ile Leu Glu Met Trp Asn Leu His Pro Ser Thr Leu Thr
        35                  40                  45

Leu Thr Trp Gln Asp Gln Tyr Glu Glu Leu Lys Asp Glu Ala Thr Ser
    50                  55                  60

Cys Ser Leu His Arg Ser Ala His Asn Ala Thr His Ala Thr Tyr Thr
65                  70                  75                  80

Cys His Met Asp Val Phe His Phe Met Ala Asp Asp Ile Phe Ser Val
                85                  90                  95

Asn Ile Thr Asp Gln Ser Gly Asn Tyr Ser Gln Glu Cys Gly Ser Phe
            100                 105                 110

Leu Leu Ala Glu Ser Ile Lys Pro Ala Pro Pro Phe Asn Val Thr Val
        115                 120                 125

Thr Phe Ser Gly Gln Tyr Asn Ile Ser Trp Arg Ser Asp Tyr Glu Asp
    130                 135                 140

Pro Ala Phe Tyr Met Leu Lys Gly Lys Leu Gln Tyr Glu Leu Gln Tyr
145                 150                 155                 160

Arg Asn Arg Gly Asp Pro Trp Ala Val Ser Pro Arg Arg Lys Leu Ile
                165                 170                 175

Ser Val Asp Ser Arg Ser Val Ser Leu Leu Pro Leu Glu Phe Arg Lys
            180                 185                 190

Asp Ser Ser Tyr Glu Leu Gln Val Arg Ala Gly Pro Met Pro Gly Ser
        195                 200                 205

Ser Tyr Gln Gly Thr Trp Ser Glu Trp Ser Asp Pro Val Ile Phe Gln
    210                 215                 220

Thr Gln Ser Glu Glu Leu Lys Glu Gly Trp Asn Gly Ser Gly Ser Arg
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335
```

```
Lys Glu Tyr Lys Cys Lys Val Ser Asn Lys Ala Leu Pro Val Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465
```

```
<210> SEQ ID NO 14
<211> LENGTH: 1499
<212> TYPE: DNA
<213> ORGANISM: Homo sapiens
<220> FEATURE:
<221> NAME/KEY: CDS
<222> LOCATION: (15)..(1493)

<400> SEQUENCE: 14

gcggccgcac cacc atg ccg cgt ggc tgg gcc gcc ccc ttg ctc ctg ctg        50
                Met Pro Arg Gly Trp Ala Ala Pro Leu Leu Leu Leu
                1               5                   10

ctg ctc cag gga ggc tgg ggc tgc ccc gac ctc gtc tgc tac acc gat        98
Leu Leu Gln Gly Gly Trp Gly Cys Pro Asp Leu Val Cys Tyr Thr Asp
        15                  20                  25

tac ctc cag acg gtc atc tgc atc ctg gaa atg tgg aac ctc cac ccc       146
Tyr Leu Gln Thr Val Ile Cys Ile Leu Glu Met Trp Asn Leu His Pro
    30                  35                  40

agc acg ctc acc ctt acc tgg caa gac cag tat gaa gag ctg aag gac       194
Ser Thr Leu Thr Leu Thr Trp Gln Asp Gln Tyr Glu Glu Leu Lys Asp
45                  50                  55                  60

gag gcc acc tcc tgc agc ctc cac agg tcg gcc cac aat gcc acg cat       242
Glu Ala Thr Ser Cys Ser Leu His Arg Ser Ala His Asn Ala Thr His
                65                  70                  75

gcc acc tac acc tgc cac atg gat gta ttc cac ttc atg gcc gac gac       290
Ala Thr Tyr Thr Cys His Met Asp Val Phe His Phe Met Ala Asp Asp
            80                  85                  90

att ttc agt gtc aac atc aca gac cag tct ggc aac tac tcc cag gag       338
Ile Phe Ser Val Asn Ile Thr Asp Gln Ser Gly Asn Tyr Ser Gln Glu
        95                  100                 105

tgt ggc agc ttt ctc ctg gct gag agc atc aag ccg gct ccc cct ttc       386
Cys Gly Ser Phe Leu Leu Ala Glu Ser Ile Lys Pro Ala Pro Pro Phe
    110                 115                 120

aac gtg act gtg acc ttc tca gga cag tat aat atc tcc tgg cgc tca       434
Asn Val Thr Val Thr Phe Ser Gly Gln Tyr Asn Ile Ser Trp Arg Ser
125                 130                 135                 140

gat tac gaa gac cct gcc ttc tac atg ctg aag ggc aag ctt cag tat       482
Asp Tyr Glu Asp Pro Ala Phe Tyr Met Leu Lys Gly Lys Leu Gln Tyr
                145                 150                 155

gag ctg cag tac agg aac cgg gga gac ccc tgg gct gtg agt ccg agg       530
```

```
Glu Leu Gln Tyr Arg Asn Arg Gly Asp Pro Trp Ala Val Ser Pro Arg
            160                 165                 170

aga aag ctg atc tca gtg gac tca aga agt gtc tcc ctc ctc ccc ctg      578
Arg Lys Leu Ile Ser Val Asp Ser Arg Ser Val Ser Leu Leu Pro Leu
        175                 180                 185

gag ttc cgc aaa gac tcg agc tat gag ctg cag gtg cgg gca ggg ccc      626
Glu Phe Arg Lys Asp Ser Ser Tyr Glu Leu Gln Val Arg Ala Gly Pro
    190                 195                 200

atg cct ggc tcc tcc tac cag ggg acc tgg agt gaa tgg agt gac ccg      674
Met Pro Gly Ser Ser Tyr Gln Gly Thr Trp Ser Glu Trp Ser Asp Pro
205                 210                 215                 220

gtc atc ttt cag acc cag tca gag gag tta aag gaa ggc tgg aac ggc      722
Val Ile Phe Gln Thr Gln Ser Glu Glu Leu Lys Glu Gly Trp Asn Gly
                225                 230                 235

tcc ggc tct aga gac aaa act cac aca tgc cca ccg tgc cca gca cct      770
Ser Gly Ser Arg Asp Lys Thr His Thr Cys Pro Pro Cys Pro Ala Pro
            240                 245                 250

gaa ctc ctg ggg gga ccg tca gtc ttc ctc ttc ccc cca aaa ccc aag      818
Glu Leu Leu Gly Gly Pro Ser Val Phe Leu Phe Pro Pro Lys Pro Lys
        255                 260                 265

gac acc ctc atg atc tcc cgg acc cct gag gtc aca tgc gtg gtg gtg      866
Asp Thr Leu Met Ile Ser Arg Thr Pro Glu Val Thr Cys Val Val Val
    270                 275                 280

gac gtg agc cac gaa gac cct gag gtc aag ttc aac tgg tac gtg gac      914
Asp Val Ser His Glu Asp Pro Glu Val Lys Phe Asn Trp Tyr Val Asp
285                 290                 295                 300

ggc gtg gag gtg cat aat gcc aag aca aag ccg cgg gag gag cag tac      962
Gly Val Glu Val His Asn Ala Lys Thr Lys Pro Arg Glu Glu Gln Tyr
                305                 310                 315

aac agc acg tac cgt gtg gtc agc gtc ctc acc gtc ctg cac cag gac     1010
Asn Ser Thr Tyr Arg Val Val Ser Val Leu Thr Val Leu His Gln Asp
            320                 325                 330

tgg ctg aat ggc aag gag tac aag tgc aag gtc tcc aac aaa gcc ctc     1058
Trp Leu Asn Gly Lys Glu Tyr Lys Cys Lys Val Ser Asn Lys Ala Leu
        335                 340                 345

cca gtc ccc atc gag aaa acc atc tcc aaa gcc aaa ggg cag ccc cga     1106
Pro Val Pro Ile Glu Lys Thr Ile Ser Lys Ala Lys Gly Gln Pro Arg
    350                 355                 360

gaa cca cag gtg tac acc ctg ccc cca tcc cgg gag gag atg acc aag     1154
Glu Pro Gln Val Tyr Thr Leu Pro Pro Ser Arg Glu Glu Met Thr Lys
365                 370                 375                 380

aac cag gtc agc ctg acc tgc ctg gtc aaa ggc ttc tat ccc agc gac     1202
Asn Gln Val Ser Leu Thr Cys Leu Val Lys Gly Phe Tyr Pro Ser Asp
                385                 390                 395

atc gcc gtg gag tgg gag agc aat ggg cag ccg gag aac aac tac aag     1250
Ile Ala Val Glu Trp Glu Ser Asn Gly Gln Pro Glu Asn Asn Tyr Lys
            400                 405                 410

acc acg cct ccc gtg ctg gac tcc gac ggc tcc ttc ttc ctc tat agc     1298
Thr Thr Pro Pro Val Leu Asp Ser Asp Gly Ser Phe Phe Leu Tyr Ser
        415                 420                 425

aag ctc acc gtg gac aag agc agg tgg cag cag ggg aac gtc ttc tca     1346
Lys Leu Thr Val Asp Lys Ser Arg Trp Gln Gln Gly Asn Val Phe Ser
    430                 435                 440

tgc tcc gtg atg cat gag gct ctg cac aac cac tac acg cag aag agc     1394
Cys Ser Val Met His Glu Ala Leu His Asn His Tyr Thr Gln Lys Ser
445                 450                 455                 460

ctc tcc ctg tcc ccg ggt aaa tca gga atg gca tca atg aca gga ggt     1442
Leu Ser Leu Ser Pro Gly Lys Ser Gly Met Ala Ser Met Thr Gly Gly
                465                 470                 475

caa caa atg ggt tct gga tct cat cat cat cat cat cat tct gga ggt     1490
```

-continued

```
Gln Gln Met Gly Ser Gly Ser His His His His His His Ser Gly Gly
            480                 485                 490

tga gaattc                                                      1499


<210> SEQ ID NO 15
<211> LENGTH: 492
<212> TYPE: PRT
<213> ORGANISM: Homo sapiens

<400> SEQUENCE: 15

Met Pro Arg Gly Trp Ala Ala Pro Leu Leu Leu Leu Leu Leu Gln Gly
1               5                   10                  15

Gly Trp Gly Cys Pro Asp Leu Val Cys Tyr Thr Asp Tyr Leu Gln Thr
            20                  25                  30

Val Ile Cys Ile Leu Glu Met Trp Asn Leu His Pro Ser Thr Leu Thr
        35                  40                  45

Leu Thr Trp Gln Asp Gln Tyr Glu Glu Leu Lys Asp Glu Ala Thr Ser
    50                  55                  60

Cys Ser Leu His Arg Ser Ala His Asn Ala Thr His Ala Thr Tyr Thr
65                  70                  75                  80

Cys His Met Asp Val Phe His Phe Met Ala Asp Asp Ile Phe Ser Val
                85                  90                  95

Asn Ile Thr Asp Gln Ser Gly Asn Tyr Ser Gln Glu Cys Gly Ser Phe
            100                 105                 110

Leu Leu Ala Glu Ser Ile Lys Pro Ala Pro Pro Phe Asn Val Thr Val
        115                 120                 125

Thr Phe Ser Gly Gln Tyr Asn Ile Ser Trp Arg Ser Asp Tyr Glu Asp
    130                 135                 140

Pro Ala Phe Tyr Met Leu Lys Gly Lys Leu Gln Tyr Glu Leu Gln Tyr
145                 150                 155                 160

Arg Asn Arg Gly Asp Pro Trp Ala Val Ser Pro Arg Arg Lys Leu Ile
                165                 170                 175

Ser Val Asp Ser Arg Ser Val Ser Leu Leu Pro Leu Glu Phe Arg Lys
            180                 185                 190

Asp Ser Ser Tyr Glu Leu Gln Val Arg Ala Gly Pro Met Pro Gly Ser
        195                 200                 205

Ser Tyr Gln Gly Thr Trp Ser Glu Trp Ser Asp Pro Val Ile Phe Gln
    210                 215                 220

Thr Gln Ser Glu Glu Leu Lys Glu Gly Trp Asn Gly Ser Gly Ser Arg
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Val Pro Ile
            340                 345                 350

Glu Lys Thr Ile Ser Lys Ala Lys Gly Gln Pro Arg Glu Pro Gln Val
```

```
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys Ser Gly Met Ala Ser Met Thr Gly Gly Gln Gln Met Gly
465                 470                 475                 480

Ser Gly Ser His His His His His His Ser Gly Gly
                485                 490


<210> SEQ ID NO 16
<211> LENGTH: 1426
<212> TYPE: DNA
<213> ORGANISM: Homo sapiens
<220> FEATURE:
<221> NAME/KEY: CDS
<222> LOCATION: (15)..(1415)

<400> SEQUENCE: 16

gcggccgcac cacc atg ccg cgt ggc tgg gcc gcc ccc ttg ctc ctg ctg       50
                Met Pro Arg Gly Trp Ala Ala Pro Leu Leu Leu Leu
                1               5                   10

ctg ctc cag gga ggc tgg ggc tgc ccc gac ctc gtc tgc tac acc gat       98
Leu Leu Gln Gly Gly Trp Gly Cys Pro Asp Leu Val Cys Tyr Thr Asp
        15                  20                  25

tac ctc cag acg gtc atc tgc atc ctg gaa atg tgg aac ctc cac ccc      146
Tyr Leu Gln Thr Val Ile Cys Ile Leu Glu Met Trp Asn Leu His Pro
    30                  35                  40

agc acg ctc acc ctt acc tgg caa gac cag tat gaa gag ctg aag gac      194
Ser Thr Leu Thr Leu Thr Trp Gln Asp Gln Tyr Glu Glu Leu Lys Asp
45                  50                  55                  60

gag gcc acc tcc tgc agc ctc cac agg tcg gcc cac aat gcc acg cat      242
Glu Ala Thr Ser Cys Ser Leu His Arg Ser Ala His Asn Ala Thr His
                65                  70                  75

gcc acc tac acc tgc cac atg gat gta ttc cac ttc atg gcc gac gac      290
Ala Thr Tyr Thr Cys His Met Asp Val Phe His Phe Met Ala Asp Asp
            80                  85                  90

att ttc agt gtc aac atc aca gac cag tct ggc aac tac tcc cag gag      338
Ile Phe Ser Val Asn Ile Thr Asp Gln Ser Gly Asn Tyr Ser Gln Glu
        95                  100                 105

tgt ggc agc ttt ctc ctg gct gag agc atc aag ccg gct ccc cct ttc      386
Cys Gly Ser Phe Leu Leu Ala Glu Ser Ile Lys Pro Ala Pro Pro Phe
    110                 115                 120

aac gtg act gtg acc ttc tca gga cag tat aat atc tcc tgg cgc tca      434
Asn Val Thr Val Thr Phe Ser Gly Gln Tyr Asn Ile Ser Trp Arg Ser
125                 130                 135                 140

gat tac gaa gac cct gcc ttc tac atg ctg aag ggc aag ctt cag tat      482
Asp Tyr Glu Asp Pro Ala Phe Tyr Met Leu Lys Gly Lys Leu Gln Tyr
                145                 150                 155

gag ctg cag tac agg aac cgg gga gac ccc tgg gct gtg agt ccg agg      530
Glu Leu Gln Tyr Arg Asn Arg Gly Asp Pro Trp Ala Val Ser Pro Arg
            160                 165                 170
```

```
aga aag ctg atc tca gtg gac tca aga agt gtc tcc ctc ctc ccc ctg      578
Arg Lys Leu Ile Ser Val Asp Ser Arg Ser Val Ser Leu Leu Pro Leu
        175                 180                 185

gag ttc cgc aaa gac tcg agc tat gag ctg cag gtg cgg gca ggg ccc      626
Glu Phe Arg Lys Asp Ser Ser Tyr Glu Leu Gln Val Arg Ala Gly Pro
    190                 195                 200

atg cct ggc tcc tcc tac cag ggg acc tgg agt gaa tgg agt gac ccg      674
Met Pro Gly Ser Ser Tyr Gln Gly Thr Trp Ser Glu Trp Ser Asp Pro
205                 210                 215                 220

gtc atc ttt cag acc cag tca gag gag tta aag gaa ggc tgg aac ggc      722
Val Ile Phe Gln Thr Gln Ser Glu Glu Leu Lys Glu Gly Trp Asn Gly
                225                 230                 235

tcc ggc tct aga gac aaa act cac aca tgc cca ccg tgc cca gca cct      770
Ser Gly Ser Arg Asp Lys Thr His Thr Cys Pro Pro Cys Pro Ala Pro
            240                 245                 250

gaa gcc ctg ggg gca ccg tca gtc ttc ctc ttc ccc cca aaa ccc aag      818
Glu Ala Leu Gly Ala Pro Ser Val Phe Leu Phe Pro Pro Lys Pro Lys
        255                 260                 265

gac acc ctc atg atc tcc cgg acc cct gag gtc aca tgc gtg gtg gtg      866
Asp Thr Leu Met Ile Ser Arg Thr Pro Glu Val Thr Cys Val Val Val
    270                 275                 280

gac gtg agc cac gaa gac cct gag gtc aag ttc aac tgg tac gtg gac      914
Asp Val Ser His Glu Asp Pro Glu Val Lys Phe Asn Trp Tyr Val Asp
285                 290                 295                 300

ggc gtg gag gtg cat aat gcc aag aca aag ccg cgg gag gag cag tac      962
Gly Val Glu Val His Asn Ala Lys Thr Lys Pro Arg Glu Glu Gln Tyr
                305                 310                 315

aac agc acg tac cgt gtg gtc agc gtc ctc acc gtc ctg cac cag gac     1010
Asn Ser Thr Tyr Arg Val Val Ser Val Leu Thr Val Leu His Gln Asp
            320                 325                 330

tgg ctg aat ggc aag gag tac aag tgc aag gtc tcc aac aaa gcc ctc     1058
Trp Leu Asn Gly Lys Glu Tyr Lys Cys Lys Val Ser Asn Lys Ala Leu
        335                 340                 345

cca gcc ccc atc gag aaa acc atc tcc aaa gcc aaa ggg cag ccc cga     1106
Pro Ala Pro Ile Glu Lys Thr Ile Ser Lys Ala Lys Gly Gln Pro Arg
    350                 355                 360

gaa cca cag gtg tac acc ctg ccc cca tcc cgg gag gag atg acc aag     1154
Glu Pro Gln Val Tyr Thr Leu Pro Pro Ser Arg Glu Glu Met Thr Lys
365                 370                 375                 380

aac cag gtc agc ctg acc tgc ctg gtc aaa ggc ttc tat ccc agc gac     1202
Asn Gln Val Ser Leu Thr Cys Leu Val Lys Gly Phe Tyr Pro Ser Asp
                385                 390                 395

atc gcc gtg gag tgg gag agc aat ggg cag ccg gag aac aac tac aag     1250
Ile Ala Val Glu Trp Glu Ser Asn Gly Gln Pro Glu Asn Asn Tyr Lys
            400                 405                 410

acc acg cct ccc gtg ctg gac tcc gac ggc tcc ttc ttc ctc tat agc     1298
Thr Thr Pro Pro Val Leu Asp Ser Asp Gly Ser Phe Phe Leu Tyr Ser
        415                 420                 425

aag ctc acc gtg gac aag agc agg tgg cag cag ggg aac gtc ttc tca     1346
Lys Leu Thr Val Asp Lys Ser Arg Trp Gln Gln Gly Asn Val Phe Ser
    430                 435                 440

tgc tcc gtg atg cat gag gct ctg cac aac cac tac acg cag aag agc     1394
Cys Ser Val Met His Glu Ala Leu His Asn His Tyr Thr Gln Lys Ser
445                 450                 455                 460

ctc tcc ctg tcc ccg ggt aaa tgagtgaatt c                            1426
Leu Ser Leu Ser Pro Gly Lys
                465
```

<210> SEQ ID NO 17
<211> LENGTH: 467

<212> TYPE: PRT
<213> ORGANISM: Homo sapiens

<400> SEQUENCE: 17

```
Met Pro Arg Gly Trp Ala Ala Pro Leu Leu Leu Leu Leu Leu Gln Gly
1               5                   10                  15

Gly Trp Gly Cys Pro Asp Leu Val Cys Tyr Thr Asp Tyr Leu Gln Thr
            20                  25                  30

Val Ile Cys Ile Leu Glu Met Trp Asn Leu His Pro Ser Thr Leu Thr
        35                  40                  45

Leu Thr Trp Gln Asp Gln Tyr Glu Glu Leu Lys Asp Glu Ala Thr Ser
    50                  55                  60

Cys Ser Leu His Arg Ser Ala His Asn Ala Thr His Ala Thr Tyr Thr
65                  70                  75                  80

Cys His Met Asp Val Phe His Phe Met Ala Asp Asp Ile Phe Ser Val
                85                  90                  95

Asn Ile Thr Asp Gln Ser Gly Asn Tyr Ser Gln Glu Cys Gly Ser Phe
            100                 105                 110

Leu Leu Ala Glu Ser Ile Lys Pro Ala Pro Pro Phe Asn Val Thr Val
        115                 120                 125

Thr Phe Ser Gly Gln Tyr Asn Ile Ser Trp Arg Ser Asp Tyr Glu Asp
    130                 135                 140

Pro Ala Phe Tyr Met Leu Lys Gly Lys Leu Gln Tyr Glu Leu Gln Tyr
145                 150                 155                 160

Arg Asn Arg Gly Asp Pro Trp Ala Val Ser Pro Arg Arg Lys Leu Ile
                165                 170                 175

Ser Val Asp Ser Arg Ser Val Ser Leu Leu Pro Leu Glu Phe Arg Lys
            180                 185                 190

Asp Ser Ser Tyr Glu Leu Gln Val Arg Ala Gly Pro Met Pro Gly Ser
        195                 200                 205

Ser Tyr Gln Gly Thr Trp Ser Glu Trp Ser Asp Pro Val Ile Phe Gln
    210                 215                 220

Thr Gln Ser Glu Glu Leu Lys Glu Gly Trp Asn Gly Ser Gly Ser Arg
225                 230                 235                 240

Asp Lys Thr His Thr Cys Pro Pro Cys Pro Ala Pro Glu Ala Leu Gly
                245                 250                 255

Ala Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400
```

```
Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465


<210> SEQ ID NO 18
<211> LENGTH: 741
<212> TYPE: DNA
<213> ORGANISM: Homo sapiens
<220> FEATURE:
<221> NAME/KEY: CDS
<222> LOCATION: (1)..(735)

<400> SEQUENCE: 18

atg ccg cgt ggc tgg gcc gcc ccc ttg ctc ctg ctg ctg ctc cag gga       48
Met Pro Arg Gly Trp Ala Ala Pro Leu Leu Leu Leu Leu Leu Gln Gly
1               5                   10                  15

ggc tgg ggc tgc ccc gac ctc gtc tgc tac acc gat tac ctc cag acg       96
Gly Trp Gly Cys Pro Asp Leu Val Cys Tyr Thr Asp Tyr Leu Gln Thr
            20                  25                  30

gtc atc tgc atc ctg gaa atg tgg aac ctc cac ccc agc acg ctc acc      144
Val Ile Cys Ile Leu Glu Met Trp Asn Leu His Pro Ser Thr Leu Thr
        35                  40                  45

ctt acc tgg caa gac cag tat gaa gag ctg aag gac gag gcc acc tcc      192
Leu Thr Trp Gln Asp Gln Tyr Glu Glu Leu Lys Asp Glu Ala Thr Ser
    50                  55                  60

tgc agc ctc cac agg tcg gcc cac aat gcc acg cat gcc acc tac acc      240
Cys Ser Leu His Arg Ser Ala His Asn Ala Thr His Ala Thr Tyr Thr
65                  70                  75                  80

tgc cac atg gat gta ttc cac ttc atg gcc gac gac att ttc agt gtc      288
Cys His Met Asp Val Phe His Phe Met Ala Asp Asp Ile Phe Ser Val
                85                  90                  95

aac atc aca gac cag tct ggc aac tac tcc cag gag tgt ggc agc ttt      336
Asn Ile Thr Asp Gln Ser Gly Asn Tyr Ser Gln Glu Cys Gly Ser Phe
            100                 105                 110

ctc ctg gct gag agc atc aag ccg gct ccc cct ttc aac gtg act gtg      384
Leu Leu Ala Glu Ser Ile Lys Pro Ala Pro Pro Phe Asn Val Thr Val
        115                 120                 125

acc ttc tca gga cag tat aat atc tcc tgg cgc tca gat tac gaa gac      432
Thr Phe Ser Gly Gln Tyr Asn Ile Ser Trp Arg Ser Asp Tyr Glu Asp
    130                 135                 140

cct gcc ttc tac atg ctg aag ggc aag ctt cag tat gag ctg cag tac      480
Pro Ala Phe Tyr Met Leu Lys Gly Lys Leu Gln Tyr Glu Leu Gln Tyr
145                 150                 155                 160

agg aac cgg gga gac ccc tgg gct gtg agt ccg agg aga aag ctg atc      528
Arg Asn Arg Gly Asp Pro Trp Ala Val Ser Pro Arg Arg Lys Leu Ile
                165                 170                 175

tca gtg gac tca aga agt gtc tcc ctc ctc ccc ctg gag ttc cgc aaa      576
Ser Val Asp Ser Arg Ser Val Ser Leu Leu Pro Leu Glu Phe Arg Lys
            180                 185                 190

gac tcg agc tat gag ctg cag gtg cgg gca ggg ccc atg cct ggc tcc      624
Asp Ser Ser Tyr Glu Leu Gln Val Arg Ala Gly Pro Met Pro Gly Ser
        195                 200                 205

tcc tac cag ggg acc tgg agt gaa tgg agt gac ccg gtc atc ttt cag      672
Ser Tyr Gln Gly Thr Trp Ser Glu Trp Ser Asp Pro Val Ile Phe Gln
```

-continued

```
    210                 215                 220

acc cag tca gag gag tta aag gaa ggc tgg aac aaa acc gaa acc tcc      720
Thr Gln Ser Glu Glu Leu Lys Glu Gly Trp Asn Lys Thr Glu Thr Ser
225                 230                 235                 240

cag gtt gct ccg gca taatga                                            741
Gln Val Ala Pro Ala
                245


<210> SEQ ID NO 19
<211> LENGTH: 245
<212> TYPE: PRT
<213> ORGANISM: Homo sapiens

<400> SEQUENCE: 19

Met Pro Arg Gly Trp Ala Ala Pro Leu Leu Leu Leu Leu Leu Gln Gly
1               5                   10                  15

Gly Trp Gly Cys Pro Asp Leu Val Cys Tyr Thr Asp Tyr Leu Gln Thr
            20                  25                  30

Val Ile Cys Ile Leu Glu Met Trp Asn Leu His Pro Ser Thr Leu Thr
        35                  40                  45

Leu Thr Trp Gln Asp Gln Tyr Glu Glu Leu Lys Asp Glu Ala Thr Ser
    50                  55                  60

Cys Ser Leu His Arg Ser Ala His Asn Ala Thr His Ala Thr Tyr Thr
65                  70                  75                  80

Cys His Met Asp Val Phe His Phe Met Ala Asp Asp Ile Phe Ser Val
                85                  90                  95

Asn Ile Thr Asp Gln Ser Gly Asn Tyr Ser Gln Glu Cys Gly Ser Phe
            100                 105                 110

Leu Leu Ala Glu Ser Ile Lys Pro Ala Pro Pro Phe Asn Val Thr Val
        115                 120                 125

Thr Phe Ser Gly Gln Tyr Asn Ile Ser Trp Arg Ser Asp Tyr Glu Asp
    130                 135                 140

Pro Ala Phe Tyr Met Leu Lys Gly Lys Leu Gln Tyr Glu Leu Gln Tyr
145                 150                 155                 160

Arg Asn Arg Gly Asp Pro Trp Ala Val Ser Pro Arg Arg Lys Leu Ile
                165                 170                 175

Ser Val Asp Ser Arg Ser Val Ser Leu Leu Pro Leu Glu Phe Arg Lys
            180                 185                 190

Asp Ser Ser Tyr Glu Leu Gln Val Arg Ala Gly Pro Met Pro Gly Ser
        195                 200                 205

Ser Tyr Gln Gly Thr Trp Ser Glu Trp Ser Asp Pro Val Ile Phe Gln
    210                 215                 220

Thr Gln Ser Glu Glu Leu Lys Glu Gly Trp Asn Lys Thr Glu Thr Ser
225                 230                 235                 240

Gln Val Ala Pro Ala
                245


<210> SEQ ID NO 20
<211> LENGTH: 1413
<212> TYPE: DNA
<213> ORGANISM: Homo sapiens
<220> FEATURE:
<221> NAME/KEY: CDS
<222> LOCATION: (1)..(1410)

<400> SEQUENCE: 20

atg ccg cgt ggc tgg gcc gcc ccc ttg ctc ctg ctg ctg ctc cag gga       48
Met Pro Arg Gly Trp Ala Ala Pro Leu Leu Leu Leu Leu Leu Gln Gly
1               5                   10                  15
```

-continued

```
ggc tgg ggc tgc ccc gac ctc gtc tgc tac acc gat tac ctc cag acg        96
Gly Trp Gly Cys Pro Asp Leu Val Cys Tyr Thr Asp Tyr Leu Gln Thr
            20                  25                  30

gtc atc tgc atc ctg gaa atg tgg aac ctc cac ccc agc acg ctc acc       144
Val Ile Cys Ile Leu Glu Met Trp Asn Leu His Pro Ser Thr Leu Thr
        35                  40                  45

ctt acc tgg caa gac cag tat gaa gag ctg aag gac gag gcc acc tcc       192
Leu Thr Trp Gln Asp Gln Tyr Glu Glu Leu Lys Asp Glu Ala Thr Ser
    50                  55                  60

tgc agc ctc cac agg tcg gcc cac aat gcc acg cat gcc acc tac acc       240
Cys Ser Leu His Arg Ser Ala His Asn Ala Thr His Ala Thr Tyr Thr
65                  70                  75                  80

tgc cac atg gat gta ttc cac ttc atg gcc gac gac att ttc agt gtc       288
Cys His Met Asp Val Phe His Phe Met Ala Asp Asp Ile Phe Ser Val
                85                  90                  95

aac atc aca gac cag tct ggc aac tac tcc cag gag tgt ggc agc ttt       336
Asn Ile Thr Asp Gln Ser Gly Asn Tyr Ser Gln Glu Cys Gly Ser Phe
            100                 105                 110

ctc ctg gct gag agc atc aag ccg gct ccc cct ttc aac gtg act gtg       384
Leu Leu Ala Glu Ser Ile Lys Pro Ala Pro Pro Phe Asn Val Thr Val
        115                 120                 125

acc ttc tca gga cag tat aat atc tcc tgg cgc tca gat tac gaa gac       432
Thr Phe Ser Gly Gln Tyr Asn Ile Ser Trp Arg Ser Asp Tyr Glu Asp
    130                 135                 140

cct gcc ttc tac atg ctg aag ggc aag ctt cag tat gag ctg cag tac       480
Pro Ala Phe Tyr Met Leu Lys Gly Lys Leu Gln Tyr Glu Leu Gln Tyr
145                 150                 155                 160

agg aac cgg gga gac ccc tgg gct gtg agt ccg agg aga aag ctg atc       528
Arg Asn Arg Gly Asp Pro Trp Ala Val Ser Pro Arg Arg Lys Leu Ile
                165                 170                 175

tca gtg gac tca aga agt gtc tcc ctc ctc ccc ctg gag ttc cgc aaa       576
Ser Val Asp Ser Arg Ser Val Ser Leu Leu Pro Leu Glu Phe Arg Lys
            180                 185                 190

gac tcg agc tat gag ctg cag gtg cgg gca ggg ccc atg cct ggc tcc       624
Asp Ser Ser Tyr Glu Leu Gln Val Arg Ala Gly Pro Met Pro Gly Ser
        195                 200                 205

tcc tac cag ggg acc tgg agt gaa tgg agt gac ccg gtc atc ttt cag       672
Ser Tyr Gln Gly Thr Trp Ser Glu Trp Ser Asp Pro Val Ile Phe Gln
    210                 215                 220

acc cag tca gag gag tta aag gaa ggc tgg aac gat gac gat gac aag       720
Thr Gln Ser Glu Glu Leu Lys Glu Gly Trp Asn Asp Asp Asp Asp Lys
225                 230                 235                 240

ggc tcc ggc gac aaa act cac aca tgc cca ccg tgc cca gca cct gaa       768
Gly Ser Gly Asp Lys Thr His Thr Cys Pro Pro Cys Pro Ala Pro Glu
                245                 250                 255

gcc ctg ggg gca ccg tca gtc ttc ctc ttc ccc cca aaa ccc aag gac       816
Ala Leu Gly Ala Pro Ser Val Phe Leu Phe Pro Pro Lys Pro Lys Asp
            260                 265                 270

acc ctc atg atc tcc cgg acc cct gag gtc aca tgc gtg gtg gtg gac       864
Thr Leu Met Ile Ser Arg Thr Pro Glu Val Thr Cys Val Val Val Asp
        275                 280                 285

gtg agc cac gaa gac cct gag gtc aag ttc aac tgg tac gtg gac ggc       912
Val Ser His Glu Asp Pro Glu Val Lys Phe Asn Trp Tyr Val Asp Gly
    290                 295                 300

gtg gag gtg cat aat gcc aag aca aag ccg cgg gag gag cag tac aac       960
Val Glu Val His Asn Ala Lys Thr Lys Pro Arg Glu Glu Gln Tyr Asn
305                 310                 315                 320

agc acg tac cgt gtg gtc agc gtc ctc acc gtc ctg cac cag gac tgg      1008
Ser Thr Tyr Arg Val Val Ser Val Leu Thr Val Leu His Gln Asp Trp
                325                 330                 335
```

```
ctg aat ggc aag gag tac aag tgc aag gtc tcc aac aaa gcc ctc cca      1056
Leu Asn Gly Lys Glu Tyr Lys Cys Lys Val Ser Asn Lys Ala Leu Pro
            340                 345                 350

gcc ccc atc gag aaa acc atc tcc aaa gcc aaa ggg cag ccc cga gaa      1104
Ala Pro Ile Glu Lys Thr Ile Ser Lys Ala Lys Gly Gln Pro Arg Glu
        355                 360                 365

cca cag gtg tac acc ctg ccc cca tcc cgg gag gag atg acc aag aac      1152
Pro Gln Val Tyr Thr Leu Pro Pro Ser Arg Glu Glu Met Thr Lys Asn
    370                 375                 380

cag gtc agc ctg acc tgc ctg gtc aaa ggc ttc tat ccc agc gac atc      1200
Gln Val Ser Leu Thr Cys Leu Val Lys Gly Phe Tyr Pro Ser Asp Ile
385                 390                 395                 400

gcc gtg gag tgg gag agc aat ggg cag ccg gag aac aac tac aag acc      1248
Ala Val Glu Trp Glu Ser Asn Gly Gln Pro Glu Asn Asn Tyr Lys Thr
            405                 410                 415

acg cct ccc gtg ctg gac tcc gac ggc tcc ttc ttc ctc tat agc aag      1296
Thr Pro Pro Val Leu Asp Ser Asp Gly Ser Phe Phe Leu Tyr Ser Lys
            420                 425                 430

ctc acc gtg gac aag agc agg tgg cag cag ggg aac gtc ttc tca tgc      1344
Leu Thr Val Asp Lys Ser Arg Trp Gln Gln Gly Asn Val Phe Ser Cys
        435                 440                 445

tcc gtg atg cat gag gct ctg cac aac cac tac acg cag aag agc ctc      1392
Ser Val Met His Glu Ala Leu His Asn His Tyr Thr Gln Lys Ser Leu
    450                 455                 460

tcc ctg tcc ccg ggt aaa tga                                          1413
Ser Leu Ser Pro Gly Lys
465                 470


<210> SEQ ID NO 21
<211> LENGTH: 470
<212> TYPE: PRT
<213> ORGANISM: Homo sapiens

<400> SEQUENCE: 21

Met Pro Arg Gly Trp Ala Ala Pro Leu Leu Leu Leu Leu Leu Gln Gly
1               5                   10                  15

Gly Trp Gly Cys Pro Asp Leu Val Cys Tyr Thr Asp Tyr Leu Gln Thr
            20                  25                  30

Val Ile Cys Ile Leu Glu Met Trp Asn Leu His Pro Ser Thr Leu Thr
        35                  40                  45

Leu Thr Trp Gln Asp Gln Tyr Glu Glu Leu Lys Asp Glu Ala Thr Ser
    50                  55                  60

Cys Ser Leu His Arg Ser Ala His Asn Ala Thr His Ala Thr Tyr Thr
65                  70                  75                  80

Cys His Met Asp Val Phe His Phe Met Ala Asp Asp Ile Phe Ser Val
                85                  90                  95

Asn Ile Thr Asp Gln Ser Gly Asn Tyr Ser Gln Glu Cys Gly Ser Phe
            100                 105                 110

Leu Leu Ala Glu Ser Ile Lys Pro Ala Pro Pro Phe Asn Val Thr Val
        115                 120                 125

Thr Phe Ser Gly Gln Tyr Asn Ile Ser Trp Arg Ser Asp Tyr Glu Asp
    130                 135                 140

Pro Ala Phe Tyr Met Leu Lys Gly Lys Leu Gln Tyr Glu Leu Gln Tyr
145                 150                 155                 160

Arg Asn Arg Gly Asp Pro Trp Ala Val Ser Pro Arg Arg Lys Leu Ile
                165                 170                 175

Ser Val Asp Ser Arg Ser Val Ser Leu Leu Pro Leu Glu Phe Arg Lys
            180                 185                 190
```

```
Asp Ser Ser Tyr Glu Leu Gln Val Arg Ala Gly Pro Met Pro Gly Ser
        195                 200                 205

Ser Tyr Gln Gly Thr Trp Ser Glu Trp Ser Asp Pro Val Ile Phe Gln
    210                 215                 220

Thr Gln Ser Glu Glu Leu Lys Glu Gly Trp Asn Asp Asp Asp Asp Lys
225                 230                 235                 240

Gly Ser Gly Asp Lys Thr His Thr Cys Pro Pro Cys Pro Ala Pro Glu
                245                 250                 255

Ala Leu Gly Ala Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470


<210> SEQ ID NO 22
<211> LENGTH: 1754
<212> TYPE: DNA
<213> ORGANISM: Mus musculus
<220> FEATURE:
<221> NAME/KEY: CDS
<222> LOCATION: (1)..(720)

<400> SEQUENCE: 22

atg ccc cgg ggc cca gtg gct gcc tta ctc ctg ctg att ctc cat gga       48
Met Pro Arg Gly Pro Val Ala Ala Leu Leu Leu Leu Ile Leu His Gly
1               5                   10                  15

gct tgg agc tgc ctg gac ctc act tgc tac act gac tac ctc tgg acc       96
Ala Trp Ser Cys Leu Asp Leu Thr Cys Tyr Thr Asp Tyr Leu Trp Thr
            20                  25                  30

atc acc tgt gtc ctg gag aca cgg agc ccc aac ccc agc ata ctc agt      144
Ile Thr Cys Val Leu Glu Thr Arg Ser Pro Asn Pro Ser Ile Leu Ser
        35                  40                  45

ctc acc tgg caa gat gaa tat gag gaa ctt cag gac caa gag acc ttc      192
Leu Thr Trp Gln Asp Glu Tyr Glu Glu Leu Gln Asp Gln Glu Thr Phe
```

```
    50                  55                  60

tgc agc cta cac agg tct ggc cac aac acc aca cat ata tgg tac acg      240
Cys Ser Leu His Arg Ser Gly His Asn Thr Thr His Ile Trp Tyr Thr
65                  70                  75                  80

tgc cat atg cgc ttg tct caa ttc ctg tcc gat gaa gtt ttc att gtc      288
Cys His Met Arg Leu Ser Gln Phe Leu Ser Asp Glu Val Phe Ile Val
                85                  90                  95

aat gtg acg gac cag tct ggc aac aac tcc caa gag tgt ggc agc ttt      336
Asn Val Thr Asp Gln Ser Gly Asn Asn Ser Gln Glu Cys Gly Ser Phe
            100                 105                 110

gtc ctg gct gag agc atc aaa cca gct ccc ccc ttg aac gtg act gtg      384
Val Leu Ala Glu Ser Ile Lys Pro Ala Pro Pro Leu Asn Val Thr Val
        115                 120                 125

gcc ttc tca gga cgc tat gat atc tcc tgg gac tca gct tat gac gaa      432
Ala Phe Ser Gly Arg Tyr Asp Ile Ser Trp Asp Ser Ala Tyr Asp Glu
    130                 135                 140

ccc tcc aac tac gtg ctg agg ggc aag cta caa tat gag ctg cag tat      480
Pro Ser Asn Tyr Val Leu Arg Gly Lys Leu Gln Tyr Glu Leu Gln Tyr
145                 150                 155                 160

cgg aac ctc aga gac ccc tat gct gtg agg ccg gtg acc aag ctg atc      528
Arg Asn Leu Arg Asp Pro Tyr Ala Val Arg Pro Val Thr Lys Leu Ile
                165                 170                 175

tca gtg gac tca aga aac gtc tct ctt ctc cct gaa gag ttc cac aaa      576
Ser Val Asp Ser Arg Asn Val Ser Leu Leu Pro Glu Glu Phe His Lys
            180                 185                 190

gat tct agc tac cag ctg cag gtg cgg gca gcg cct cag cca ggc act      624
Asp Ser Ser Tyr Gln Leu Gln Val Arg Ala Ala Pro Gln Pro Gly Thr
        195                 200                 205

tca ttc agg ggg acc tgg agt gag tgg agt gac ccc gtc atc ttt cag      672
Ser Phe Arg Gly Thr Trp Ser Glu Trp Ser Asp Pro Val Ile Phe Gln
    210                 215                 220

acc cag gct ggg gag ccc gag gca ggc tgg gac ggc tcc ggc tct aga      720
Thr Gln Ala Gly Glu Pro Glu Ala Gly Trp Asp Gly Ser Gly Ser Arg
225                 230                 235                 240

gagccccgcg gaccgacaat caagccctgt cctccatgca aatgcccagg taagtcacta    780

gaccagagct ccactcccgg gagaatggta agtgctataa acatccctgc actagaggat    840

aagccatgta cagatccatt tccatctctc ctcatcagca cctaacctcg agggtggacc    900

atccgtcttc atcttccctc caaagatcaa ggatgtactc atgatctccc tgagccccat    960

agtcacatgt gtggtggtgg atgtgagcga ggatgaccca gatgtccaga tcagctggtt   1020

tgtgaacaac gtggaagtac acacagctca gacacaaacc catagagagg attacaacag   1080

tactctccgg gtggtcagtg ccctccccat ccagcaccag gactggatga gtggcaaggc   1140

tttcgcatgc gccgtcaaca acaaagacct cccagcgccc atcgagagaa ccatctcaaa   1200

acccaaaggt gagagctgca gcctgactgc atgggggctg ggatgggcat aaggataaag   1260

gtctgtgtgg acagccttct gcttcagcca tgacctttgt gtatgtttct accctcacag   1320

ggtcagtaag agctccacag gtatatgtct tgcctccacc agaagaagag atgactaaga   1380

aacaggtcac tctgacctgc atggtcacag acttcatgcc tgaagacatt tacgtggagt   1440

ggaccaacaa cgggaaaaca gagctaaact acaagaacac tgaaccagtc ctggactctg   1500

atggttctta cttcatgtac agcaagctga gagtggaaaa gaagaactgg gtggaaagaa   1560

atagctactc ctgttcagtg gtccacgagg gtctgcacaa tcaccacacg actaagagct   1620

tctcccggac tccgggtaaa tgagctcagc acccacaaaa ctctcaggtc caaagagaca   1680

cccacactca tctccatgct tcccttgtat aaataaagca cccagcaatg cctgggacca   1740
```

```
tgtaatagga attc                                                       1754


<210> SEQ ID NO 23
<211> LENGTH: 240
<212> TYPE: PRT
<213> ORGANISM: Mus musculus

<400> SEQUENCE: 23

Met Pro Arg Gly Pro Val Ala Ala Leu Leu Leu Leu Ile Leu His Gly
1               5                   10                  15

Ala Trp Ser Cys Leu Asp Leu Thr Cys Tyr Thr Asp Tyr Leu Trp Thr
            20                  25                  30

Ile Thr Cys Val Leu Glu Thr Arg Ser Pro Asn Pro Ser Ile Leu Ser
        35                  40                  45

Leu Thr Trp Gln Asp Glu Tyr Glu Glu Leu Gln Asp Gln Glu Thr Phe
    50                  55                  60

Cys Ser Leu His Arg Ser Gly His Asn Thr Thr His Ile Trp Tyr Thr
65                  70                  75                  80

Cys His Met Arg Leu Ser Gln Phe Leu Ser Asp Glu Val Phe Ile Val
                85                  90                  95

Asn Val Thr Asp Gln Ser Gly Asn Asn Ser Gln Glu Cys Gly Ser Phe
            100                 105                 110

Val Leu Ala Glu Ser Ile Lys Pro Ala Pro Pro Leu Asn Val Thr Val
        115                 120                 125

Ala Phe Ser Gly Arg Tyr Asp Ile Ser Trp Asp Ser Ala Tyr Asp Glu
    130                 135                 140

Pro Ser Asn Tyr Val Leu Arg Gly Lys Leu Gln Tyr Glu Leu Gln Tyr
145                 150                 155                 160

Arg Asn Leu Arg Asp Pro Tyr Ala Val Arg Pro Val Thr Lys Leu Ile
                165                 170                 175

Ser Val Asp Ser Arg Asn Val Ser Leu Leu Pro Glu Glu Phe His Lys
            180                 185                 190

Asp Ser Ser Tyr Gln Leu Gln Val Arg Ala Ala Pro Gln Pro Gly Thr
        195                 200                 205

Ser Phe Arg Gly Thr Trp Ser Glu Trp Ser Asp Pro Val Ile Phe Gln
    210                 215                 220

Thr Gln Ala Gly Glu Pro Glu Ala Gly Trp Asp Gly Ser Gly Ser Arg
225                 230                 235                 240


<210> SEQ ID NO 24
<211> LENGTH: 795
<212> TYPE: DNA
<213> ORGANISM: Mus musculus
<220> FEATURE:
<221> NAME/KEY: CDS
<222> LOCATION: (19)..(783)

<400> SEQUENCE: 24

ctgcaggtcg acaccacc atg ccc cgg ggc cca gtg gct gcc tta ctc ctg       51
                    Met Pro Arg Gly Pro Val Ala Ala Leu Leu Leu
                    1               5                   10

ctg att ctc cat gga gct tgg agc tgc ctg gac ctc act tgc tac act       99
Leu Ile Leu His Gly Ala Trp Ser Cys Leu Asp Leu Thr Cys Tyr Thr
            15                  20                  25

gac tac ctc tgg acc atc acc tgt gtc ctg gag aca cgg agc ccc aac      147
Asp Tyr Leu Trp Thr Ile Thr Cys Val Leu Glu Thr Arg Ser Pro Asn
        30                  35                  40

ccc agc ata ctc agt ctc acc tgg caa gat gaa tat gag gaa ctt cag      195
Pro Ser Ile Leu Ser Leu Thr Trp Gln Asp Glu Tyr Glu Glu Leu Gln
```

```
    45                  50                  55

gac caa gag acc ttc tgc agc cta cac agg tct ggc cac aac acc aca        243
Asp Gln Glu Thr Phe Cys Ser Leu His Arg Ser Gly His Asn Thr Thr
60                  65                  70                  75

cat ata tgg tac acg tgc cat atg cgc ttg tct caa ttc ctg tcc gat        291
His Ile Trp Tyr Thr Cys His Met Arg Leu Ser Gln Phe Leu Ser Asp
                80                  85                  90

gaa gtt ttc att gtc aat gtg acg gac cag tct ggc aac aac tcc caa        339
Glu Val Phe Ile Val Asn Val Thr Asp Gln Ser Gly Asn Asn Ser Gln
            95                  100                 105

gag tgt ggc agc ttt gtc ctg gct gag agc atc aaa cca gct ccc ccc        387
Glu Cys Gly Ser Phe Val Leu Ala Glu Ser Ile Lys Pro Ala Pro Pro
        110                 115                 120

ttg aac gtg act gtg gcc ttc tca gga cgc tat gat atc tcc tgg gac        435
Leu Asn Val Thr Val Ala Phe Ser Gly Arg Tyr Asp Ile Ser Trp Asp
    125                 130                 135

tca gct tat gac gaa ccc tcc aac tac gtg ctg agg ggc aag cta caa        483
Ser Ala Tyr Asp Glu Pro Ser Asn Tyr Val Leu Arg Gly Lys Leu Gln
140                 145                 150                 155

tat gag ctg cag tat cgg aac ctc aga gac ccc tat gct gtg agg ccg        531
Tyr Glu Leu Gln Tyr Arg Asn Leu Arg Asp Pro Tyr Ala Val Arg Pro
                160                 165                 170

gtg acc aag ctg atc tca gtg gac tca aga aac gtc tct ctt ctc cct        579
Val Thr Lys Leu Ile Ser Val Asp Ser Arg Asn Val Ser Leu Leu Pro
            175                 180                 185

gaa gag ttc cac aaa gat tct agc tac cag ctg cag gtg cgg gca gcg        627
Glu Glu Phe His Lys Asp Ser Ser Tyr Gln Leu Gln Val Arg Ala Ala
        190                 195                 200

cct cag cca ggc act tca ttc agg ggg acc tgg agt gag tgg agt gac        675
Pro Gln Pro Gly Thr Ser Phe Arg Gly Thr Trp Ser Glu Trp Ser Asp
    205                 210                 215

ccc gtc atc ttt cag acc cag gct ggg gag ccc gag gca ggc tgg gac        723
Pro Val Ile Phe Gln Thr Gln Ala Gly Glu Pro Glu Ala Gly Trp Asp
220                 225                 230                 235

ggc agc gga cac cac cat cat cac cac ggt agc ggc gac tat aaa gac        771
Gly Ser Gly His His His His His His Gly Ser Gly Asp Tyr Lys Asp
                240                 245                 250

gat gac gat aag tagtgagaat tc                                          795
Asp Asp Asp Lys
            255


<210> SEQ ID NO 25
<211> LENGTH: 255
<212> TYPE: PRT
<213> ORGANISM: Mus musculus

<400> SEQUENCE: 25

Met Pro Arg Gly Pro Val Ala Ala Leu Leu Leu Leu Ile Leu His Gly
1               5                   10                  15

Ala Trp Ser Cys Leu Asp Leu Thr Cys Tyr Thr Asp Tyr Leu Trp Thr
            20                  25                  30

Ile Thr Cys Val Leu Glu Thr Arg Ser Pro Asn Pro Ser Ile Leu Ser
        35                  40                  45

Leu Thr Trp Gln Asp Glu Tyr Glu Glu Leu Gln Asp Gln Glu Thr Phe
    50                  55                  60

Cys Ser Leu His Arg Ser Gly His Asn Thr Thr His Ile Trp Tyr Thr
65                  70                  75                  80

Cys His Met Arg Leu Ser Gln Phe Leu Ser Asp Glu Val Phe Ile Val
                85                  90                  95
```

```
Asn Val Thr Asp Gln Ser Gly Asn Asn Ser Gln Glu Cys Gly Ser Phe
            100                 105                 110

Val Leu Ala Glu Ser Ile Lys Pro Ala Pro Pro Leu Asn Val Thr Val
        115                 120                 125

Ala Phe Ser Gly Arg Tyr Asp Ile Ser Trp Asp Ser Ala Tyr Asp Glu
    130                 135                 140

Pro Ser Asn Tyr Val Leu Arg Gly Lys Leu Gln Tyr Glu Leu Gln Tyr
145                 150                 155                 160

Arg Asn Leu Arg Asp Pro Tyr Ala Val Arg Pro Val Thr Lys Leu Ile
                165                 170                 175

Ser Val Asp Ser Arg Asn Val Ser Leu Leu Pro Glu Glu Phe His Lys
            180                 185                 190

Asp Ser Ser Tyr Gln Leu Gln Val Arg Ala Ala Pro Gln Pro Gly Thr
        195                 200                 205

Ser Phe Arg Gly Thr Trp Ser Glu Trp Ser Asp Pro Val Ile Phe Gln
    210                 215                 220

Thr Gln Ala Gly Glu Pro Glu Ala Gly Trp Asp Gly Ser Gly His His
225                 230                 235                 240

His His His His Gly Ser Gly Asp Tyr Lys Asp Asp Asp Asp Lys
                245                 250                 255


<210> SEQ ID NO 26
<211> LENGTH: 792
<212> TYPE: DNA
<213> ORGANISM: Mus musculus
<220> FEATURE:
<221> NAME/KEY: CDS
<222> LOCATION: (1)..(786)

<400> SEQUENCE: 26

atg aaa ttc tta gtc aac gtt gcc ctt gtt ttt atg gtc gtg tac att       48
Met Lys Phe Leu Val Asn Val Ala Leu Val Phe Met Val Val Tyr Ile
1               5                   10                  15

tct tac atc tat gcc ggc agc gga cac cac cat cat cac cac ggt agc       96
Ser Tyr Ile Tyr Ala Gly Ser Gly His His His His His His Gly Ser
            20                  25                  30

ggc gac tat aaa gac gat gac gat aag ggt tcc gga tgc ctg gac ctc      144
Gly Asp Tyr Lys Asp Asp Asp Asp Lys Gly Ser Gly Cys Leu Asp Leu
        35                  40                  45

act tgc tac act gac tac ctc tgg acc atc acc tgt gtc ctg gag aca      192
Thr Cys Tyr Thr Asp Tyr Leu Trp Thr Ile Thr Cys Val Leu Glu Thr
    50                  55                  60

cgg agc ccc aac ccc agc ata ctc agt ctc acc tgg caa gat gaa tat      240
Arg Ser Pro Asn Pro Ser Ile Leu Ser Leu Thr Trp Gln Asp Glu Tyr
65                  70                  75                  80

gag gaa ctt cag gac caa gag acc ttc tgc agc cta cac agg tct ggc      288
Glu Glu Leu Gln Asp Gln Glu Thr Phe Cys Ser Leu His Arg Ser Gly
                85                  90                  95

cac aac acc aca cat ata tgg tac acg tgc cat atg cgc ttg tct caa      336
His Asn Thr Thr His Ile Trp Tyr Thr Cys His Met Arg Leu Ser Gln
            100                 105                 110

ttc ctg tcc gat gaa gtt ttc att gtc aat gtg acg gac cag tct ggc      384
Phe Leu Ser Asp Glu Val Phe Ile Val Asn Val Thr Asp Gln Ser Gly
        115                 120                 125

aac aac tcc caa gag tgt ggc agc ttt gtc ctg gct gag agc atc aaa      432
Asn Asn Ser Gln Glu Cys Gly Ser Phe Val Leu Ala Glu Ser Ile Lys
    130                 135                 140

cca gct ccc ccc ttg aac gtg act gtg gcc ttc tca gga cgc tat gat      480
Pro Ala Pro Pro Leu Asn Val Thr Val Ala Phe Ser Gly Arg Tyr Asp
145                 150                 155                 160
```

```
atc tcc tgg gac tca gct tat gac gaa ccc tcc aac tac gtg ctg agg      528
Ile Ser Trp Asp Ser Ala Tyr Asp Glu Pro Ser Asn Tyr Val Leu Arg
                165                 170                 175

ggc aag cta caa tat gag ctg cag tat cgg aac ctc aga gac ccc tat      576
Gly Lys Leu Gln Tyr Glu Leu Gln Tyr Arg Asn Leu Arg Asp Pro Tyr
            180                 185                 190

gct gtg agg ccg gtg acc aag ctg atc tca gtg gac tca aga aac gtc      624
Ala Val Arg Pro Val Thr Lys Leu Ile Ser Val Asp Ser Arg Asn Val
        195                 200                 205

tct ctt ctc cct gaa gag ttc cac aaa gat tct agc tac cag ctg cag      672
Ser Leu Leu Pro Glu Glu Phe His Lys Asp Ser Ser Tyr Gln Leu Gln
    210                 215                 220

gtg cgg gca gcg cct cag cca ggc act tca ttc agg ggg acc tgg agt      720
Val Arg Ala Ala Pro Gln Pro Gly Thr Ser Phe Arg Gly Thr Trp Ser
225                 230                 235                 240

gag tgg agt gac ccc gtc atc ttt cag acc cag gct ggg gag ccc gag      768
Glu Trp Ser Asp Pro Val Ile Phe Gln Thr Gln Ala Gly Glu Pro Glu
                245                 250                 255

gca ggc tgg gac tag tga gaattc                                       792
Ala Gly Trp Asp
            260


<210> SEQ ID NO 27
<211> LENGTH: 260
<212> TYPE: PRT
<213> ORGANISM: Mus musculus

<400> SEQUENCE: 27

Met Lys Phe Leu Val Asn Val Ala Leu Val Phe Met Val Val Tyr Ile
1               5                   10                  15

Ser Tyr Ile Tyr Ala Gly Ser Gly His His His His His His Gly Ser
            20                  25                  30

Gly Asp Tyr Lys Asp Asp Asp Asp Lys Gly Ser Gly Cys Leu Asp Leu
        35                  40                  45

Thr Cys Tyr Thr Asp Tyr Leu Trp Thr Ile Thr Cys Val Leu Glu Thr
    50                  55                  60

Arg Ser Pro Asn Pro Ser Ile Leu Ser Leu Thr Trp Gln Asp Glu Tyr
65                  70                  75                  80

Glu Glu Leu Gln Asp Gln Glu Thr Phe Cys Ser Leu His Arg Ser Gly
                85                  90                  95

His Asn Thr Thr His Ile Trp Tyr Thr Cys His Met Arg Leu Ser Gln
            100                 105                 110

Phe Leu Ser Asp Glu Val Phe Ile Val Asn Val Thr Asp Gln Ser Gly
        115                 120                 125

Asn Asn Ser Gln Glu Cys Gly Ser Phe Val Leu Ala Glu Ser Ile Lys
    130                 135                 140

Pro Ala Pro Pro Leu Asn Val Thr Val Ala Phe Ser Gly Arg Tyr Asp
145                 150                 155                 160

Ile Ser Trp Asp Ser Ala Tyr Asp Glu Pro Ser Asn Tyr Val Leu Arg
                165                 170                 175

Gly Lys Leu Gln Tyr Glu Leu Gln Tyr Arg Asn Leu Arg Asp Pro Tyr
            180                 185                 190

Ala Val Arg Pro Val Thr Lys Leu Ile Ser Val Asp Ser Arg Asn Val
        195                 200                 205

Ser Leu Leu Pro Glu Glu Phe His Lys Asp Ser Ser Tyr Gln Leu Gln
    210                 215                 220

Val Arg Ala Ala Pro Gln Pro Gly Thr Ser Phe Arg Gly Thr Trp Ser
```

225 230 235 240

Glu Trp Ser Asp Pro Val Ile Phe Gln Thr Gln Ala Gly Glu Pro Glu
245 250 255

Ala Gly Trp Asp
260

<210> SEQ ID NO 28
<211> LENGTH: 20
<212> TYPE: DNA
<213> ORGANISM: Artificial
<220> FEATURE:
<223> OTHER INFORMATION: PCR Primer

<400> SEQUENCE: 28
gccagatcgc ctcctgatta 20

<210> SEQ ID NO 29
<211> LENGTH: 20
<212> TYPE: DNA
<213> ORGANISM: Artificial
<220> FEATURE:
<223> OTHER INFORMATION: PCR Primer

<400> SEQUENCE: 29
catgctcaca gtgccccttt 20

<210> SEQ ID NO 30
<211> LENGTH: 20
<212> TYPE: DNA
<213> ORGANISM: Artificial
<220> FEATURE:
<223> OTHER INFORMATION: PCR Primer

<400> SEQUENCE: 30
ctcccccctt gaacgtgact 20

<210> SEQ ID NO 31
<211> LENGTH: 20
<212> TYPE: DNA
<213> ORGANISM: Artificial
<220> FEATURE:
<223> OTHER INFORMATION: PCR Primer

<400> SEQUENCE: 31
ttgcccctca gcacgtagtt 20

<210> SEQ ID NO 32
<211> LENGTH: 28
<212> TYPE: DNA
<213> ORGANISM: Artificial
<220> FEATURE:
<223> OTHER INFORMATION: PCR Primer

<400> SEQUENCE: 32
agagccagat tatctctttc tacctcag 28

<210> SEQ ID NO 33
<211> LENGTH: 20
<212> TYPE: DNA
<213> ORGANISM: Artificial
<220> FEATURE:
<223> OTHER INFORMATION: PCR Primer

<400> SEQUENCE: 33
cctttttcgc cttgctgttg 20

<210> SEQ ID NO 34
<211> LENGTH: 40
<212> TYPE: PRT
<213> ORGANISM: artificial
<220> FEATURE:
<223> OTHER INFORMATION: peptide linker
<220> FEATURE:
<221> NAME/KEY: MISC_FEATURE
<222> LOCATION: (6)..(40)
<223> OTHER INFORMATION: The 35 Xaa represent up to 7 repetitions of the five amino acid sequence Ser-Gly-Gly-Gly-Gly, i.e., the amino acid sequence Ser-Gly-Gly-Gly-Gly may be present in 1, 2, 3, 4, 5, 6, 7, or 8 copies

<400> SEQUENCE: 34

```
Ser Gly Gly Gly Gly Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa
        35                  40
```

<210> SEQ ID NO 35
<211> LENGTH: 551
<212> TYPE: PRT
<213> ORGANISM: Homo sapiens

<400> SEQUENCE: 35

```
Met Ala Ala Pro Ala Leu Ser Trp Arg Leu Pro Leu Leu Ile Leu Leu
1               5                   10                  15

Leu Pro Leu Ala Thr Ser Trp Ala Ser Ala Ala Val Asn Gly Thr Ser
            20                  25                  30

Gln Phe Thr Cys Phe Tyr Asn Ser Arg Ala Asn Ile Ser Cys Val Trp
        35                  40                  45

Ser Gln Asp Gly Ala Leu Gln Asp Thr Ser Cys Gln Val His Ala Trp
    50                  55                  60

Pro Asp Arg Arg Arg Trp Asn Gln Thr Cys Glu Leu Leu Pro Val Ser
65                  70                  75                  80

Gln Ala Ser Trp Ala Cys Asn Leu Ile Leu Gly Ala Pro Asp Ser Gln
                85                  90                  95

Lys Leu Thr Thr Val Asp Ile Val Thr Leu Arg Val Leu Cys Arg Glu
            100                 105                 110

Gly Val Arg Trp Arg Val Met Ala Ile Gln Asp Phe Lys Pro Phe Glu
        115                 120                 125

Asn Leu Arg Leu Met Ala Pro Ile Ser Leu Gln Val Val His Val Glu
    130                 135                 140

Thr His Arg Cys Asn Ile Ser Trp Glu Ile Ser Gln Ala Ser His Tyr
145                 150                 155                 160

Phe Glu Arg His Leu Glu Phe Glu Ala Arg Thr Leu Ser Pro Gly His
                165                 170                 175

Thr Trp Glu Glu Ala Pro Leu Leu Thr Leu Lys Gln Lys Gln Glu Trp
            180                 185                 190

Ile Cys Leu Glu Thr Leu Thr Pro Asp Thr Gln Tyr Glu Phe Gln Val
        195                 200                 205

Arg Val Lys Pro Leu Gln Gly Glu Phe Thr Thr Trp Ser Pro Trp Ser
    210                 215                 220

Gln Pro Leu Ala Phe Arg Thr Lys Pro Ala Ala Leu Gly Lys Asp Thr
225                 230                 235                 240

Ile Pro Trp Leu Gly His Leu Leu Val Gly Leu Ser Gly Ala Phe Gly
```

-continued

```
            245                 250                 255

Phe Ile Ile Leu Val Tyr Leu Leu Ile Asn Cys Arg Asn Thr Gly Pro
        260                 265                 270

Trp Leu Lys Lys Val Leu Lys Cys Asn Thr Pro Asp Pro Ser Lys Phe
    275                 280                 285

Phe Ser Gln Leu Ser Ser Glu His Gly Gly Asp Val Gln Lys Trp Leu
    290                 295                 300

Ser Ser Pro Phe Pro Ser Ser Ser Phe Ser Pro Gly Gly Leu Ala Pro
305                 310                 315                 320

Glu Ile Ser Pro Leu Glu Val Leu Glu Arg Asp Lys Val Thr Gln Leu
                325                 330                 335

Leu Leu Gln Gln Asp Lys Val Pro Glu Pro Ala Ser Leu Ser Ser Asn
            340                 345                 350

His Ser Leu Thr Ser Cys Phe Thr Asn Gln Gly Tyr Phe Phe His
        355                 360                 365

Leu Pro Asp Ala Leu Glu Ile Glu Ala Cys Gln Val Tyr Phe Thr Tyr
    370                 375                 380

Asp Pro Tyr Ser Glu Glu Asp Pro Asp Glu Gly Val Ala Gly Ala Pro
385                 390                 395                 400

Thr Gly Ser Ser Pro Gln Pro Leu Gln Pro Leu Ser Gly Glu Asp Asp
                405                 410                 415

Ala Tyr Cys Thr Phe Pro Ser Arg Asp Asp Leu Leu Leu Phe Ser Pro
            420                 425                 430

Ser Leu Leu Gly Gly Pro Ser Pro Pro Ser Thr Ala Pro Gly Gly Ser
        435                 440                 445

Gly Ala Gly Glu Glu Arg Met Pro Pro Ser Leu Gln Glu Arg Val Pro
    450                 455                 460

Arg Asp Trp Asp Pro Gln Pro Leu Gly Pro Pro Thr Pro Gly Val Pro
465                 470                 475                 480

Asp Leu Val Asp Phe Gln Pro Pro Pro Glu Leu Val Leu Arg Glu Ala
                485                 490                 495

Gly Glu Glu Val Pro Asp Ala Gly Pro Arg Glu Gly Val Ser Phe Pro
            500                 505                 510

Trp Ser Arg Pro Pro Gly Gln Gly Glu Phe Arg Ala Leu Asn Ala Arg
        515                 520                 525

Leu Pro Leu Asn Thr Asp Ala Tyr Leu Ser Leu Gln Glu Leu Gln Gly
    530                 535                 540

Gln Asp Pro Thr His Leu Val
545                 550
```